US007732162B2

(12) United States Patent
Hoffman et al.

(10) Patent No.: US 7,732,162 B2
(45) Date of Patent: *Jun. 8, 2010

(54) INHIBITORS OF GLUTAMINYL CYCLASE FOR TREATING NEURODEGENERATIVE DISEASES

(75) Inventors: Torsten Hoffman, Halle/Saale (DE); Stephan Schilling, Halle/Saale (DE); Andre J. Niestroj, Sennewitz (DE); Hans-Ulrich Demuth, Haale/Saale (DE); Ulrich Heiser, Halle/Saale (DE); Mirko Buchholz, Halle/Saale (DE)

(73) Assignee: Probiodrug AG, Halle (Salle) (DE)

( * ) Notice: Subject to any disclaimer, the term of this patent is extended or adjusted under 35 U.S.C. 154(b) by 263 days.

This patent is subject to a terminal disclaimer.

(21) Appl. No.: 11/685,881

(22) Filed: Mar. 14, 2007

(65) Prior Publication Data

US 2007/0191366 A1    Aug. 16, 2007

Related U.S. Application Data

(63) Continuation-in-part of application No. 10/839,017, filed on May 5, 2004, now Pat. No. 7,381,537.

(60) Provisional application No. 60/468,014, filed on May 5, 2003.

(51) Int. Cl.
   *C12Q 1/34*    (2006.01)
(52) U.S. Cl. .......................... 435/18; 435/69.2
(58) Field of Classification Search ............ 435/18, 435/69.2
   See application file for complete search history.

(56) References Cited

U.S. PATENT DOCUMENTS

| 5,552,426 | A | 9/1996 | Lunn et al. |
| 6,316,449 | B1 | 11/2001 | Bratton et al. |
| 6,670,364 | B2 | 12/2003 | Laborde et al. |
| 6,677,365 | B2 | 1/2004 | Laborde et al. |
| 7,109,347 | B2 | 9/2006 | von Hoersten et al. |
| 7,381,537 | B2 * | 6/2008 | Demuth et al. ............ 435/18 |
| 2004/0224875 | A1 | 11/2004 | Schilling et al. |
| 2004/0229848 | A1 | 11/2004 | Demuth et al. |
| 2008/0260688 | A1 * | 10/2008 | Buchholz et al. ........... 424/85.2 |
| 2008/0262063 | A1 * | 10/2008 | Buchholz et al. ........... 514/394 |
| 2008/0262065 | A1 * | 10/2008 | Buchholz et al. ........... 514/397 |
| 2008/0267911 | A1 * | 10/2008 | Buchholz et al. ........... 424/85.2 |
| 2008/0267912 | A1 * | 10/2008 | Buchholz et al. ........... 424/85.2 |
| 2008/0286231 | A1 * | 11/2008 | Buchholz et al. ........... 424/85.2 |
| 2008/0286810 | A1 * | 11/2008 | Demuth et al. ............ 435/7.8 |
| 2008/0292582 | A1 * | 11/2008 | Buchholz et al. ........... 424/85.2 |
| 2009/0018087 | A1 * | 1/2009 | Schilling et al. ........... 514/19 |
| 2009/0068699 | A1 * | 3/2009 | Schilling et al. ........... 435/29 |

FOREIGN PATENT DOCUMENTS

| EP | 0253310 | 10/1994 |
| EP | 0443983 | 2/1996 |
| EP | 0459136 | 12/1996 |
| EP | 0539086 | 12/1997 |
| EP | 0502314 | 5/1998 |
| EP | 0454511 | 6/1998 |
| EP | 0403159 | 3/2000 |
| EP | 0503785 | 4/2001 |
| EP | 1262552 | 4/2002 |
| WO | WO8906242 | 7/1989 |
| WO | WO9012870 | 11/1990 |
| WO | WO9012871 | 11/1990 |
| WO | WO9014840 | 12/1990 |
| WO | WO9221333 | 12/1992 |
| WO | WO9320061 | 10/1993 |
| WO | WO9325534 | 12/1993 |
| WO | WO9407890 | 4/1994 |
| WO | WO9409016 | 4/1994 |
| WO | WO9413641 | 6/1994 |
| WO | WO9417197 | 8/1994 |
| WO | WO9420109 | 9/1994 |
| WO | WO9502601 | 1/1995 |
| WO | WO9502602 | 1/1995 |
| WO | WO9512594 | 5/1995 |
| WO | WO9526342 | 10/1995 |
| WO | WO9526349 | 10/1995 |
| WO | WO9526350 | 10/1995 |
| WO | WO9526352 | 10/1995 |
| WO | WO9531986 | 11/1995 |

(Continued)

OTHER PUBLICATIONS

Bateman et al., "Post-Translational Modifrication of Bovine Pro-Opiomelanocortin", The Journal of Biological Chemistry, 1990, 265:22130-22136.

(Continued)

*Primary Examiner*—Ralph Gitomer
(74) *Attorney, Agent, or Firm*—Sonnenschein Nath & Rosenthal LLP

(57) ABSTRACT

The present invention provides novel physiological substrates of mammalian glutaminyl cyclase (QC, EC 2.3.2.5), new effectors of QC, methods for screening for such effectors, and the use of such effectors and pharmaceutical compositions comprising such effectors for the treatment of conditions that can be treated by modulation of QC-activity. Preferred compositions additionally comprise inhibitors of DP IV or DP IV-like enzymes for the treatment or alleviation of conditions that can be treated by modulation of QC- and DP IV-activity.

19 Claims, 54 Drawing Sheets

FOREIGN PATENT DOCUMENTS

| | | |
|---|---|---|
| WO | WO9608485 | 3/1996 |
| WO | WO9614318 | 5/1996 |
| WO | WO09620946 | 7/1996 |
| WO | WO9621655 | 7/1996 |
| WO | WO9625435 | 8/1996 |
| WO | WO9712615 | 4/1997 |
| WO | WO9723214 | 7/1997 |
| WO | WO9723215 | 7/1997 |
| WO | WO9723216 | 7/1997 |
| WO | WO9732873 | 9/1997 |
| WO | WO9801157 | 1/1998 |
| WO | WO9805337 | 2/1998 |
| WO | WO9806703 | 2/1998 |
| WO | WO9810757 | 3/1998 |
| WO | WO9840102 | 9/1998 |
| WO | WO9844955 | 10/1998 |
| WO | WO9846559 | 10/1998 |
| WO | WO9850044 | 11/1998 |
| WO | WO9850075 | 11/1998 |
| WO | WO9901416 | 1/1999 |
| WO | WO9907351 | 2/1999 |
| WO | WO9907413 | 2/1999 |
| WO | WO9913878 | 3/1999 |
| WO | WO9927944 | 6/1999 |
| WO | WO9941224 | 8/1999 |
| WO | WO9945963 | 9/1999 |
| WO | WO9948891 | 9/1999 |
| WO | WO9953922 | 10/1999 |
| WO | WO9957119 | 11/1999 |
| WO | WO9957120 | 11/1999 |
| WO | WO9960024 | 11/1999 |
| WO | WO0000197 | 1/2000 |
| WO | WO0029023 | 5/2000 |
| WO | WO0046195 | 8/2000 |
| WO | WO0046196 | 8/2000 |
| WO | WO0046198 | 8/2000 |
| WO | WO0046199 | 8/2000 |
| WO | WO0056711 | 9/2000 |
| WO | WO0063250 | 10/2000 |
| WO | WO0072880 | 12/2000 |
| WO | WO0110831 | 2/2001 |
| WO | WO0110833 | 2/2001 |
| WO | WO0112176 | 2/2001 |
| WO | WO0112598 | 2/2001 |
| WO | WO0126656 | 4/2001 |
| WO | WO0132640 | 5/2001 |
| WO | WO0134594 | 5/2001 |
| WO | WO0157226 | 8/2001 |
| WO | WO0162801 | 8/2001 |
| WO | WO0181295 | 11/2001 |
| WO | WO0192204 | 12/2001 |
| WO | WO0194321 | 12/2001 |
| WO | WO0198262 | 12/2001 |
| WO | WO0198289 | 12/2001 |
| WO | WO0213821 | 2/2002 |
| WO | WO0221509 | 3/2002 |
| WO | WO0227418 | 4/2002 |
| WO | WO0234718 | 5/2002 |
| WO | WO0241842 | 5/2002 |
| WO | WO0246222 | 6/2002 |
| WO | WO0246237 | 6/2002 |
| WO | WO02060900 | 8/2002 |
| WO | WO02070509 | 9/2002 |
| WO | WO02072542 | 9/2002 |
| WO | WO02074240 | 9/2002 |
| WO | WO02081463 | 10/2002 |
| WO | WO02088306 | 11/2002 |
| WO | WO02088307 | 11/2002 |
| WO | WO02094881 | 11/2002 |
| WO | WO03012141 | 2/2003 |
| WO | WO03014162 | 2/2003 |
| WO | WO03015691 | 2/2003 |
| WO | WO03016466 | 2/2003 |
| WO | WO03037376 | 5/2003 |
| WO | WO03039467 | 5/2003 |
| WO | WO03040174 | 5/2003 |
| WO | WO03040183 | 5/2003 |
| WO | WO03045128 | 6/2003 |
| WO | WO03048204 | 6/2003 |
| WO | WO03051374 | 6/2003 |
| WO | WO03053368 | 7/2003 |
| WO | WO03055514 | 7/2003 |
| WO | WO03063760 | 8/2003 |
| WO | WO03070760 | 8/2003 |
| WO | WO03074081 | 9/2003 |
| WO | WO03077858 | 9/2003 |
| WO | WO03086310 | 10/2003 |
| WO | WO03089460 | 10/2003 |
| WO | WO03104437 | 12/2003 |
| WO | WO2004009062 | 1/2004 |
| WO | WO2004024090 | 3/2004 |
| WO | WO2004024770 | 3/2004 |
| WO | WO2004024921 | 3/2004 |
| WO | WO2004026851 | 4/2004 |
| WO | WO2004028522 | 4/2004 |
| WO | WO2004029629 | 4/2004 |
| WO | WO2004029630 | 4/2004 |
| WO | WO2004031400 | 4/2004 |
| WO | WO2004032868 | 4/2004 |
| WO | WO2004039371 | 5/2004 |
| WO | WO2004044204 | 5/2004 |
| WO | WO2004056727 | 7/2004 |
| WO | WO2004067561 | 8/2004 |
| WO | WO2004069182 | 8/2004 |
| WO | WO2004071408 | 8/2004 |
| WO | WO2004078908 | 9/2004 |
| WO | WO2004080419 | 9/2004 |
| WO | WO2004084830 | 10/2004 |
| WO | WO2004089351 | 10/2004 |
| WO | WO2004089366 | 10/2004 |
| WO | WO2004092189 | 10/2004 |
| WO | WO2004098631 | 11/2004 |
| WO | WO2004108895 | 12/2004 |
| WO | WO2005000216 | 1/2005 |
| WO | WO2005007199 | 1/2005 |
| WO | WO2005007614 | 1/2005 |
| WO | WO20005000193 | 1/2005 |
| WO | WO2005009421 | 2/2005 |
| WO | WO2005011599 | 2/2005 |
| WO | WO2005018424 | 3/2005 |
| WO | WO2005025516 | 3/2005 |
| WO | WO2005025616 | 3/2005 |
| WO | WO2005028511 | 3/2005 |
| WO | WO2005070429 | 4/2005 |
| WO | WO2005055996 | 6/2005 |
| WO | WO2005072705 | 8/2005 |
| WO | WO2005079756 | 9/2005 |
| WO | WO2005079779 | 9/2005 |
| WO | WO2005080435 | 9/2005 |
| WO | WO2005081872 | 9/2005 |
| WO | WO2005097103 | 10/2005 |
| WO | WO2005102390 | 11/2005 |
| WO | WO2005105133 | 11/2005 |
| WO | WO2005105998 | 11/2005 |
| WO | WO2005120571 | 12/2005 |
| WO | WO2005123775 | 12/2005 |
| WO | WO2006008661 | 1/2006 |
| WO | WO2006010965 | 2/2006 |
| WO | WO2006014478 | 2/2006 |
| WO | WO2006014638 | 2/2006 |
| WO | WO2006016644 | 2/2006 |
| WO | WO2006021409 | 3/2006 |
| WO | WO2006021413 | 3/2006 |
| WO | WO2006026408 | 3/2006 |

| | | |
|---|---|---|
| WO | WO2006036291 | 4/2006 |
| WO | WO2006039470 | 4/2006 |
| WO | WO2006039807 | 4/2006 |
| WO | WO2006042103 | 4/2006 |
| WO | WO2006046644 | 5/2006 |
| WO | WO2006055178 | 5/2006 |
| WO | WO2006058059 | 6/2006 |
| WO | WO2006058236 | 6/2006 |
| WO | WO2006060473 | 6/2006 |
| WO | WO2006066049 | 6/2006 |
| WO | WO2006066089 | 6/2006 |
| WO | WO2006066171 | 6/2006 |
| WO | WO2006066233 | 6/2006 |
| WO | WO2006074265 | 7/2006 |
| WO | WO2006081171 | 8/2006 |
| WO | WO2006085961 | 8/2006 |
| WO | WO2006091988 | 8/2006 |
| WO | WO2006094674 | 9/2006 |
| WO | WO2006095041 | 9/2006 |
| WO | WO2006097624 | 9/2006 |
| WO | WO2006103116 | 10/2006 |
| WO | WO2006118959 | 11/2006 |
| WO | WO2006125202 | 11/2006 |
| WO | WO2006137354 | 12/2006 |

OTHER PUBLICATIONS

Bhatia et al, "Pathophysiology of Acute Pancreatitis", Pancreatology, 2005, 5:132-144.

Bhatia et al, "Treatment With Bindarit, A Blocker Of Mcp-1 Synthesis, Protects Mice Against Acute Pancreatis, American Journal of Physiology Gastrointestinal Liver Physiology", 2005, 288, G1259-G1265.

Booth et al., "Human Glutaminyl Cyclase and Bacterial Zinc Aminopeptidase Share A Common Fold And Active Site, BMC Biology", 2004, 2:1-9.

Citron, β-Secretase Inhibition for the Treatment of Alzheimer's Disease - Promise and Challenge, Trends in Pharmacological Sciences, 2004, 25:92-97.

Coll et al., "Hiv-lnfected Patients With Lipodystrophy Have Higher Rates of Carotid Altherosclerosis: The Role of Monocyte Chemoattractant Protein-1", Cytokine+, 2006, 34:51-55.

Galimberti et al., "Intrathecal Chemokine Synthesis in Mild Cognitive Impairment and Alzheimer Disease", Arch Neurol, 2006, 63:538-543.

Galimberti et al., "Serum MCP-1 Levels are Increased in Mild Cognitive Impairment and Mild Alzheimer's Disease," Neurobiology of Aging, 2006, 27:1763-1768.

Garden et al., "Formation of N-Pyroglutamyl Peptides from N-Glu and N-Gln Precursors in Aplysia Neurons", Journal of Neurochemistry, 1999, 72:676-681.

Gerard and Rollins, "Chemokines and Disease", Nature Immunology, 2001, 2:108-115.

Ghiso et al., "Chromosome 13 Dementia Syndromes as Models of Neurodegeneration", Amyloid, 2001, 8:277-284.

Glabe C, "Avoiding Collateral Damage in Alzheimer's Disease Treatment", Science, 2006, 314:602-603.

Gololobov et al., "Substrate and Inhibitor Specificity of Glutamine Cyclotransferase (QC)", Biol Chem Hoppe-Seyler, 1996, 377:395-398.

Gong et al., "An Antagonist of Monocyte Chemoattractant Protein 1 (Mcp-1) Inhibits Arthritis In The Mrl-Lpr Mouse Model", J Exp Med, 1997, 186:131-137.

Gosling et al., "Mcp-1 Deficiency Reduces Susceptibility To Atherosclerosis In Mice That Overexpress Human Apolipoprotein B", J Clin Invest, 1999 103:773-778.

Gu et al., "Absence of Monocyte Chemoattractant Protein-1 Reduces Atherosclerosis In Low Density Lipoprotein Receptor-Deficient Mice", Molecular Cell, 1998, 2:275-281.

Hardy and Selkoe, THe Amyloid Hypothesis of Alzheimer's Disease: Progress and Problems on the Road to Therapeutics, Science, 2002, 297:353-356.

Harigaya et al., "Amyloid β Protein Starting Pyroglutamate at Position 3 Is a Major Component of the Amyloid Deposits in the Alzheimer's Disease Brain", Biochemical and Biophysical Research Communications, 2000, 276:422-427.

Hashimoto et al.,"CLAC: A Novel Alzheimer Amyloid Plague Component Derived From a Transmembrane Precursor, CLAC-P/Collagen Type XXV", The EMBO Journal, 2002, 21:1524-1534.

He and Barrow, The Aβ 3-Pyroglutamyl and 11-Pyroglutamyl Peptides Found in Senile Plague Have Greater β-Sheet Forming and Aggregation Propensities in Vitro than Full-Lenth Aβ; Biochemistry, 1999, 38:10871-1877.

Hemmerich et al., "Indentification of Residues in the Monocyte Chemotactic Protein-1 That Contact the MCP-1 Receptor, CCR2", Biochemistry, 1999, 38:13013-13025.

Hosoda et al., "Quantification of Modified Amyloid βPeptides in Alzheimer Disease and Down Syndrome Brains", Journal of Neuropathology and Experimental Neurology, 1998, 57:1089-1095.

Huang et al., "Crystal Structures of Human Glutaminyl Cyclase, an Enzyme Responsible for Protein N- Terminal Pyroglutamate Formation," PNAS, 2005, 102:13117-13122.

Huse et al., "62-Secretase Processing in the Trans-Golgi Network Preferentially Generates Truncated Amyloid Species that Accumulate in Alzheimer's Disease Brain", The Journal of Biological Chemistry, 2002, 277:18:16278-16284.

Inoshima et al., "Anti-Monocyte Chemoattractant Protein-1 Gene Therapy Attenuates Pulmonary Fibrosis in Mice", Am J Physiol Lung Cell Mol Physiol, 2004, 286:L1038-L1044.

Ishizuka et al., "Identification of Monocyte Chemoattractant Protein-1 in Senile Plaques and Reactive Microglia of Alzheimer's Disease", Psychiatry and Clinical Neurosciences, 1997, 51:135-138.

Iwatsubo et al., Full-Lenth Amyloid-β(1-42(43)) and Amino-Terminally Modified and Truncated Amyloid-β42(43 Deposit in Diffuse Plaques, American Journal of Pathology, 1996, 149:1823-1830.

Janelsins et al., "Early Correlation of Microglial Activiation with Enhanced Tumor Necrosis Factor-Alpha and Monocyte Chemoattractant Protein-1 Expression Specifically Within the Entorhinal Cortex of Triple Transgenic Alzheimer's Disease Mice", Journal of Neuroinflammation, 2005, 2:23.

Katabuchi et al., "Characterization of Macrophages in the Decidual Atherotic Spiral Artery With Specifal Reference to the Cytology of Foam Cells", Med Electron Micross, 2003, 36:253-262.

Kitamoto et al., "Stress and Vascular Responses: Anti-Inflammatory Therapeutic Strategy Against Atherosclerosis and Restenosis After Coronary Intervention", J Pharmacol Sci, 2003, 91:192-196.

Kuo et al., "Isolation, Chemical Characterization, and Quantitation of Aβ 3-Pyroglutamyl Peptide from Neuritic Plagues and Vascular Amyloid Deposits", Biochemical and Biophysical Research Communications, 1997, 237:188-191.

Li et al., "Mcp-1 Overexpressed In Tuberous Sclerosis Lesions Acts As A Paracrine Factor For Tumor Development", J Exp Med, 2005, 202:617-624.

Luini et al., "Species-Specificity of Monocyte Chemotactic Protein-1 and -3", Cytokine, 1994, 6:28-31.

Masure et al., "Expression of a Human Mutant Monocyte Chemotactic Protein 3 in Pichia Pastoris and Characterization as an MCP-3 Receptor Antagonis", Journal of Interferon and Cytokine Research, 1995, 15:955-963.

Meda et al., "β-Amyloid (25-35) Peptide and IFN-y Synergistically Induce the Production of the Chemotactic Cytokine MCP-1/JE in Monocytes and Microglial Cells", The Journal of Immunology, 1996, 157:1213-1218.

Miravalle et al., "Amino-Terminally Truncated AβPeptide Species Are the Main Component of Coton Woll Plaques", Biochemistry, 2005, 44:10810-10821.

Misquitta et al., "Inhibition Studies of Glutaminyl Cyclase", FASEB Journal, vol. 15, p. 1159, No. 5, A1159, 2001.

Misquitta et al., "Characterization of the Inhibition of Glutaminyl Cyclase by Imidazole Derivatives and Phenanthrolines", FASEB Journal, 2002, vol. 16, No. 4, p. A157.

Ogata et al., "The Role of Monocyte Chemoattractant Protein-1 (Mcp-1) in The Pathogenesis Of Collagen- Induced Arthritis In Rats", Journal Of Pathology, 1997, 182:106-114.

Ohta et al., "Monocyte Chemoattractant Protein-1 Expression Correlates With Macrophage Infiltration And Tumor Vascularity In Human Gastric Carcinomas", International Journal Of Oncology, 2003, 22:773-778.

Park et al., "Hiv-1 Tat Promotes Monocyte Chemoattractant Protein-1 Secretion Followed By Transmigration Of Monocytes", Blood, 2001, 97:352-358.

Patton et al., "Amyloid-βPeptide Remnants in An-1792-Immunized Alzheimer's Disease Patients", The American Journal of Pathology, 2006, 169:1048-63.

Pearson and Peers, "Physiological Roles for Amyloid βPeptides", J Physiol, 2006, 575:5-10.

Piccini et al, "β-Amyloid Is Different in Normal Aging and in Alzheimer Disease", The Jounral of Biological Chemistry, 2005, 34186-34192.

Proost et al., "Posttranslational Modifications Affect the Activity of the Human Monocyte Chemotactic Proteins MCP-1 and MCP-2: Identification of MCP-2(6-76) as a Natural Chemokine Inhibitor", J. Immunol, 1998, 160:4034-4041.

Rogers and Lue, "Microglial Chemotaxis, Activation, and Phagocytosis of Amyloid -Peptide as Linked Phenomena in Alzheimer's Disease", Neurochemistry International, 2001, 39:333-340.

Russo et al., "Heterogeneity of Water-Soluable Amyloid β-Peptide in Alzheimer's Disease and Down's Syndrome Brains", Federation of European Biochemical Socienties Letters, 1997, 409:411-16.

Russo et al., "Identification of Amino-Terminally and Phosphotyrosine-Modified Carboxy-Terminal Fragments of the Amyloid Precursor Protein in Alzheimer's Disease and Down's Syndrome Brain", Neurobiology of Disease, 2001, 8:173-180.

Russo et al., "Presenilin-1 Mutations in Alzheimer's Disease", Nature, 2000, 405:531-532.

Russo et al., "Pyroglutamate-Modified Amyloid β-Peptides - AN3(pE) - Strongly Affected Cultured Neuron and Astrocyte Survival", Journal of Neurochemistry, 2002, 82:1480-1489.

Saido, "Alzheimer's Disease as Proteolytic Disorders: Anabolism and Catabolism of β-Amyloid", Neurobiology of Aging, 1998, 19:S69-S75.

Saido, "Involvement of Polyglutamine Endolysis Followed by Pyroglutamate Formation in the Pathogenesis of Triplet Repeat/ Polyglutamine-Expansion Diseases", Medical Hypothese, 2000, 54:427-429.

Saiura et al., "Antimonocyte Chemoattractant Protein-1 Gene Therapy Attenuates Graft Vasculopathy", Arterioscler Thromb Basc Biol., 2004, 24:1886-1890.

Schilling et al., "Glutaminyl Cyclases Unfold Glutamyl Cyclase Activity Under Mild Acid Conditions", FEBS Letters, 2004, 563:191-196.

Schilling et al., "Substrate Specificity Of Glutaminyl Cyclases From Plants And Animals", J Biol Chem., 2003, 278:50:49773-49779.

Schilling et al., "Isolation and Characterization of the Glutaminyl Cyclases from Solanum Tuberosum and Arabidopsis Thaliana: Implications for Physiological Functions", Biol. Chem., 2007, vol. 388, pp. 145-153.

Schilling et al., "On the Seeding and Oligomerization of pGlu-Amyloid Peptides (in vitro)", American Chemical Society, 2006, vol. 45, No. 41.

Schilling et al., "Isolation, Catalytic Properties, and Comopetitive Inhibitors of the Zinc-Dependent Murine Glutaminyl Cyclase", Biochemistry, 2005, 44:13415-13424.

Schilling et al., "Identification of Human Glutaminyl Cyclase as a Metalloenzyme", The Journal of Biological Chemistry, 2003, vol. 278, No. 50:49773-49779.

Schilling et al., "Heterologous Expression and Characterization of Human Glutaminyl Cyclase: Evidence for a Disulfide Bond with Importance for Catalytic Activity", Biochemistry, 2002, 41:10849-10857.

Selkoe, "Alzheimer's Disease: Genes, Proteins, and Therapy", Physiological Reviews, 2001, 81:741-766.

Sergeant et al., "Truncated Beta-Amyloid Peptide Species in Pre-Clinical Alzheimer's Disease as New Targets for the Vaccination Approach", Journal of Neurochemistry, 2003, 85:1581-1591.

Szczepanik et al., "IL-4, IL-10 and IL-13 Modulate Aβ(1-42)-Induced Cytokine and Chemokine Production in Primary Murine Microglia and a Human Monocyte Cell Line", Jounal of Neuroimmunology, 2001, 113:49-62.

Tekirian et al., "N-Terminal Heterogeneity Of Parenchymal And Cerebrovascular Aβ Deposits", Journal Of Neuropathology And Experimental Neurology, 1998, 57:76-94.

Twardzik and Peterkovsky, "Glutamic Acid as a Precursor to N-Terminal Pyroglutamic Acid in Mouse Plasmacytoma Protein", Proc. Nat. Acad. Sci. USA, 1972, 69:274-277.

Uguccioni et al., "Actions of the Chemotactic Cytokines MCP-1, MCP-2, MCP-3, Rantes, MIP-y and MIP-1β on Human Nonocytes", Eur J. Immunol., 1995, 25:64-68.

Van Damme et al., "The Role of CD26/DPP IV in Chemokine Processing", Chem Immunol, 1999, 72:42-56.

Wada et al., "Gene Therapy Via Blockade Of Monocyte Chemoattractant Protein-1 For Renal Fibrosis", J Am Soc Nephrol, 2004, 15:940-948.

White et al.,"Excitatory Monocyte Chemoattractant Protein-1 Signaling Is Up-Regulated In Sensory Neurons After Chronic Compression Of The Dorsal Root Ganglion", PNAS USA, 2005, 102:14092-14097.

Xia and Hyman, "Chemokines/Chemokine Receptors in the Central Nervous System and Alzheimer's Disease", Journal of NeuroVirology, 1999, 5:32-41.

Yamamoto et al., Overexpression of Monocyte Chemotactic Protein-1/CCL2 in β-Amyloid Precursor Protein Transgenic Mice Show Accelerated Diffuse β-Amyloid Deposition, American Journal of Pathology, 2005, 166:1475-1485.

Zhang et al., "Sructure/Activity Analysis of Human Monocyte Chemoattractant Protein-1 (MCP-1) by Mutagenesis", The Journal of Biological Chemistry, 1994, 269:15918-15924.

Misquitta et al., "Inhibition Studies of Glutaminyl Cyclase", FASEB Journal, 2001, vol. 15, No. 5, p. 1159.

* cited by examiner

```
hQC      MAGGRHRRVVGTLHLLLLVAALPWASRGVSPSASAWPEEKNYHQPAILNSSALRQIAEGT
SGAP     -----------------------------------------APDIPLANVKAHLTQLS
hGCP II  --------------------------ANEYAYRRGIAEAVGLPSIPVHPIGYYDAQ-K
                                                  * *         ::  .

hQC      SISEMWQNDLQPLLIERYPGSPGSYAARQHIMQRIQRLQADWVLEIDTFLSQTPYGYRSF
SGAP     TIAAN--NGGN-----RAHGRPGYKASVDYVKAKLD--AAGYTTTLQQFTSGGATGYNLI
hGCP II  LLEKM--GGSAP---PDSSWRGSLKVPYNVGPGFTGNFSTQKVKMHIHSTNEVTRIYNVI
             :   ..       .   ..:        :   .       . .  *. :

hQC      SNIISTLNPTAKRHLVLACHYDSKYFSHWNNRVFVGATDSAVPCAMMLELAR---ALDKK
SGAP     ANWPG-GDP--NKVLMAGAHLDS--VSSG-----AGINDNGSGSAAVLETAL---AVSRA
hGCP II  GTLRGAVEP--DRYVILGGHRDS-----W----VFGGIDPQSGAAVVHEIVRSFGTLKKE
         ..  .  :*  .: ::  . * **            *  *    .* : * .    ::.:

hQC      LLSLKTVSDSKPDLSLQLIFFDGEEAFLHWSPQDSLYGSRHLAAKMASTPHPPGARGTSQ
SGAP     GY--Q------PDKHLRFAWWGAEELGLIGS---KFY----------VNNLPSADR--SK
hGCP II  GW--R------PRRTILFASWDAEEFGLLGS---TEW------------AEENSR-LLQ
                :     *    : :   :..** * *    . :               *   :

hQC      LHGMDLLVLLDLIGAPNPTFPNFF--PNSARWFERLQAIEHELH---ELGLLKDHSLEGR
SGAP     LAG----YLNFDMIGSPNPGYFVYDDDPVIEKTFKNYFAGLNVPT---EIETEGDGRSDHA
hGCP II  ERG-VAYINADSSIEGNYTLRVDCT-PLMYSLVHNLTKELKSPDEGFEGKSLYESWTKKS
            *     :  *     *         *        ...    :       *    :   .

hQC      Y---FQNYSY----G-G-----VIQDD-HIPFLRRGVP-VLHLIPSPFPEVWHTMDDNEE
SGAP     P---FKNVGVP--VG-G-----LFTGAGYTKSAAQAQK-WGGTAGQAFDRCYHSSCDSLS
hGCP II  PSPEFSGMPRISKLGSGNDFEVFFQRLGIASGRARYTKNWETNKFSGYP-LYHSVYETYE
             *..      *  *     .:           :         . :   :*:  :. .

hQC      NLDESTID-N-LNKILQVFVLEYLHL----
SGAP     NINDTALDRNSDAAAHAIWTLSSGTGEPPT
hGCP II  -LVEKFYD--PMFKYHLTVAQVRGGMVFEL
          : :.  *                 .
```

Figure 23
QC-inhibitor diminishes pGlu-Aβ formation *in vitro*
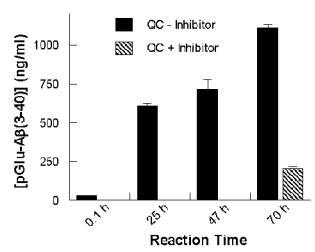
QC-inhibitor reduces pGlu-Aβ formation in cell culture
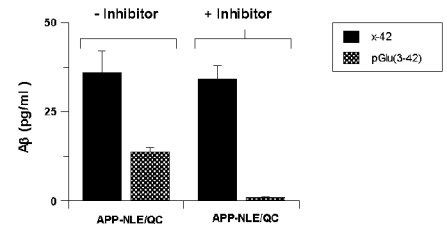
QC-inhibitor reduces pGlu-Aβ formation in traumatic animal model
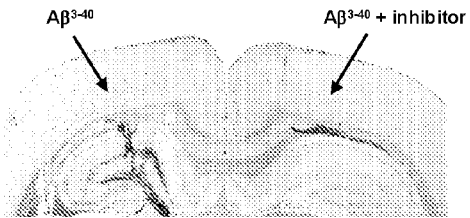
pGlu-Aβ is generated by alternative β-site cleaving enzyme(s)
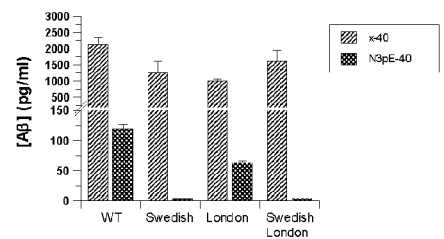

Figure 31
A
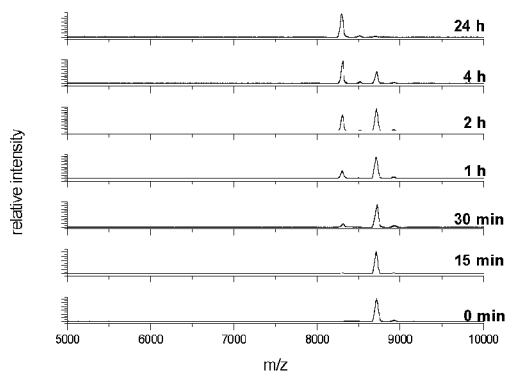
B
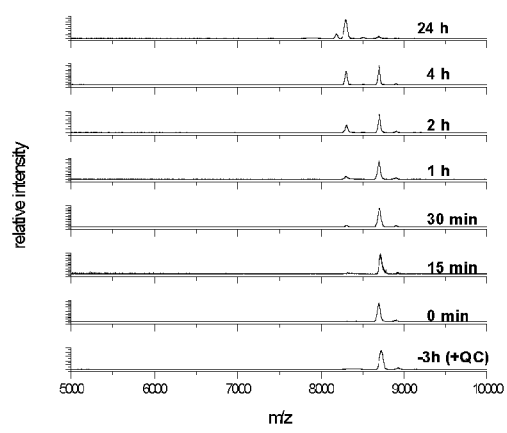

Figure 34
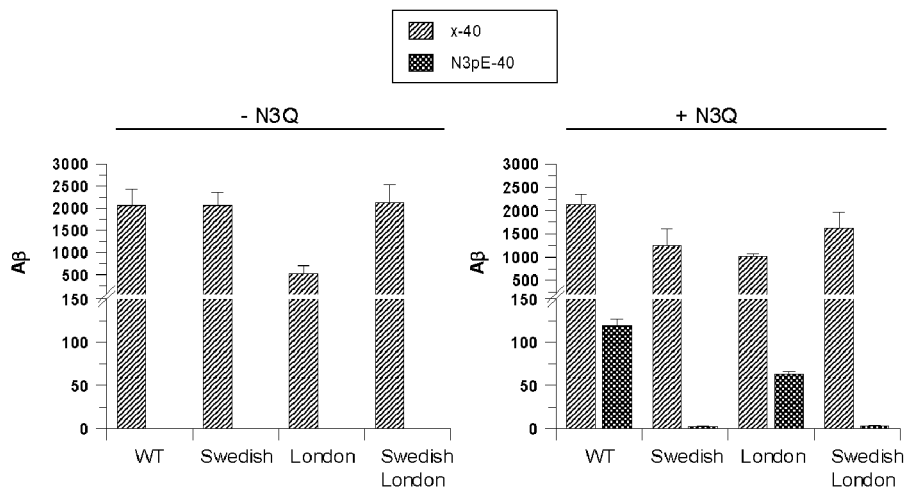
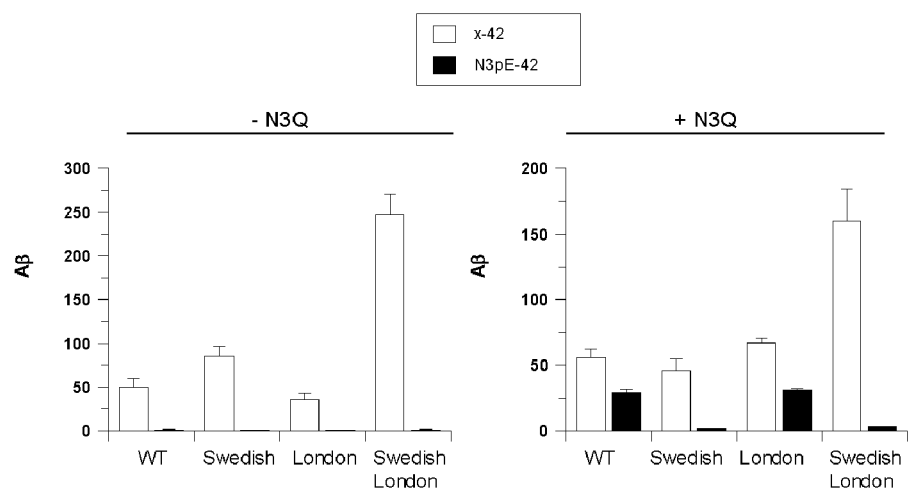
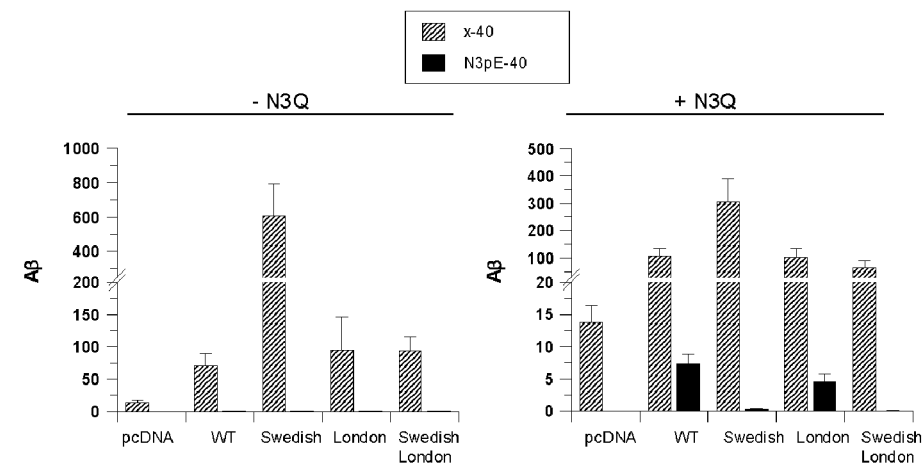

Figure 35
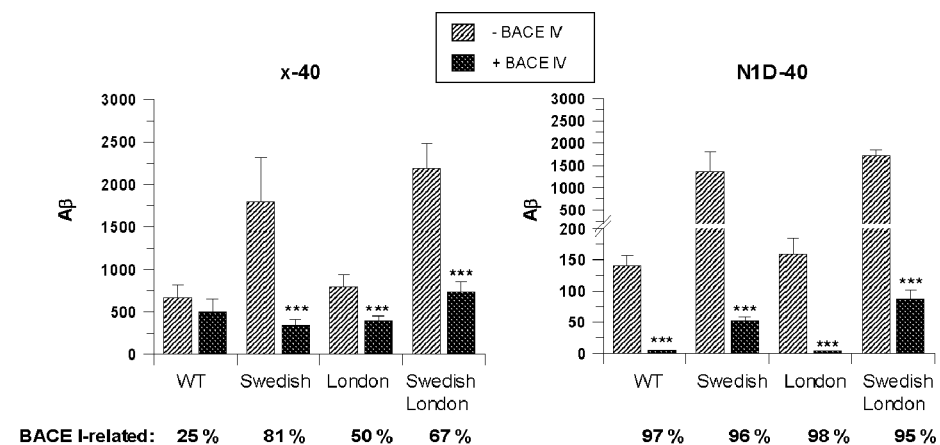
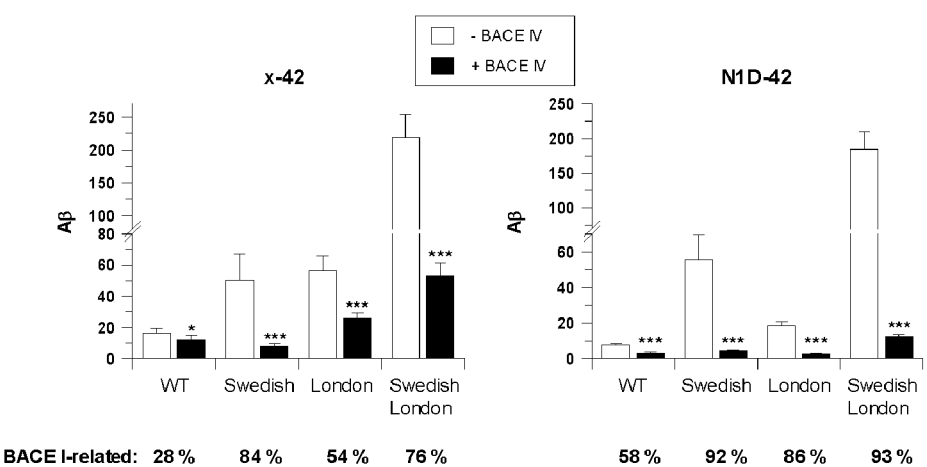
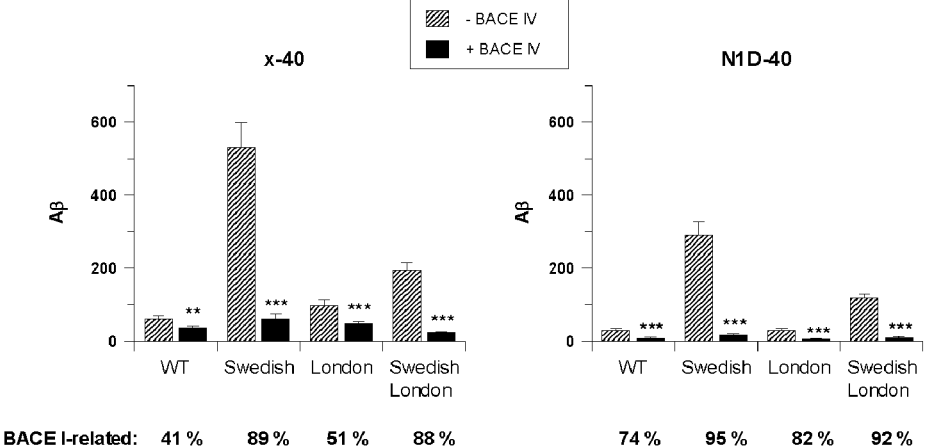

INHIBITORS OF GLUTAMINYL CYCLASE FOR TREATING NEURODEGENERATIVE DISEASES

CROSS REFERENCE TO RELATED APPLICATIONS

The present application is a continuation-in-part of U.S. patent application Ser. No. 10/839,017, filed May 5, 2004, now issued as U.S. Pat. No. 7,381,537, which in turn claims priority to U.S. Provisional Application 60/468,014, filed May 5, 2003, each of which is incorporated herein by reference for all purposes to the extent permitted by law.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-proline, pGlu*) under liberation of ammonia and the intramolecular cyclization of N-terminal glutamate residues into pyroglutamic acid under liberation of water.

The present invention identifies mammalian QCs as metalloenzymes, provides novel physiological substrates of QC in mammals and the use of effectors of QC and pharmaceutical compositions comprising effectors of QC for the treatment of conditions that can be medicated by modulation of QC-activity. Additionally, it is shown that metal interaction is a useful approach for development of QC inhibitors.

In a further embodiment, the present invention provides the use of effectors of QC activity in combination with other agents, which are useful for the treatment of neurodegenerative diseases.

A screening method is also provided for the identification and selection of effectors of QC activity.

BACKGROUND

Alzheimer's disease (AD) is the most frequent neurodegenerative disorder in developed countries, accounting for 60-70% of all dementia cases. Around 5% of all people over the age of 65 years are suffering from AD. Due to a close correlation to age the number of patients is dramatically increasing worldwide. Around 5% of all people above the age of 65 years are suffering from AD while about 30-50% over the age of 80 are affected. In the US alone an estimated 4.5 million patients (in Germany 1.5 million) have Alzheimer's disease. This number is expected to grow to up to 16 million people in 2050. The spending in 2005 was 91 billion US-$ for medication and nursing in the USA. With respect to the increasing life expectancy, the development of a treatment strategy is the present therapeutic challenge and due to a close correlation to age, the number of patients is dramatically increasing worldwide. Even after two decades of intense research, there is currently no treatment available, which rebuilds or even sustains the cognitive function of the patients in a long-lasting manner.

Present endeavors for potential new causal treatments include application of (i) intercalating substances to prevent aggregation of neurotoxic Aβ peptides,
(ii) the inhibition of the enzymes responsible for Aβ formation, or
(iii) clearance of the Aβ-aggregates by vaccination approaches (reviewed in: Hardy and Selkoe (2002) Science 297, 353-356 and Citron (2004) Trends Pharmacol Sci. 25, 92-97).

With regard to vaccination, recent results point to dramatic adverse effects: phase II trials failed because of a high percentage of aseptic encephalitis cases (Patton, et al. (2006) Am J Pathol. 169, 1048-63). Also, the apparently straightforward approach to develop β-secretase (BACE-1) and γ-secretase inhibitors is hampered by their importance for basic cellular processes, e.g. is BACE-1 activity essential for myelination of axons (Glabe, C. (2006) Science 314, 602-603). Also, APP and even Aβ seem to fulfill important physiological functions (Pearson and Peers (2006) J Physiol. 575, 5-10), which might obstruct therapeutic strategies to suppress Aβ generation in general.

A characteristic symptom of AD is the progressive cognitive impairment, characterized by loss of memory, function, language abilities, judgment and executive functioning. Later disease stages are often associated with severe behavioral symptoms (aggression, delusions, hallucinations, disturbed day-night cycle) and the loss of activities of daily living. Reasons for the observed cognitive decline are molecular and histopathological changes in the brain. The earliest events are loss of synaptic contacts in the entorhinal cortex. At later stages, there is also a significant loss of cholinergic neurons in basal forebrain nuclei, a finding that led to the cholinergic theory behind memory loss in this disease and which was the basis for the development of a first symptomatic treatment. Pathological hallmarks of the disease are extracellular amyloid deposits consisting mainly of the amyloid beta peptide (neuritic plaques), and intracellular neurofibrillary tangles which are formed by the hyperphosphorylated microtubule-associated protein tau. The cerebral cortex and the hippocampal regions are particularly affected. According to the amyloid hypothesis, initial amyloid aggregates are caused by intracellular Aβ accumulation, which then initiates the pathophysiologic cascade including plaque formation, neuroinflammation and tangle-formation (Selkoe (2001) Physiol. Rev. 81, 741-766).

The core of amyloid plaques in AD consists of multimeric aggregates of a polypeptide of 40 or 42 residues (4 kDa), depending on the cleavage site of γ-secretase, called amyloid beta or Aβ. The peptide is generated from the amyloid precursor protein (APP), a class 1 transmembrane protein which is highly expressed in neuronal cells, by successive proteolysis of a β- and γ-secretase (FIG. 22-1). In contrast, cleavage of APP by α-secretase precludes generation of Aβ. Therefore, α-cleavage is the physiological, non-amyloidogenic counterpart to the processing by the other secretases of the amyloidogenic pathway.

Depending on the chain length, Aβ peptides display different neurotoxicity, i.e. the longer form Aβ(1-42) is particularly important for developing Alzheimer's disease. It has been shown in vitro that Aβ(1-42)-peptides aggregate more rapidly than Aβ(1-40) peptides. Furthermore, analysis of brains derived from patients with sporadic Alzheimer's disease and Down's syndrome, who inevitably develop AD as a result of the presence of a third APP gene, has shown that Aβ(1-42) peptides deposit at the beginning and in a highly selective manner in senile plaques. These findings provided strong evidence that aggregation and deposition of Aβ(1-42) peptides may be a common initiating event in all forms of AD.

So, in the last decades, research was focused on the C-terminal part of the Aβ-peptides and the influence of C-terminal modifications on AD development and progression. More recently, research was started on N-terminal modifications of Aβ(1-40) and Aβ(1-42). Several new studies have shown that the Aβ-peptides deposited in brains of AD patients are heterogeneous at the N-terminus. The N-terminus of Aβ is generated by β-secretase cleavage at position Asp1 (β-cleavage)

and to a much lesser extent at Glu11 (β'-cleavage) of Aβ. However, it has been shown, that the peptides in plaques display pronounced heterogeneity in terms of the N-terminal amino acid. The L-aspartate residues, normally present at positions 1 and 7 in β-amyloid peptides, can be isomerized to iso-aspartate or racemized to form D-aspartate. More importantly, the glutamates are cyclized to pyroglutamic acid (pGlu) in truncated peptides starting at position 3 or 11. Analysis of brains from AD or DS patients show that the core of amyloid plaques consists of β-amyloid peptides containing N-terminal pyroglutamate, e.g. pGlu3-Aβ(3-40/42) and pGlu11-Aβ(11-40/42). These shortened and modified peptides can account for about 50% of the whole Aβ deposited in plaques (Harigaya, et al. (2000) BBRC 276, 422-427; Sergeant, et al. (2003) J. Neurochem. 85, 1581-1591; Russo, et al. (1997) FEBS Lett. 409, 411-416; Kuo, et al. (1997), BBRC 237, 188-191). Moreover, they are reported to be more neurotoxic and to aggregate more rapidly than full-length isoforms in vitro (Schilling, et al. (2006), Biochemistry 45, 12393-12399; Russo, et al. (2002), J. Neurochem. 82, 1480-1489; He and Barrow (1999), Biochemistry 38, 10871-10877). In a recent study, normal-aged (NA) elderly persons with plaque deposits, but without showing Alzheimer's pathology, could be distinguished from patients suffering from sporadic Alzheimer's disease by characterization of the composition of Aβ species (Piccini, et al. (2005), J. Biol. Chem., 34186-34192). In water-soluble brain fractions of patients with AD, a significantly higher amount of N-terminally truncated, pGlu-modified Aβ peptides was detected, suggesting that accumulation of these species represents a nidus for development of neurodegeneration. A correlation of the insoluble pGlu-Aβ concentration with the state of disease progression was also reported very recently (Güntert, et al. (2006) Neuroscience, 143, 461-475). Additionally, elevated levels of N-truncated Aβ peptides were identified in familial AD cases caused by presenilin mutations. In fact, this further substantiates the relevance of N-modified Aβ for the severity of the disease (Miravalle, et al. (2005), Biochemistry 44, 10810-10821; Russo, et al. (2000), Nature 405, 531-532). Finally, it is important to consider that pGlu-modified Aβ peptides are resistant to degradation by extracellular aminopeptidases. Therefore, pyroglutamate-modified Aβ species have, a prolonged half-life in vivo, which favors accumulation and formation of neurotoxic aggregates (Saido (1998) Neurobiol. Aging, 19, S69-S75). Taken together, the results indicate that the pGlu3-Aβ peptides play an important, probably even the decisive, role in the development of Alzheimer's disease.

Glutaminyl Cyclases—Catalysts of Pyroglutamyl Formation In Vivo

Several bioactive hormones, e.g. Thyrotropin-Releasing Hormone (TRH) or Gastrin, possess a N-terminal pyroglutamic acid residue, which is generated from glutamine during prohormone maturation. Glutaminyl cyclases (QCs) have been identified to catalyze the cyclization of N-terminal glutaminyl residues in plants and animals under concomitant release of ammonia (Messer, (1963), Nature 4874, 1299; Fischer and Spiess, (1987), PNAS 84, 3628-3632).

A QC was first isolated by Messer from the latex of the tropical plant Carica papaya in 1963 (Messer, M. (1963) Nature 4874, 1299). 24 years later, a corresponding enzymatic activity was discovered in animal pituitary (Busby, W. H. J. et al. (1987) J Biol Chem 262, 8532-8536; Fischer, W. H. and Spiess, J. (1987) Proc Natl Acad Sci USA 84, 3628-3632). For the mammalian QCs, the conversion of Gln into pGlu by QC could be shown for the precursors of TRH and GnRH (Busby, W. H. J. et al. (1987) J Biol Chem 262, 8532-8536; Fischer, W. H. and Spiess, J. (1987) Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. (1995) J Neuroendocrinol 7, 445-453). In contrast, the physiological function of the plant QC is less clear. In case of the enzyme from C. papaya, a role in the plant defense against pathogenic microorganisms was suggested (El Moussaoui, A. et al. (2001) Cell Mol Life Sci 58, 556-570). Recently, other QCs from plants were identified by sequence comparisons (Dahl, S. W. et al. (2000) Protein Expr Purif 20, 27-36; Schilling, S. et al. (2007) Biol Chem 388, 145-153) The physiological function of these enzymes, is presumably the pGlu-formation at the N-terminus of pathogenesis-related proteins. The QCs known from plants and animals show a strict specificity for L-Glutamine at the N-terminal position of the substrates and their kinetic behavior was found to obey the Michaelis-Menten equation mostly (Pohl, T. et al. (1991) Proc Natl Acad Sci USA 88, 10059-10063; Consalvo, A. P. et al. (1988) Anal Biochem 175, 131-138; Gololobov, M. Y. et al. (1996) Biol Chem Hoppe Seyler 377, 395-398, Schilling, S. et al. (2003) Biol Chem 384, 1583-1592). A comparison of the primary structures of the QC from C. papaya and of the highly conserved QCs from mammals, however, did not reveal any sequence homology (Dahl, S. W. et al. (2000) Protein Expr Purif 20, 27-36). Whereas the plant QCs appear to belong to a new enzyme family (Dahl, S. W. et al. (2000) Protein Expr Purif 20, 27-36), the mammalian QCs were found to have a pronounced sequence homology to bacterial aminopeptidases (Bateman, R. C. et al. (2001) Biochemistry 40, 11246-11250), leading to the conclusion that the QCs from plants and animals have different evolutionary origins.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are described as useful pesticides.

First tissue distribution studies of mammalian QCs revealed that they are mainly expressed in brain and some peripheral glands, e.g. thyroid and thymus. The enzyme is expected to be directed to the regulated secretory pathway of the expressing cells where the hormone maturation process takes place (Bockers, et al. (1995), J. Neuroendocrinol. 7, 445-453). Upon stimulation, QCs appear to be secreted from the cells together with the mature hormones.

Mammalian QCs were isolated and characterized from human, bovine and murine sources (Pohl, et al. (1991), PNAS 88, 10059-19963; Schilling, et al. (2002), Biochemistry 41, 10849-10857; Schilling, et al. (2005), Biochemistry 44, 13415-13424). The open reading frames of the enzymes consist of 361 (human, bovine) or 362 (murine) amino acids with an overall sequence identity of about 80%. The mature proteins are glycosylated. Human QC has been shown to be highly specific for the L-configuration of glutamine at the N-terminal amino acid position. Free glutamine was not converted (Schilling, et al. (2003) Biol Chem 384, 1583-1592). Other restrictions, however, were not observed, implying that the enzyme is responsible for N-terminal conversion of the very heterogenous group of pGlu-hormones and proteins (Schilling, et al. (2003), Biol. Chem. 384, 1583-1592). Initial mechanistic studies on human QC pointed to an involvement of histidinyl residues in the binding and conversion of the substrate as indicated by diethyl pyrocarbonate inhibition and site directed mutagenesis (Bateman, et al. (2001), Biochemistry 40, 11246-11250). Later evidence showed that mammalian QCs are structurally related to zinc-dependent aminopeptidases and that the residues for complexation of the active site metal ions are also conserved in human QC. Furthermore, 1,10-phenanthroline, dipicolinic acid and imidazole inhibited human QC, implying a metal-dependent catalysis of the enzyme (Schilling, et al. (2003), J. Biol. Chem. 278, 49773-49779). Determination of metal content of human and murine QC and crystallization revealed a single zinc-dependent catalytic in human and murine QC mechanism (Huang, et al. (2005), PNAS 102, 13117-13122; Schilling, et al. (2005), Biochemistry 44, 13415-13424).

In contrast to the physiological QC-substrates, glutamic acid is the precursor of pGlu at the N-terminus of Aβ. Initially, it was suggested that cyclization of glutamic acid proceeds spontaneously (Hashimoto, et al. (2002), EMBO J. 21, 1524-1534). The identification of QCs in brain regions vulnerable to AD, however, triggered research by the present inventors on the catalytic properties of QC. Indeed, catalysis of pGlu-Aβ(3-11) and pGlu-Aβ(3-21) generation could be demonstrated in vitro (Schilling, et al. (2004), FEBS Lett. 563, 191-196). Interestingly, the pH-dependence of catalysis reveals an optimal substrate conversion under mildly acidic conditions, which contrasts with the basic pH-optimum for cyclization of glutaminyl peptides. This, in fact, supports a conversion of glutamic acid at the N-terminus of Aβ in the secretory pathway, were an acidic pH environment has been described. Pyroglutamate present at the N-terminus of the C-terminal fragments supports such a conclusion (Russo, et al. (2001), Neurobiol. Dis. 8, 173-180). Additionally, an involvement of QC in conversion of glutamic acid into pGlu is supported by the following observations:

1. APP, the precursor of Aβ, and QC are highly abundant in brain tissue,
2. QC and APP are expressed in the secretory pathway,
3. Obviously, Aβ is generated at least partially in secretory compartments. Hence, QC and Aβ (or the C-terminal Fragment of APP) might be colocalized intracellularly at high concentrations of both species, thus promoting conversion. Other peptides and proteins originating from high-level QC expressing tissue are known carrying N-terminal pGlu originating from glutamic acid, e.g. the pituitary-derived hormone β-Lipotropin (β-LPH) or immunoglobulins and the amyloidogenic ADan and ABri peptides as well (Bateman, et al. (1991) J. Biol. Chem. 265, 22130-22136; Twardzik and Peterkovsky (1972) PNAS 69, 274-7, Ghiso, et al. (2001) Amyloid 8, 277-284). (see also FIG. 22-2).

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"-chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard and Rollins (2001) Nat. Immunol 2, 108-115; Bhatia, et al. (2005) Pancreatology. 5, 132-144; Kitamoto, et al. (2003) J Pharmacol Sci. 91, 192-196). The MCP family, as one family of chemokines, consists of four members (MCP-1-4), displaying a preference for attracting monocytes but showing differences in their potential (Luini, et al. (1994) Cytokine 6, 28-31; Uguccioni, et al. (1995) Eur J Immunol 25, 64-68). In the following both cDNA as well as amino acid sequences of MCP-1-4 are indicated:

```
Human MCP-1 (CCL2) (GeneBank Accession: M24545)
cDNA (300 bp)
                                                         SEQ ID NO: 4
   1 atgaaagtct ctgccgccct tctgtgcctg ctgctcatag cagccacctt cattcccaa 61 gggctcgctc agccagatgc aatcaatgcc ccagtcacct gctgttataa cttcaccaat 121 aggaagatct cagtgcagag gctcgcgagc tatagaagaa tcaccagcag caagtgtccc 181 aaagaagctg tgatcttcaa gaccattgtg gccaaggaga tctgtgctga ccccaagcag 241 aagtgggttc aggattccat ggaccacctg gacaagcaaa cccaaactcc gaagacttga Protein (Signal Sequence in bold: 23 aa; Mature MCP-1: 76 aa)
                                                         SEQ ID NO: 5
MKVSAALLCLLLIAATFIPQGLAQPDAINAPVTCCYNFTNRKISVQRLASYRRITSSKCPKEAVIFKTI

VAKEICADPKQKWVQDSMDHLDKQTQTPKT

Human MCP-2 (CCL8) (GeneBank Accession: Y10802)
cDNA (300 bp)
                                                         SEQ ID NO: 6
   1 atgaaggttt ctgcagcgct tctgtgcctg ctgctcatgg cagccacttt cagccctcag 61 ggacttgctc agccagattc agtttccatt ccaatcacct gctgctttaa cgtgatcaat 121 aggaaaattc ctatccagag gctggagagc tacacaagaa tcaccaacat ccaatgtccc 181 aaggaagctg tgatcttcaa gacccaacgg ggcaaggagg tctgtgctga ccccaaggag 241 agatgggtca gggattccat gaagcatctg gaccaaatat ttcaaaatct gaagccatga Protein (Signal Sequence in bold: 23 aa; Mature MCP-2: 76 aa)
```

-continued

SEQ ID NO: 7
MKVSAALLCLLLMAATFSPQGLAQPDSVSIPITCCENVINRKIPIQRLESYTRITNIQCPKEAVIFKTQ

RGKEVCADPKERWVRDSMKHLDQIFQNLKP

Human MCP-3 (CCL7) (GeneBank Accession: X71087)
cDNA (300 bp)
SEQ ID NO: 8

```
  1 atgaaagcct ctgcagcact tctgtgtctg ctgctcacag cagctgcttt cagcccccag 61 gggcttgctc agccagttgg gattaatact tcaactacct gctgctacag atttatcaat 121 aagaaaatcc ctaagcagag gctggagagc tacagaagga ccaccagtag ccactgtccc 181 cgggaagctg taatcttcaa gaccaaactg gacaaggaga tctgtgctga ccccacacag 241 aagtgggtcc aggactttat gaagcacctg gacaagaaaa cccaaactcc aaagctttga
```

Protein (Signal Sequence in bold: 23 aa; Mature MCP-3: 76 aa)
SEQ ID NO: 9
MKASAALLCLLLTAAAFSPQGLAQPVGINTSTTCCYRFINKKIPKQRLESYRRTTSSHCPREAVIFKTK

LDKEICADPTQKWVQDFMKHLDKKTQTPKL

MCP-4 (CCL13) (GeneBank Accession: U46767)
cDNA (297 bp)
SEQ ID NO: 10

```
  1 atgaaagtct ctgcagtgct tctgtgcctg ctgctcatga cagcagcttt caaccccag 61 ggacttgctc agccagatgc actcaacgtc ccatctactt gctgcttcac atttagcagt 121 aagaagatct ccttgcagag gctgaagagc tatgtgatca ccaccagcag gtgtcccag 181 aaggctgtca tcttcagaac caaactgggc aaggagatct gtgctgaccc aaaggagaag 241 tgggtccaga attatatgaa acacctgggc cggaaagctc acaccctgaa gacttga
```

Protein (Signal Sequence in bold: 23 aa; Mature MCP-4: 75 aa)
SEQ ID NO: 11
MKVSAVLLCLLLMTAAFNPQGLAQPDALNVPSTCCFTFSSKKISLQRLKSYVITTSRCPQKAVIFRTKL

GKEICADPKEKWVQNYMKHLGRKAHTLKT

The inventors have shown that the mature form of human and rodent MCP-1 is posttranslationally modified by Glutaminyl Cyclase (QC), resulting in the formation of an N-terminal pyroglutamyl (pGlu) residue. The N-terminal pGlu modification confers resistance against N-terminal degradation by aminopeptidases, which is of importance, since chemotactic potency of MCP-1 is mediated by its N-terminus (Van Damme, J., et al., (1999) Chem Immunol 72, 42-56). Artificial elongation or degradation leads to a loss of function although MCP-1 still binds to its receptor (CCR2) (Proost, P., et al., (1998), J Immunol 160, 4034-4041; Zhang, Y. J., et al., (1994), J Biol. Chem. 269, 15918-15924; Masure, S., et al., 1995, J Interferon Cytokine Res. 15, 955-963; Hemmerich, S., et al., (1999) Biochemistry 38, 13013-13025).

Due to the major role of MCP-1 in a number of disease conditions, an anti-MCP-1 strategy is urgently needed. Therefore, small orally available compounds inhibiting the action of MCP-1 are promising candidates for a drug development. Inhibitors of Glutaminyl Cyclase are small orally available compounds, which target the important step of pGlu-formation at the N-terminus of MCP-1 (Cynis, H., et al., (2006) Biochim. Biophys. Acta 1764, 1618-1625; Buchholz, M., et al., (2006) J Med Chem 49, 664-677). In consequence, after application of a QC-inhibitor the N-terminus of MCP-1 is not protected by a pGlu-residue possessing a glutamine-proline motif, which can be cleaved by dipeptidylpeptidases, e.g. dipeptidylpeptidase 4 and fibroblast activating protein (FAP, Seprase), abundantly existing on the endothelium and within the blood circulation. This leads to the formation of N-terminal truncated MCP 1 unfolding an antagonistic action at the CCR2 and therefore, inhibiting monocyte-related disease conditions.

As mentioned above, Monocyte chemoattractant protein 1 (MCP-1, CCL2) belongs to a family of potent chemotactic cytokines (CC chemokines), that regulate the trafficking of leukocytes, especially monocytes, macrophages and T-cells, to sites of inflammation (Charo, I. F. and Taubman, M. B. (2004) Circ. Res. 95, 858-866). Besides its role in, e.g. vascular disease, compelling evidence points to a role of MCP 1 in Alzheimer's disease (AD) (Xia, M. Q. and Hyman, B. T. (1999) J Neurovirol. 5, 32-41). The presence of MCP-1 in senile plaques and in reactive microglia, the residential macrophages of the CNS, has been observed in brains of patients suffering from AD (Ishizuka, K., et al., (1997) Psychiatry Clin. Neurosci. 51, 135-138). Stimulation of monocytes and microglia with Amyloid-β protein (Aβ) induces chemokine secretion in vitro (Meda, L., et al., (1996) J Immunol 157, 1213-1218; Szczepanik, A. M., et al., (2001) J Neuroimmunol. 113, 49-62) and intracerebroventricular infusion of Aβ (1-42) into murine hippocampus significantly increases MCP-1 in vivo. Moreover, Aβ deposits attract and activate microglial cells and force them to produce inflammatory mediators such as MCP-1, which in turn leads to a feed back to induce further chemotaxis, activation and tissue damage. At the site of Aβ deposition, activated microglia also phagocyte Aβ peptides leading to activation (Rogers, J. and Lue, L. F. (2001) Neurochem. Int. 39, 333-340).

Examination of chemokine expression in the 3×Tg mouse model for AD revealed that neuronal inflammation precedes plaque formation and MCP-1 is upregulated by a factor of 11. Furthermore, the upregulation of MCP-1 seems to correlate with the occurrence of first intracellular Aβ deposits (Janelsins, M. C., et al., (2005) J Neuroinflammation. 2, 23). Crossbreeding of the Tg2575 mouse model for AD with a MCP-1 overexpressing mouse model has shown an increased microglia accumulation around Aβ deposits and that this accumulation was accompanied by increased amount of diffuse plaques compared to single-transgenic Tg2576 littermates (Yamamoto, M., et al. (2005) Am. J Pathol. 166, 1475-1485).

MCP-1 levels are increased in CSF of AD patients and patients showing mild cognitive impairment (MCI) (Galimberti, D., et al., (2006) Arch. Neurol. 63, 538-543). Furthermore, MCP-1 shows an increased level in serum of patients with MCI and early AD (Clerici, F., et al., (2006) Neurobiol. Aging 27, 1763-1768).

SUMMARY OF THE INVENTION

The present invention provides novel physiological substrates of QC in mammals. Novel substrates are the glutamic acid precursers of amyloid peptides, e.g. Aβ(3-40), Aβ(3-42), [Gln3]Aβ(3-40), [Gln3]Aβ(3-42), [Glu11]Aβ(11-40), [Glu11]Aβ(11-42), [Gln11]Aβ(11-40), [Gln11]Aβ(11-42), [Gln$^1$]ABri, [Gln$^1$]ADan, [Gln$^1$]Gastrins (17 and 34), [Gln$^1$] Neurotensin, [Gln$^1$]FPP, [Gln$^1$]TRH, [Gln$^1$]GnRH, [Gln$^1$] CCL 2, [Gln$^1$]CCL 7, [Gln$^1$]CCL 8, [Gln$^1$]CCL 13, [Gln$^1$] CCL 16, [Gln$^1$]CCL 18, [Gln$^1$]ELA, [Gln$^1$]Fractalkine, [Gln$^1$]Orexin A, [Gln$^3$]glucagon(3-29) and [Gln$^5$]substance P(5-11) and the use of effectors of QC and pharmaceutical compositions comprising effectors of QC for the treatment of conditions that can be treated by modulation of QC activity.

It was shown by inhibition studies that human QC is a metal-dependent transferase. QC apoenzyme could be reactivated most efficiently by zinc ions, and the metal-binding motif of zinc-dependent aminopeptidases is also present in human QC. Compounds interacting with the active-site bound metal are potent inhibitors.

Unexpectedly, it was shown by the inventors that recombinant human QC as well as QC-activity from brain extracts catalyze both the N-terminal glutaminyl as well as glutamate cyclization. Most striking is the finding, that cyclase-catalyzed Glu1-conversion is favored around pH 6.0 while Gln1-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

The present invention relates to effectors of QC activity and use thereof for the treatment and/or prevention of a disease or disorder selected from the group consisting of a. neurodegenerative diseases, e.g. mild cognitive impairment (MCI), Alzheimer's disease, neurodegeneration in Down Syndrome, Familial British Dementia, Familial Danish Dementia, multiple sclerosis, b. chronic and acute inflammations, e.g. rheumatoid arthritis, atherosclerosis, restenosis, pancreatitis, c. fibrosis, e.g. lung fibrosis, liver fibrosis, renal fibrosis, d. cancer, e.g. cancer/hemangioendothelioma proliferation, gastric carcinomas, e. metabolic diseases, e.g. hypertension, f. and other inflammatory diseases, e.g. neuropathic pain, graft rejection/graft failure/graft vasculopathy, HIV infections/AIDS, gestosis, tuberous sclerosis.

In particular, the present invention pertains to the use of effectors of QC activity for the preparation of a medicament for the prevention, alleviation and/or treatment of Alzheimer's disease in a human subject.

Further, by administration of effectors of QC activity to a mammal it can be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

Furthermore, by administration of effectors of QC activity to a mammal it can be possible to suppress the proliferation of myeloid progenitor cells.

In addition, administration of QC inhibitors can lead to suppression of male fertility.

In a preferred embodiment, the present invention provides the use of effectors of QC activity in combination with inhibitors of DP IV or DP IV-like enzymes for the treatment or alleviation of conditions that can be treated by modulation of QC- and/or DP IV-activity.

The present invention provides pharmaceutical compositions for parenteral, enteral or oral administration, comprising at least one effector of QC optionally in combination with customary carriers and/or excipients; or comprising at least one effector of QC in combination with at least one DP IV-inhibitor, optionally in combination with customary carriers and/or excipients.

Screening methods are also provided for the identification and selection of effectors of QC.

BRIEF DESCRIPTION OF THE DRAWINGS

Further understanding of these and other aspects of the present invention will be had by reference to the figures wherein:

FIG. 21 Sequence alignment of human QC (hQC) and other M28 family members of the metallopeptidase Clan MH. Multiple sequence alignment was performed using ClustalW at ch.EMBnet.org with default settings. The conservation of the zinc-ion ligating residues is shown for human QC (hQC; GenBank X71125), the Zn-dependent aminopeptidase from *Streptomyces griseus* (SGAP; Swiss-Prot P80561), and within the N-acetylated-alpha-linked acidic dipeptidase (NAALADase I) domain (residues 274-587) of the human Glutamate carboxypeptidase II (hGCP II; Swiss-Prot Q04609). The amino acids involved in metal binding are typed in bold and underlined. In case of human QC, these residues are the putative counterparts to the peptidases.

FIG. 22-1 is a schematic representation of the proteolytic processing of the amyloid precursor protein APP. Cleavage by β-secretase (beta site cleaving enzyme, BACE) and γ-secretase (a complex consisting of PEN-2, presenilin, APH-1 and Nicastrin) in the amyloidogenic pathway leads to formation of Aβ(1-40) or (1-42). Degradation by α-secretases (likely candidates are the enzymes ADAM-10 and TACE) results in liberation of the extracellular part of the protein, sAPPα, and precludes the generation of neurotoxic peptides.

FIG. 22-2 illustrates the events leading to the formation and elimination of pGlu-Aβ peptides. Formation of Aβ(1-40/42) and Aβ(11-40/42) is catalyzed by β- and γ-secretase(s). Aβ(1-x) peptides are truncated N-terminally by aminopeptidases leading to demasking of glutamic acid at position 3. Alternatively, the N-truncated variant(s) are generated by alternative ⊕-secretase cleavage (dotted trace). isoAsp-Aβ (non-catalyzed) formation results in massively slower cleavage by aminopeptidases. Subsequently, the N-terminal Glu-residues are prone to cyclization by QC. The resulting pGlu-peptides display a diminished solubility and are highly prone to aggregation. The intracellular Aβ concentration is presumably regulated by degradation (Neprilysin, NEP; aminopeptidases, AP) and secretion. A dysfunction in homeostasis, i.e., diminished degradation (aging) or elevated generation (mutations in the APP or presenilin genes) leads to accumulation of degradation-resistant pGlu-Aβ peptides. Cyclization of Aβ into pGlu-Aβ by QC has been demonstrated.

FIG. 23: summarizes the most relevant results for an involvement of Glutaminyl Cyclase in pGlu-Aβ generation and Aβ deposition.

FIG. 24-1: Assessment of QC-catalyzed pGlu-Aβ (3-40) formation by recombinant human QC. Reactions were carried out in 0.1 M Mes buffer, pH 6.5. The inhibitor concentration was 5 μM. The pGlu-Aβ concentration was determined using a specific ELISA.

FIG. 24-2: Schematic representation of the APP-constructs used for assessment of pGlu-Aβ formation. The constructs were initially described by Shirotani and coworkers (Shirotani, et al (2002) Neurosci Lett 327, 25-28). Caused by deletion of two amino acids, processing of the APP-NLE and -NLQ results directly in formation of pGlu-Aβ(3-40/42), which can be quantified in the culture medium. The APP constructs encode the Swedish (KM595/596NL) and London (V642I) mutation.

FIG. 24-3: pGlu-Aβ formation after expression of APP-NLE in HEK293 cells. Significant pGlu-Aβ formation was observed, if QC and APP-NLE are co-expressed. Less pGlu-Aβ is formed in case of an addition of recombinant human QC to the medium, indicating that QC-catalyzed pGlu-Aβ formation occurs primarily intracellularly. The results indicate that pGlu-Aβ formation is favored under conditions of the secretory pathway.

FIG. 24-4: Aβ concentration determined in the medium of A) HEK293 cells and B) βTC3 cells. The different APP plasmid or mTRH-Aβ constructs were transiently expressed. The QC-inhibitor 1-(3-(1H-imidazole-1-yl)propyl)-3-(3,4-dimethoxy-phenyl)thiourea hydrochloride reduced the pGlu-Aβ concentration significantly.

FIG. 24-5 Aβ concentration determined in the medium of A) HEK293 cells and B) βTC3 cells. Human QC and APP constructs were co-expressed transiently.

FIG. 24-6 Analysis of fibril formation from Aβ species, which differ at the N- and C-terminus.

A) Fibril formation from monomeric Aβ(1-42) (circles), Aβ(3-42) (triangles) and pGlu-Aβ(3-42) (squares) analyzed using flow cytometry. Reactions were carried out in 50 mM sodium acetate, pH 5.5 containing 2 mM DTT and 100 mM NaCl at a peptide concentration of 10 μM. Fibril formation from a mixture of unlabeled (80%) and Alexa Fluor 488 labeled (20%) Aβ peptides.

B) Fibril formation from unlabeled Aβ peptides followed by incubation with a labeled 4G8 antibody and analysis using flow cytometry. C) Comparison of monomeric Aβ(1-42) (80% unlabeled, 20% Alexa-Fluor labeled) (circles), with a sample consisting of 70% monomeric, unlabeled Aβ(1-42), 20% monomeric. Alexa-Fluor labeled Aβ(1-42) and 10% monomeric unlabeled pGlu-Aβ(3-42) (squares). D) Kinetics of aggregation of Aβ(1-40) (circles), Aβ(3-40) (triangles) and pGlu-Aβ(3-40) (squares) monitored by ThT fluorescence. For pGlu-Aβ(3-40), an initial lag phase was not observed under the applied conditions, indicating an influence of the pGlu-residue on the formation of seeds.

Figure 7:
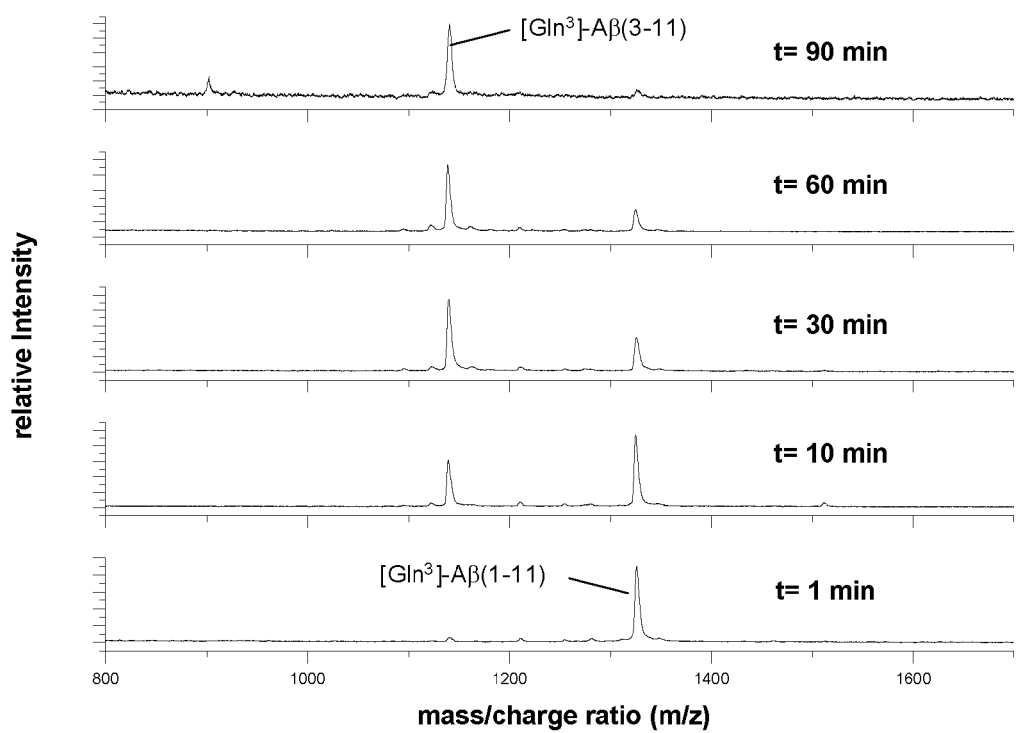
FIG. 7 shows the formation of [Gln3]-Aβ(3-11) from [Gln3]Aβ(1-11) catalysed by DPIV. At the times indicated, samples were removed, from the assay tube, mixed with matrix solution (1:1 v/v) and subsequently the mass spectra recorded.
Figures 1, 24:
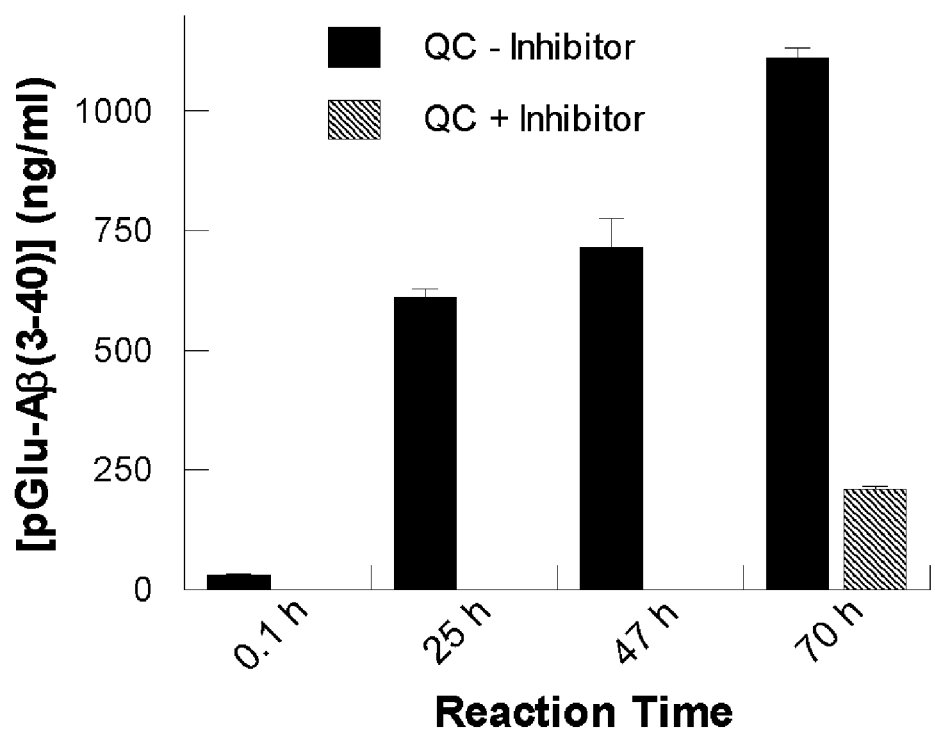
Figures 2, 24:
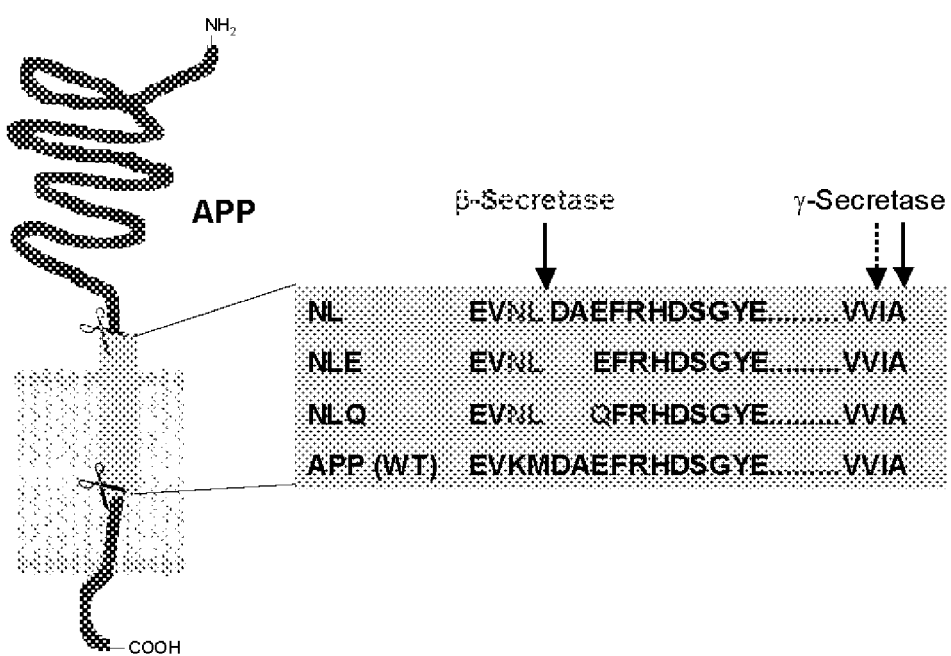
Figures 3, 24:
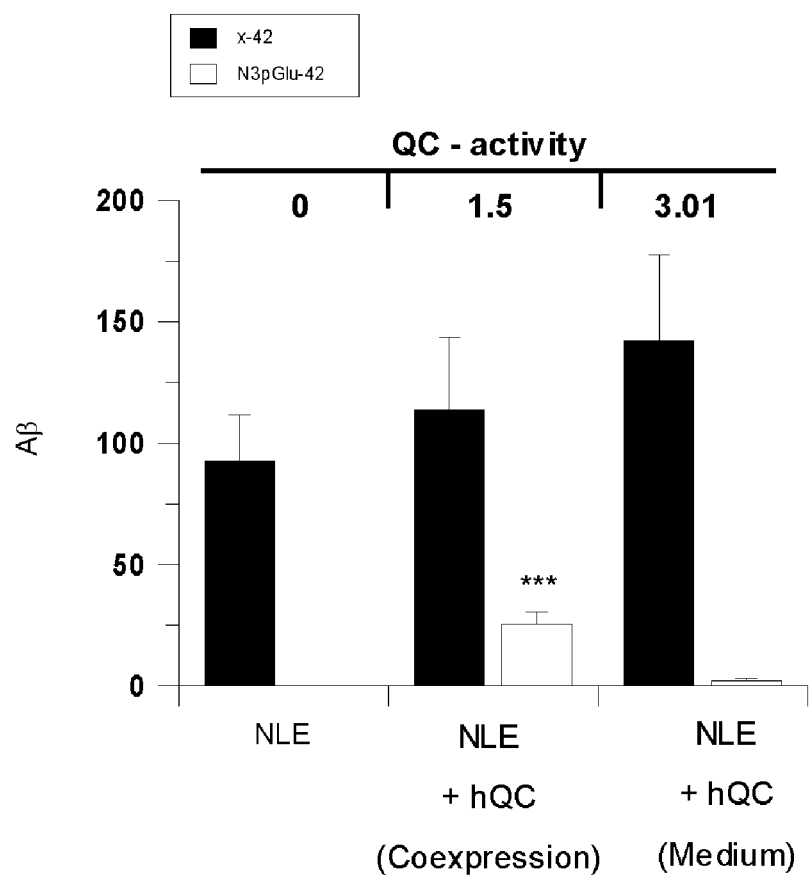
Figures 4, 24:
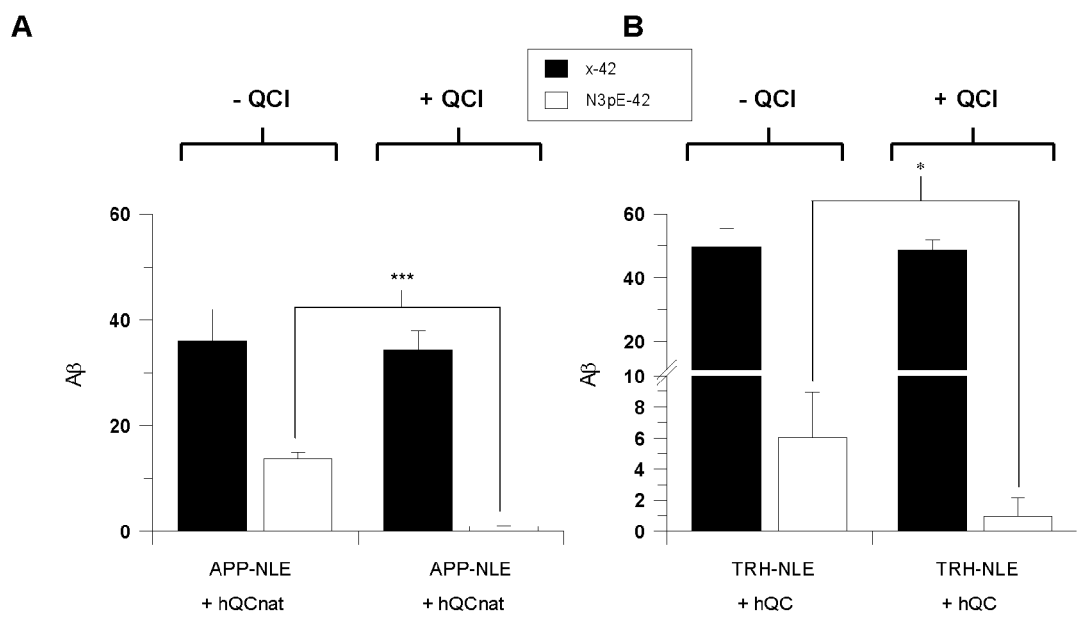
Figure 24:
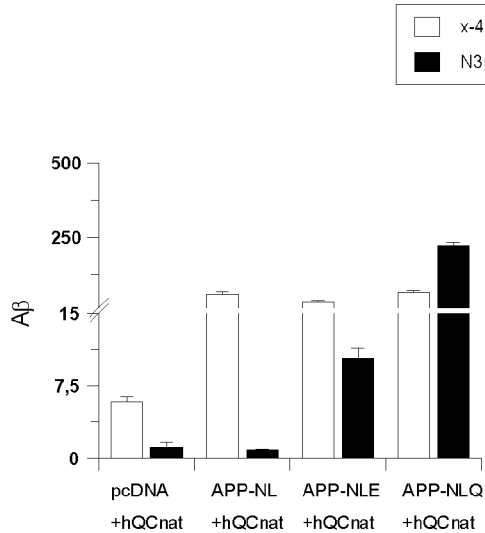
Figure 5:
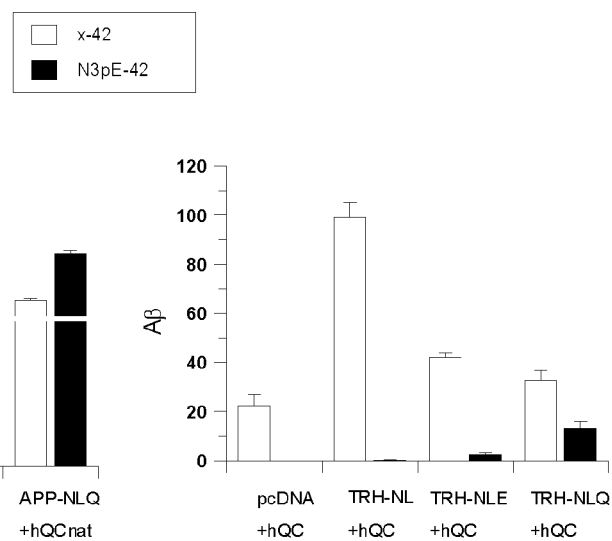
Figures 6, 24:
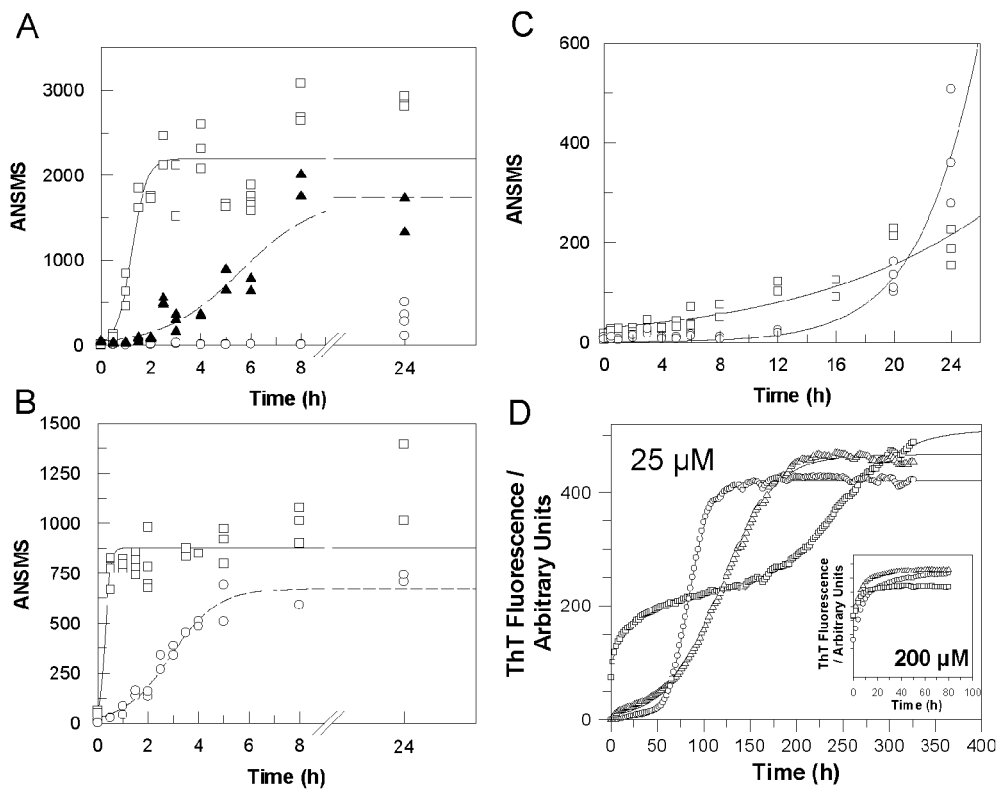
Figures 7, 24:
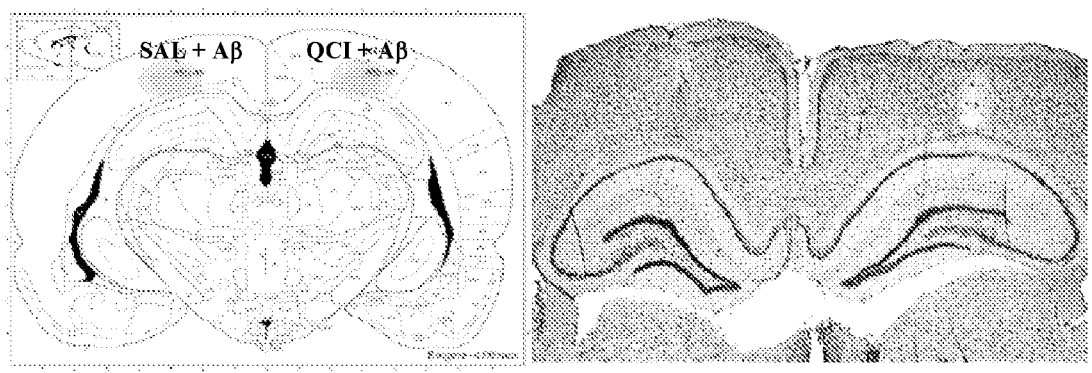
Figures 8, 24:
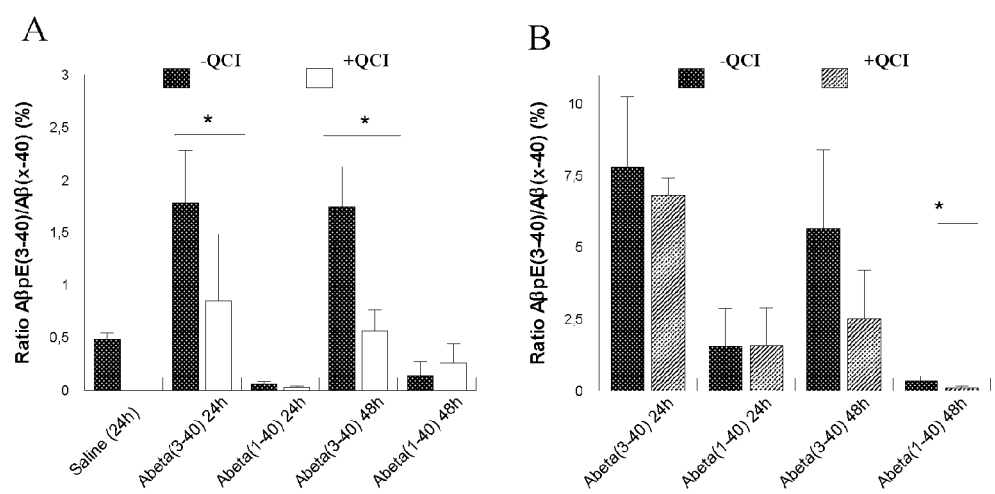
Figures 9, 24:

FIG. 24-7 Illustration of the injection paradigm for analysis of QC-inhibitor efficacy in a rat model of traumatic brain injury. The injection sites are indicated.

Figure 8:
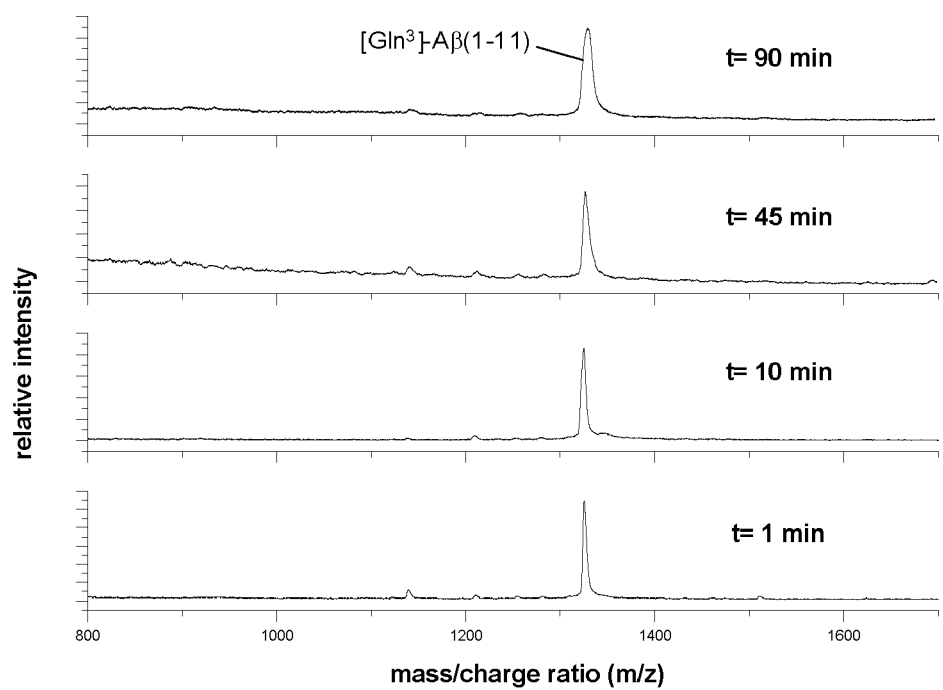
FIG. 8 shows the prevention of the cleavage of [Gln3]Aβ (1-11) by the DP IV-inhibitor Val-Pyrrolidide (Val-Pyrr). At the times indicated, samples were removed from the assay tube, mixed with matrix solution (1:1 v/v) and subsequently the mass spectra recorded.

FIG. 24-8: Ratio of pGlu-Aβ and total Aβ in the 2% SDS-fraction after sequential Aβ extraction from rat brain. Each concentration was determined using ELISA:

The QC-inhibitor 1-(3-(1H-imidazole-1-yl)propyl)-3-(3,4-dimethoxy-phenyl)thiourea hydrochloride reduced the ratio after co-injection with Aβ: A) 5 μL 1M solution, B) 5 μL 0.2 M solution.

Figure 9:
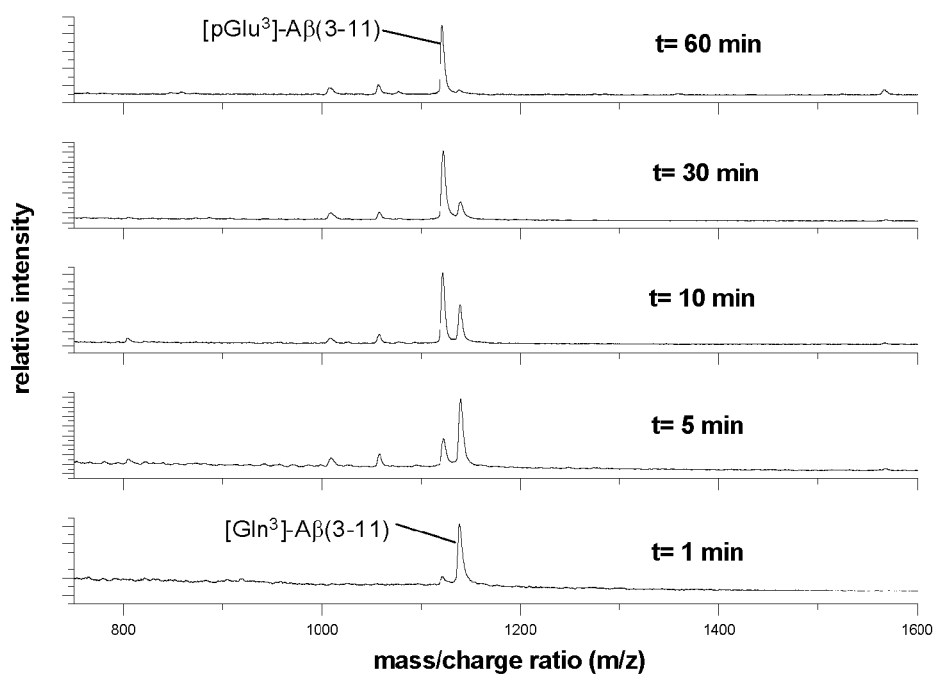
FIG. 9 shows the formation of [pGlu3]Aβ(3-11) from [Gln3]Aβ(3-11) catalyzed by QC. At the times indicated, samples were removed from the assay tube, mixed with matrix solution (1:1 v/v) and subsequently the mass spectra recorded.

FIG. 24-9: pGlu-Aβ immunostaining (dark coloration) after injection of Aβ(3-40) into the deep cortex of rats. In the right hemisphere (here: left side), Aβ was injected, preceded by a saline infusion. In the other hemisphere, 1-(3-(1H-imidazole-1-yl)propyl)-3-(3,4-dimethoxy-phenyl)thiourea hydrochloride was injected instead of saline. 1-(3-(1H-imidazole-1-yl)propyl)-3-(3,4-dimethoxy-phenyl)thiourea hydrochloride suppresses pGlu-Aβ formation by inhibition of QC, which is, accordingly, responsible for pGlu-Aβ formation in this traumatic rat model.

Figure 1:
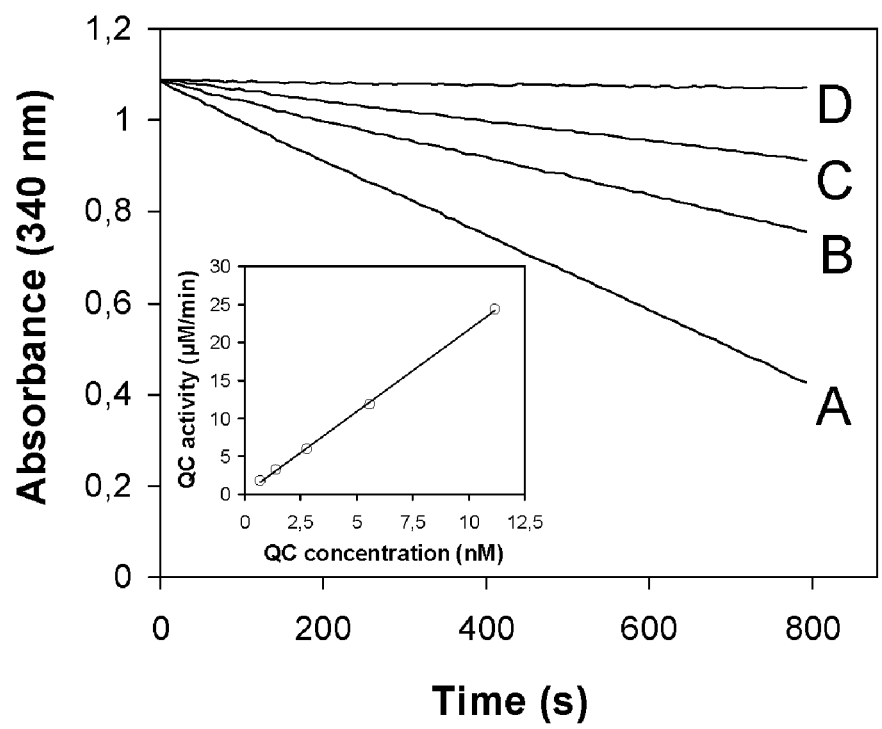
FIG. 1 shows progress curves of the cyclization of H-Gln-Ala-OH, catalyzed by human QC, monitoring the decrease in absorbance at 340 nm. The samples contained 0.3 mM NADH/H$^+$, 14 mM α-Ketoglutaric acid, 30 U/ml glutamic dehydrogenase and 1 mM H-Gln-Ala-OH. From curve A-D, varying concentrations of QC were applied: A, 10 mU/ml, B, 5 mU/ml, C, 2.5 mU/ml. In case of curve D, QC was omitted. A linear relationship was obtained between the QC concentration and the observed activity (inset).
Figures 1, 25:
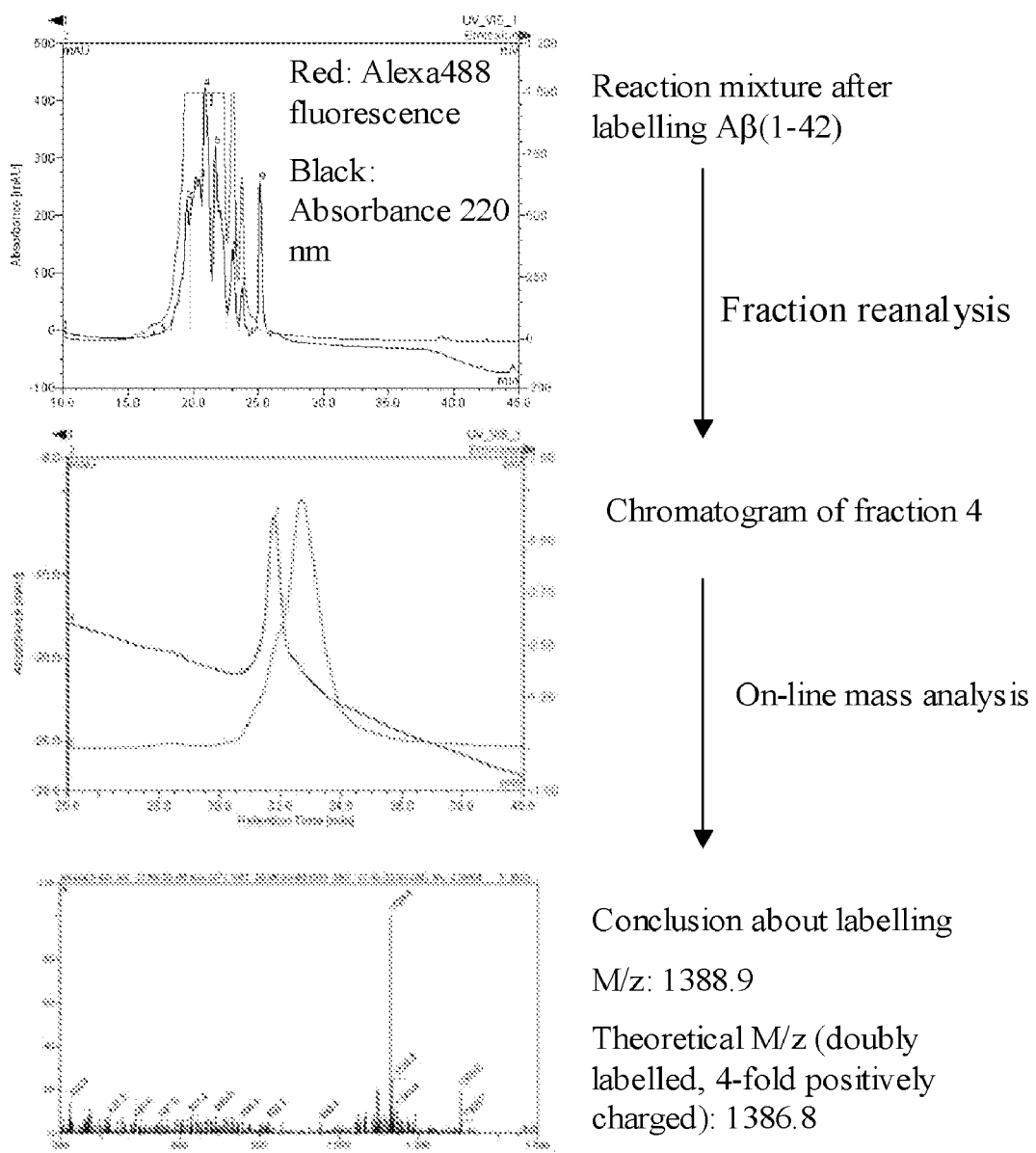
Figures 2, 25:
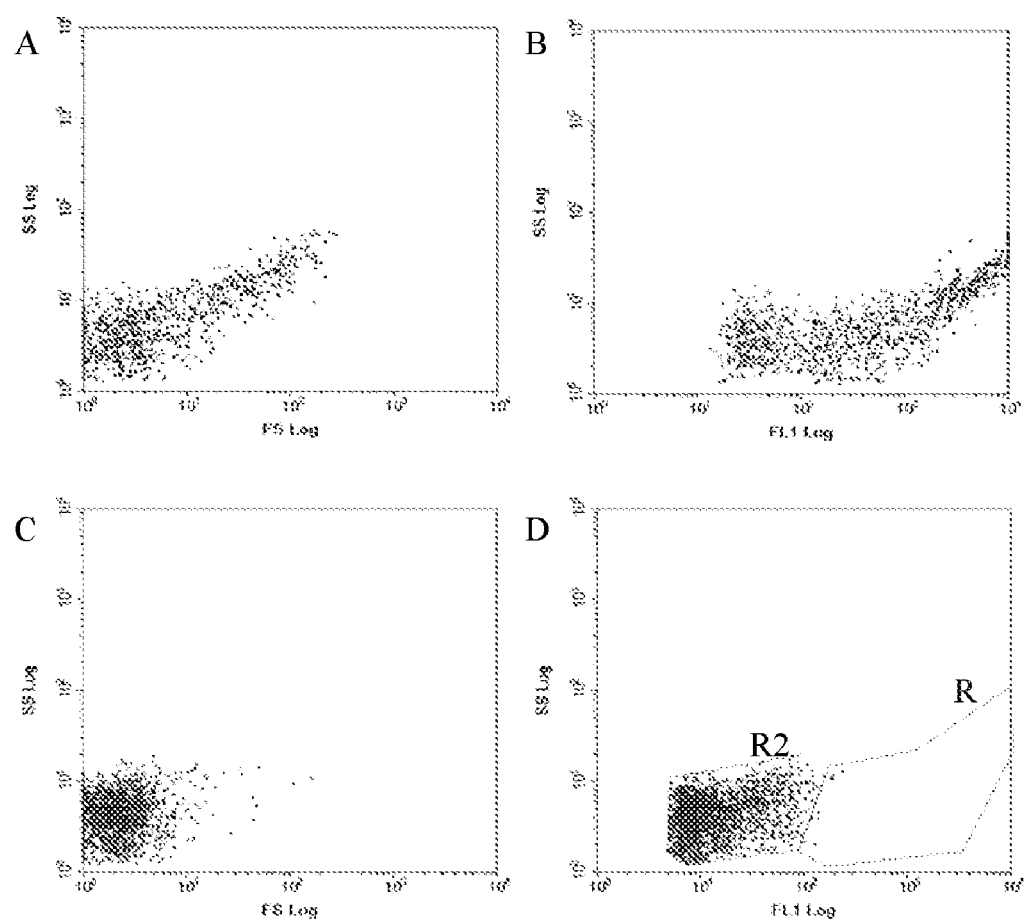

FIG. 25-1: Determination of degree of labeling, exemplified illustrated for Aβ (1-42).

Figure 2:
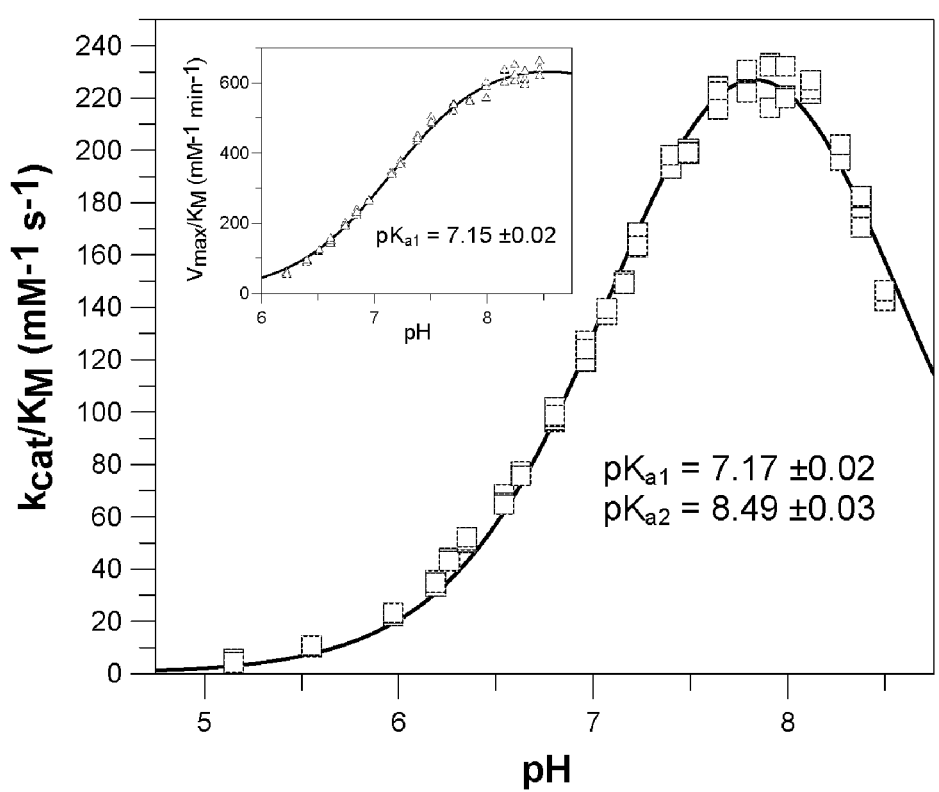
FIG. 2 shows the pH dependence of human and papaya (inset) QC, determined under first-order rate conditions using Gln-βNA as substrate. In case of human QC, a buffer system providing a constant ionic strength according to Ellis and Morrison was used, consisting of 25 mM MES, 25 mM acetic acid and 50 mM Tris (Ellis, K. J. and Morrison, J. F. 1982 Methods Enzymol. 87, 405-426). Due to a slightly inhibiting effect of Tris, papaya QC was investigated using a 50 mM Mops buffer. The ionic strength was adjusted to 0.05 M by addition of NaCl. The rate profiles were evaluated by fitting to a model that is based on dissociating groups. The determined pKa-values are in excellent agreement with the pKa of the substrate, which was determined by titration (7.16±0.01).

FIG. 25-2: Detection of in vitro assembled Aβ fibrils (A, B) and oligomers (C, D) by flow cytometry.

FS Log: forward scatter; SS Log: side scatter; FL1 Log: fluorescence 1 channel. The different size distributions (FS Log/SS Log dot-blots) of fibrils (A) and oligomers (C) correlate with signal intensity in the FL1 channel (B, D; regions R1 and R2) and allow a differentiation of these structures in a single experiment. It should be noted that the assay does not detect any monomeric species, i.e., at time point 0 after reaction start, no signal can be observed, which also becomes evident from the data displayed in FIG. 24-6.

Figure 26:
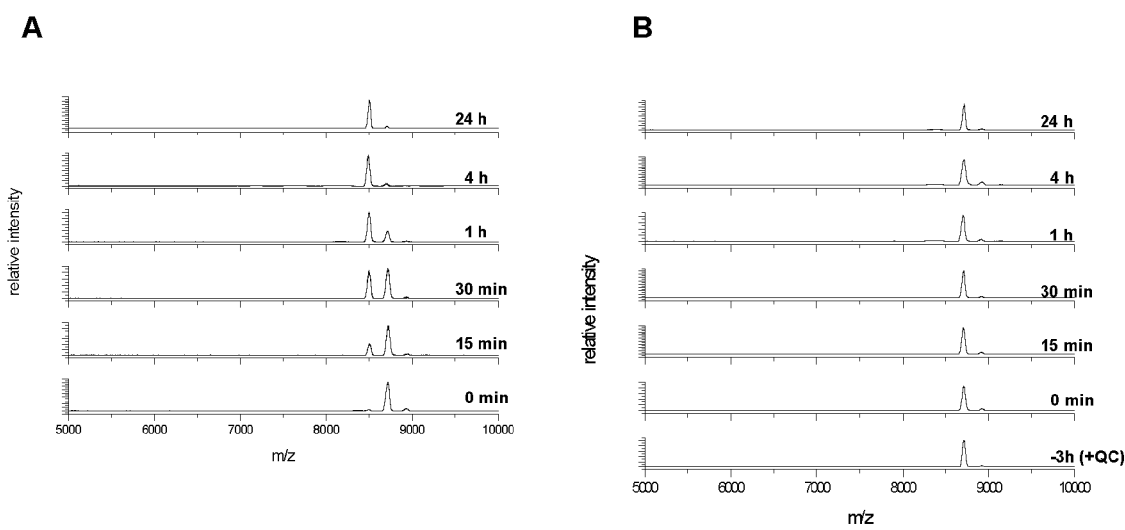

FIG. 26: shows the incubation of MCP-1(1-76) bearing an N-terminal glutaminyl (A) or Pyroglutamyl (5-oxo-L-Prolyl) residue (B) with recombinant human DP4 for 24 h. For cyclization of N-terminal glutamine into pyroglutamate, MCP-1 was incubated with recombinant human QC 3 h prior to assay start. The DP4 cleavage products were analyzed after 0 min, 15 min, 30 min, 1 h, 4 h and 24 h using Maldi-TOF mass spectrometry.

Figure 27:
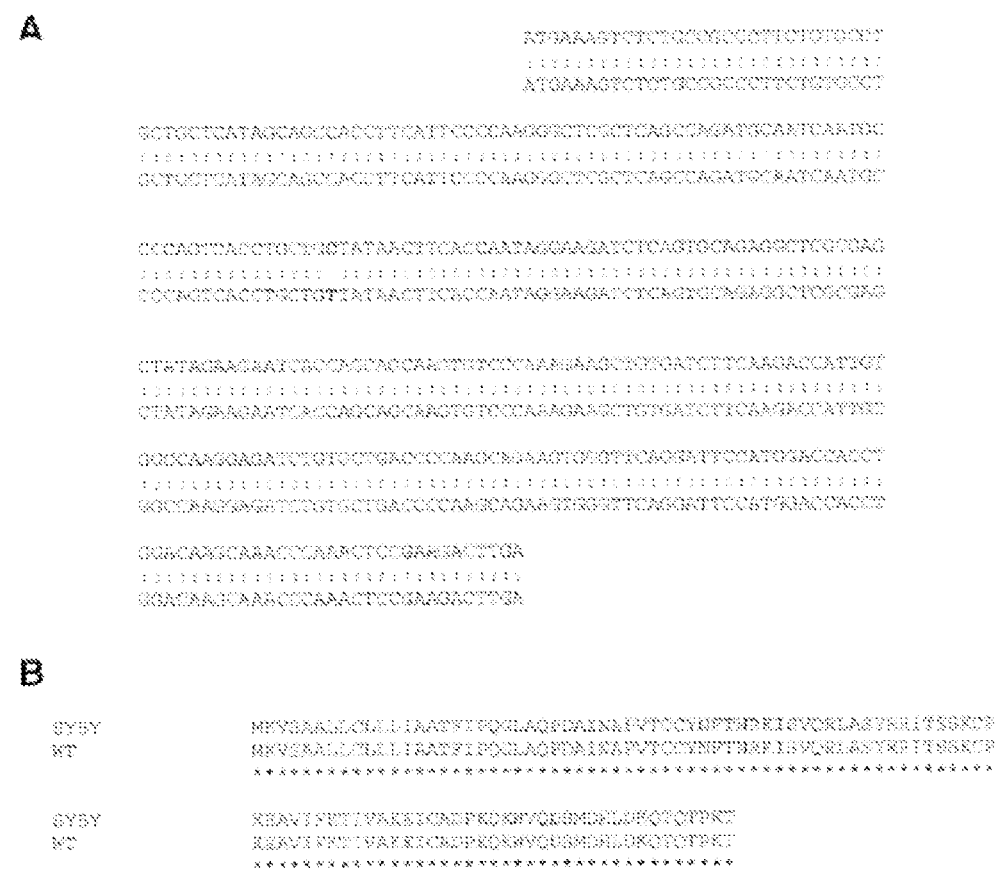

FIG. 27 shows the nucleotide (A) and amino acid (B) alignment of human MCP-1 isolated from SH-SY5Y (upper lane) and human MCP-1 genebank accession M24545 (lower lane). Single nucleotide polymorphism is depicted in bold.

Figure 27C:
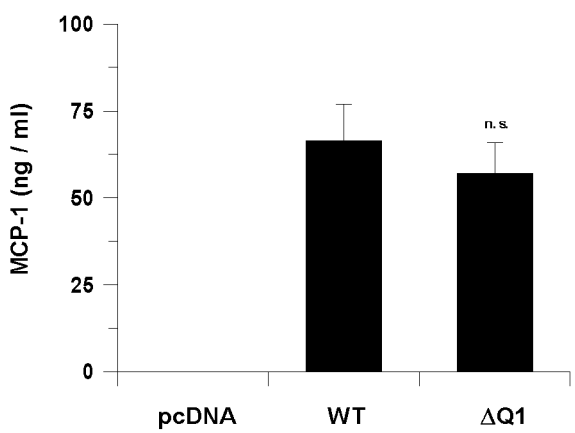

FIG. 27C shows the concentration of human MCP-1 (1-76) (WT) and mutant human MCP-1 lacking the N-terminal pGlu residue (ΔQ1) in the supernatant of transfected HEK293 cells in comparison to vector transfected control (pcDNA). (n.s.: not significant, Student's t-test; n=6). The concentrations were determined applying a specific ELISA technique.

Figure 27D:
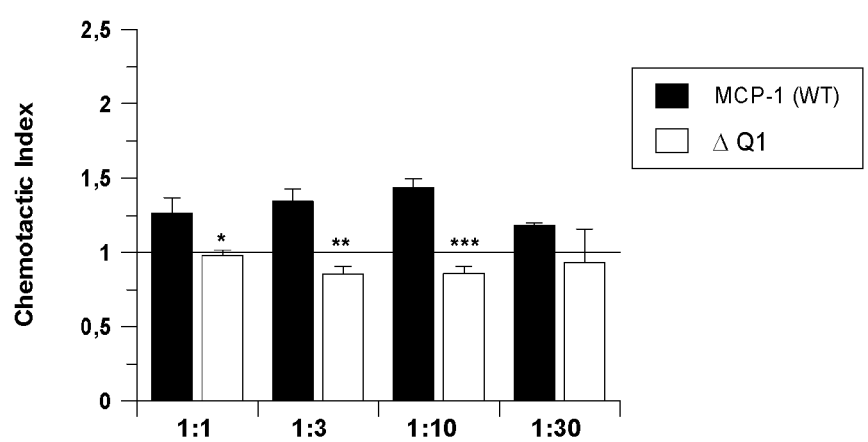

FIG. 27D: Migration of THP-1 monocytes towards the generated supernatant of HEK293 cells, transfected with MCP-1 (WT) or MCP-1 (ΔQ1) in dilutions 1:1, 1:3, 1:10 and 1:30. (*, P<0.05; , P<0.01; *, P<0.001; Student's t-test, n=3)

Figure 28A:
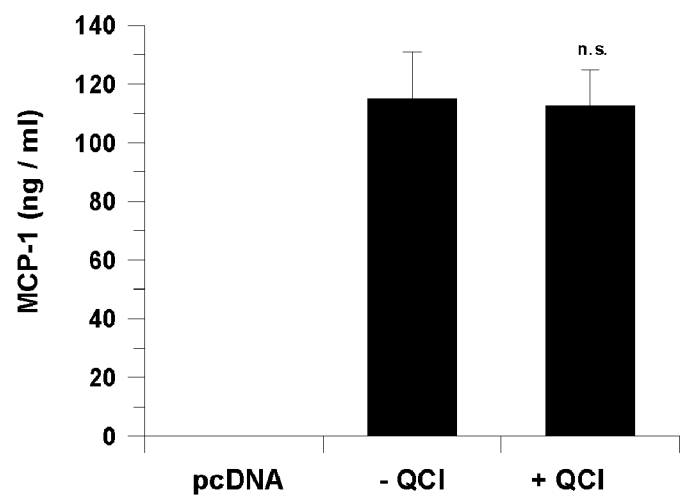

FIG. 28A shows the concentration of human MCP-1(1-76) (WT) in the supernatant of transfected HEK293 cells in absence and presence of 10 μM 1-(3-(1H-imidazol-1-yl)propyl)-3-(3,4-dimethoxyphenyl)thiourea hydrochloride in comparison to vector transfected control (pcDNA) (n.s.: not significant; Student's t-test; n=6). The concentrations were determined applying a specific ELISA technique.

Figure 28B:
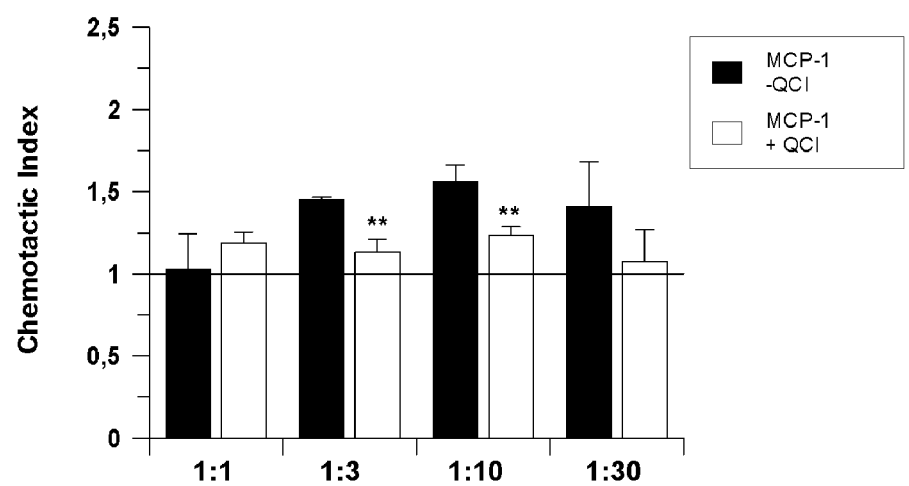

FIG. 28B shows the migration of THP-1 monocytes towards the generated supernatant of HEK293 cells, transfected with MCP-1 (WT) and treated in absence (closed bars) or presence (open bars) of 10 μM 1-(3-(1H-imidazol-1-yl) propyl)-3-(3,4-dimethoxyphenyl)thiourea hydrochloride in dilutions 1:1, 1:3, 1:10 and 1:30. (**, P<0.01; Student's t-test, n=3)

Figure 29:
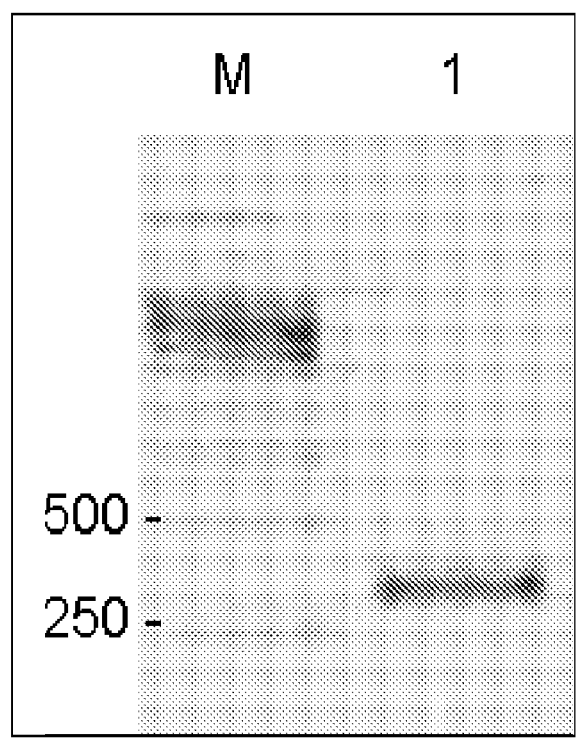

FIG. 29 shows the isolation of human MCP-1 cDNA from human neuroblastoma cell line SH-SY5Y applying a standard RT-PCR technique. (M:DNA standard in bp; 1: full length human MCP-1 isolated from SH-SY5Y).

Figure 30A:
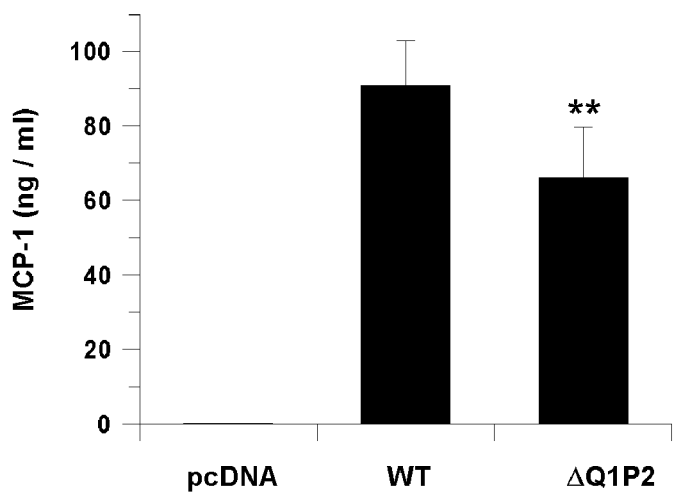

FIG. 30A shows the concentration of human MCP-1 (1-76) (WT) and mutant human MCP-1 lacking the two N-terminal amino acids (ΔQ1P2) in the supernatant of transfected HEK293 cells in comparison to vector transfected control (pcDNA) (**, P<0.01; Student's t-test; n=6). The concentrations were determined applying a specific ELISA technique.

Figure 30B:
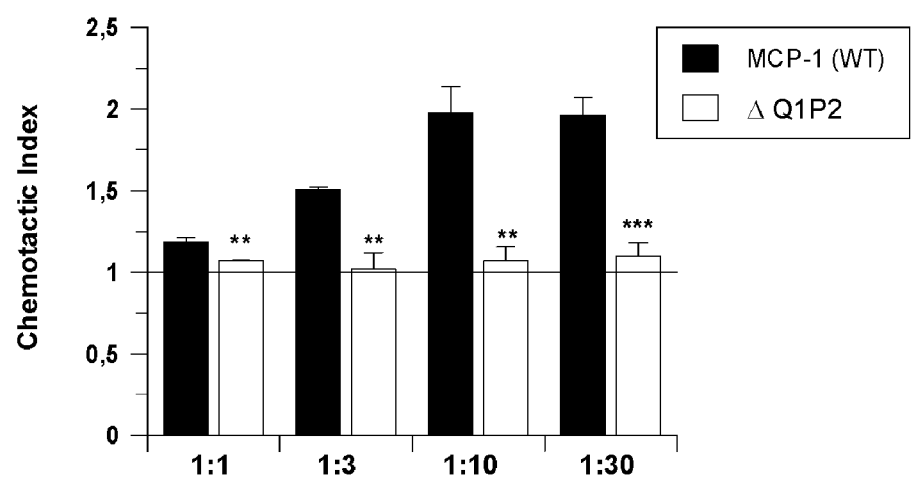

FIG. 30B shows the migration of THP-1 monocytes towards the generated supernatant of HEK293 cells, transfected with MCP-1 (WT) or MCP-1 (ΔQ1P) in dilutions 1:1, 1:3, 1:10 and 1:30. (, P<0.01; *, P<0.001; Student's t-test, n=3).

FIG. 31 shows the incubation of MCP-1(1-76) bearing an N-terminal glutaminyl (A) or Pyroglutamyl (5-oxo-L-Prolyl) residue with human synovial fibroblast MMP-1 (Calbiochem) for 24 h. For cyclization of N-terminal glutamine into pyroglutamate MCP-1 was incubated with recombinant human QC 3 h prior to assay start. The MMP-1 cleavage products were analyzed after 0 min, 15 min, 30 min, 1 h, 2 h, 4 h and 24 h using Maldi-TOF mass spectrometry.

Figure 32:
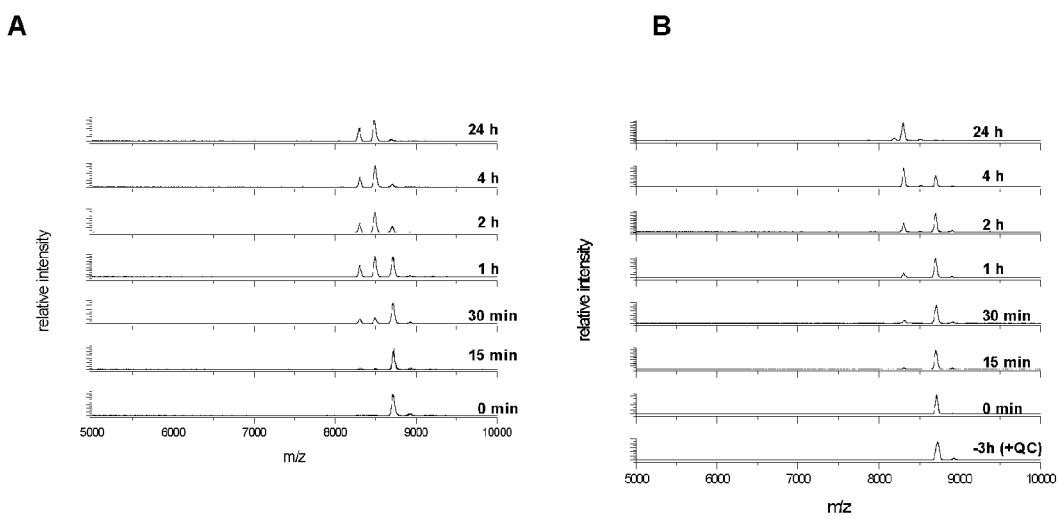
Figure 33:
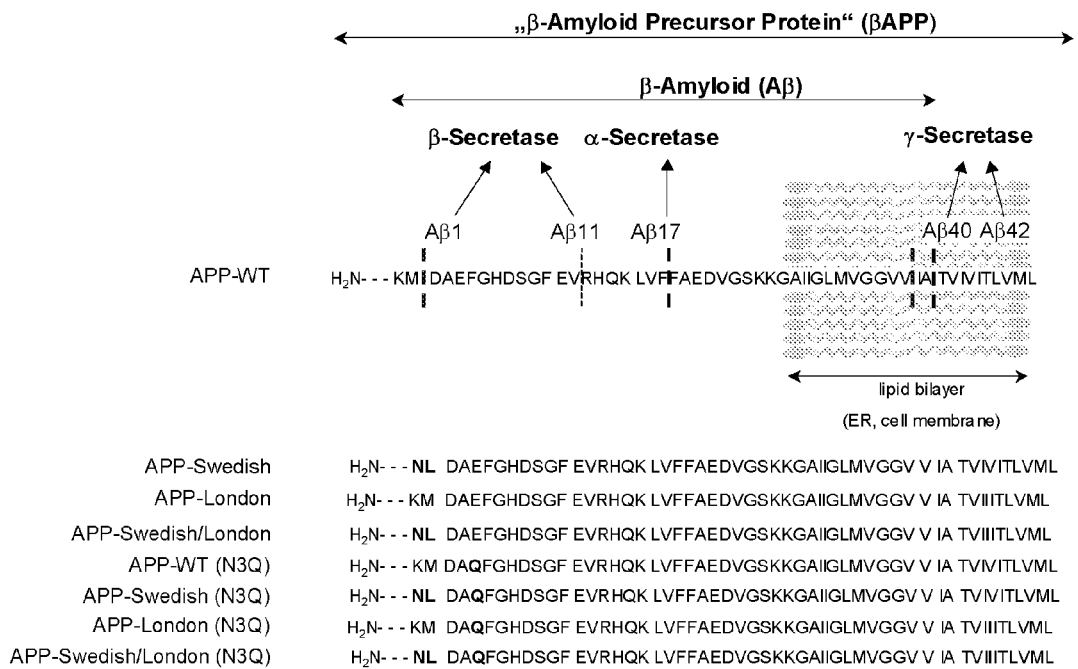

FIG. 32 shows the incubation of MCP-1(1-76) carrying an N-terminal glutaminyl (A) or Pyroglutamyl (5-oxo-L-Prolyl) with human synovial fibroblast MMP-1 and recombinant human DP4 for 24 h. For cyclization of N-terminal glutamine into pyroglutamate, MCP-1 was incubated with recombinant human QC 3 h prior to assay start. Resulting MMP-1 cleavage products were analyzed after 0 min, 15 min, 30 min, 1 h, 2 h, 4 h and 24 h using Maldi-TOF mass spectrometry FIG. 33 shows the schematic representation of the different APP constructs implicated in the studies to delineate formation of N-truncated peptides in cell culture studies. APPwt is the wild-type protein, APPsw contains the "swedish" mutation (KM595/596NL) APPLondon contains a single mutation (V642I) and APP Swedish/London both (KM595/596NL and V642I). In addition, constructs were generated which contained additionally a mutation which enables convenient detection of pGlu-Aβ formation (E599Q), if Aβ(3-40) or Aβ(3-42) is generated, caused by a rapid, QC-catalyzed cyclization of glutamine.

FIG. 34 shows the Aβ concentrations in the conditioned media of HEK-293 cells (A-D) and LNZ-308 cells (E and F), following transient expression of APP constructs either carrying the N3Q mutation (E599Q; B,D,F) or the wild type sequence (E599) at this amino acid position. The ELISAs (IBL, Hamburg, Germany) either detected total Aβ(x-40) or Aβ(x-42), denoted as x-40 or x-42, respectively, or pGlu-Aβ (3-40) and pGlu-Aβ(3-42) denoted as N3pE-40 and N3pE-42, respectively. The N3Q mutation does not influence the relative Aβ concentrations, comparing the x-40 and x-42 levels in cases of N3Q and the other constructs.

FIG. 35 shows the Aβ concentrations in the conditioned media of HEK-293 cells (A-D) and LNZ-308 cells (E and F), following transient expression of APP constructs (FIG. 33). The ELISAs (IBL, Hamburg, Germany) either detected total Aβ(x-40) or Aβ(x-42), denoted as x-40 or x-42, respectively, or Aβ(1-40) and Aβ(1-42) denoted as N1D-40 and N1D-42, respectively. The cells were transfected with the APP DNA constructs and afterwards, cells were maintained in presence or absence of a BACE I inhibitor. As can be concluded from the data, BACE I inhibition does significantly suppress the formation of Aβ(1-40/42), indicating that BACE I generates preferably N-terminally intact Aβ (D597 of the APP is the N-terminal amino acid). In contrast, analysing the total Aβ concentrations, it is obvious that the inhibition of BACE I did not impact the Aβ concentration to a similar extent. This, in turn, implies that there are N-terminally different Aβ species are generated in the cells, which are not due to BACE I cleavage.

Figure 36:
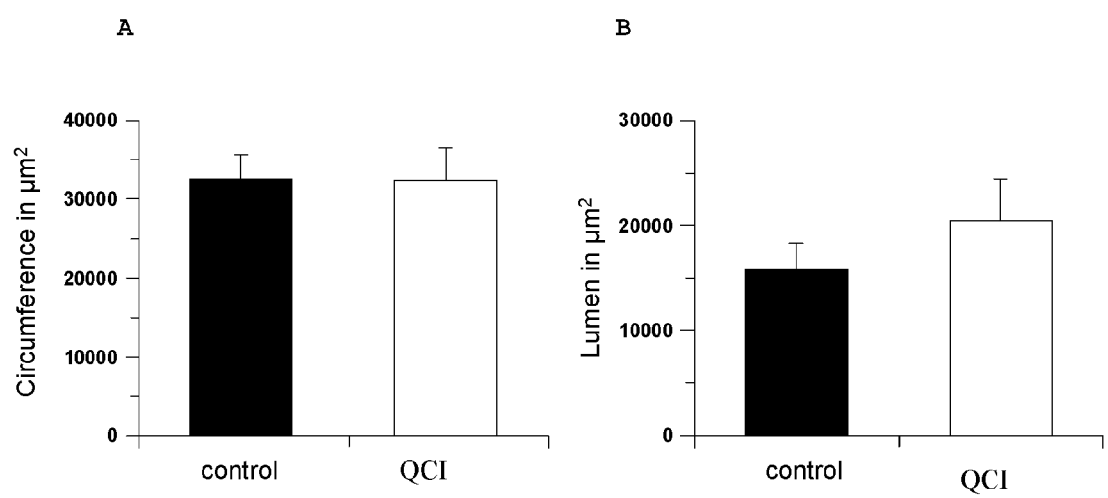

FIG. 36 shows the quantification of the vascular remodeling of the cuffed vessel wall segments of untreated ApoE3 Leiden mice (black bars) and mice, which were treated (open bars) with 1-(3-(1H-imidazol-1-yl)propyl)-3-(3,4-dimethoxyphenyl)thiourea hydrochloride. Mice were sacrificed 14 days after cuff placement. Expressed is the vascular circumference (A) i.e. the total area within the outer diameter of the vessel segment and the remaining lumen (B) in μm².

Figure 37:
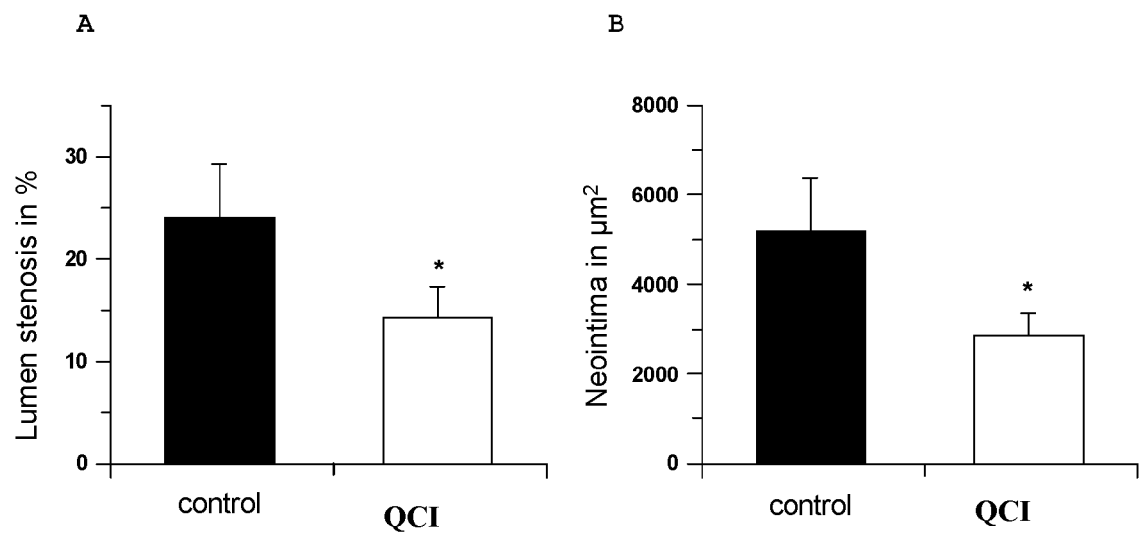
Figure 38:
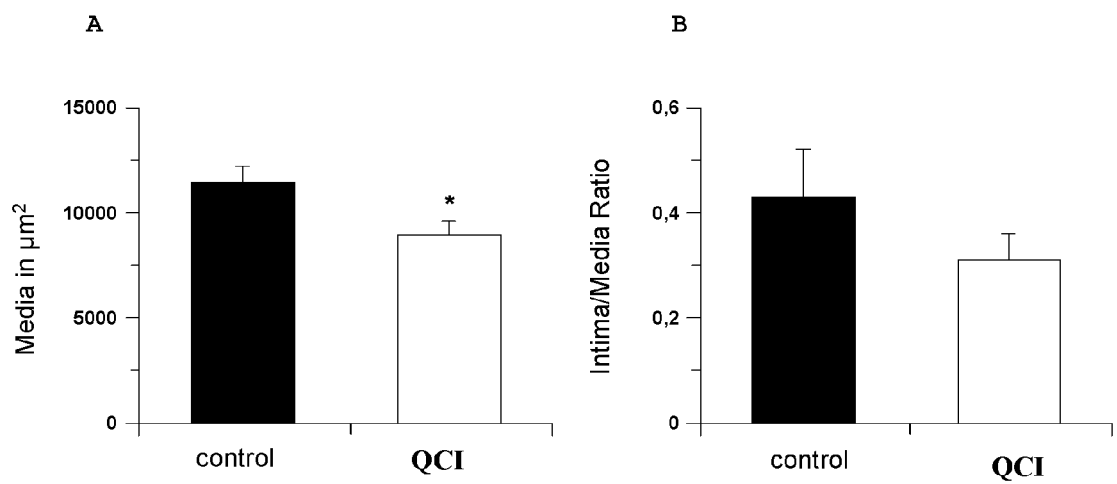
Figure 39:
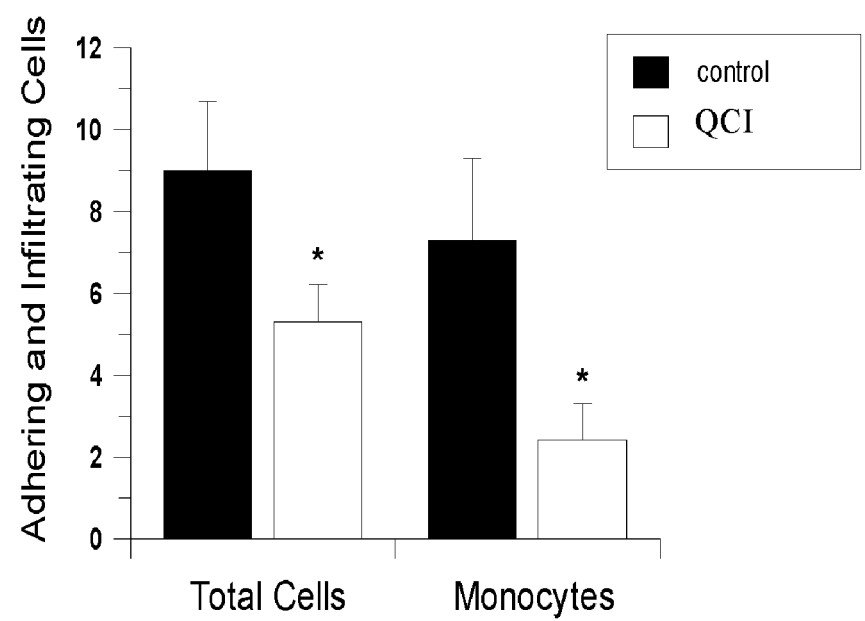

FIG. 37 shows the quantification of the vascular remodeling of the cuffed vessel wall segments of untreated ApoE3 Leiden mice (black bars) or mice treated with (open bars) 1-(3-(1H-imidazol-1-yl)propyl)-3-(3,4-dimethoxyphenyl) thiourea hydro-chloride. Mice were sacrificed 14 days after cuff placement. Expressed is the lumen stenosis A in % and the area of neointima B in μm². (*, P<0.05, Student's t-test):

FIG. 38 shows the quantification of the vascular remodeling of the cuffed vessel wall segments of untreated ApoE3 Leiden mice (black bars) or mice, which were treated with (open bars) of 1-(3-(1H-imidazol-1-yl)propyl)-3-(3,4-dimethoxyphenyl)thiourea hydrochloride. Mice were sacrificed 14 days after cuff placement. Expressed is the area of the media A in μm² and the intima/media ratio B. (*, P<0.05, Student's t-test):

FIG. 39 shows adhering and infiltrating cells per cross section in absence (black bars) or presence (open bars) of 1-(3-(1H-imidazol-1-yl)propyl)-3-(3,4-dimethoxyphenyl) thiourea hydrochloride treatment. Total number of adhering cells per cross section was counted in the cross section of the cuffed femoral arteries harvested two days after cuff placement. Within the total population of adhering cells a specific staining for monocytes/macrophages was used to identify the adhering and infiltrating monocytes. (*, P<0.05, Student's t-test).

Figure 40:
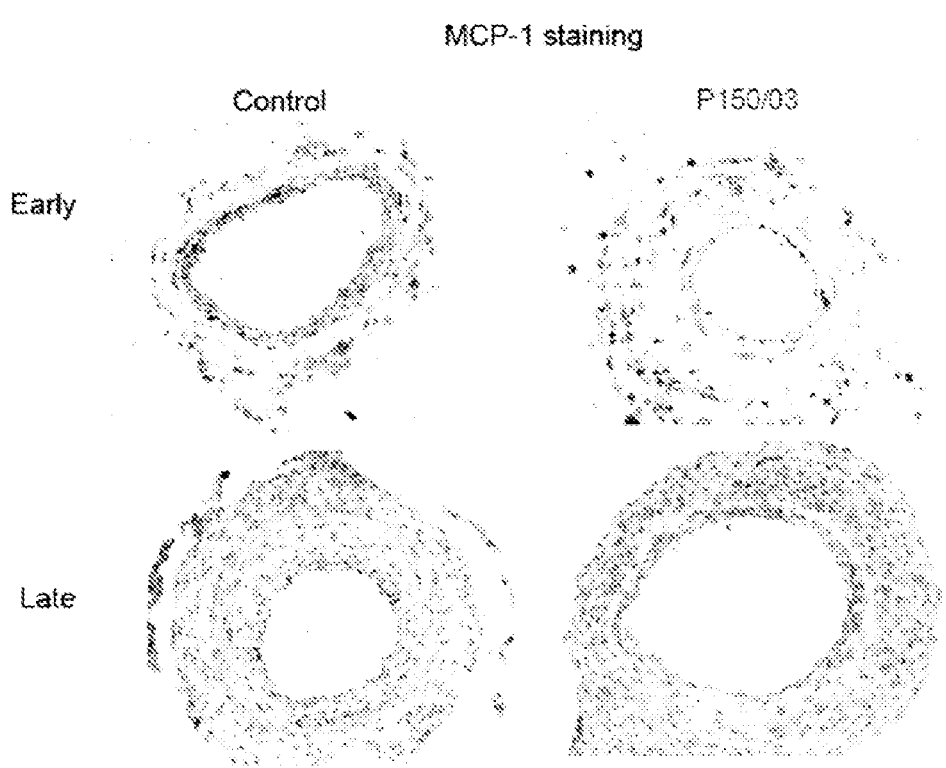

FIG. 40 shows examples of MCP-1 staining by immunohistochemistry of lesions at the early time point (2 days) and the late time point (14 days) in untreated mice (control) and mice, which were treated with 1-(3(1H-imidazol-1-yl)propyl)-3-(3,4-dimethoxyphenyl)thiourea hydrochloride (P150/03).

Figure 41:
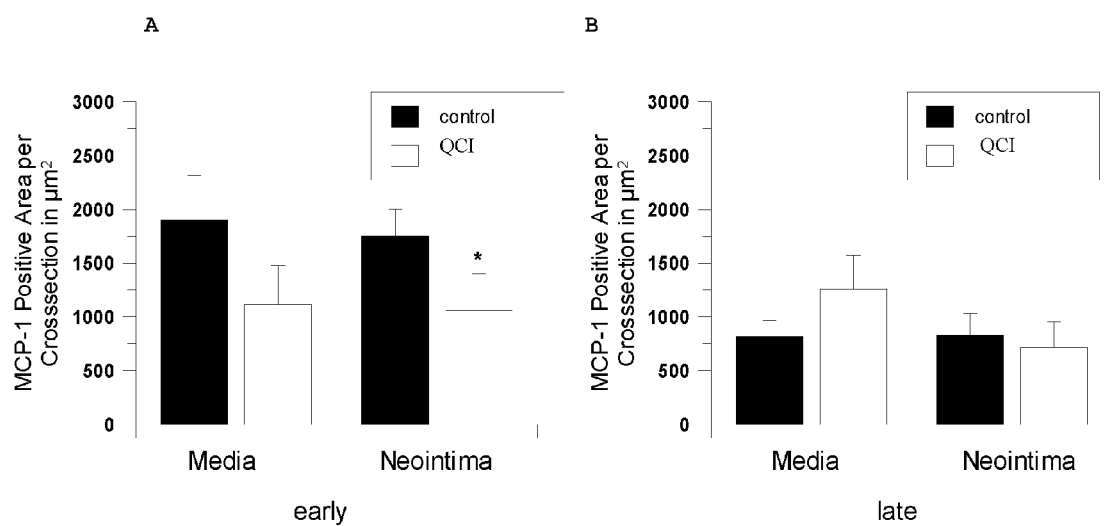

FIG. 41 shows the quantification of MCP-1 staining in cross sections of mice sacrificed after 2 days (early time point) A or after 14 days (late time point) B within the media and neointima in absence (black bars) and presence (open bars) of 1-(3-(1H-imidazol-1-yl)propyl)-3-(3,4-dimethoxyphenyl)thiourea hydrochloride treatment. (*, P<0.05; Student's t-test).

Figure 42:
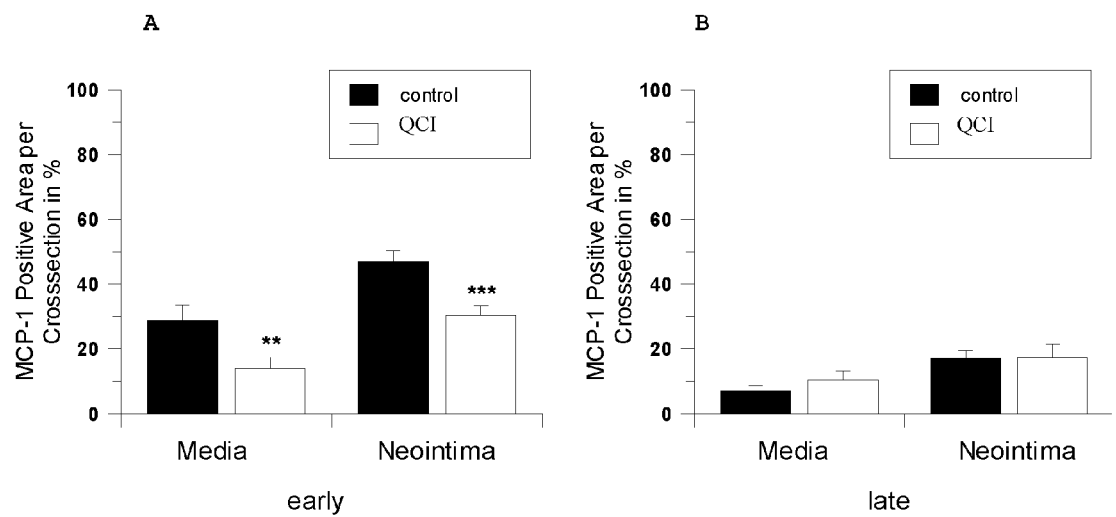

FIG. 42 shows the relative amount of MCP-1 staining (%) in cross sections of mice sacrificed after 2 days (early time point) (A) or after 14 days (late time point) (B) within the media and neointima in absence (black bars) and presence (open bars) of 1-(3-(1H-imidazol-1-yl)propyl)-3-(3,4-dimethoxyphenyl)thiourea hydrochloride treatment. (*, P<0.05; Student's t-test).

Figure 43:
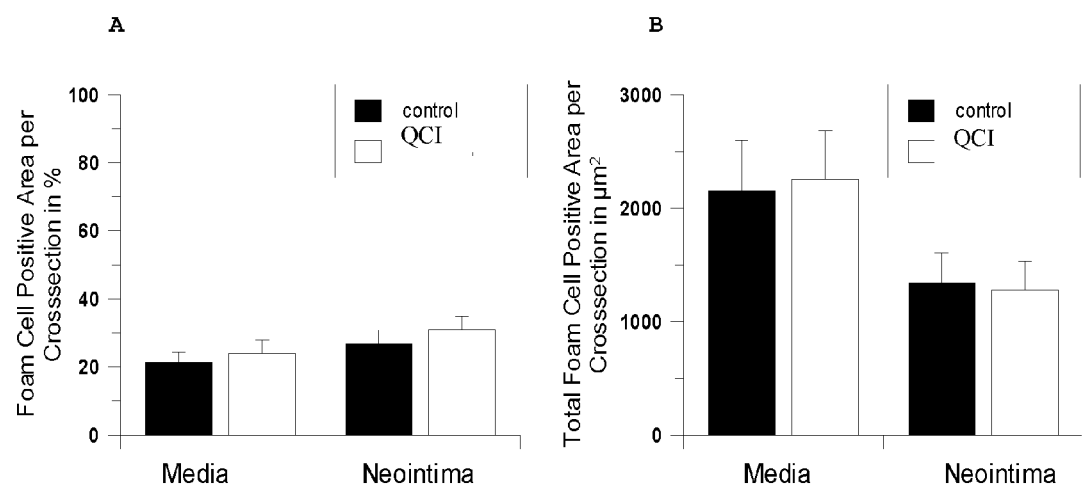

FIG. 43 shows the quantification of the accelerated atherosclerosis in the vessel wall based on the quantification of monocyte/macrophage staining using marker AIA31240. Presented are cross sections of mice sacrificed at the late time point (14 days) treated in absence (black bars) and presence (open bars) of 1-(3-(1H-imidazol-1-yl)propyl)-3-(3,4-dimethoxyphenyl)thiourea hydrochloride. Foam cell accumulation is illustrated as (A) foam cell positive area/cross section in % and (B) foam cell positive area/cross section in $\mu m^2$.

PEPTIDE SEQUENCES

The peptides mentioned and used herein have the following sequences:

Aβ(1-42) (SEQ ID NO: 20):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-Ile-Ala

Aβ(1-40) (SEQ ID NO: 21):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val

Aβ(3-42) (SEQ ID NO: 22):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val-Ile-Ala

Aβ(3-40) (SEQ ID NO: 23):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Aβ(1-11)a (SEQ ID NO: 24):
Asp-Ala-Glu-Phe-Arg-His-Asp-Ser-Gly-Tyr-Glu-NH₂

Aβ(3-11)a (SEQ ID NO: 25):
Glu-Phe-Arg-His-Asp-Ser-Gly-Tyr-Glu-NH₂

Aβ(1-21)a (SEQ ID NO: 26):
Asp-Ala-Glu-Phe-Arg-His-Asp-Ser-Gly-Tyr-Glu-Val-

His-His-Gln-Lys-Leu-Val-Phe-Phe-Ala-NH₂

Aβ(3-21)a (SEQ ID NO: 27):
Glu-Phe-Arg-His-Asp-Ser-Gly-Tyr-Glu-Val-His-His-

Gln-Lys-Leu-Val-Phe-Phe-Ala-NH₂

[Gln3]Aβ(3-40) (SEQ ID NO: 28):
Gln-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

[Gln3]Aβ(3-21)a (SEQ ID NO: 29):
Gln-Phe-Arg-His-Asp-Ser-Gly-Tyr-Glu-Val-His-His-

Gln-Lys-Leu-Val-Phe-Phe-Ala-NH₂

[Gln3]Aβ1-11a (SEQ ID NO: 30):
Asp-Ala-Gln-Phe-Arg-His-Asp-Ser-Gly-Tyr-Glu-NH₂

[Gln3]Aβ3-11a (SEQ ID NO: 31):
Gln-Phe-Arg-His-Asp-Ser-Gly-Tyr-Glu-NH₂

Aβ(11-42) (SEQ ID NO: 32):
Glu-Val-His-His-Gln-Lys-Leu-Val-Phe-Phe-Ala-Glu-

Asp-Val-Gly-Ser-Asn-Lys-Gly-Ala-Ile-Ile-Gly-Leu-

Met-Val-Gly-Gly-Val-Val-Ile-Ala

Aβ(1-40) (SEQ ID NO: 33):
Glu-Val-His-His-Gln-Lys-Leu-Val-Phe-Phe-Ala-Glu-

Asp-Val-Gly-Ser-Asn-Lys-Gly-Ala-Ile-Ile-Gly-Leu-

Met-Val-Gly-Gly-Val-Val

DETAILED DESCRIPTION OF THE INVENTION

The present invention provides effectors of glutaminyl cyclase (QC) for
 a) the treatment of diseases in mammals that can be treated by modulation of QC activity in vivo and/or
 b) the modulation of physiological processes based on the action of pGlu-containing peptides caused by modulation of QC activity.

Furthermore, the present invention provides compounds for the inhibition of glutaminyl cyclase (QC, EC 2.3.2.5) and/or QC-like enzymes in a mammal and the use of inhibitors of QC activity for the treatment of pathological conditions related to QC activity. In particular, inhibitors of QC activity for the prevention, treatment and/or alleviation of Alzheimer's disease are provided.

The present invention also provides a new method for the treatment of Alzheimer's disease and Down syndrome. The N-termini of amyloid β-peptides deposited in Alzheimer's disease and Down syndrome brain bear pyroglutamic acid. The pGlu formation is an important event in the development and progression of the disease since the modified amyloid β-peptides show an enhanced tendency to β-amyloid aggregation and toxicity, likely worsening the onset and progression of the disease (Russo, C. et al. 2002 J Neurochem 82, 1480-1489).

In the natural Aβ-peptides (3-40/42), glutamic acid is present as an N-terminal amino acid. There was no enzymatic conversion of Glu to pGlu known to date. Moreover, spontaneous cyclization of Glu-peptides to pGlu-peptides has not been observed as yet. Therefore, one aspect of the present invention was to determine the role of QC in Alzheimer's disease and Down syndrome. This aspect was addressed by the synthesis of Aβ(3-11) and Aβ(1-11), containing the amino acid glutamine instead of glutamic acid at position three, the determination of the substrate characteristics of these modified amyloid β-peptides against QC, DP IV and DP IV-like enzymes and aminopeptidases and the use of inhibitors of QC to prevent the formation of pGlu from a N-terminal glutaminyl residue of the amyloid β-derived peptides Aβ(3-11) and Aβ(1-11). The results are shown in example 8. The applied method is described in example 3.

To date, there are no hints indicating an involvement of QC in the progression of the disease, because glutamic acid is the N-terminal amino acid in Aβ (3-40/42, or 11-40/42). However, QC is the only known enzyme capable of forming pGlu at the N-terminus of peptides. Other aspects of the present invention concern the following findings and discoveries:

a) In a side reaction, QC catalyzes the cyclization of glutamic acid to pyroglutamic acid at very low rates,
b) Glutamic acid of APP or its subsequently formed amyloid-β-peptides is converted into glutamine post-translationally by an unknown enzymatic activity and in a second step, QC catalyzes the cyclization of glutamine into pyroglutamic acid after processing of the amyloid β-peptide N-terminus,
c) Glutamic acid is converted into glutamine post-translationally by a chemical catalysis or autocatalysis and subsequently, QC catalyzes the cyclization of glutamine to pyroglutamic acid after processing of the amyloid β-peptide N-terminus,
d) There are mutations in the APP gene, which encode the amyloid β-protein, leading to Gln instead of Glu in position 3. After translation and processing of the N-terminus, QC catalyzes the cyclization of glutamine to pyroglutamic acid,
e) Glutamine is incorporated into the nascent peptide chain of APP, due to a malfunction of an unknown enzymatic activity and subsequently, QC catalyzes the cyclization of N-terminally glutamine to pyroglutamic acid after processing of the amyloid β-peptide N-terminus.

In this regard the present inventors conducted several extensive studies in order to 1) validate the involvement of QC in generation of pGlu-Aβ(3-40/42) and II) to demonstrate that QC inhibitors can be used to suppress pGlu-Aβ formation in the studies. The most relevant results are illustrated in FIG. 23 and are the following:

1. QC-catalyzed pGlu-Aβ(3-40) formation was suppressed by QC-inhibitor 1-(3-(1H-imidazole-1-yl)propyl)-3-(3,4-dimethoxy-phenyl)thiourea hydrochloride in vitro, applying Aβ(3-40) and recombinant human glutaminyl cyclase,
2. 1-(3-(1H-imidazole-1-yl)propyl)-3-(3,4-dimethoxy-phenyl)thiourea hydrochloride was used successfully to suppress generation of pGlu-Aβ(3-42) in a cell culture experiment based on APP expression,
3. In an animal trial based on traumatic brain injury, Aβ(3-40) and Aβ(1-40) were injected into the deep cortex of the rat. Following that pGlu-Aβ formation was assessed by immunohistochemistry and pGlu-specific ELISAs. The QC inhibitor 1-(3-(1H-imidazole-1-yl)propyl)-3-(3,4-dimethoxy-phenyl)thiourea hydrochloride reduced the pGlu-Aβ(3-40) formation significantly.
4. In addition to the effect as shown by the present invention, i.e. that the QC-catalyzed pGlu-Aβ formation was suppressed by the QC inhibitor, it was also shown that MCP-1 is an additional target of the QC inhibitors of the present invention, thus leading surprisingly to additive or even synergistic effects of the present QC-inhibitor.

Hence, in one particularly important embodiment of the present invention, use of the QC inhibitors, in particular 1-(3-(1H-imidazole-1-yl)propyl)-3-(3,4-dimethoxy-phenyl)thiourea hydrochloride for the treatment of Alzheimer's disease is claimed. The QC inhibitors would work especially well for the treatment of Alzheimer's disease, or prevention or alleviation thereof, as both the Aβ peptides as well as MCP-1, which play an important role in inflammatory processes in Alzheimer's disease, are targets of the QC inhibitors of the invention.

It is only due to the present invention that it could be shown that QC inhibitors would target both MCP-1 and Aβ, both being involved in mechanisms underlying Alzheimer's disease.

It could therefore be shown by the present invention that QC inhibitors are particularly useful for the alleviation or prevention of Alzheimer's disease.

Thus, the present invention clearly discloses the applicability of QC inhibitors in vivo for the treatment of QC-related diseases, in particular Alzheimer's disease.

In parallel to the above studies, substance development was initiated to search for inhibitory leads that display a disease-relevant tissue distribution. The studies as conducted are described in detail in the Examples section of the present invention.

Further, as shown by the present inventors, QC is involved in the critical step in all five cases a) to e) listed above, namely the formation of pyroglutamic acid that favors the aggregation of amyloid β-peptides. Thus, an inhibition of QC leads to a prevention of the precipitation of the plaque-forming Aβ(3-40), Aβ(3-42), Aβ(11-40) or Aβ(11-42), causing the onset and progression of Alzheimer's disease and Down Syndrome, independently of the mechanism by which cyclization occurs.

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so-called Dutch type cerebroarterial amyloidosis mutation.

The β-amyloid peptides with a pyroglutamic acid residue in position 3, 11 and/or 22 have been described to be more cytotoxic and hydrophobic than Aβ(1-40), Aβ(1-42) or Aβ(1-43) (Saido, (2000) Medical Hypotheses 54, 427-429).

The multiple N-terminal variations can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase processing. In all cases, cyclization can take place according to a)-e) as described above.

So far, there was no experimental evidence supporting the enzymatic conversion of Glu1-peptides into pGlu-peptides by an unknown glutamyl cyclase (EC) corresponding to pathway a) (Garden, R. W. et al., (1999) J Neurochem 72, 676-681; Hosoda R. et al. (1998) J Neuropathol Exp Neurol. 57, 1089-1095). To date, no such enzyme activity has been identified, capable to cyclize Glu1-peptides which are protonated N-terminally and possess a negatively charged Glu1 γ-carboxylate moiety under mildly alkaline and neutral pH-conditions.

QC-activity against Gln1-substrates is dramatically reduced below pH 7.0. In contrast, it appears that Glu1- conversion can occur at acidic reaction conditions (Iwatsubo, T. et al., (1996) Am J Pathol 149, 1823-1830; Russo, C. et al., (1977) FEBS Lett 409, 411-416; Russo, C. et al., (2001) Neurobiol Dis 8, 173-180; Tekirian, T. L. et al., (1998) J Neuropathol Exp Neurol. 57, 76-94; Russo, C. et al., (2002) J Neurochem 82, 1480-1489; Hosoda, R. et al., (1998) J Neuropathol Exp Neurol. 57, 1089-1095; Garden, R. W. et al., (1999) J Neurochem 72, 676-681).

According to the present invention, it was investigated whether QC is able to recognize and to turnover amyloid-β derived peptides under mildly acidic conditions. Therefore, the peptides [Gln3]Aβ(1-11)a, Aβ(3-11)a, [Gln3]Aβ(3-11)a, Aβ(3-21)a, [Gln3]Aβ(3-21)a, [Gln3]Aβ3-40, Aβ(3-40) and Aβ(3-42) as potential substrates of the enzyme were synthesized and investigated. These sequences were chosen for mimicking natural N-terminally and C-terminally truncated [Glu3]Aβ peptides and [Gln3]Aβ peptides which could occur due to posttranslational Glu-amidation.

In the present invention it was shown that papaya and human QC catalyze both glutaminyl and glutamyl cyclization. Apparently, the primary physiological function of QC is to finish hormone maturation in endocrine cells by glutamine cyclization prior or during the hormone secretion process. Such secretory vesicles are known to be acidic in pH. Thus, a side activity of the enzyme in the narrow pH-range from 5.0 to 7.0 could be its newly discovered glutamyl cyclase activity transforming also Glu-Aβ peptides (FIGS. 15-17, FIG. 24-1). In the pathology of neurodegenerative disorders, in particular Alzheimer's disease, this glutamyl cyclization is of relevance.

Figure 17:
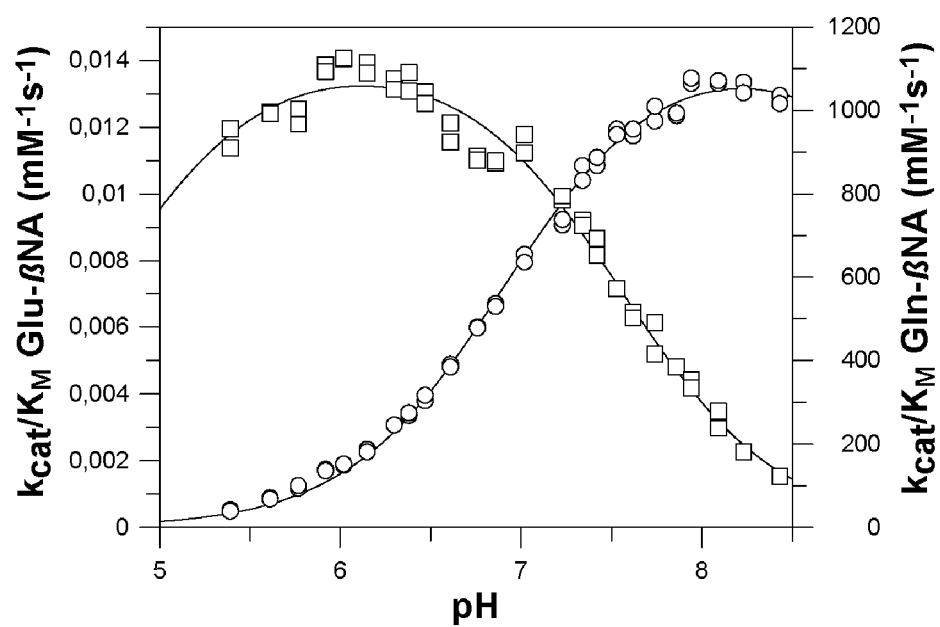
FIG. 17 shows the pH-dependence of the QC-catalyzed conversion of Gln-βNA (circles) and Glu-βNA (squares), determined under first-order rate-law conditions (S<<$K_M$). Substrate concentrations were 0.01 mM and 0.25 mM, respectively. For both determinations, a three-component buffer system was applied consisting of 0.05 M acetic acid, 0.05 M pyrophosphoric acid and 0.05 M Tricine. All buffers were adjusted to equal conductivity by addition of NaCl, in order to avoid differences in ionic strength. The data were fitted to equations that account for two dissociating groups revealing pKa-values of 6.91±0.02 and 9.5±0.1 for Gln-βNA and 4.6±0.1 and 7.55±0.02 for Glu-βNA. The pKa-values of the respective substrate amino groups, determined by titration, were 6.97±0.01 (Gln-βNA) and 7.57±0.05 (Glu-βNA). All determinations were carried out at 30° C.

Investigating the pH-dependency of this enzymatic reaction, the inventors found that the unprotonated N-terminus was essential for the cyclization of $Gln^1$-peptides and accordingly that the $pK_a$-value of the substrate was identical to the $pK_a$-value for QC-catalysis (see FIG. 17). Thus, QC stabilizes the intramolecular nucleophilic attack of the unprotonated α-amino moiety on the γ-carbonyl carbon electrophilically activated by amidation (Scheme 1 below).

In contrast to the monovalent charge present on N-terminal glutamine containing peptides, the N-terminal Glu-residue in Glu-containing peptides is predominantly bivalently charged around neutral pH. Glutamate exhibits $pK_a$-values of about 4.2 and 7.5 for the γ-carboxylic and for the α-amino moiety, respectively. That is, at neutral pH and above, although the α-amino nitrogen is in part or fully unprotonated and nucleophilic, the γ-carboxylic group is unprotonated, and so exercising no electrophilic carbonyl activity. Hence, intramolecular cyclization is impossible.

However, in the pH-range of about 5.2-6.5, between their respective $pK_a$-values, the two functional groups are present both in non-ionized forms, in concentrations of about 1-10% (—NH$_2$) or 10-1% (—COOH) of total N-terminal Glu-containing peptide. As a result, over a mildly acidic pH-range species of N-terminal Glu-peptides are present which carry both groups uncharged, and, therefore, it is possible that QC could stabilize the intermediate of intramolecular cyclization to pGlu-peptide, i.e. if the γ-carboxylic group is protonated, the carbonyl carbon is electrophilic enough to allow nucleophilic attack by the unprotonated α-amino group. At this pH the hydroxyl ion functions as a leaving group (Scheme 3 below). These assumptions are corroborated by the pH-dependence data obtained for the QC catalyzed conversion of Glu-βNA (see example 11). In contrast to glutamine conversion of Gln-βNA by QC, the pH-optimum of catalysis shifts to the acidic range around pH 6.0, i.e. the pH-range, in which substrate molecule species are simultaneously abundant carrying a protonated γ-carboxyl and unprotonated α-amino group. Furthermore, the kinetically determined $pK_a$-value of 7.55±0.02 is in excellent agreement with that of the α-amino group of Glu-βNA, determined by titration (7.57±0.05).

Physiologically, at pH 6.0 the second-order rate constant (or specificity constant, $k_{cat}/K_M$) of the QC-catalyzed glutamate cyclization might be in the range of 8,000 fold slower than the one for glutamine cyclization (FIG. 17). However, the nonenzymatic turnover of both model substrates Glu-βNA and Gln-βNA is negligible, being conform with the observed negligible pGlu-peptide formation in the present invention. Hence, for the pGlu-formation by QC an acceleration of at least $10^8$ can be estimated from the ratio of the enzymatic versus non-enzymatic rate constants (comparing the second-order rate constants for the enzyme catalysis with the respective nonenzymatic cyclization first-order rate constants the catalytic proficiency factor is $10^9$-$10^{10}$ M$^{-1}$ for the Gln- and the Glu-conversion, respectively). The conclusion from these data is, that in vivo only an enzymatic path resulting pGlu-formations seems conceivable.

Figure 10:
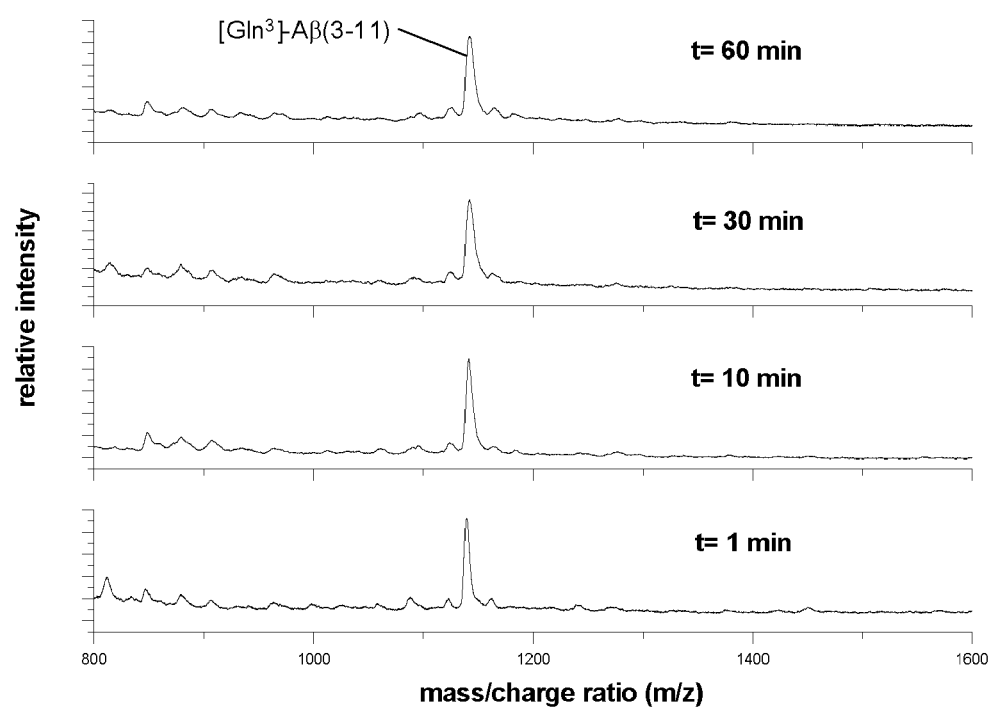
FIG. 10 shows the inhibition of the formation of [pGlu3] Aβ(3-11) from [Gln3]Aβ(3-11) by the QC-inhibitor 1,10-phenanthroline. At the times indicated, samples were removed from the assay tube, mixed with matrix solution (1:1 v/v) and subsequently the mass spectra recorded.
Figure 15:
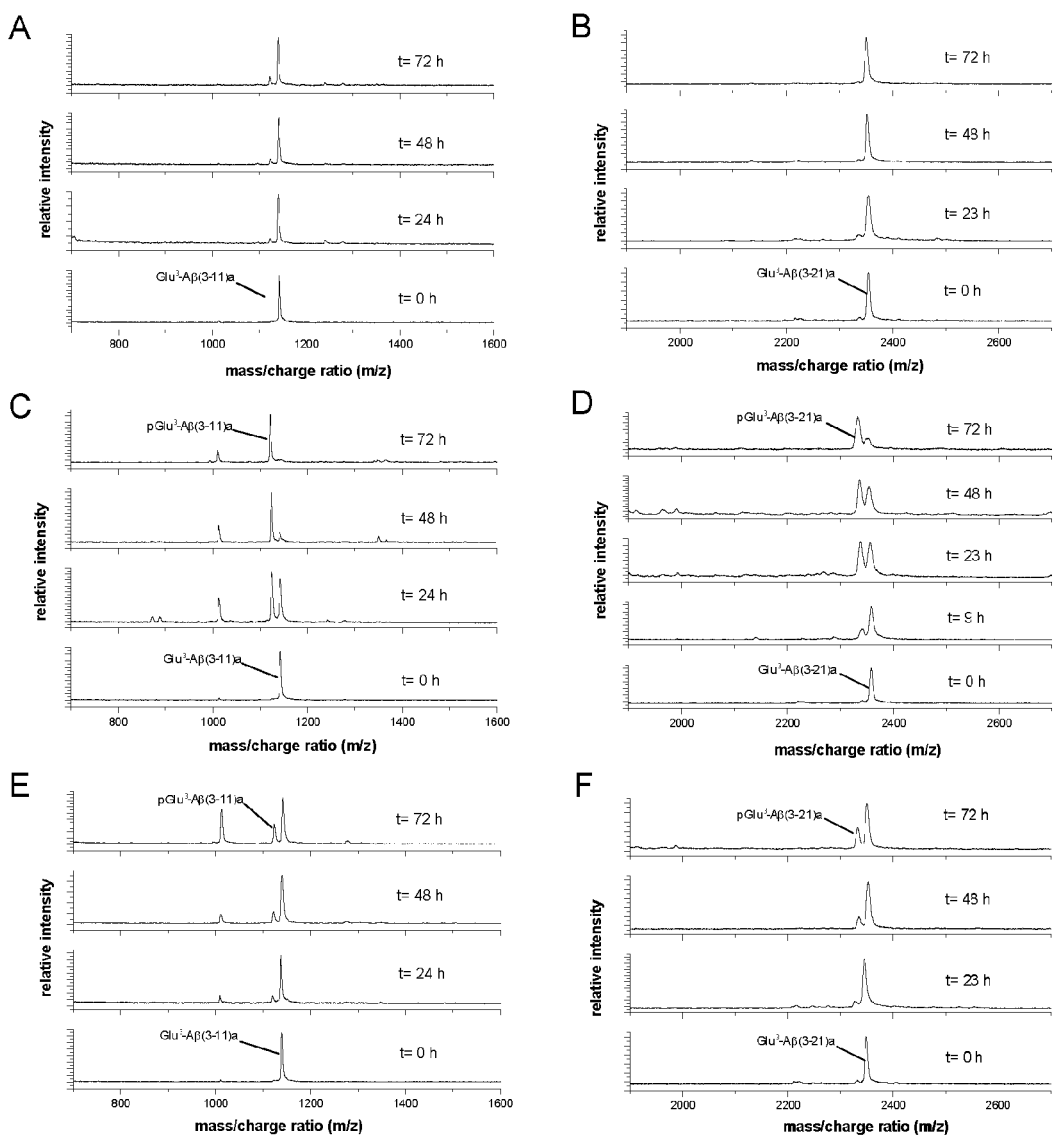
FIGS. 15 A and B show mass spectra of [Glu3]Aβ(3-11)a and [Glu3]Aβ(3-21)a incubated with recombinant human QC, that was boiled for 10 min before use. C and D show mass spectra of [Glu3]Aβ(3-11) and [Glu3]Aβ(3-21)a in presence of active human QC resulting in the formation of [pGlu3]Aβ (3-11)a and [pGlu3]Aβ(3-21)a, respectively. E and F show Mass spectra of [Glu3]Aβ(3-11)a and [Glu3]Aβ(3-21)a in presence of active QC and 5 mM Benzimidazole suppressing the formation of [pGlu3].

Since QC is highly abundant in the brain and taking into account the high turnover rate of 0.9 min$^{-1}$ recently found for the maturation of 30 μM of (Gln-)TRH-like peptide (Prokai, L., Prokai-Tatrai, K., Ouyang, X., Kim, H. S., Wu, W. M., Zharikova, A., and Bodor, N. (1999) *J Med Chem* 42, 4563-4571), one can predict a cyclization half-life of about 100 hours for an appropriate glutamate-substrate, similar reaction conditions provided. Moreover, given compartmentalization and localization of brain QC/EC in the secretory pathway, the actual in vivo enzyme and substrate concentrations and reaction conditions might be even more favorable for the enzymatic cyclization in the intact cell. And, if N-terminal Glu is transformed to Gln a much more rapid pGlu-formation mediated by QC could be expected. In vitro, both reactions were suppressed by applying inhibitors of QC/EC-activity (FIGS. 9, 10 and 15).

In summary, the present invention shows that human QC, which is highly abundant in the brain, is a likely catalyst to the formation of the amyloidogenic pGlu-Aβ peptides from Glu-Aβ and Gln-Aβ precursors, which make up more than 50% of the plaque deposits found in Alzheimer's disease. These findings identify QC/EC as a player in senile plaque formation and thus as a novel drug target in the treatment of Alzheimer's disease.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

More specifically, the aforementioned other agent is selected from the group consisting of beta-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of
- (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
- (b) Selective serotonin re-uptake inhibitors (SSRI's), e.g. citalopram, fluoxetine, fluvoxamine, escitalopram, sertraline, paroxetine,
- (c) Tricyclic antidepressants, e.g. amitryptiline, clomipramine, desipramine, doxepin, imipramine
- (d) Monoamine oxidase (MAO) inhibitors,
- (e) Azapirones, e.g. buspirone, tandopsirone,
- (f) Serotonin-norepinephrine reuptake inhibitors (SNRI's), e.g. venlafaxine, duloxetine,
- (g) Mirtazapine,
- (h) Norepinephrine reuptake inhibitors (NRI's), e.g. reboxetine,
- (i) Bupropione,
- (j) Nefazodone,
- (k) beta-blockers,
- (l) NPY-receptor ligands: NPY agonists or antagonists.

In a further embodiment, the other agent may be, for example, an anti-multiple sclerosis drug selected from the group consisting of
- a) dihydroorotate dehydrogenase inhibitors, e.g. SC-12267, teriflunomide, MNA-715, HMR-1279 (syn. to HMR-1715, MNA-279),
- b) autoimmune suppressant, e.g. laquinimod,
- c) paclitaxel,
- d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-1 L-12-antibody,
- e) peptide nucleic acid (PNA) preparations, e.g. reticulose,
- f) interferon alpha, e.g. Alfaferone, human alpha interferon (syn. to Omniferon, Alpha Leukoferon),
- g) interferon beta, e.g. Frone, interferon beta-1a like Avonex, Betron (Rebif), interferon beta analogs, interferon beta-transferrin fusion protein, recombinant interferon beta-1b like Betaseron,
- h) interferon tau,
- i) peptides, e.g. AT-008, AnergiX.MS, Immunokine (alpha-Immunokine-NNSO3), cyclic peptides like ZD-7349,
- j) therapeutic enzymes, e.g. soluble CD8 (sCD8),
- k) multiple sclerosis-specific autoantigen-encoding plasmid and cytokine-encoding plasmid, e.g. BHT-3009;
- l) inhibitor of TNF-alpha, e.g. BLX-1002, thalidomide, SH-636,
- m) TNF antagonists, e.g. solimastat, lenercept (syn. to RO-45-2081, Tenefuse), onercept (sTNFR1), CC-1069,
- n) TNF alpha, e.g. etanercept (syn. to Enbrel, TNR-001)
- o) CD28 antagonists, e.g. abatacept,
- p) Lck tyrosine kinase inhibitors,
- q) cathepsin K inhibitors,
- r) analogs of the neuron-targeting membrane transporter protein taurine and the plant-derived calpain inhibitor leupeptin, e.g. Neurodur,
- s) chemokine receptor-1 (CCR1) antagonist, e.g. BX-471,
- t) CCR2 antagonists,
- u) AMPA receptor antagonists, e.g. ER-167288-01 and ER-099487, E-2007, talampanel,
- v) potassium channel blockers, e.g. fampridine,
- w) tosyl-proline-phenylalanine small-molecule antagonists of the VLA-4/VCAM interaction, e.g. TBC-3342,
- x) cell adhesion molecule inhibitors, e.g. TBC-772,
- y) antisense oligonucleotides, e.g. EN-101,
- z) antagonists of free immunoglobulin light chain (IgLC) binding to mast cell receptors, e.g. F-991,
- aa) apoptosis inducing antigens, e.g. Apogen MS,
- bb) alpha-2 adrenoceptor agonist, e.g. tizanidine (syn. to Zanaflex, Ternelin, Sirdalvo, Sirdalud, Mionidine),
- cc) copolymer of L-tyrosine, L-lysine, L-glutamic acid and L-alanine, e.g. glatiramer acetate (syn. to Copaxone, COP-1, copolymer-),
- dd) topoisomerase II modulators, e.g. mitoxantrone hydrochloride,
- ee) adenosine deaminase inhibitor, e.g. cladribine (syn. to Leustatin, Mylinax, RWJ-26251),
- ff) interleukin-10, e.g. ilodecakin (syn. to Tenovil, Sch-52000, CSIF),
- gg) interleukin-12 antagonists, e.g. lisofylline (syn. to CT-1501R, LSF, lysofylline),
- hh) Ethanaminum, e.g. SRI-62-834 (syn. to CRC-8605, NSC-614383),
- ii) immunomodulators, e.g. SAIK-MS, PNU-156804, alpha-fetoprotein peptide (AFP), IPDS,
- jj) retinoid receptor agonists, e.g. adapalene (syn. to Differin, CD-271),
- kk) TGF-beta, e.g. GDF-1 (growth and differentiation factor 1),
- ll) TGF-beta-2, e.g. BetaKine,
- mm) MMP inhibitors, e.g. glycomed,
- nn) phosphodiesterase 4 (PDE4) inhibitors, e.g. RPR-122818,
- oo) purine nucleoside phosphorylase inhibitors, e.g. 9-(3-pyridylmethyl)-9-deazaguanine, peldesine (syn. to BCX-34, TO-200),
- pp) alpha-4/beta-1 integrin antagonists, e.g. ISIS-104278,
- qq) antisense alpha4 integrin (CD49d), e.g. ISIS-17044, ISIS-27104,
- rr) cytokine-inducing agents, e.g. nucleosides, ICN-17261,
- ss) cytokine inhibitors,
- tt) heat shock protein vaccines, e.g. HSPPC-96,
- uu) neuregulin growth factors, e.g. GGF-2 (syn. to neuregulin, glial growth factor 2),
- vv) cathepsin S-inhibitors,
- ww) bropirimine analogs, e.g. PNU-56169, PNU-63693,
- xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Suitable cysteine protease inhibitors are inhibitors of cathepsin B. Inhibitors of cathepsin B and compositions containing such inhibitors are described, e.g. in WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.) and DNP-004089 (De Novo Pharmaceuticals Ltd.).

Inhibitors of gamma secretase and compositions containing such inhibitors are described, e.g. in WO2005/008250, WO2006/004880, U.S. Pat. No. 7,122,675, U.S. Pat. No. 7,030,239, U.S. Pat. No. 6,992,081, U.S. Pat. No. 6,982,264, WO2005/097768, WO2005/028440, WO2004/101562, U.S. Pat. No. 6,756,511, U.S. Pat. No. 6,683,091, WO03/066592, WO03/014075, WO03/013527, WO02/36555, WO01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. No. 6,713,276, U.S. Pat. No. 6,686,449, WO03/091278, U.S. Pat. No. 6,649,196, U.S. Pat. No. 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124,305; U.S. Pat. No. 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613; WO2006/009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk A/S).

Other preferred DP IV-inhibitors are (i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;

(ii) peptide structures, disclosed in WO 03/002593, e.g. tripeptides;

(iii) peptidylketones, disclosed in WO 03/033524;

(vi) substituted aminoketones, disclosed in WO 03/040174;

(v) topically active DP IV-inhibitors, disclosed in WO 01/14318;

(vi) prodrugs of DP IV-inhibitors, disclosed in WO 99/67278 and WO 99/67279; and (v) glutaminyl based DP IV-inhibitors, disclosed in WO 03/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S)-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221,752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N2-(diphenylacetyl)-(R)—N-[1-(4-hydroxy-phenyl)ethyl]arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth) and CI-101 7/(PD-151832) (Pfizer Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (Whanln).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); Epi-Cept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-CI-kynurenine (4-CI-KYN)), 7-chloro-kynurenic acid (7-CI-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include AT$_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-4177 of the formula

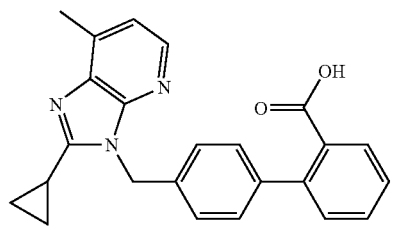

the compound with the designation SC-52458 of the following formula

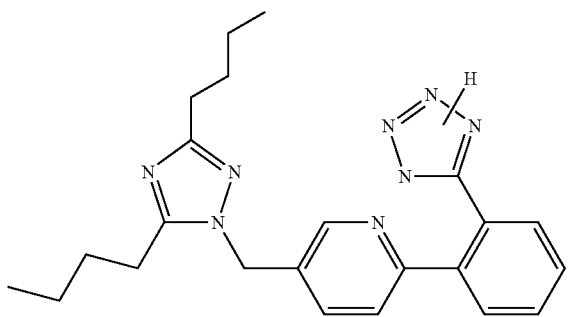

and the compound with the designation the compound ZD-8731 of the formula

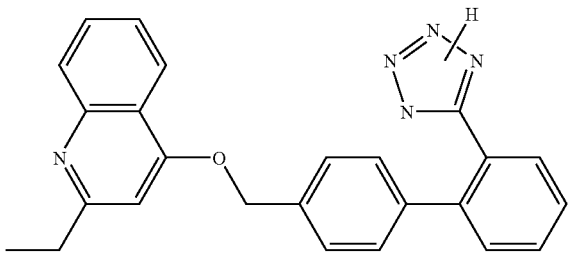

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorthalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:
- a QC inhibitor, in particular QCI, in combination with Atorvastatin for the treatment and/or prevention of atherosclerosis
- a QC inhibitor, in particular QCI in combination with immunosuppressive agents, preferably rapamycin for the prevention and/or treatment of restenosis
- a QC inhibitor, in particular QCI in combination with immunosuppressive agents, preferably paclitaxel for the prevention and/or treatment of restenosis
- a QC inhibitor, in particular QCI in combination with AChE inhibitors, preferably Donepezil, for the prevention and/or treatment of Alzheimer's disease
- a QC inhibitor, in particular QCI in combination with interferones, preferably Aronex, for the prevention and/or treatment of multiple sclerosis
- a QC inhibitor, in particular QCI in combination with interferones, preferably betaferon, for the prevention and/or treatment of multiple sclerosis
- a QC inhibitor, in particular QCI in combination with interferones, preferably Rebif, for the prevention and/or treatment of multiple sclerosis
- a QC inhibitor, in particular QCI in combination with Copaxone, for the prevention and/or treatment of multiple sclerosis.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

In a preferred embodiment of the present invention, it was found that amyloid β-derived peptides are a substrate of dipeptidyl peptidase IV (DP IV) or DP IV-like enzymes, preferably dipeptidyl peptidase II (DPII). DP IV, DP II or other DP IV-like enzymes release a dipeptide from the N-terminus of the modified amyloid β-peptide (1-11) generating amyloid β-peptide (3-11) with glutamine as the N-terminal amino acid residue. The results are shown in example 8.

DP IV-like enzymes, which have been identified so far, include e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), DPL1 (DPX, DP6), DPL2 and DPP 9 described in review articles by Sedo & Malik (Sedo and Malik 2001, *Biochim Biophys Acta*, 36506, 1-10) and Abbott and Gorrell (Abbott, C. A. and Gorrell, M. D. 2002 In: Langner & Ansorge (ed.), Ectopeptidases. Kluwer Academic/Plenum Publishers, New York, 171-195). Recently, the cloning and characterization of dipeptidyl peptidase 10 (DPP 10) was reported (Qi, S. Y. et al., Biochemical Journal Immediate Publication. Published on 28 Mar. 2003 as manuscript BJ20021914).

Prior to cleavage by DP II, DPIV or other DP IV-like enzymes, the peptide bond between aspartic acid (residue 1 of amyloid β-peptide) and alanine (residue 2 of amyloid β-peptide) may be isomerised yielding an isoaspartyl residue as described in the literature (Kuo, Y.-M. et al., (1997) *BBRC* 237, 188-191; Shimizu, T. et al., (2000) *Arch. Biochem. Biophys.* 381, 225-234).

These isoaspartyl residues render the amyloid β-peptide resistant against aminopeptidase degradation and consequently the core plaques contain high amounts of isoAsp$^1$-amyloid β-peptides, which suggests a reduced turnover at the N-terminus.

However, in the present invention it is demonstrated for the first time, that the N-terminal dipeptide H-isoAsp$^1$-Ala$^2$-OH can be released by dipeptidyl peptidases especially under acidic conditions. Furthermore, it was shown that isomerization can precede also cleavage by β-secretase, and that isomerization may accelerate proteolytic processing, thus leading to liberation of an N-terminal isoaspartyl bond of isoAsp$^1$-amyloid β-peptides which subsequently is subject to turnover by DP II, DPIV or DP IV-like enzymes (Momand, J. and Clarke, S. (1987) *Biochemistry* 26, 7798-7805; Kuo, Y.-M. et al., (1997) *BBRC* 237, 188-191). Accordingly, inhibition of isoaspartyl formation may lead to the reduction of cleavage by β-secretase and, in turn, to a reduced formation of amyloid β-peptides. In addition, blockage of the isoAsp$^1$-amyloid β-peptide turnover by inhibition of DP II, DPIV or DP IV-like enzymes would prevent the exposure of [Glu$^3$]Aβ to QC/EC-catalyzed formation of [pGlu$^3$]Aβ.

In a third embodiment of the present invention, a combination of inhibitors of DP IV-activity and of inhibitors of QC can be used for the treatment of Alzheimer's disease and neurodegeneration in Down Syndrome.

The combined effect of DP IV and/or DP IV-like enzymes and of QC is illustrated as follows:
a) DP IV and/or DP IV-like enzymes cleave Aβ(1-40/42), a dipeptide comprising H-Asp-Ala-OH and Aβ(3-40/42) are released,
b) In a side reaction, QC catalyzes the cyclization of glutamic acid to pyroglutamic acid at very low rates,
c) Glutamic acid is converted into glutamine at the N-terminus post-translationally by an unknown enzymatic activity and subsequently, QC catalyzes the cyclization of glutamine into pyroglutamic acid after processing of the amyloid β-peptide N-terminus, d) Glutamic acid is converted into glutamine post-translationally by a chemical catalysis or autocatalysis and in a second step, QC catalyzes the cyclization of glutamine into pyroglutamic acid after processing of the amyloid β-peptide N-terminus, e) There are mutations in the APP gene, which encode the amyloid β-protein, leading to Gln instead of Glu in position 3 of Aβ, After translation and processing of the N-terminus, QC catalyzes the cyclization of glutamine to pyroglutamic acid, f) Glutamine is incorporated into the nascent peptide chain of APP, due to a malfunction of an unknown enzymatic activity and subsequently, QC catalyzes the cyclization of N-terminally glutamine to pyroglutamic acid after processing of the amyloid β-peptide N-terminus, The N-terminal Gln-exposure to QC-activity can also be triggered by different peptidase activities. Aminopeptidases can remove sequentially Asp and Ala from the N-terminus of Aβ(1-40/42), thus unmasking amino acid three that is prone to cyclization. Dipeptidyl peptidases, such as DP I, DP II, DP IV, DP 8, DP 9 and DP 10, remove the dipeptide Asp-Ala in one step. Hence, inhibition of aminopeptidase- or dipeptidylpeptidase-activity is useful to prevent the formation of Aβ(3-40/42).

Under certain disease conditions, e.g. Alzheimers disease with pronounced neuroinflammation involving MCP-1 mediated microglial activation, inhibition of DPIV and DPIV-like enzymes is not indicated. In those cases, QC-inhibition is required for suppression of pGlu-Aβ formation and MCP-1 inactivation caused by N-terminal cleavage as described in example 16.

Another aspect of the present invention is the identification of new molecular pathways leading to generation of substrates of QC and, in turn, to pGlu-peptides.

In particular, generation of N-terminally modified Aβ peptides was subject of the invention. It can be shown, that formation of pGlu-Aβ depends strongly on the APP protein sequence surrounding the cleavage site of β-secretase (BACE). N-terminally truncated and pGlu-modified peptides are formed in high amounts, if the APP displays the wild-type sequence at the cleavage site. N-terminally pGlu-modified peptides are formed at lower concentrations, if the so-called swedish mutation was present at the cleavage site of BACE.

The results clearly point to a direct, presumably an endoproteolytic, formation of the N-terminus of N-truncated peptides. These alternative processing pathways lead to the identification of other target proteases exhibiting β-secretase activity, which are potential targets to treat the formation of N-truncated Aβ peptides, preferably Aβ(3-42) and Aβ(3-40). The experiments are outlined in Example 18.

The combined effect of inhibitors of DP IV and/or DP IV-like enzymes and of activity lowering effectors of QC is illustrated in the following way:

a) The inhibitors of DP IV and/or DP IV-like enzymes inhibit the conversion of Aβ(1-40/42) to Aβ(3-40/42).

b) An N-terminal exposure of glutamic acid is thereby prevented and no conversion to glutamine, either by enzymatic or by chemical catalysis, subsequently leading to pyroglutamic acid formation, is possible.

c) Inhibitors of QC prevent in addition the formation pyroglutamic acid from any residual modified Aβ(3-40/42) molecules and those modified Aβ(3-40/42) molecules, which are generated by mutations of the APP gene.

Within the present invention, a similar combined action of DP IV or DP IV-like enzymes and QC was demonstrated for further peptide hormones, such as glucagon, CC chemokines and substance P.

Glucagon is a 29-amino acid polypeptide released from pancreatic islet alpha-cells that acts to maintain euglycemia by stimulating hepatic glycogenolysis and gluconeogenesis. Despite its importance, there remains controversy about the mechanisms responsible for glucagon clearance in the body. Pospisilik et al. assessed the enzymatic metabolism of glucagon using sensitive mass spectrometric techniques to identify the molecular products. Incubation of glucagon with purified porcine dipeptidyl peptidase IV (DP IV) yielded sequential production of glucagon(3-29) and glucagon(5-29). In human serum, degradation to glucagon3-29 was rapidly followed by N-terminal cyclization of glucagon, preventing further DP IV-mediated hydrolysis. Bioassay of glucagon, following incubation with purified DP IV or normal rat serum demonstrated a significant loss of hyperglycemic activity, while a similar incubation in DP IV-deficient rat serum did not show any loss of glucagon bioactivity. The specific DP IV inhibitor, isoleucyl thiazolidine, blocked glucagon degradation, monitored by mass spectrometry and bioassay. These results identify DP IV as a primary enzyme involved in the degradation and inactivation of glucagon. These findings have important implications for the determination of glucagon levels in human plasma (Pospisilik et al., *Regul Pept* 2001 Jan. 12; 96(3): 133-41).

Human Monocyte Chemotactic Protein (MCP)-2 has originally been isolated from stimulated osteosarcoma cells as a chemokine coproduced with MCP-1 and MCP-3. Van Coillie et al. (Van Coillie, E. et al. 1998 *Biochemistry* 37, 12672-12680) cloned a 5'-end extended MCP-2 cDNA from a human testis cDNA library. It encoded a 76 residue MCP-2 protein, but differed from the reported bone marrow-derived MCP-2 cDNA sequence in codon 46, which coded for a Lys instead of a Gln. This MCP-2Lys46 variant, caused by a single nucleotide polymorphism (SNP), was biologically compared with MCP-2Gln46. The coding regions were sub-cloned into the bacterial expression vector pHEN1, and after transformation of *Escherichia coli*, the two MCP-2 protein variants were recovered from the periplasm. Edman degradation revealed a Gln residue at the $NH_2$ terminus instead of a pGlu. rMCP-2Gln46 and rMCP-2Lys46 and the $NH_2$-terminal cyclic counterparts were tested on monocytic cells in calcium mobilization and chemotaxis assays. No significant difference in biological activity was observed between the rMCP-2Gln46 and rMCP-2Lys46 isoforms. However, for both MCP-2 variants the $NH_2$-terminal pyroglutamate was shown to be essential for chemotaxis, but not for calcium mobilization. $NH_2$-terminal truncation of rMCP-2Lys46 by the serine protease CD26/dipeptidyl peptidase IV (CD26/DPP IV) resulted in the release of the $NH_2$-terminal Gln-Pro dipeptide, whereas synthetic MCP-2 with an amino-terminal pGlu remained unaffected. CD26/DPP IV-clipped rMCP-2Lys46(3-76) was almost completely inactive in both chemotaxis and signaling assays. These observations indicated that the $NH_2$-terminal pGlu in MCP-2 is necessary for chemotactic activity but also that it protects the protein against degradation by CD26/DPP IV (van Coillie, E. et al. *Biochemistry* 1998 37, 12672-80).

Within the present invention, it was determined by LC/MS-analysis that the formation of the N-terminal pyroglutamate residue determined in glucagon(3-29) (Pospisilik et al., 2001), and in MCP-2 isoforms (van Coillie et al., 1998), is catalyzed by QC.

In addition, it was proven by LC/MS-investigation that after N-terminal DP IV-catalyzed removal of the two dipeptides Lys-Pro and Arg-Pro from substance P the remaining [Gln5]substanceP(5-11) is transformed by QC to [pGlu5]substanceP(5-11).

DEFINITIONS

In the peptides of the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Enzyme Inhibitors, in Particular Inhibitors of QC

Reversible enzyme inhibitors: comprise competitive inhibitors, non-competitive reversible inhibitors, slow-binding or tight-binding inhibitors, transition state analogues and multisubstrate analogues.

Competitive Inhibitors Show i) non-covalent interactions with the enzyme, ii) compete with substrate for the enzyme active site, The principal mechanism of action of a reversible enzyme inhibitor and the definition of the dissociation constant can be visualized as follows:

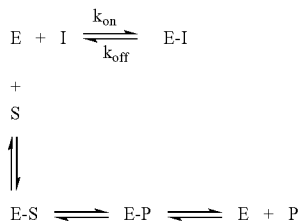

The formation of the enzyme-inhibitor [E-I] complex prevents binding of substrates, therefore the reaction cannot proceed to the normal physiological product, P. A larger inhibitor concentration [I] leads to larger [E-I], leaving less free enzyme to which the substrate can bind.

Non-Competitive Reversible Inhibitors i) bind at a site other than active site (allosteric binding site)

ii) cause a conformational change in the enzyme which decreases or stops catalytic activity.

Slow-Binding or Tight-Binding Inhibitors i) are competitive inhibitors where the equilibrium between inhibitor and enzyme is reached slowly, ii) (kon is slow), possibly due to conformational changes that must occur in the enzyme or inhibitor a) are often transition state analogues b) are effective at concentrations similar to the enzyme concentration (subnanomolar KD values)

c) due to koff values being so low these types of inhibitors are "almost" irreversible.

Transition State Analogues are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogues

For a reaction involving two or more substrates, a competitive inhibitor or transition state analogue can be designed which contains structural characteristics resembling two or more of the substrates.

Irreversible enzyme inhibitors: drive the equilibrium between the unbound enzyme and inhibitor and enzyme inhibitor complex (E+I<--->E-I) all the way to the E-I-side with a covalent bond (~100 kcal/mole), making the inhibition irreversible.

Affinity Labeling Agents

Active-site directed irreversible inhibitors (competitive irreversible inhibitor) are recognized by the enzyme (reversible, specific binding) followed by covalent bond formation, and i) are structurally similar to substrate, transition state or product allowing for specific interaction between drug and target enzyme, ii) contain reactive functional group (e.g. a nucleophile, —COCH$_2$Br) allowing for covalent bond formation.

The reaction scheme below describes an active-site directed reagent with its target enzyme where $K_D$ is the dissociation constant and $k_{inactivation}$ is the rate of covalent bond formation.

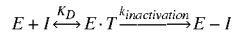

Mechanism-based enzyme inactivators (also called suicide inhibitors) are active-site directed reagents (unreactive) which binds to the enzyme active site where it is transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

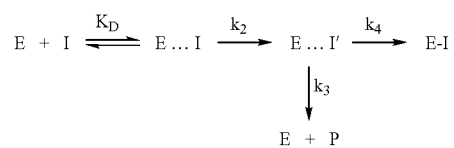

Inactivation (covalent bond formation, $k_4$) must occur prior to dissociation ($k_3$) otherwise the now reactive inhibitor is released into the environment. The partition ratio, $k_3/k_4$: ratio of released product to inactivation should be minimized for efficient inactivation of the system and minimal undesirable side reactions.

A large partition ratio (favors dissociation) leads to non-specific reactions.

Uncompetitive enzyme inhibitors: As a definition of uncompetitive inhibitor (an inhibitor which binds only to ES complexes) the following equilibria equation can be assumed:

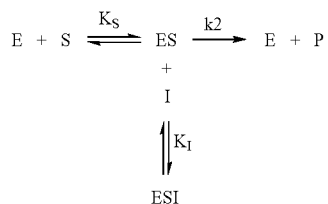

The ES complex dissociates the substrate with a dissociation constant equal to Ks, whereas the ESI complex does not dissociate it (i.e has a Ks value equal to zero). The Km's of Michaelis-Menten type enzymes are expected to be reduced. Increasing substrate concentration leads to increasing ESI concentration (a complex incapable of progressing to reaction products) therefore the inhibition cannot be removed.

Preferred according to the present invention are competitive enzyme inhibitors.

Most preferred are competitive reversible enzyme inhibitors.

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

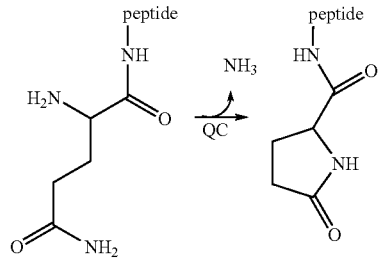

Scheme 2: Cyclization of L-homoglutamine by QC

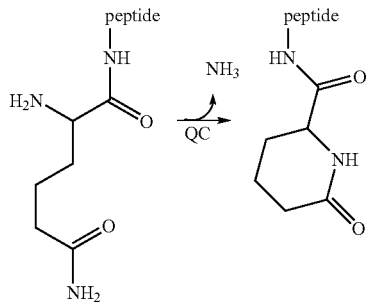

The term "EC" as used herein comprises the side activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

The term "metal-dependent enzyme" as used herein is defined as enzyme(s), that require a bound metal ion in order to fulfill their catalytic function and/or require a bound metal ion in order to form the catalytically active structure.

Molecules that bind to enzymes and increase or decrease their activities are called "effectors". Effectors can modify enzymatic activity because enzymes can assume both active and inactive conformations: activators are positive effectors and inhibitors are negative effectors. Effectors bind at regulatory sites, or allosteric sites (from the Greek for "another shape"), a term used to emphasize that the regulatory site is an element of the enzyme distinct from the catalytic site and to differentiate this form of regulation from competition between substrates and inhibitors at the catalytic site.

According to the individual embodiments of the present invention, either activators or inhibitors are preferred.

More preferred are inhibitors of QC. Most preferably, the QC-inhibitors are competitive inhibitors. Even preferred are QC-inhibitors, which bind to the active-site bound metal ion of QC.

Potency of QC Inhibition

In light of the correlation with QC inhibition, in preferred embodiments, the subject method and medical use utilize an agent with an $IC_{50}$ for QC inhibition of 10 μM or less, more preferably of 1 μM or less, even more preferably of 0.1 μM or less or 0.01 μM or less, or most preferably 0.001 μM or less. Indeed, inhibitors with Ki values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DIV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

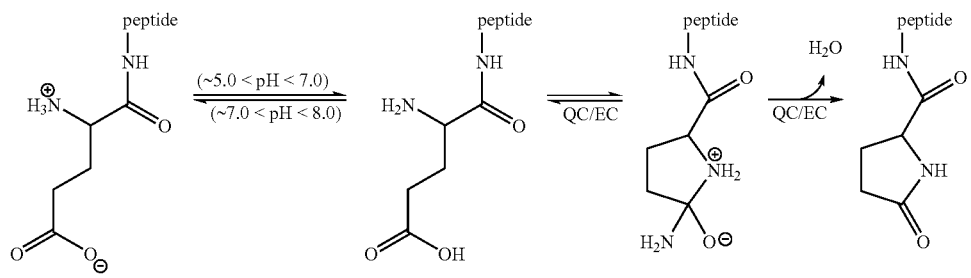

Scheme 3: N-terminal cyclization of uncharged glutamyl peptides by QC (EC)

Another aspect of the present invention is the identification of new physiological substrates of QC. These were identified by performing cyclization experiments with mammalian peptides as described in example 5. Prior, human QC and papaya QC were isolated as described in example 1. The applied methods are described in example 2, and the peptide synthesis employed is outlined in example 6. The results of the study are shown in Table 1.

TABLE 1

New physiological substrates of glutaminyl cyclase

| | Human QC | | | Papaya QC | | |
|---|---|---|---|---|---|---|
| Substrate | $K_M$ (µM) | $k_{cat}$ (s$^{-1}$) | $k_{cat}/K_M$ (mM$^{-1}$ s$^{-1}$) | $K_M$ (µM) | $k_{cat}$ (s$^{-1}$) | $k_{cat}/K_M$ (mM$^{-1}$ s$^{-1}$) |
| [Gln$^1$]-Gastrin | 31 ± 1 | 54.1 ± 0.6 | 1745.2 ± 36.9 | 34 ± 2 | 25.8 ± 0.5 | 759 ± 30 |
| [Gln$^1$]-Neurotensin | 37 ± 1 | 48.8 ± 0.4 | 1318.9 ± 24.8 | 40 ± 3 | 35.7 ± 0.9 | 893 ± 44 |
| [Gln$^1$]-FPP | 87 ± 2 | 69.6 ± 0.3 | 800.0 ± 14.9 | 232 ± 9 | 32.5 ± 0.4 | 140 ± 4 |
| [Gln$^1$]-TRH | 90 ± 4 | 82.8 ± 1.2 | 920.0 ± 27.6 | n.d. | n.d. | n.d. |
| [Gln$^1$]-GnRH | 53 ± 3 | 69.2 ± 1.1 | 1305.7 ± 53.2 | 169 ± 9 | 82.5 ± 1.9 | 488.2 ± 14.8 |
| [Gln$^3$]-glucagon(3-29) | | | * | | | * |
| [Gln$^5$]-substance P(5-11) | | | * | | | * |

(*, determined qualitatively by MALDI-TOF experiments)

All analyses were performed in the optimal range of activity and stability of either human or plant QC, as demonstrated in example 4.

The amino acid sequences of physiological active peptides having an N-terminal glutamine residue and being therefore substrates for the QC enzyme are listed in Table 2:

TABLE 2

Amino acid sequences of physiological active peptides with an N-terminal glutamine residue

| Peptide | Amino acid sequence | Function |
|---|---|---|
| ABri (SEQ ID NO: 34) | EASNCFA IRHFENKFAV ETLIC SRTVKKNIIEEN | Pyroglutamated form plays a role in Familial British Dementia |
| ADan (SEQ ID NO: 35) | EASNCFA IRHFENKFAV ETLIC FNLFLNSQEKHY | Pyroglutamated form plays a role in Familial Danish Dementia |
| Gastrin 17 (SEQ ID NO: 38) Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin (SEQ ID NO: 39) Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/neuromodulator in the central and peripheral nervous systems. |
| GnRH (SEQ ID NO: 40) Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16) (SEQ ID NO: 41) Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) (SEQ ID NO: 42) Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |

TABLE 2-continued

Amino acid sequences of physiological active peptides with an N-terminal glutamine residue

| Peptide | Amino acid sequence | Function |
| --- | --- | --- |
| CCL18 (small inducible cytokine A18) (SEQ ID NO: 43) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) (SEQ ID NO: 44) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible cytokine A7) (SEQ ID NO: 45) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) (SEQ ID NO: 46) Swiss-Prot: O43612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P (SEQ ID NO: 47) | RPK PQQFFGLM | Belongs to the tachykinins. Tachykinins are active peptides which excite neurons, evoke behavioral responses, are potent vasodilators and secretagogues, and contract (directly or indirectly) many smooth muscles. |
| QYNAD (SEQ ID NO: 48) | Gln-Tyr-Asn-Ala-Asp | Acts on voltage-gated sodium channels. |

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid β-peptides 1-40 (42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) *Mol. Cell* 2, 275-281; Gosling, J., et al., (1999) *J Clin. Invest* 103, 773-778); rheumatoid arthritis (Gong, J. H., et al., (1997) *J Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

MCP-1 levels are increased in CSF of AD patients and patients showing mild cognitive impairment (MCI) (Galimberti, D., et al., (2006) Arch. Neurol. 63, 538-543). Furthermore, MCP-1 shows an increased level in serum of patients with MCI and early AD (Clerici, F., et al., (2006) Neurobiol. Aging 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of QC-inhibitors for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Heliobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, artherosclerosis and multiple sclerosis.

The present invention also provides a method of treatment of the aforementioned diseases comprising the administration of a therapeutically active amount of at least one QC-inhibitor to a mammal, preferably a human.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson disease and Chorea Huntington, comprising the administration of a therapeutically active amount of at least one QC-inhibitor to a mammal, preferably a human.

Even preferably, the present invention provides a method of treatment and corresponding uses for the treatment of rheumatoid arthritis, atherosclerosis, pancreatitis and restenosis.

In a further embodiment, the present invention provides a general way to reduce or inhibit the enzymatic activity of QC. Examples of inhibitory compounds are also provided.

Figure 18:
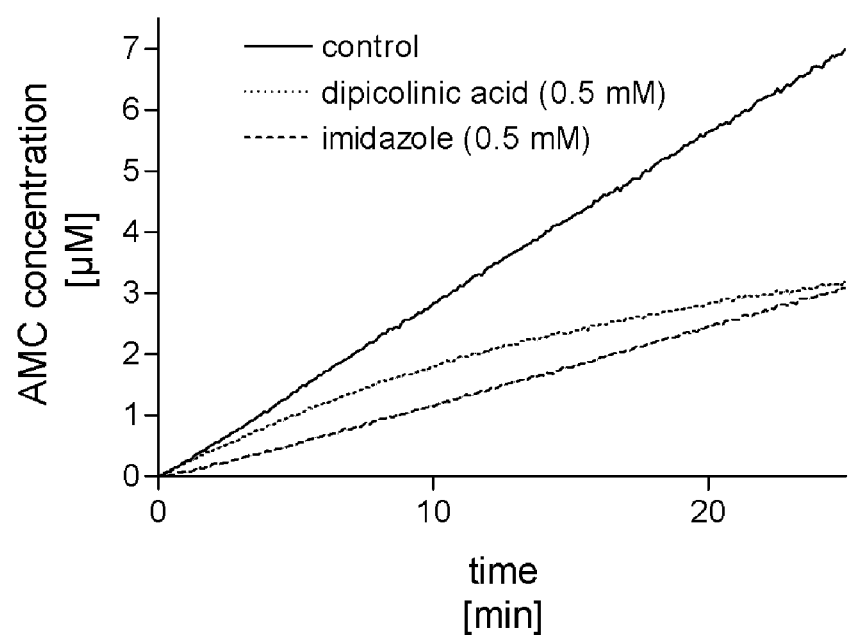
FIG. 18 shows progress curves of human QC-catalyzed cyclization of H-Gln-AMC in presence of imidazole, dipicolinic acid and in absence of an inhibitory compound. The hyperbolic shape of the curve in presence of dipicolinic acid indicates metal ion remove from the active site of QC.
Figure 19:
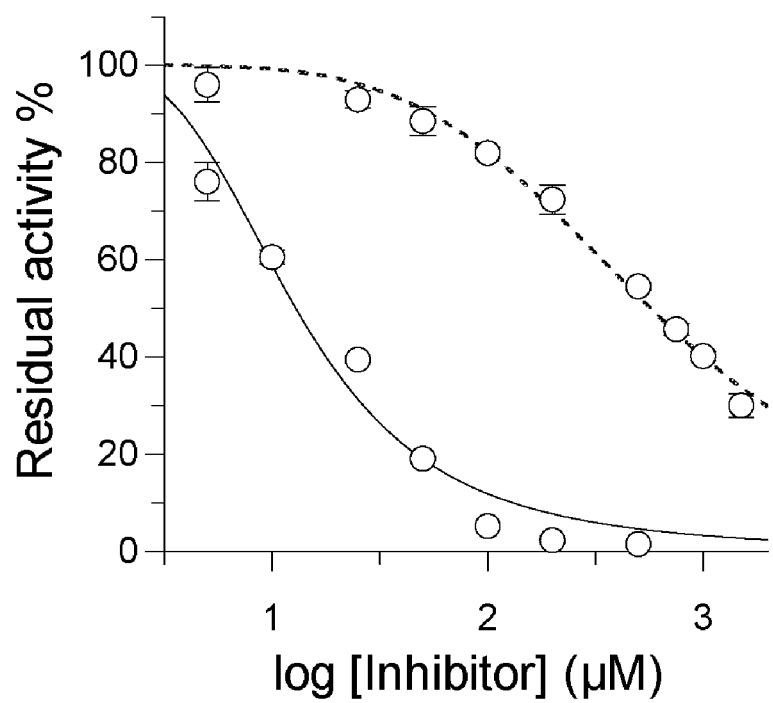
FIG. 19 shows the time-dependent inactivation of human QC by the heterocyclic chelator 1,10-phenanthroline. After incubation of the QC-enzyme with the inhibitor in absence of substrate (continuous line), a reduced enzymatic activity was observed compared to samples that were not preincubated with inhibitor (dotted trace), indicating metal ion remove from the active site of QC.
Figure 20:
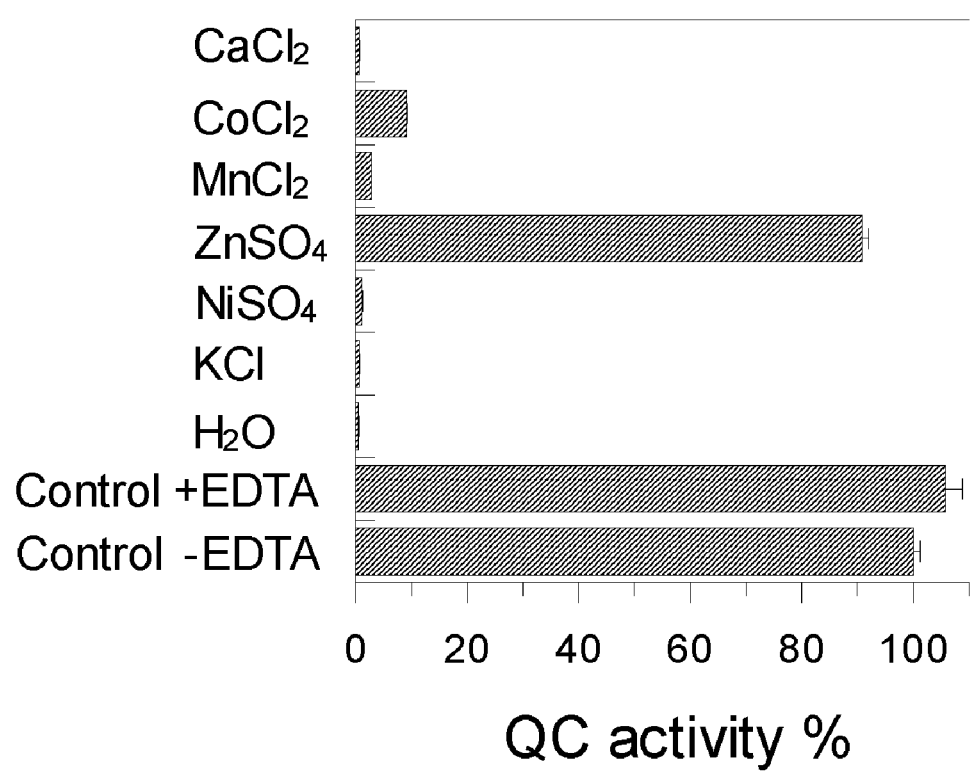
FIG. 20 shows the reactivation of human QC with monovalent- and divalent metal ions. QC was inactivated by addition of 2 mM dipicolinic acid in 50 mM Bis-Tris, pH 6.8. Subsequently, the enzyme was subjected to dialysis against 50 mM Bis-Tris, pH 6.8, containing 1.0 mM EDTA. Reactivation of the enzymes was achieved by incubation of the inactivated enzyme sample with metal ions at a concentration of 0.5 mM, in presence of 0.5 mM EDTA in order to avoid an unspecific reactivation by traces of metal ions present in buffer solutions. Controls are given by enzyme samples that were not inactivated, but also dialyzed against EDTA solution as the inactivated enzyme (+EDTA) and enzyme samples that were dialyzed against buffer solutions without added EDTA (−EDTA).
Figures 1, 22:
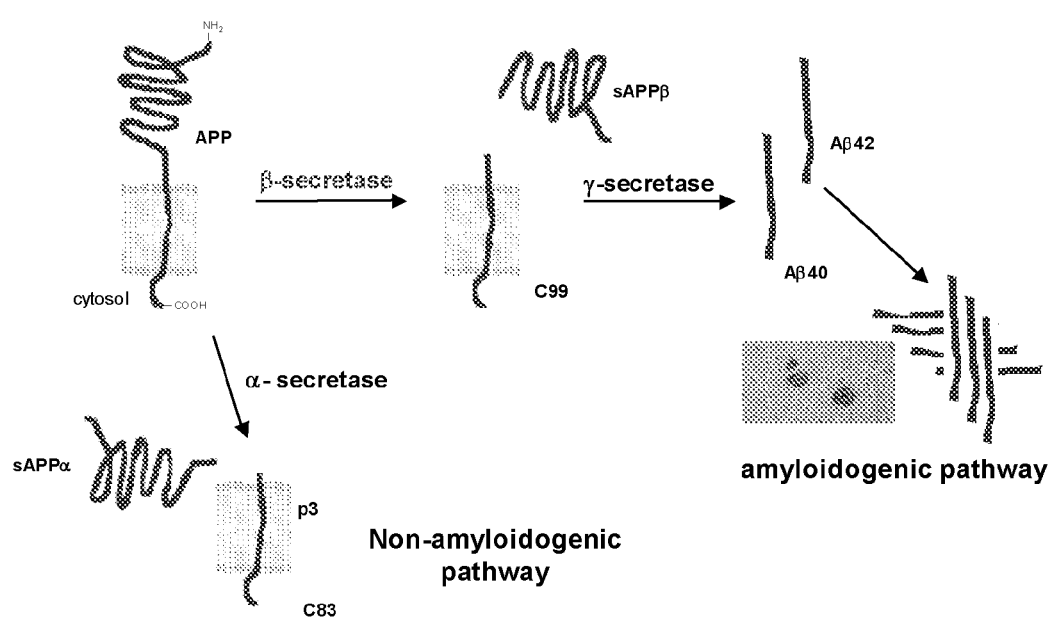
Figures 2, 22:
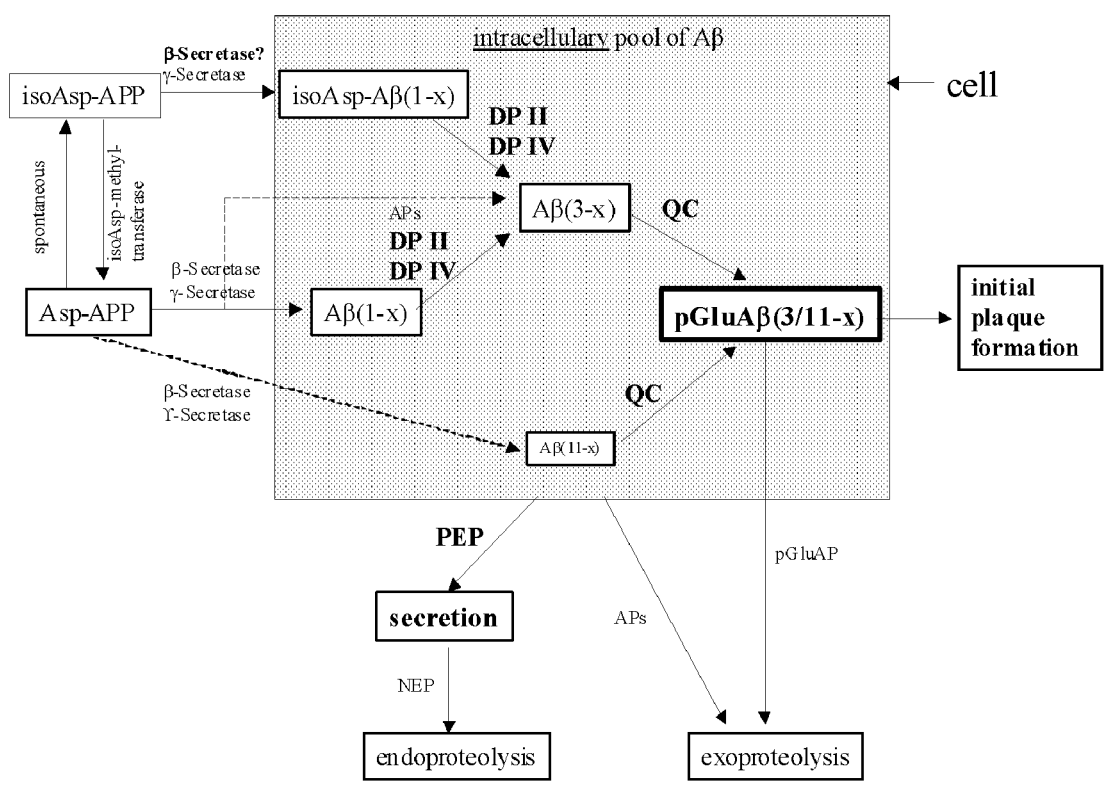

Inhibition of a mammalian QC was only detected initially for 1,10-phenanthroline and reduced 6-methylpterin (Busby, W. H. J. et al. 1987 *J Biol Chem* 262, 8532-8536). EDTA did not inhibit QC, thus it was concluded that QC is not a metal-dependent enzyme (Busby, W. H. J. et al. 1987 *J Biol Chem* 262, 8532-8536, Bateman, R. C. J. et al. 2001 *Biochemistry* 40, 11246-11250, Booth, R. E. et al. 2004 *BMC Biology* 2). In the present invention, however, it is shown that human QC and other animal QCs are metal-dependent enzymes, as revealed by the inhibition characteristics of QC by 1,10-phenanthroline, dipicolinic acid, 8-hydroxy-quinoline and other chelators (FIGS. 18,19) and by the reactivation of QC by transition metal ions (FIG. 20). Finally, the metal dependence is outlined by a sequence comparison to other metal-dependent enzymes, showing a conservation of the chelating amino acid residues also in human QC (FIG. 21). The interaction of compounds with the active-site bound metal ion represents a general way to reduce or inhibit QC activity.

In the present invention many imidazole derivatives were analyzed concerning their ability to inhibit the human QC as a member of the highly conserved mammalian QC's (for details see example 2).

EXAMPLES OF QC-INHIBITORS

QC-inhibitors, which are suitable for uses and methods according to the present invention are disclosed in WO 2005/075436, which is incorporated herein in its entirety with regard to the structure, synthesis and methods of use of the QC-inhibitors.

In particular:
A suitable compound, that of formula 1* shown below, is a inhibitor of QC:

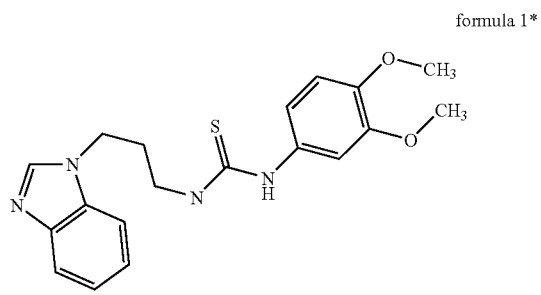

formula 1*

In a further embodiment, the inhibitors of QC (EC) are those of formula 1a,

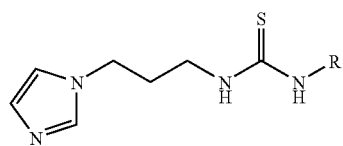

(1a)

wherein R is defined in examples 1 to 53.

| Example | R | ESI-MS (M + H) | Res. Act. (%) | IC$_{50}$ (µM) | K$_i$ (µM) |
|---|---|---|---|---|---|
| 1 | Methyl | 199.3 | 4.3 | | 13 |
| 2 | tert-Butyl | 241.4 | 60.7 | | 14.7 |
| 3 | Benzyl | 275.4 | 60.9 | | 5.67 |
| 4 | Phenyl | 261.4 | 42.3 | | 4.4 |
| 5 | 4-(fluoro)-phenyl | 279.35 | 42.0 | | 4.73 |
| 6 | 4-(chloro)-phenyl | 295.80 | | | 1.2 |
| 7 | 4-(ethyl)-phenyl | 289.41 | 28.7 | | 2.78 |
| 8 | 4-(trifluoromethyl)-phenyl | 329.4 | 38.5 | | 3.93 |
| 9 | 4-(methoxy-carbonyl)-Phenyl | 319.4 | | | 1.19 |
| 10 | 4-(acetyl)-phenyl | 303.4 | 17.0 | | 1.70 |
| 11 | 4-(methoxy)-phenyl | 291.4 | 9.7 | | 0.70 |
| 12 | bicyclo[2.2.1]hept-5-en-2-yl | 277.5 | 16.0 | | |
| 13 | 3,4-(dimethoxy)-phenyl | 321.5 | 0.7 | 0.22 | 0.06 |
| 14 | 2,4-(dimethoxy)-phenyl | 321.5 | 2.2 | | 0.57 |
| 15 | 3,5-(dimethoxy)-phenyl | 321.5 | 2.86 | | 0.75 |
| 16 | 2-(methoxy-carbonyl)-Phenyl | 319.4 | | | |
| 17 | 4-(oxazol-5-y)-phenyl | 328.5 | 3.64 | | 0.86 |
| 18 | 4-(pyrazol-1-yl)-phenyl | 327.4 | | | |
| 19 | 4-(isopropyl)-phenyl | 303.5 | 8.7 | | |
| 20 | 4-(piperidine-1-sulfonyl)-Phenyl | 408.6 | 8.5 | | 2.27 |
| 21 | 4-(morpholin-4-yl)-phenyl | 346.5 | 9.0 | | |
| 22 | 4-(cyano)-phenyl | 286.4 | 9.0 | | 2.89 |
| 23 | 2,3-dihydro-benzo[1,4]dioxin-6-yl | 319.4 | 4.17 | | 1.12 |
| 24 | benzo[1,3]dioxol-5-yl | 305.4 | 16.7 | | 5.66 |
| 25 | 3,4,5(trimethoxy)-phenyl | 351.5 | 1.7 | | 0.34 |
| 26 | 3-(methoxy)-phenyl | 291.4 | 6.8 | | 1.86 |
| 27 | 4-(ethoxy)-phenyl | 305.5 | 7.2 | | 0.89 |
| 28 | 4-(benzyloxy)-phenyl | 367.5 | | | 0.98 |
| 29 | 4-(methoxy)-benzyl | 305.5 | | | 3.93 |
| 30 | 3,4-(dimethoxy)-benzyl | 335.5 | | | 1.55 |
| 31 | 2-(methoxy-carbonyl)-thiophene-3-yl | 325.5 | | | |
| 32 | 3-(ethoxy-carbonyl)-4,5,6,7-tetrahydrobenzo[b]thiophene2-yl | 392.6 | | | |
| 33 | 2-(methoxy-carbonyl)-4-(methyl)-thiophene-3-yl | 339.5 | | | |
| 34 | Benzo[c][1,2,5]thiazol-4-yl | 319.5 | | | |
| 35 | Benzo[c][1,2,5]thiazol-5-yl | 319.5 | 4.4 | | 1.37 |
| 36 | 5-(methyl)-3-(phenyl)-isooxazol-4-yl | 342.5 | | | |
| 37 | 3,5-(dimethyl)-isooxazol-4-yl | 280.4 | | | |
| 38 | 4-(iodo)-phenyl | 387.3 | 23.5 | | 2.12 |
| 39 | 4-(bromo)-phenyl | 340.3 | | | 2.52 |
| 40 | 4-(methyl)-phenyl | 275.4 | 31.3 | | 2.14 |
| 41 | Naphthalen-1-yl | 311.5 | 26.7 | | 2.79 |
| 42 | 4-(nitro)-phenyl | 306.4 | 31.1 | | 2.68 |
| 43 | Butyl | 241.4 | 53.8 | 14.0 | |
| 44 | Cyclooctyl | 295.5 | 33.1 | 9.1 | |
| 45 | Furan-2-ylmethyl | 265.4 | 61.4 | 10.0 | |
| 46 | Tetrahydrofuran-2-ylmethyl | 269.4 | 46.0 | 12.8 | |
| 47 | Benzo[1,3]dioxol-5-ylmethyl | 319.4 | 42.7 | | 6.1 |
| 48 | 2-(morpholin-4-yl)-ethyl | 298.5 | 55.0 | 13.3 | |
| 49 | 4-(methylsulfanyl)-phenyl | 307.5 | 19.1 | | 1.66 |
| 50 | 4-(dimethylamino)-phenyl | 304.5 | | | 2.03 |
| 51 | 4-(trifluoromethoxy)-phenyl | 345.4 | 14.2 | | |
| 52 | Benzoyl | 288.3 | | | |
| 53 | Pyridin-4-yl | 261.1 | | | |

Further suitable inhibitors of QC (EC) are those of formula 1b,

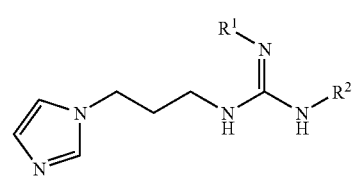

(1b)

wherein R¹ and R² are defined in examples 54 to 95.

| Example | R¹ | R² | ESI-MS (M + H) | Res. Act. (%) | $K_i$ (μM) |
|---|---|---|---|---|---|
| 54 | Cyano | Methyl | 207.3 | | 1.5 |
| 55 | Cyano | 3,4-(dimethoxy)-phenyl | 329.4 | | 1.36 |
| 56 | Cyano | 2,4-(dimethoxy)-phenyl | 329.4 | | |
| 57 | Cyano | 3,5-(dimethoxy)-phenyl | 329.4 | | 0.91 |
| 58 | Cyano | 2,3-dihydrobenzo[b][1,4]dioxin-7-yl | 327.4 | | 0.64 |
| 59 | Cyano | Benzo[d][1,3]dioxol-6-yl | 313.4 | | 0.73 |
| 60 | Cyano | 3,4,5-(trimethoxy)-phenyl | 359.4 | | 0.88 |
| 61 | Cyano | 3-(methoxy)-phenyl | 299.4 | | |
| 62 | Cyano | 4-(ethoxy)-phenyl | 313.4 | | |
| 63 | Cyano | 4-(benzyloxy)-phenyl | 375.5 | | |
| 64 | Cyano | Phenyl | 269.4 | | 1.02 |
| 65 | Cyano | 4-(methoxy)-phenyl | 299.4 | | 0.70 |
| 66 | Cyano | 4-(acetyl)-phenyl | 311.4 | | |
| 67 | Cyano | 4-(nitro)-phenyl | 314.4 | | |
| 68 | Cyano | Benzyl | 283.4 | 22.5 | 8.17 |
| 69 | Cyano | Naphthalen-1-yl | 319.4 | | |
| 70 | Cyano | 4-(fluoro)-phenyl | 387.3 | | |
| 71 | Cyano | 4-(iodo)-phenyl | 395.3 | | |
| 72 | Cyano | 4-(bromo)-phenyl | 348.3 | | |
| 73 | Cyano | Cyclooctyl | 289.4 | | |
| 74 | Cyano | tert-butyl | 249.3 | | |
| 75 | Cyano | 4-(methyl)-phenyl | 283.3 | | 1.34 |
| 76 | Cyano | 4-(methylthio)-phenyl | 315.5 | | |
| 77 | Cyano | 4-(ethyl)-phenyl | 297.4 | | |
| 78 | Cyano | 4-(dimethylamino)-phenyl | 312.4 | | |
| 79 | Cyano | Butyl | 249.4 | | |
| 80 | Cyano | Trityl | 435.6 | | |
| 81 | Cyano | (Benzo[d][1,3]dioxol-6yl)methyl | 327.4 | | 1.53 |
| 82 | Cyano | (tetrahydrofuran-2yl)methyl | 277.4 | | |
| 83 | Cyano | 4-(trifluoromethyl)-phenyl | 334.4 | | |
| 84 | Cyano | (furan-2-yl)methyl | 273.4 | | |
| 85 | Cyano | 2-(morpholin-4-yl)-ethyl | 306.4 | | |
| 86 | Cyano | 4-(oxazol-5yl)-phenyl | 336.4 | | |
| 87 | Cyano | Pyridin-3-yl | 270.4 | | |
| 88 | Cyano | 4-(cyano)-phenyl | 294.4 | | |
| 89 | Cyano | 4-(trifluoromethoxy)-phenyl | 353.4 | | |
| 90 | Cyano | 4-(piperidinosulfonyl)-phenyl | 416.6 | | |
| 91 | Cyano | 4-(1H-pyrazol-1-yl)phenyl | 335.4 | | |
| 92 | H | 3,4-(dimethoxy)-phenyl | 304.4 | | 204.5 |
| 93 | Methyl | 3,4-(dimethoxy)-phenyl | 318.4 | | 3.62 |
| 94 | Cyano | 2,3,4-(trimethoxy)-phenyl | 358.1 | | |
| 95 | Cyano | Cycloheptyl | 288.2 | | |

Further suitable inhibitors of QC (EC) are those of formula 1c,

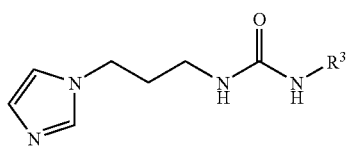
(1c)

wherein R³ is defined in examples 96 to 102.

| Example | R³ | ESI-MS (M + H) | Res. Act. (%) | IC$_{50}$ (μM) | $K_i$ (μM) |
|---|---|---|---|---|---|
| 96 | Ethyl | 197.3 | | | 19.2 |
| 97 | 6-fluoro-4H-benzo[d][1,3]dioxin-8-yl | 321.4 | 19.0 | 12.0 | |
| 98 | 3-(cylopentyloxy)-4-(methoxy)-phenyl | 359.4 | 2.87 | | 0.62 |

-continued

| Example | R³ | ESI-MS (M + H) | Res. Act. (%) | IC$_{50}$ (μM) | $K_i$ (μM) |
|---|---|---|---|---|---|
| 99 | 4-(heptyloxy)-phenyl | 359.5 | 5.6 | 9.9 | |
| 100 | 3,4-dihydro-2H-benzo[b][1,4]dioxepin-7-yl | 317.4 | | | |
| 101 | 4-(butoxy)-phenyl | 317.4 | | | |
| 102 | 3,4-(dimethoxy)-phenyl | 305.4 | | | 0.46 |

Further suitable inhibitors of QC (EC) are those of formula 1d,

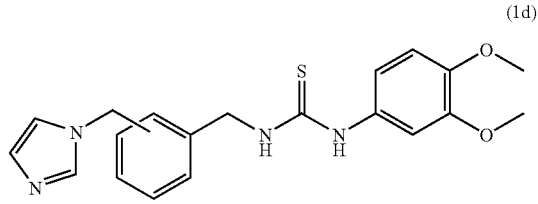
(1d)

wherein the position on the ring is defined in examples 103 to 105.

| Example | Position of the Benzyl-substitution | ESI-MS (M + H) | Res. Act. (%) | $K_i$ (μM) |
|---|---|---|---|---|
| 103 | 2 | 383.5 | 16.27 | 4.84 |
| 104 | 3 | 383.5 | | 3.52 |
| 105 | 4 | 383.5 | | 1.86 |

Further suitable inhibitors of QC (EC) are those of formula 1e,

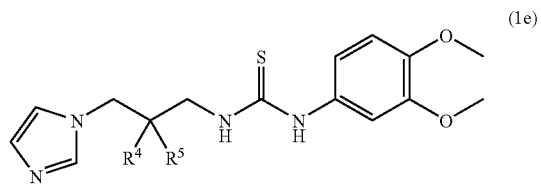

wherein $R^4$ and $R^5$ are defined in examples 106 to 109.

| Example | $R^4$ | $R^5$ | ESI-MS (M + H) | Res.Act. (%) | $IC_{50}$ (μM) | $K_i$ (μM) |
|---|---|---|---|---|---|---|
| 106(S) | H | Methyl | 335.5 | | | 0.76 |
| 107(R) | Methyl | H | 335.5 | | | 0.35 |
| 108 | Methyl | Methyl | 349.5 | | | |
| 109 | —CH$_2$—CH$_2$— | | 347.5 | | | 7.85 |

Further suitable inhibitors of QC (EC) are those of formula 1f,

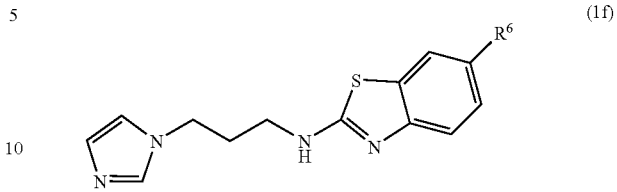

wherein $R^6$ is defined in examples 110 to 112.

| Example | $R^6$ | ESI-MS (M + H) | Res. Act. (%) | $IC_{50}$ (μM) | $K_i$ (μM) |
|---|---|---|---|---|---|
| 110 | H | 259.4 | | | 3.00 |
| 111 | Chloro | 293.8 | | | 3.35 |
| 112 | Methoxy | 289.4 | | | 1.57 |

Further suitable inhibitors of QC (EC) are those of formula 1g,

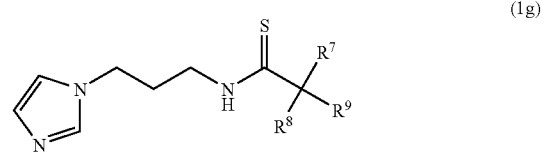

wherein $R^7$, $R^8$ and $R^9$ are defined in examples 113 to 132.

| Example | $R^7$ | $R^8$ | $R^9$ | ESI-MS (M + H) | Res.Act (%) | $K_i$ (μM) |
|---|---|---|---|---|---|---|
| 113 | Phenyl | H | H | 260.4 | | 4.62 |
| 114 | Thiophen-2-yl | H | H | 266.5 | | 3.29 |
| 115(R) | Phenyl | Methyl | H | 274.5 | 21.2 | 7.34 |
| 116(S) | Phenyl | H | Methyl | 274.5 | 8.1 | 3.51 |
| 117 | Phenyl | H | Ethyl | 288.5 | | 3.57 |
| 118 | Phenyl | H | Phenyl | 336.5 | 13.5 | 4.48 |
| 119 | 3,4-(dimethoxy)-Phenyl | H | H | 320.5 | | 0.39 |
| 120 | 3,4-(dimethoxy)-Phenyl | Methyl | Methyl | 347.2 | | |
| 121 | 4-(chloro)-phenyl | —CH$_2$—CH$_2$—CH$_2$— | | 334.9 | | 4.88 |
| 122 | 4-(chloro)-phenyl | —CH$_2$—C$_2$H$_4$—CH$_2$— | | 349.0 | | 7.3 |
| 123 | 4-(methoxy)-phenyl | —CH$_2$—C$_3$H$_6$—CH$_2$— | | 358.6 | | 2.78 |
| 124 | 4-(methoxy)-phenyl | —CH$_2$—CH$_2$— | | 316.5 | | 0.39 |
| 125 | 3,4-(dimethoxy)-Phenyl | —CH$_2$—CH$_2$— | | 346.5 | | 0.09 |
| 126 | 3,4,5-(trimethoxy)-Phenyl | —CH$_2$—CH$_2$— | | 376.6 | | |
| 127 | 2,3,4-(trimethoxy)-Phenyl | —CH$_2$—CH$_2$— | | 376.6 | | |
| 128 | 2-(methoxy)-phenyl | —CH$_2$—CH$_2$— | | 316.5 | | |
| 129 | 3-(methoxy)-phenyl | —CH$_2$—CH$_2$— | | 316.5 | | |
| 130 | 2,3-(dimethoxy)-Phenyl | —CH$_2$—CH$_2$— | | 346.5 | | |
| 131 | 3,5-(dimethoxy)-Phenyl | —CH$_2$—CH$_2$— | | 346.5 | | |
| 132 | 2,5-(dimethoxy)-Phenyl | —CH$_2$—CH$_2$— | | 346.5 | | |

Further suitable inhibitors of QC (EC) are those of formula 1h,

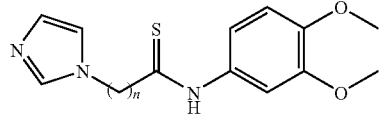

(1h)

wherein n is defined in examples 133 to 135.

| Example | N | ESI-MS (M + H) | $K_i$ (μM) |
|---|---|---|---|
| 133 | 3 | 306.4 | |
| 134 | 4 | 320.5 | 0.99 |
| 135 | 5 | 334.5 | |

Further suitable inhibitors of QC (EC) are those of formula 1i,

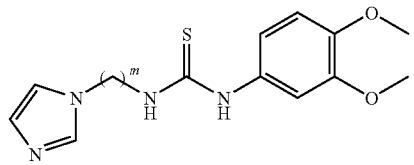

(1i)

wherein m is defined in examples 136 and 137.

| Example | m | ESI-MS (M + H) | Res. Act. (%) | $K_i$ (μM) |
|---|---|---|---|---|
| 136 | 2 | 307.4 | | 17.6 |
| 137 | 4 | 335.5 | 2.19 | 0.55 |

Further suitable inhibitors of QC (EC) are those of formula 138 to 141.

| Example | Structure | ESI-MS (M + H) | Res.Act. (%) | $IC_{50}$ (μM) | $K_i$ (μM) |
|---|---|---|---|---|---|
| 138 | 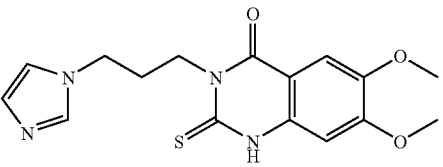 | 347.5 | | | |
| 139 | 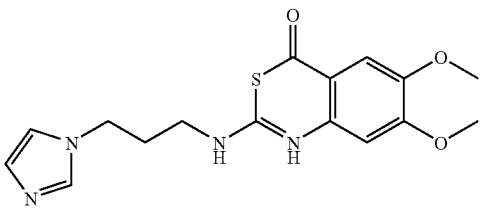 | 347.2 | | | |
| 140 | 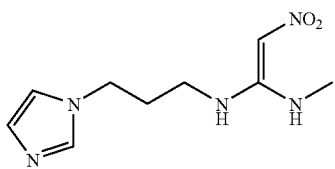 | 226.3 | 13.8 | | 20.5 |
| 141 | 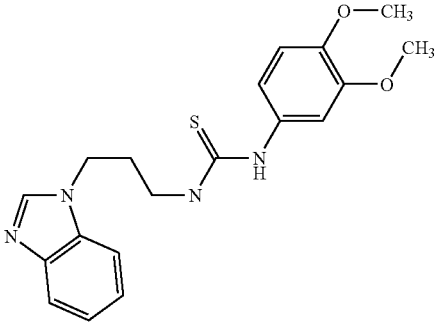 | 370.4 | | | |

Surprisingly, during characterization of the enzymatic activity it was discovered that besides an N-terminal glutaminyl residue, N-terminal β-homo-glutaminyl residues also fulfill properties as substrates of QCs from plants and mammals. The N-terminal β-homo-glutaminyl residue was converted into a five-membered lactam ring by catalysis of human and papaya QC, respectively. The results are described in example 5. The applied method is illustrated in example 2 and the peptide synthesis was performed as described in example 6.

Another preferred embodiment of the present invention comprises screening methods for effectors of QC.

A preferred screening method for identifying effectors modifying the activity of QC from a group of compounds comprises the steps of:
  a) Contacting said compounds with QC under conditions, which would permit binding therebetween;
  b) Adding a substrate of QC;
  c) Monitoring the conversion of the substrate or optionally measuring the residual QC activity; and
  d) Calculating changes in the substrate conversion and/or enzyme activity of QC to identify an activity modifying effector.

Another preferred screening method relates to a method for the identification and selection of effectors which interact directly or indirectly with the active-site bound metal ion of QC and comprises the following steps:
  a) Contacting said compounds with QC under conditions, which would permit binding therebetween;
  b) Adding a substrate of QC, which is subject to conversion by QC;
  c) Monitoring the conversion of the substrate or optionally measuring the residual QC activity; and
  d) Calculating changes in the substrate conversion and/or enzyme activity of QC wherein changes may be used to identify an activity modifying effector of QC.

Preferred for the use in the above-described screening methods are mammalian QC, mammalian QC-like enzymes or Papaya QC. Especially preferred is mammalian QC, since the effectors identified by these screening methods shall be used for the treatment of diseases in mammals, especially in humans. Most preferred are human QC and/or human isoQC.

The agents selected by the above-described screening methods can work by decreasing the conversion of at least one substrate of QC (negative effectors, inhibitors), or by increasing the conversion of at least one substrate of QC (positive effectors, activators).

The compounds of the present invention can be converted into acid addition salts, especially pharmaceutically acceptable acid addition salts.

The salts of the compounds of the invention may be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

In a further embodiment, the present invention provides a method of preventing or treating a condition mediated by modulation of the QC enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition mediated by modulation of the QC activity in a subject. The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The effectors of QC activity administered according to the invention may be employed in pharmaceutically administrable formulations or formulation complexes as inhibitors or in combination with inhibitors, substrates, pseudosubstrates, inhibitors of QC expression, binding proteins or antibodies of those enzyme proteins that reduce the QC protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The doctor providing treatment is thereby given the opportunity to respond differently to the individual situation of patients: he is able to adjust precisely, on the one hand, the speed of the onset of action and, on the other hand, the duration of action and especially the intensity of action.

A preferred treatment method according to the invention represents a new approach for the prevention or treatment of a condition mediated by modulation of the QC enzyme activity in mammals. It is advantageously simple, susceptible of commercial application and suitable for use, especially in the treatment of diseases that are based on unbalanced concentration of physiological active QC substrates, e.g. listed in Tables 1 and 2, in mammals and especially in human medicine.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending upon their endogenous stability and their bioavailability, one or more doses of the compounds can be given per day in order to achieve the desired normalisation of the blood glucose values. For example, such a dosage range in humans may be in the range of from about 0.01 mg to 250.0 mg per day, preferably in the range of from about 0.01 to 100 mg of compound per kilogram of body weight.

By administering effectors of QC activity to a mammal it could be possible to prevent or alleviate or treat conditions selected from
  g. neurodegenerative diseases, e.g. mild cognitive impairment (MCI), Alzheimer's disease, neurodegeneration in Down Syndrome, Familial British Dementia, Familial Danish Dementia, multiple sclerosis,
  h. chronic and acute inflammations, e.g. rheumatoid arthritis, atherosclerosis, restenosis, pancreatitis,
  i. fibrosis, e.g. lung fibrosis, liver fibrosis, renal fibrosis,
  j. cancer, e.g. cancer/hemangioendothelioma proliferation, gastric carcinomas,
  k. metabolic diseases, e.g. hypertension,
  l. and other inflammatory diseases, e.g. neuropathic pain, graft rejection/graft failure/graft vasculopathy, HIV infections/AIDS, gestosis, tuberous sclerosis.

In particular, the present invention pertains to the use of effectors of QC activity for the preparation of a medicament for the prevention, alleviation and/or treatment of Alzheimer's disease in a human subject.

Further, by administration of effectors of QC activity to a mammal it can be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

Furthermore, by administration of effectors of QC activity to a mammal it can be possible to suppress the proliferation of myeloid progenitor cells.

In addition, administration of QC inhibitors can lead to suppression of male fertility.

The compounds used according to the invention can accordingly be converted in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The substances can be used as medicaments in the form of dragées, capsules, bitable capsules, tablets, drops, syrups or also as suppositories or as nasal sprays.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly disperse silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

EXAMPLES OF PHARMACEUTICAL FORMULATIONS

1. Capsules Containing 100 mg of a Compound of the Invention Per Capsule

For approximately 10,000 capsules a solution of the following composition is prepared:

| | |
|---|---|
| compound of the invention | 1.0 kg |
| glycerol | 0.5 kg |
| polyethylene glycol | 3.0 kg |
| water | 0.5 kg |
| | 5.0 kg |

The solution is introduced into soft gelatin capsules in a manner known per se. The capsules are suitable for chewing or swallowing.

2. Tablets or Coated Tables or Dragées Containing 100 mg of a Compound of the Invention The following amounts refer to the preparation of 100,000 tablets:

| | |
|---|---|
| compound of the invention, finely ground | 10.0 kg |
| glucose | 4.35 kg |
| lactose | 4.35 kg |
| starch | 4.50 kg |
| cellulose, finely ground | 4.50 kg |

The above constituents are mixed and then provided with a solution prepared from

| | |
|---|---|
| polyvinylpyrrolidone | 2.0 kg |
| polysorbate | 0.1 kg |
| and water | approx. 5.0 kg | and granulated in a manner known per se by grating the moist mass and, after the addition of 0.2 kg of magnesium stearate, drying it. The finished tablet mixture of 30.0 kg is processed to form convex tablets weighing 300 mg. Ideally, the tablets can be coated or sugar-coated in a manner known per se.

The pharmaceutical compositions defined throughout the specification advantageously contain a combination of at least one effector of QC activity, preferably a QC-inhibitor, and at least one other agent, which is useful for the treatment of the aforementioned conditions. Most preferred are pharmaceutical compositions, which are useful for the treatment of Alzheimer's disease and neurodegeneration Down syndrome.

In the examples below, the following abbreviations are used:
AD Alzheimer's disease
AUC area under the concentration-time curve
AUC($t_0$-t) area under the concentration-time curve from the first to the last time point sampled
AUC$_{(0-t)}$ area under the concentration-time curve from t=0 to the last time point calc. calculated
CETP cholestryl ester transfer protein
CvD cardiovascular disease
d day
DP4 dipeptidylpeptidase 4 (CD26)
DS Down syndrome
EDT 1,2-ethanedithiol
eNOS endothelial nitric oxide synthase
Fmoc 9-Fluorenylmethyloxocarbonyl-
g gram
Gln glutamine
h hour
HDL high density lipoproteins
HFIP 1,1,1,3,3,3-Hexafluoro-2-propanol
HIV human immunodeficiency virus
HMG-CoA 3-Hydroxy-3-Methylglutaryl-Coenzyme-A
H-NMR hydrogen nuclear magnetic resonance spectroscopy
HSA human serum albumine
ICAM intercellular adhesion molecule
IL interleukin
kg kilogram
L liter
LC-MS liquid chromatography coupled with mass spectrometry
LDL low density lipoproteins
LPS lipopolysaccharide
M molar
Maldi-TOF matrix-assisted laser desorption/ionization time-of-flight
µM micromolar
MCP-1 monocyte chemoattractant protein 1
min minute
MIP macrophage inflammatory protein
mL milliliter
mM millimolar
MMP-1 matrix metalloproteinase 1
MW molecular weight
n sample size
Na sodium
ng nanogram
NMM N-Methylmorpholine
No Number
PCTA percutaneous transluminal coronary angioplasty
pGlu pyroglutamate
PPAR-α Peroxisome proliferator-activated receptor alpha
ppm parts per million
QC Glutaminyl Cyclase
RT room temperature
SD standard deviation
Ser(ψMe,Mepro) Pseudoprolyl-
SPE solid phase extraction
TBTU 2-(1H-Benzotriazole-1-yl)-1,1,3,3-tetramethylammonium-tetrafluoroborate
TFA Trifluoro acetic acid
TIS Triisopropylsilane
TNF-α tumor necrosis factor α
ThT ThioflavinT
VCAM vascular adhesion molecule

Example 1

Preparation of Human and Papaya QC

Host Strains and Media

*Pichia pastoris* strain X33 (AOX1, AOX2), used for the expression of human QC was grown, transformed and analyzed according to the manufacturer's instructions (Invitrogen). The media required for *P. pastoris*, i.e. buffered glycerol (BMGY) complex or methanol (BMMY) complex medium, and the fermentation basal salts medium were prepared according to the manufacturer's recommendations.

Molecular Cloning of Plasmid Vectors Encoding the Human QC

All cloning procedures were done applying standard molecular biology techniques. For expression in yeast, the vector pPICZαB (Invitrogen) was used. The pQE-31 vector (Qiagen) was used to express the human QC in *E. coli*. The cDNA of the mature QC starting with codon 38 was fused in frame with the plasmid encoded 6× histidine tag. After amplification utilizing the primers pQCyc-1 and pQCyc-2 (Table 1) and subcloning, the fragment was inserted into the expression vector employing the restriction sites of SphI and HindIII.

Transformation of *P. pastoris* and Mini-Scale Expression

Plasmid DNA was amplified in *E. coli* JM109 and purified according to the recommendations of the manufacturer (Qiagen). In the expression plasmid used, pPICZαB, three restriction sites are provided for linearization. Since SacI and BstXI cut within the QC cDNA, PmeI was chosen for linearization. 20-30 μg plasmid DNA was linearized with PmeI, precipitated by ethanol, and dissolved in sterile, deionized water. 10 μg of the DNA was then applied for transformation of competent *P. pastoris* cells by electroporation according to the manufacturers instructions (BioRad). Selection was done on plates containing 150 μg/ml Zeocin. One transformation using the linearized plasmid yielded several hundred transformants.

In order to test the recombinant yeast clones for QC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h up to 72 h. Subsequently, QC activity in the supernatant was determined. The presence of the fusion protein was confirmed by western blot analysis using an antibody directed against the 6× histidine tag (Qiagen). Clones that displayed the highest QC activity were chosen for further experiments and fermentation.

Large-Scale Expression in a Fermenter

Expression of the QC was performed in a 5 l reactor (Biostat B. B. Braun biotech), essentially as described in the "*Pichia* fermentation process guidelines" (Invitrogen). Briefly, the cells were grown in the fermentation basal salts medium supplemented with trace salts, and with glycerol as the sole carbon source (pH 5.5). During an initial batch phase for about 24 h and a subsequent fed-batch phase for about 5 h, cell mass was accumulated. Once a cell wet weight of 200 g/l was achieved, induction of QC expression was performed using methanol applying a three-step feeding profile for an entire fermentation time of approximately 60 h. Subsequently, cells were removed from the QC-containing supernatant by centrifugation at 6000×g, 4° C. for 15 min. The pH was adjusted to 6.8 by addition of NaOH, and the resultant turbid solution was centrifuged again at 37000×g, 4° C. for 40 min. In cases of continued turbidity, an additional filtration step was applied using a cellulose membrane (pore width 0.45 μm).

Purification of 6× Histidine Tagged QC Expressed in *P. pastoris*

The His-tagged QC was first purified by immobilized metal affinity chromatography (IMAC). In a typical purification, 1000 ml of culture supernatant were applied to a Ni$^{2+}$-loaded Chelating Sepharose FF column (1.6×20 cm, Pharmacia), that was equilibrated with 50 mM phosphate buffer, pH 6.8, containing 750 mM NaCl, at a flow rate of 5 ml/min. After washing with 10 column volumes of equilibration buffer and 5 column volumes of equilibration buffer containing 5 mM histidine, the bound protein was eluted by a shift to 50 mM phosphate buffer, pH 6.8, containing 150 mM NaCl and 100 mM histidine. The resulting eluate was dialyzed against 20 mM Bis-Tris/HCl, pH 6.8, at 4° C. overnight. Subsequently, the QC was further purified by anion exchange chromatography on a Mono Q6 column (BioRad), equilibrated with dialysis buffer. The QC-containing fraction was loaded onto the column using a flow rate of 4 ml/min. The column was then washed with equilibration buffer containing 100 mM NaCl. The elution was performed by two gradients resulting in equilibration buffer containing 240 mM and 360 mM NaCl in 30 or 5 column volumes, respectively. Fractions of 6 ml were collected and the purity was analyzed by SDS-PAGE. Fractions containing homogenous QC were pooled and concentrated by ultrafiltration. For long-term storage (−20° C.), glycerol was added to a final concentration of 50%. Protein was quantified according to the methods of Bradford or Gill and von Hippel (Bradford, M. M. 1976 *Anal Biochem* 72, 248-254; Gill, S. C. and von Hippel, P. H. 1989 *Anal Biochem* 182, 319-326.).

Expression and Purification of QC in *E. coli*

The construct encoding the QC was transformed into M15 cells (Qiagen) and grown on selective LB agar plates at 37° C. Protein expression was carried out in LB medium containing 1% glucose and 1% ethanol at room temperature. When the culture reached an $OD_{600}$ of approximately 0.8, expression was induced with 0.1 mM IPTG overnight. After one cycle of freezing and thawing, cells were lysed at 4° C. by addition of 2.5 mg/ml lysozyme in 50 mM phosphate buffer, pH 8.0, containing 300 mM NaCl and 2 mM histidine for approximately 30 min. The solution was clarified by centrifugation at 37000×g, 4° C. for 30 min, followed by a filtration applying a glass frit (DNA separation) and two additional filtration steps applying cellulose filters for crude and fine precipitates. The supernatant (approx. 500 ml) was applied onto a Ni$^{2+}$-affinity column (1.6×20 cm) at a flow rate of 1 ml/min. Elution of QC was carried out with 50 mM phosphate buffer containing 150 mM NaCl and 100 mM histidine. The QC-containing fraction was concentrated by ultrafiltration.

Purification of QC from Papaya Latex

QC from papaya latex was prepared using the BioCAD 700E (Perseptive Biosystems, Wiesbaden, Germany) with a modified version of a previously reported method (Zerhouni, S. et al. 1989 *Biochim Biophys Acta* 138, 275-290). 50 g latex was dissolved in water and centrifugated as described therein. Inactivation of proteases was performed with S-methyl methanethiosulfonate, and the resultant crude extract was dialyzed. After dialysis, the entire supernatant was loaded onto a (2152.5 cm i.d.) SP Sepharose Fast Flow column, equilibrated with 100 mM sodium acetate buffer, pH 5.0 (flow rate 3 ml/min). Elution was performed in three steps by increasing sodium acetate buffer concentration at a flow rate of 2 ml/min. The first step was a linear gradient from 0.1 to 0.5 M acetate buffer in 0.5 column volumes. The second step was a linear increase in buffer concentration from 0.5 to 0.68 M in four column volumes. During the last elution step, one column volume of 0.85 M buffer was applied. Fractions (6 ml) containing the highest enzymatic activity were pooled. Concentration and buffer changes to 0.02 M Tris/HCl, pH 8.0 were performed via ultrafiltration (Amicon; molecular mass cutoff of the membrane 10 kDa).

Ammonium sulfate was added to the concentrated papaya enzyme, obtained from the ion exchange chromatography step to a final concentration of 2 M. This solution was applied onto a (2152.5 cm i.d.) Butyl Sepharose 4 Fast Flow column (flow rate 1.3 ml/min, equilibrated with 2 M ammonium sulfate, 0.02 M Tris/HCl, pH 8.0. Elution was performed in three steps with decreasing concentrations of ammonium sulfate. During the first step a linear gradient from 2 to 0.6 M ammonium sulfate, 0.02 M Tris/HCl, pH 8.0 was applied for 0.5 column volumes at a flow rate of 1.3 ml/min. The second step was a linear gradient from 0.6 to 0 M ammonium sulfate, 0.02 M Tris/HCl, pH 8.0, in 5 column volumes at a flow rate of 1.5 ml/min. The last elution step was carried out by applying 0.02 M Tris/HCl at pH 8.0 for 2 column volumes at a flow rate of 1.5 ml/min. All fractions containing QC activity were pooled and concentrated by ultrafiltration. The resultant homogenous QC was stored at −70° C. Final protein concentrations were determined using the method of Bradford, compared to a standard curve obtained with bovine serum albumin.

Example 2

Assays for Glutaminyl Cyclase Activity

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hørsholm, Denmark) in 0.2 M Tris/HCl, pH 8.0 containing 20 mM EDTA and an appropriately diluted aliquot of QC in a final volume of 250 μl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 μmol pGlu-βNA from H-Gln-βNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 μl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, which was derived by adapting a previous discontinuous assay (Bateman, R. C. J. 1989 *J Neurosci Methods* 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 μl. Reactions were started by addition of QC and persued by monitoring of the decrease in absorbance at 340 nm for 8-15 min. Typical time courses of product formation are presented in FIG. 1.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 3

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 μl) were mixed with equal volumes of the matrix solution. For matrix solution we used DHAP/DAHC, prepared by solving 30 mg 2′,6′-dihydroxyacetophenone (Aldrich) and 44 mg diammonium hydrogen citrate (Fluka) in 1 ml acetonitrile/ 0.1% TFA in water (1/1, v/v). A small volume (≈1 μl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 μl 0.1 M sodium acetate buffer, pH 5.2 or 0.1 M Bis-Tris buffer, pH 6.5 at 30° C. Peptides were applied in 0.5 mM [Aβ3-11a] or 0.15 mM [Aβ3-21a] concentrations, and 0.2 U Q was added all 24 hours. In case of Aβ3-21a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls did either contain no QC or heat deactivated enzyme. For the inhibitor studies the sample composition was the same as described above, with exception of the inhibitory compound added (5 mM benzimidazole or 2 mM 1,10-phenanthroline).

Example 4 pH Dependence

The pH-dependence of catalysis of human and papaya QC was investigated under first-order rate conditions, thus reflecting the impact of the proton concentration on the specificity constant $k_{cat}/K_M$. For this purpose, the coupled enzymatic assay using pyroglutamyl aminopeptidase as auxiliary enzyme and Gln-βNA as substrate was used. Pyroglutamyl aminopeptidase was shown to be active and stable between pH 5.5-8.5 (Tsuru, D. et al. 1978 *J Biochem (Tokyo)* 84, 467-476). Hence, the assay enabled the study of QC catalysis in this pH-region. The rate profiles obtained were fit to classical bell shaped curves, as shown in FIG. 2. The human QC bears a very narrow pH-dependence with an optimum at about pH 7.8-8.0. The rate tended to decrease at more basic pH. This is in contrast to the rate profile observed with papaya QC, which showed no drop in activity up to pH 8.5 (FIG. 2, inset). However, both enzymes had their optimum of specificity at pH 8. Surprisingly, evaluation of the curves revealed identical $pK_a$-values in the acidic range of 7.17±0.02 and 7.15±0.02 for human and papaya QC, respectively.

The reduction of the activity of human QC at basic pH-values was obviously due to dissociation of a group with a $pK_a$ of approximately 8.5. In case of papaya QC, there was no excessive data point collection in the basic pH-range possible to enable a reliable determination of the second $pK_a$ value. This is supported by fitting of the data to a single dissociation model, resulting in an almost identical $pK_a$-value ($pK_a$ 7.13±0.03) compared to fitting the data to a double dissociation model. This indicates that both $pK_a$-values are fairly separated.

pH Stability

Figure 3:
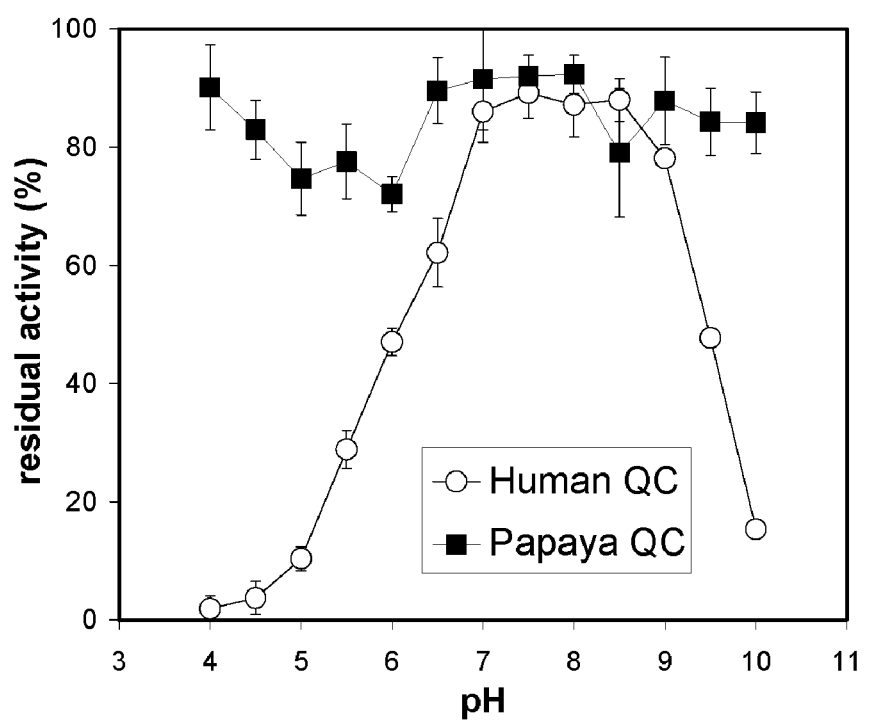
FIG. 3 shows the effect of the pH on the stability of the QC from Papaya latex and human QC. An enzyme stock solution was diluted 20-fold in 0.1 M buffer of various pH values (pH 4-7 sodium citrate, pH 7-10 sodium phosphate). Enzyme solutions were incubated at 30° C. for 30 min and subsequently enzymatic activity was analyzed according to the standard protocol.

The stability of the glutaminyl cyclases was investigated by incubating the plant and animal enzymes at 30° C. for 30 min at different pH values between pH 4-10. Afterwards, QC activity was determined under standard conditions. The results are shown in FIG. 3.

The QC from papaya latex was stable in the pH-range studied, without an obvious trend for instability in the acidic or basic range. In contrast, human QC only showed a comparable stability in the pH-range between 7 and 8.5, exhibiting a remarkable instability at pH values above pH 8.5 and below pH 6. Thus, the region around pH 8 seems to be optimal for activity and stability of plant and human QC and a suitable pH-value for performing a substrate specificity comparison of the QCs.

Example 5

Determination of Substrate Specificity of QC

Spectrophotometric Assay

The continuous spectrophotometric assay was performed as described in example 2. Accordingly, QC activity is reflected by a decrease in absorbance at 340 nm caused by the ammonia release and subsequent consumption of NADH/H$^+$ due to formation of glutamate from α-ketoglutaric acid. As shown in FIG. 1, linear progress curves were monitored and there was a linear relationship between the measured activity and the concentration of QC. Furthermore, the kinetic parameters obtained for H-Gln-Gln-OH using the continuous assay presented here (Table 1) were in good agreement with those obtained using the discontinuous method ($K_M$=175±18 μM, $k_{cat}$=21.3±0.6 s$^{-1}$). In addition, the kinetic parameters for conversion of the substrates H-Gln-Ala-OH, H-Gln-Glu-OH, H-Gln-Gln-OH, H-Gln-OtBu and H-Gln-NH$_2$ by papaya QC shown in Table 1 correspond well to those determined using a direct method at pH 8.8 and 37° C. (Gololobov, M. Y. et al. 1996 *Biol Chem Hoppe Seyler* 377, 395-398). Hence, it is quite obvious that the novel continuous assay provides reliable results.

Di-, Tri- and Dipeptide-Surrogates

Utilizing the novel continuous assay described above, about 30 compounds were tested as potential substrates of QC from *C. papaya* and human. The results are displayed in Table 5. By comparison of the specificities it was shown, that nearly all of the short peptide substrates are more efficiently converted by papaya QC compared to the human enzyme. Interestingly, for both enzymes substrates with large hydrophobic residues in the second position are the most potent ones, as shown by the specificities of H-Gln-Tyr-Ala-OH, H-Gln-Phe-Ala-NH$_2$ and H-Gln-Trp-Ala-NH$_2$ compared to those of other tripeptides or by the reactivities of the chromophoric substrates H-Gln-AMC, H-Gln-βNA and H-Gln-Tyr-OH in comparison to dipeptide substrates. For papaya QC, this finding is in agreement with earlier results showing that the specificity is in correlation with the size of the second amino acid residue (Gololobov, M. Y. et al. 1996 *Biol Chem Hoppe Seyler* 377, 395-398). The only striking difference in specificity of the plant and animal QC was observed in case of H-Gln-OtBu. Whereas the ester was converted by papaya QC with similar specificity compared to dipeptide substrates, it was converted about one order of magnitude slower by human QC.

Oligopeptides

Besides several dipeptides and tripeptides, a number of oligopeptides was tested upon conversion by papaya and human QC (Table 5). Interestingly, the overall difference in the specificities between human and plant QC for a set of tetrapeptides was not that large as it was observed for dipeptide and tripeptide substrates. This indicates that the amino acids in the 3$^{rd}$ and 4$^{th}$ position still affect the kinetic behavior especially of human QC. An exception, however, comprise the peptides with a proline residue in the second amino acid position which show noticeably reduced $k_{cat}/K_M$ values in a set of tetrapeptides of the structure H-Gln-$X_{aa}$-Tyr-Phe-NH$_2$ (Table 5). The reduction in specificity was more pronounced for human QC, leading to an approximately 8-fold difference in the $k_{cat}/K_M$-value as compared to papaya QC.

Slightly reduced specificities of human QC were also observed for conversion of substrates with a positively charged amino acid C-terminal of glutamine, as indicated by the specificities for H-Gln-Arg-Tyr-Phe-NH$_2$, H-Gln-Arg-Tyr-Phe-NH$_2$ and H-Gln-Lys-Arg-Leu-NH$_2$ as compared to other tetrapeptides. Apparently, the reduced specificity was mainly due to a lower turnover number. This effect was not observed with the plant enzyme.

TABLE 5

Kinetic evaluation of peptide substrates of human and Papaya QC

| | Human QC | | | | Papaya QC | | | |
| --- | --- | --- | --- | --- | --- | --- | --- | --- |
| Substrate | $K_M$ (μM) | $k_{cat}$ (s$^{-1}$) | $K_i^*$ (mM) | $k_{cat}/K_M$ (mM$^{-1}$ s$^{-1}$) | $K_M$ (μM) | $k_{cat}$ (s$^{-1}$) | $K_i^*$ (mM) | $k_{cat}/K_M$ (mM$^{-1}$ s$^{-1}$) |
| H-Gln-OH | n.r. | n.r. | n.d. | n.r. | n.d. | n.d. | n.d. | 0.23 ± 0.1 |
| H-Gln-AMC | 54 ± 2 | 5.3 ± 0.1 | n.d. | 98 ± 2 | 42 ± 1 | 39.4 ± 0.4 | n.d. | 938 ± 13 |

TABLE 5-continued

Kinetic evaluation of peptide substrates of human and Papaya QC

| | Human QC | | | | Papaya QC | | | |
|---|---|---|---|---|---|---|---|---|
| Substrate | $K_M$ (µM) | $k_{cat}$ ($s^{-1}$) | $K_i$* (mM) | $k_{cat}/K_M$ ($mM^{-1} s^{-1}$) | $K_M$ (µM) | $k_{cat}$ ($s^{-1}$) | $K_i$* (mM) | $k_{cat}/K_M$ ($mM^{-1} s^{-1}$) |
| H-Gln-βNA | 70 ± 3 | 20.6 ± 0.5 | 1.21 ± 0.07 | 294 ± 6 | 38 ± 3 | 51.4 ± 1.4 | 1.20 ± 0.08 | 1353 ± 70 |
| H-Gln-OtBu | 1235 ± 74 | 6.7 ± 0.2 | n.i. | 5.4 ± 0.2 | 223 ± 9 | 49.4 ± 0.6 | n.i. | 222 ± 6 |
| H-Gln-NH₂ | 409 ± 40 | 12.8 ± 0.5 | n.i. | 31 ± 2 | 433 ± 13 | 44.8 ± 0.4 | n.i. | 103 ± 2 |
| H-Gln-Gly-OH | 247 ± 10 | 13.2 ± 0.2 | n.i. | 53 ± 1 | 641 ± 20 | 45.8 ± 0.4 | n.i. | 71 ± 2 |
| H-Gln-Ala-OH | 232 ± 5 | 57.2 ± 0.4 | n.i. | 247 ± 4 | 158 ± 8 | 69.8 ± 1.0 | n.i. | 442 ± 16 |
| H-Gln-Gln-OH | 148 ± 5 | 20.7 ± 0.2 | n.i. | 140 ± 2 | 44 ± 3 | 43.2 ± 0.7 | n.i. | 982 ± 51 |
| H-Gln-Glu-OH | 359 ± 10 | 24.7 ± 0.2 | n.i. | 58 ± 1 | 106 ± 5 | 50.3 ± 0.6 | n.i. | 475 ± 17 |
| H-Gln-Val-OH | 196 ± 5 | 17.2 ± 0.1 | n.i. | 88 ± 2 | n.d. | n.d. | n.i. | n.d. |
| H-Gln-Tyr-OH | 211 ± 5 | 94 ± 1 | n.i. | 446 ± 6 | n.d. | n.d. | n.i. | n.d. |
| H-Gln-Glu-Tyr-NH₂ | 79 ± 2 | 45.1 ± 0.4 | n.i. | 524 ± 8 | 103 ± 4 | 53.6 ± 0.7 | n.i. | 520 ± 13 |
| H-Gln-Gly-Pro-OH | 130 ± 5 | 25.3 ± 0.2 | n.i. | 195 ± 7 | 333 ± 15 | 41.7 ± 0.5 | n.i. | 125 ± 4 |
| H-Gln-Tyr-Ala-OH | 101 ± 4 | 125 ± 1 | n.i. | 930 ± 27 | 63 ± 3 | 104.0 ± 1.0 | n.i. | 1650 ± 63 |
| H-Gln-Phe-Ala-NH₂ | 69 ± 3 | 109 ± 1 | n.i. | 1811 ± 64 | 111 ± 5 | 132.1 ± 0.6 | n.i. | 1190 ± 48 |
| H-Gln-Trp-Ala-NH₂ | 50 ± 2 | 47.0 ± 0.7 | n.i. | 940 ± 24 | 78 ± 5 | 151.8 ± 2.6 | n.i. | 1946 ± 91 |
| H-Gln-Arg-Gly-Ile-NH₂ | 143 ± 4 | 33.5 ± 0.4 | n.i. | 234 ± 4 | 123 ± 10 | 49.2 ± 1.7 | n.i. | 400 ± 19 |
| H-Gln-Asn-Gly-Ile-NH₂ | 172 ± 5 | 56.6 ± 0.5 | n.i. | 329 ± 7 | 153 ± 9 | 51.4 ± 0.9 | n.i. | 336 ± 14 |
| H-Gln-Ser-Tyr-Phe-NH₂ | 55 ± 3 | 52.8 ± 0.8 | n.i. | 960 ± 38 | 135 ± 6 | 64.9 ± 1.0 | n.i. | 481 ± 14 |
| H-Gln-Arg-Tyr-Phe-NH₂ | 55 ± 2 | 29.6 ± 0.3 | n.i. | 538 ± 14 | 124 ± 6 | 48.9 ± 0.7 | n.i. | 394 ± 13 |
| H-Gln-Pro-Tyr-Phe-NH₂ | 1889 ± 152 | 31.7 ± 1.2 | n.i. | 17 ± 1 | 149 ± 14 | 18.8 ± 0.6 | n.i. | 126 ± 8 |
| H-Gln-His-Tyr-Phe-NH₂ | 68 ± 3 | 55.4 ± 0.7 | n.i. | 815 ± 26 | 92 ± 7 | 75.9 ± 1.4 | n.i. | 825 ± 48 |
| H-Gln-Gln-Tyr-Phe-NH₂ | 41 ± 2 | 41.4 ± 0.4 | n.i. | 1010 ± 40 | 45 ± 2 | 52.9 ± 0.7 | n.i. | 1176 ± 37 |
| H-Gln-Glu-Tyr-Phe-NH₂ | 47 ± 4 | 46 ± 1 | n.i. | 979 ± 62 | 100 ± 4 | 54.6 ± 0.6 | n.i. | 546 ± 16 |
| H-Gln-Glu-Ala-Ala-NH₂ | 77 ± 4 | 46 ± 1 | n.i. | 597 ± 18 | 102 ± 4 | 53.7 ± 0.6 | n.i. | 526 ± 15 |
| H-Gln-Glu-Tyr-Ala-NH₂ | 69 ± 2 | 42.1 ± 0.4 | n.i. | 610 ± 12 | 113 ± 5 | 44.7 ± 0.5 | n.i. | 396 ± 13 |
| H-Gln-Glu-Ala-Phe-NH₂ | 39 ± 3 | 39 ± 1 | n.i. | 1000 ± 51 | 81 ± 3 | 48.5 ± 0.45 | n.i. | 599 ± 17 |
| H-Gln-Glu-Asp-Leu-NH₂ | 55 ± 2 | 45.8 ± 0.5 | n.i. | 833 ± 21 | 107 ± 6 | 58.5 ± 0.4 | n.i. | 547 ± 27 |
| H-Gln-Lys-Arg-Leu-NH₂ | 54 ± 3 | 33.4 ± 0.5 | n.i. | 619 ± 25 | 118 ± 6 | 48.2 ± 0.8 | n.i. | 408 ± 14 |

(n.r., not reactive; n.i., no inhibition; n.d., not determined; *, for substrate inhibition)

Figure 4:
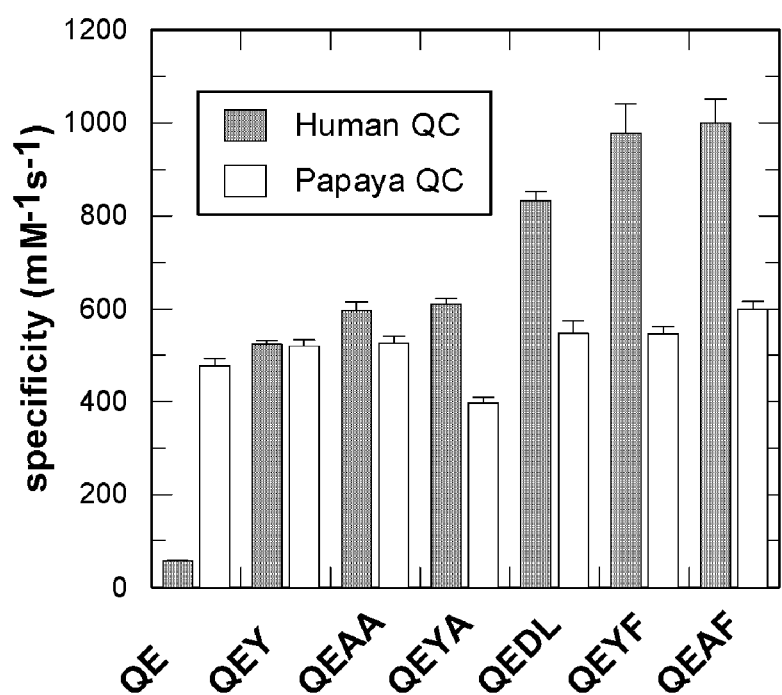
FIG. 4 shows the comparison of the specificity constant kcat/K$_M$ for a set of substrates containing glutamate in the second amino acid position. Whereas an increase in specificity of human QC was detected from the di- to the tetrapeptides, no change was observed in case of papaya QC.

The results obtained with the tetrapeptides give also rise to another conclusion. As already pointed out, papaya QC showed a higher selectivity for dipeptides. For some of the tetrapeptides, however, higher specificity-constants were observed with human QC, as shown in FIG. 4 providing a plot of the data given in Table 5, for a set of peptides containing glutamate in the second amino acid position. Furthermore, as the chain length increases from di- to tetrapeptides, the selectivity of human QC increases, in contrast to the results obtained with papaya QC. Additionally, the highest selectivity of human QC was recorded for the peptides containing bulky hydrophobic residues in the $3^{rd}$ and $4^{th}$ amino acid position, which indicate hydrophobic interactions with the enzyme. By comparison of the kinetic parameters for the respective peptides, the changes seem to be mainly due to lower $K_M$-values, the turnover numbers for conversion of the peptides were found to be similar. Thus, the higher selectivity of human QC for longer peptides is considered to be the result of tighter binding of the more hydrophobic substrates to the enzyme.

The differences between human and plant QC observed with peptides containing hydrophobic amino acids in the $3^{rd}$ and $4^{th}$ position becomes also evident by a comparison of the specificity constants of the enzymes towards H-Gln-Arg-Gly-Ile-NH₂ and H-Gln-Arg-Tyr-Phe-NH₂ or H-Gln-Gln-OH and H-Gln-Gln-Tyr-Phe-OH.

Human QC was also found to be more selective for homologous substrates containing N-terminal Gln and an increasing number of C-terminal Ala residues (Table 6). While the selectivity of human QC increased with substrate length, there was no such a trend with the papaya QC. Since human QC was less specific for a peptide containing a Ser residue in the sequence, also the nature of the side chain seems to be of importance (table 6).

TABLE 6

Influence of substrate length on the activity of human and Papaya QC

| | Human QC | | | Papaya QC | | |
|---|---|---|---|---|---|---|
| Substrate | $K_M$ (μM) | $k_{cat}$ (s$^{-1}$) | $k_{cat}/K_M$ (mM$^{-1}$ s$^{-1}$) | $K_M$ (μM) | $k_{cat}$ (s$^{-1}$) | $k_{cat}/K_M$ (mM$^{-1}$ s$^{-1}$) |
| H-Gln-Ala-NH$_2$ | 155 ± 9 | 40.1 ± 0.9 | 259 ± 9 | 212 ± 21 | 62.8 ± 3.0 | 296 ± 15 |
| H-Gln-Ala-Ala-NH$_2$ | 87 ± 3 | 76.3 ± 0.7 | 877 ± 22 | 164 ± 6 | 83.2 ± 1.0 | 507 ± 12 |
| H-Gln-Ala-Ala-Ala-Ala-NH$_2$ | 65 ± 3 | 60.5 ± 0.7 | 1174 ± 43 | 197 ± 8 | 74.6 ± 1.0 | 379 ± 10 |
| H-Gln-Ala-Ala-Ser-Ala-Ala-NH$_2$ | 79 ± 6 | 55.3 ± 1.6 | 700 ± 33 | 216 ± 6 | 78.5 ± 1.0 | 363 ± 5 |

Influence of Ionic Strength on Catalysis

Another parameter that was investigated concerning its influence on the substrate specificity was ionic strength. For that purpose, the kinetic parameters for cyclization of several substrates were determined in presence and absence of 0.5 M KCl (Table 7). Surprisingly, the selectivity for substrates with unchanged backbone did not change significantly by addition of the salt case of QC from papaya latex and human QC. However, the specificity constants of the human QC for H-Gln-Alan-OH and H-Gln-Glu-OH decreased by addition of KCl. As indicated by the individual kinetic parameters, this effect was due to an increasing $K_M$ and an only slightly decreasing $k_{cat}$-value. In case of papaya QC, there was no effect on either parameter detected. The effect seemed not to be due to the negatively charged substrate as such, since unchanged parameters were found for the negatively charged peptide H-Gln-Glu-Asp-Leu-NH$_2$. An interesting effect of the salt addition was found for the positively charged substrates H-Gln-Arg-Gly-Ile-NH$_2$ and H-Gln-Lys-Arg-Leu-NH$_2$. In case of plant and human QC, a positive effect on catalysis was determined mainly due to a smaller $K_M$ value and a slightly higher turnover number.

TABLE 7

Influence of ionic strength on catalysis of human and Papaya QC

| | Substrate | $K_M$ (mM) | $k_{cat}$ (s$^{-1}$) | $k_{cat}/K_M$ (mM$^{-1}$s$^{-1}$) | $K_i$ (mM) | $K_M$ (mM) | $k_{cat}$ (s$^{-1}$) | $k_{cat}/K_M$ (mM$^{-1}$s$^{-1}$) | $K_i$ (mM) |
|---|---|---|---|---|---|---|---|---|---|
| | | 0.05 M Tricine-NaOH, pH 8.0 | | | | 0.05 M Tricine-NaOH, pH 8.0, 0.5 M KCl | | | |
| Papaya QC | H-Gln-NH$_2$ | 0.434 ± 0.015 | 43.4 ± 0.4 | 100 ± 3 | n.i. | 0.446 ± 0.010 | 45.2 ± 0.3 | 101 ± 2 | n.i. |
| | H-Gln-βNA | 0.036 ± 0.002 | 48.8 ± 1.0 | 1356 ± 50 | 1.14 ± 0.05 | 0.032 ± 0.002 | 47.2 ± 0.8 | 1475 ± 70 | 1.33 ± 0.07 |
| | H-Gln-Ala-OH | 0.137 ± 0.007 | 69.7 ± .9 | 509 ± 19 | n.i. | 0.143 ± 0.005 | 68.1 ± 0.6 | 480 ± 12 | n.i. |
| | H-Gln-Glu-OH | 0.098 ± 0.005 | 45.0 ± 0.5 | 459 ± 18 | n.i. | 0.094 ± 0.003 | 44.4 ± 0.3 | 472 ± 12 | n.i. |
| | H-Gln-Trp-Ala-NH$_2$ | 0.079 ± 0.005 | 138 ± 3 | 1747 ± 73 | n.i. | 0.072 ± 0.004 | 133 ± 3 | 1847 ± 61 | n.i. |
| | H-Gln-Arg-Gly-Ile-NH$_2$ | 0.106 ± 0.008 | 52.9 ± 1.2 | 499 ± 26 | n.i. | 0.065 ± 0.005 | 48.4 ± 1.0 | 745 ± 42 | n.i. |
| | H-Gln-Lys-Arg-Leu-NH$_2$ | 0.102 ± 0.007 | 50 ± 1 | 493 ± 22 | n.i. | 0.053 ± 0.002 | 58.1 ± 0.7 | 1096 ± 28 | n.i. |
| | H-Gln-Glu-Asp-Leu-NH$_2$ | 0.109 ± 0.005 | 52.4 ± 0.7 | 481 ± 16 | n.i. | 0.094 ± 0.003 | 53.6 ± 0.5 | 570 ± 13 | n.i. |
| | | 0.05 M Tris-HCl, pH 8.0 | | | | 0.05 M Tris-HCl, pH 8.0, 0.5 M KCl | | | |
| Human QC | H-Gln-NH$_2$ | 0.442 ± 0.030 | 12.8 ± 0.3 | 29 ± 1 | n.i. | 0.401 ± 0.014 | 12.2 ± 0.1 | 30 ± 1 | n.i. |
| | H-Gln-βNA | 0.076 ± 0.004 | 21.7 ± 0.5 | 285 ± 8 | 1.39 ± 0.08 | 0.063 ± 0.003 | 20.0 ± 0.4 | 318 ± 9 | 0.97 ± 0.04 |
| | H-Gln-Ala-OH | 0.269 ± 0.007 | 54.4 ± 0.5 | 202 ± 3 | n.i. | 0.357 ± 0.012 | 47.6 ± 0.6 | 133 ± 3 | n.i. |
| | H-Gln-Glu-OH | 0.373 ± 0.015 | 21.4 ± 0.3 | 57 ± 2 | n.i. | 0.607 ± 0.036 | 18.9 ± 0.5 | 31 ± 1 | n.i. |
| | H-Gln-Trp-Ala-NH$_2$ | 0.054 ± 0.003 | 50.8 ± 0.6 | 941 ± 41 | n.i. | 0.056 ± 0.002 | 50.0 ± 0.4 | 893 ± 25 | n.i. |
| | H-Gln-Arg-Gly-Ile-NH$_2$ | 0.166 ± 0.013 | 31 ± 1 | 187 ± 9 | n.i. | 0.091 ± 0.005 | 29.8 ± 0.5 | 327 ± 12 | n.i. |
| | H-Gln-Lys-Arg-Leu-NH$_2$ | 0.051 ± 0.003 | 29.4 ± 0.5 | 577 ± 24 | n.i. | 0.034 ± 0.001 | 31.6 ± 0.3 | 929 ± 19 | n.i. |
| | H-Gln-Glu-Asp-Leu-NH$_2$ | 0.060 ± 0.002 | 46.6 ± 0.5 | 777 ± 18 | n.i. | 0.061 ± 0.002 | 45.6 ± 0.5 | 748 ± 16 | n.i. |

Physiological Substrates

In earlier studies, conversion of [Gln$^1$]-TRH and [Gln$^1$]-GnRH by QC was already shown for the QC from bovine and porcine pituitary (Busby, W. H. J. et al. 1987 *J Biol Chem* 262, 8532-8536; Fischer, W. H. and Spiess, J. 1987 *Proc Natl Acad Sci USA* 84, 3628-3632). In addition to these already investigated pituitary hormones, three potential physiological substrates of human QC were synthesized and tested upon conversion, namely [Gln$^1$]Gastrin, [Gln$^1$]Neurotensin, and [Gln$^1$]FPP. The kinetic parameters for their conversion are listed in Table 1. Interestingly, the glutaminyl peptides are converted to the respective pyroglutamyl peptides with increasing specificity constants depending on their size, i.e., the first largest peptide pro-gastrin with 17 amino acids followed by pro-neurotensin, pro-GnRH, pro-TRH and pro-FPP. These findings correspond to the data obtained with the synthetic peptides.

Surprisingly, the longer substrates are also converted with higher selectivity by the plant enzyme, a result that contrasts in part with the findings for the shorter oligopeptides. Possibly, there are secondary binding interactions between substrate and enzyme far distant from the active site.

The conversion of Gln-MCP-1, as revealed by the resistance against degradation by DPIV, is provided in FIG. 26. MCP-1 is thus the largest QC substrate described thus far, substantiating that there are no size-restrictions for the accessibility of substrates to the active site of QC.

Peptides Comprising Modified Amino Acids

In order to further investigate the specificity and selectivity of the QCs, peptides were synthesized comprising either a modified N-terminal glutaminyl residue or a modified amino acid in the second position. The conversion of these peptides was investigated qualitatively utilizing MALDI-TOF mass spectrometry (see also example 3). Due to the cyclization of the glutaminyl residue or its analog, respectively, a mass difference of the substrate and the product of catalysis is detected. In cases of ammonia liberation of one mole per mole of substrate, the conversion was also analyzed quantitatively using the spectrophotometric assay.

Figure 5:
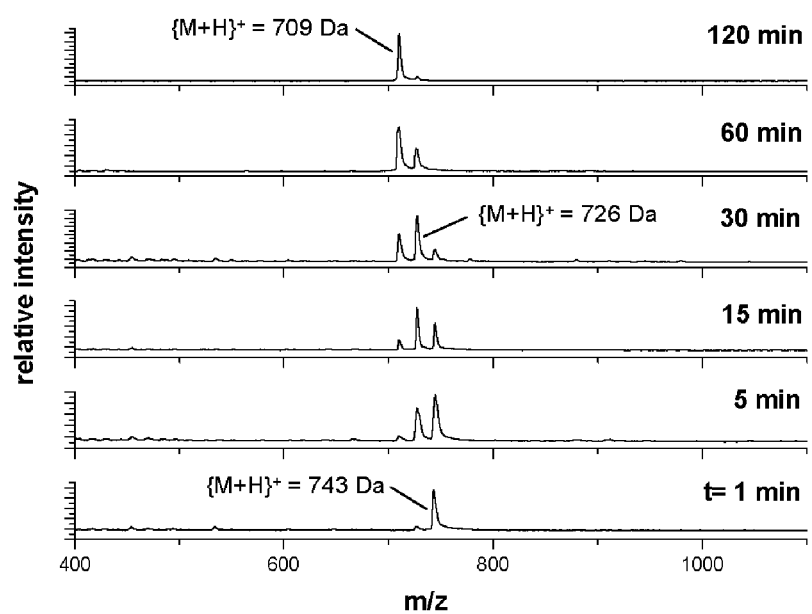
FIG. 5 shows the formation of pGlu-Lys(pGlu)-Arg-Leu-Ala-NH2 from H-Gln-Lys(Gln)-Arg-Leu-Ala-NH2, catalyzed by human QC. Substrate conversion is monitored by a time-dependent change in the m/z ratio due to the expulsion of ammonia. The sample composition was 0.5 mM substrate, 38 nM QC in 40 mM Tris/HCl, pH 7.7. At the times indicated, samples were removed from the assay tube, mixed with matrix solution (1:1 v/v) and subsequently the mass spectra recorded. A very similar dependence was observed in case of papaya QC.

H-Gln-Lys(Gln)-Arg-Leu-Ala-NH$_2$. This N-terminally branched peptide, comprising two glutaminyl residues at the N-terminus that are bound to a lysyl residue via a peptide- and partial isopeptide bond, was converted by human (FIG. 5) and papaya QC (not shown) in an apparently identical manner. Both glutaminyl residues were converted into pyroglutamic acid, without any detectable preference for a distinct residue, as indicated by the consistent substrate conversion (FIG. 5). Thus, the selectivity of the QCs for the differently bound glutaminyl residues differs not fundamentally.

Figure 6:
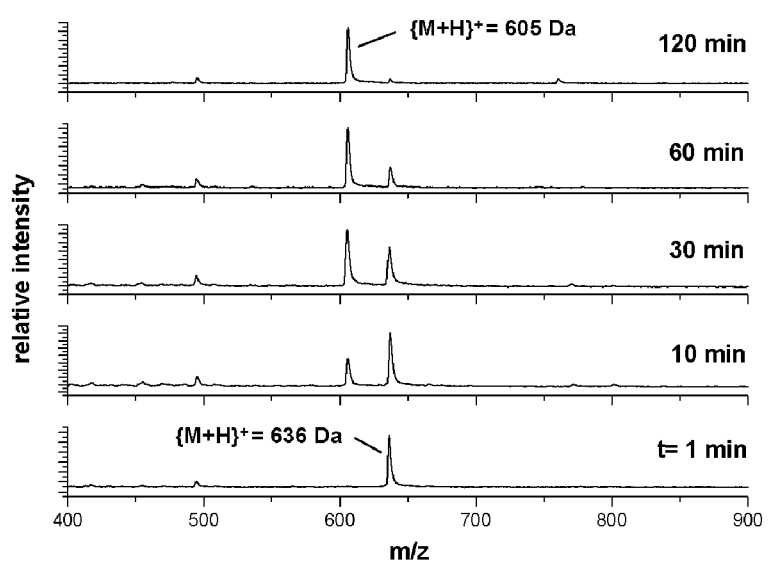
FIG. 6 shows the formation of pGlu-Phe-Lys-Ala-Glu-NH2 from H-Gln(NMe)-Phe-Lys-Ala-Glu-NH2 catalyzed by papaya QC. Substrate conversion is monitored by a time-dependent change in the m/z ratio due to the expulsion of methylamine. The sample composition was 0.5 mM substrate, 0.65 µM papaya QC in 40 mM Tris/HCl, pH 7.7. At the times indicated, samples were removed from the assay tube, mixed with matrix solution (1:1 v/v) and subsequently the mass spectra recorded. No substrate conversion was observed in samples without papaya QC or by applying up to 1.5 µM human QC to the substrate (not shown).

H-Gln(NMe)-Phe-Lys-Ala-Glu-NH$_2$. The methylated glutaminyl residue was only converted into a pyroglutamyl residue by papaya QC (FIG. 6). Additionally, an inhibition of the human QC by the peptide was not detected, indicating that the methylated residue is not recognized by human QC.

H-Glu(OMe)-βNA and H-Glu-βNA. None of these compounds were converted by papaya or human QC. These fluorogenic substrates were analyzed fluorometrically, utilizing pyroglutamyl aminopeptidase as auxiliary enzyme. The O-methylated glutamate residue, however, showed a remarkable instability in both, Tris and Tricine buffers tending to a non-enzymatically catalyzed cyclization. Furthermore, activity of both QCs against H-Gln-AMC as substrate was not inhibited by the longer peptides H-Glu(OMe)-Phe-Lys-Arg-Leu-Ala-NH$_2$ or H-Glu-Phe-Lys-Arg-Leu-Ala-NH$_2$, indicating that glutamic acid or derivates are not recognized by both QC forms. Furthermore, the result implies that not only the negative charge of the glutamic acid residue is the reason for the repulsion of the peptide from the active site.

H-Gln-cyclo(Nε-Lys-Arg-Pro-Ala-Gly-Phe). The conversion of H-Gln-cyclo(Nε-Lys-Arg-Pro-Ala-Gly-Phe), which contains an intramolecular partial isopeptide bond was analyzed quantitatively, revealing $K_M$-values of 240±14 μM and 133±5 μM for human and papaya QC, respectively. Due to the higher turnover number of conversion by papaya QC (49.4±0.6 s$^{-1}$) compared to human QC (22.8±0.6 s$^{-1}$), the plant enzyme exhibits with 372±9 mM$^{-1}$ min$^{-1}$ an approximately 4-fold higher $k_{cat}/K_M$-value than the human QC. Thus, the specificity constant is in case of the papaya QC only slightly smaller compared to substrates having a similar size, such as H-Gln-Ala-Ala-Ser-Ala-Ala-NH$_2$. The $k_{cat}/K_M$-value for human QC, however, was found with 95±3 mM$^{-1}$s$^{-1}$ to be approximately one order of magnitude smaller in comparison with substrates of similar size (Table 5).

H-βhomoGln-Phe-Lys-Arg-Leu-Ala-NH$_2$. The N-terminal β-homoglutaminyl residue was converted into a five-membered lactam ring by catalysis of human and papaya QC, respectively. The concomitant liberation of ammonia was analyzed spectrophotometrically and by MALDI-tof analysis as described before. There was no liberation of ammonia detected when QC was omitted or boiled, indicating a specific catalysis of the cyclization. Interestingly, the QC from *C. papaya* ($K_M$=3.1±0.3 mM, $k_{cat}$=4.0±0.4 s$^{-1}$) and human ($K_M$=2.5±0.2 mM, $k_{cat}$=3.5±0.1 s$^{-1}$) catalyze the conversion of this peptide with almost identical $k_{cat}/K_M$ values of 1.4±0.1 and 1.3±0.1 mM$^{-1}$s$^{-1}$, respectively. Thus, the cyclization of the β-homoglutamine residue is catalyzed with an approximately 1000-fold reduced efficiency compared to peptides of similar size containing a glutaminyl residue at their N-terminus. This shows that the constitution of the α-carbon of the substrate is important for substrate recognition by the QC forms, but not essential. The essential requirement for being a substrate is a γ-amide group and an unprotonated N-terminal amino group in distance and angle prone for cyclization, a requirement that is fulfilled by N-terminal glutaminyl and β-homoglutaminyl residues.

Figure 16:
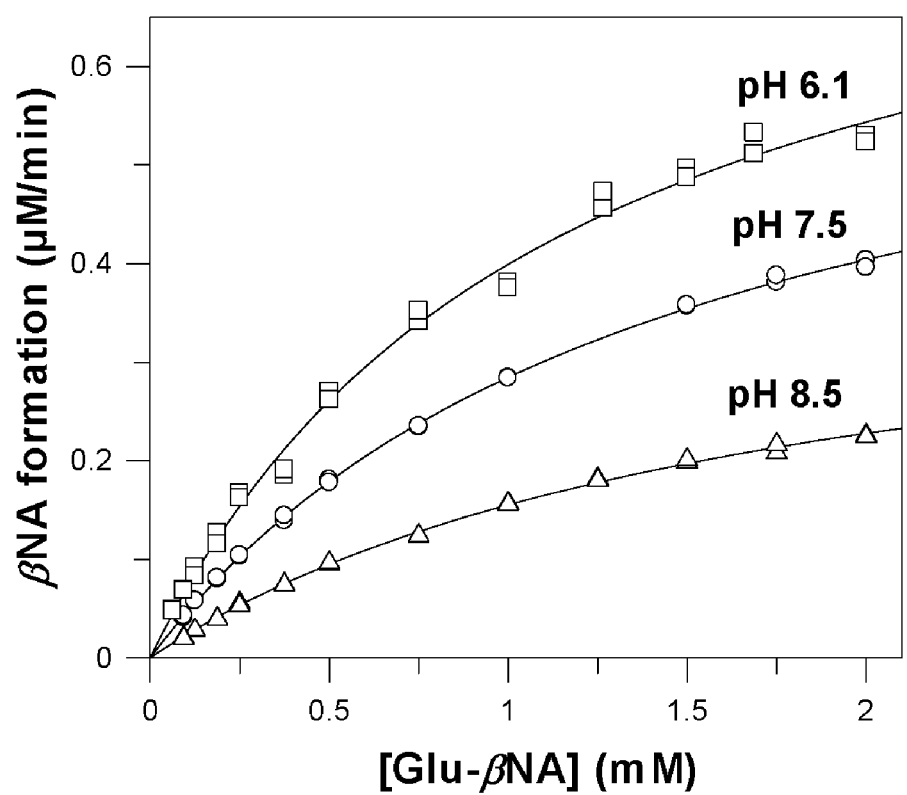
FIG. 16 shows reaction rates of papaya QC-catalyzed Glu-βNA-conversion plotted against the substrate concentration. The initial rates were measured in 0.1 M pyrophosphate buffer, pH 6.1 (squares), 0.1 M phosphate buffer, pH 7.5 (circles) and 0.1 M borate buffer, pH 8.5 (triangles). The kinetic parameters were as follows: $K_M$=1.13±0.07 mM, kcat=1.13±0.04 min−1 (pH 6.1); $K_M$=1.45±0.03 mM, kcat=0.92±0.01 min−1 (pH 7.5); $K_M$=1.76±0.06 mM, kcat=0.56±0.01 min−1 (pH 8.5).

The relaxed substrate specificity described here with amide substrates is in line with the identification of the EC activity of QC depicted in FIGS. 15-17 and represents the basis for the conversion of glutamic acid in vivo, as shown in FIG. 23.

Example 6

Synthesis of the QC Substrates

Oligopeptides. Peptides were synthesized semiautomatically in 0.5 mmol scale using a peptide synthesizer (Labortec SP650, Bachem, Switzerland) as previously described (Schilling, S. et al. 2002 *Biochemistry* 41, 10849-10857). Longer peptides were synthesized in 25 μmol scale using the automated Symphony peptide synthesizer (Rainin Instrument Co.) as described (Manhart, S. et al. 2003 *Biochemistry* 42, 3081-3088). For all peptide couplings modified Fmoc-protocols of solid-phase peptide synthesis were employed using 2-(1H-Benzotriazole-1-yl)-1,1,3,3-tetramethyluronium tetrafluoroborate (TBTU; Novabiochem)/base (diisopropyl ethylamine or N-methyl-morpholine; Merck) or in case of difficult couplings N-[(Dimethylamino)-1H-1,2,3-triazolo[4,5-b]pyridin-1-ylmethylene]-N-methyl-methanamminium hexafluorophosphate N-oxide (4,5) (HATU; Applied Biosystems)/diisopropyl ethylamine as activating reagents were used. After cleavage from the resin by trifluoroacetic acid (TFA; Merck) containing cocktail, the crude peptides were purified by preparative HPLC with acid free solvents in order to avoid further cyclization of the N-terminal glutamine. Preparative HPLC was performed with a linear gradient of acetonitrile (Merck) in water (5-40% or 65% acetonitrile over 40 min) on a 250-21 Luna RP 18 column (Phenomenex). To confirm peptide purity and identity analytical HPLC and ESI-MS was employed.

Glu(NH—$NH_2$)-Ser-Pro-Thr-Ala-$NH_2$. The linear precursor peptide (Fmoc-Glu-Ser-Pro-Thr-Ala-$NH_2$) was synthesized according to standard Fmoc-procedures (Schilling, S. et al. 2002 *Biochemistry* 41, 10849-10857) on Rink amide MBHA resin (Novabiochem). After cleavage of the Fmoc-protected peptide from the resin, the peptide was precipitated with diethyl ether (Merck), filtered and dried. HMBA-AM resin (1.16 mmol/g, Novabiochem) was used for coupling of the γ-carboxylic acid group of glutamic acid of the precursor peptide (3 eq.) in dichloromethane (DCM, Merck). Dicyclohexylcarbodiimide (DCC, Serva) (4 eq.) and dimethylaminopyridine (DMAP, Aldrich) (0.1 eq) were used as coupling reagents. After 12 hours the resin was filtered, washed with DCM and the reaction was repeated. After deprotection of the N-terminal Fmoc-group by employing 20% piperidine in DMF (3×5 min) the peptide resin was treated with a 5% hydrazine solution (20 ml/g) for 1.5 hours. The resin was filtered and washed with dimethylformamide (DMF, Roth, Germany) and TFA. Following evaporation, the crude peptide was precipitated with ether giving 76% yield.

H-Gln-Lys(Gln)-Arg-Leu-Ala-$NH_2$. The linear peptide was synthesized according to standard Fmoc/$^t$Bu-procedure on Rink amide MBHA (Schilling, S. et al. 2002 *Biochemistry* 41, 10849-10857) using Fmoc-Lys (Fmoc)-OH as penultimate amino acid coupling. After deprotection of the two amino protecting groups of lysine with 20% piperidine (Merck) in DMF, 4 eq. Fmoc-Gln(Trt)-OH were coupled. Standard cleavage procedure resulted in 95% yield.

H-Gln(NMe)-Phe-Lys-Ala-Glu-$NH_2$. Fmoc-Gln(NMe)-OH was synthesized starting from Fmoc-Glu-OtBu loaded on Fmoc-MI-AM (Novabiochem) resin. After swelling with DCM, the resin (0.5 g) washed with DMF and deprotected with 20% piperidine solution in DMF. The resin was given into 5 ml DMF and 5 eq. Fmoc-Glu-OtBu, 5 eq. HATU and 10 eq. DIPEA were added subsequently and shaked for 6 hours. After filtration and washing, the product was cleaved according to standard TFA cleavage conditions. The peptide H-Gln(NMe)-Phe-Lys-Ala-Glu-$NH_2$ was synthesized as described (Schilling, S. et al. 2002 *Biochemistry* 41, 10849-10857). Fmoc-Gln(NMe)-OH was coupled with HATU/DIPEA overnight. Standard cleavage procedure resulted in 78% of the crude peptide.

H-Glu(OMe)-β-naphthylamide, H-Gln-Val-OH, H-Gln-Tyr-OH. Boc-protected dipeptides were synthesized applying standard mixed anhydride procedure by using isobutyl chlorocarbonate (Merck). The C-terminal methylesters Boc-Gln-Tyr-OMe and Boc-Gln-Val-OMe were saponified by 1N NaOH in dioxane. The Boc-protected peptides were deprotected by HCl/dioxane solution for 10 min. After evaporation the residue was crystallized with several solvents giving 60-70% of a solid compound.

H-Gln-cyclo(Nε-Lys-Arg-Pro-Ala-Gly-Phe). The linear precursor Boc-Gln(Trt)-Lys-Arg(Pmc)-Ala-Gly-Phe-OH was synthesized on acid sensitive 2-chlorotrityl resin. Coupling was carried out using a standard protocol of Fmoc/$^t$Bu-strategy using Fmoc-Lys(Mtt)-OH. After cleavage with 3% TFA solution in DCM (10 times 5 min), the solution was neutralized with 10% pyridine (Merck) in methanol (MeOH; Merck), washed 3 times with DCM and MeOH, evaporated to 5% of the volume and the crude peptide was precipitated with icecold water. Following, the crude peptide was cyclized using DCC/N-hydroxybenzotriazole (HOBt; Aldrich) activation. The crude peptide was dissolved in dry dichloromethane (0.2 mmol/50 ml), 0.2 mmol N-methylmorpholine and 0.4 mmol 1-hydroxybenzotriazole were added. This solution was added dropwise to a solution of 0.4 mmol dicyclohexylcarbodiimide in 250 ml dichloromethane at 0° C. Stirring overnight at room temperature completed the reaction. After filtration of N,N'-dicyclohexylurea, the solvent was removed by evaporation. The residue was dissolved in ethyl acetate and washed several times with 1N HCl, saturated solution of $NaHCO_3$ and water. The solution was dried over anhydrous $Na_2SO_4$, filtered and evaporated to dryness in vacuo.

Example 7

Characterization of Effectors of QC

Imidazole Derivatives

Imidazole and benzimidazole derivatives carrying substitutents in different positions of the 5-membered ring were tested as inhibitors of QC (Table 3). The constitution of the numbers refers to the imidazole ring. The applied methods are described in example 2.

C-4(5) and C-4,5 derivatives. The compounds carrying substitutions in either in the constitutionally equivalent 4- or 5-position of the imidazole ring or in both positions showed a diminished potency for inhibition of human QC. The only exception, however, comprised N-ω-acetylated histamine that proved to be one of the most potent inhibitory compounds. Small substitutents in these positions had only little effect on binding as indicated by the similar inhibition constant of 5-hydroxymethyl-4-methyl-imidazole compared to imidazole. Larger and more bulky groups attached to these sites diminished or abolished binding of the compound by the enzyme. Some of the other substitutents tested are known to exert negative inductive or mesomeric effects that are capable to reduce the electron density in the imidazole ring, which also contributes to poorer binding constants. The difference in the $K_i$-values of L-histidine and histidinamide also indicate some influence of the charge on binding. Evidence for electrostatic repulsion of charged substrates were already shown in the substrate specificity studies, i.e. human QC converted glutaminamide to products readily, but no reactivity was observed for free glutamine as substrate.

C-2 derivatives. All derivatives tested inhibited QC weaklier than imidazole. Any substitution bigger than a proton hinders proper QC-binding. Only due to the methyl group in 2-methyl-benzimidazole, the inhibition constant drops about one order of magnitude. A very similar relation was shown by comparison of the $K_i$-values for benzimidazole and 2-amino-benzimidazole. Additionally, the results indicate that the influence is not related to electronic alterations.

N-1 derivatives. Among the imidazole derivatives tested on inhibition of human QC, most compounds that had improved $K_i$-values compared to imidazole showed alterations at one nitrogen atom. These compounds also contained one of the most effective QC inhibitors, 1-benzylimidazole. Interestingly, only little alterations of this structure led to a loss of inhibitory quality, as can be seen for 1-benzoylimidazole and phenylimidazole, which was inactive under the experimental conditions. Also in this case, the observed changes did not seem to be caused by a reduced electron density of the imidazole ring due to the negative mesomeric effect of the phenyl group, because also the bulky trimethyl-silyl group, exhibiting a positive inductive effect showed reduced binding compared to other residues. Interestingly, one of the less effective compounds of this group was 1-aminopropyl-imidazole. The basic amino group causes the small efficacy of this compound, since the sterically similar compounds 1-methylimidazole and 1-vinylimidazole showed improved binding to the active site. Thus, the positively charged amino group accounts for the smaller $K_i$-value, a result that is corroborated by a comparison of the $K_i$-values of N-ω-acetylated histamine (Table 3) and histamin (Table 4).

Effect of 3.4 and 3.5 derivatization. The imidazole derivatives that contained substitutents in positions 4(5) or both were shown to have a restricted efficiency for binding to the enzyme. The effects of the specific substitutions were specified by comparison of the inhibitory constants of L-histamine and the two intermediates in the biological degradation of histamine, 3-methyl-4-histamine and 3-methyl-5-histamine (Table 4). L-Histamine revealed a $K_i$ value that was about one order of magnitude smaller compared to its acetylated counterpart. Methylation of one nitrogen resulted in a considerable improvement of efficacy in case of 3-methyl-4-histamine. Methylation leading to 3-methyl-5-histamine, however, resulted in a complete loss of inhibitory activity. Thus, the observed effect seems to be mainly caused by a sterical hindrance of binding due to the derivatisation of the carbon adjacent to the basic nitrogen. Presumably, the basic nitrogen plays a key role for binding to the enzyme.

Example 8

Formation of Aβ3-40/42 Derivatives

The measurements were carried out with two short N-terminal peptide sequences of Aβ3-40/42, [Gln³]-Aβ1-11 (sequence: DAQFRHDSGYE) and [Gln³]Aβ3-11, which contain a glutamine instead of an glutamic acid residue in the third position. Cleavage by DP IV and cyclization of the N-terminal glutamine residue by QC of the two peptides was tested using MALDI-TOF mass spectrometry. Measurements were carried out using purified DP IV (porcine kidney) or crude porcine pituitary homogenate as sources of QC as well as for both enzymes for measurements of consecutive catalysis.

Results

1. Formation of [Gln³]Aβ3-11a from [Gln³]Aβ1-11a Catalysed by DPIV and its Prevention by the DP IV-Inhibitor Val-Pyrrolidide (Val-Pyrr)

DPIV or DPIV-like activity cleaves [Gln³]Aβ1-11a under formation of [Gln³]Aβ3-11a (FIG. 7). The residue in the third position is uncovered by this cleavage and becomes therefore accessible for modification by other enzymes, i.e. QC. As expected, catalysis can be completely prevented by Val-Pyrr (FIG. 8).

2. Formation of [pGlu³]Aβ3-11a from [Gln³]Aβ3-11a by Catalysis of QC in Pituitary Homogenate and Prevention by 1,10-Phenanthroline Glutaminyl cyclase present in the homogenate of porcine pituitary catalyzes conversion of [Gln³]Aβ3-11a to [pGlu³]Aβ3-11a (FIG. 9). Formation of [pGlu³]Aβ3-11a was inhibited by addition of 1,10-phenanthroline (FIG. 10).

Figure 11:
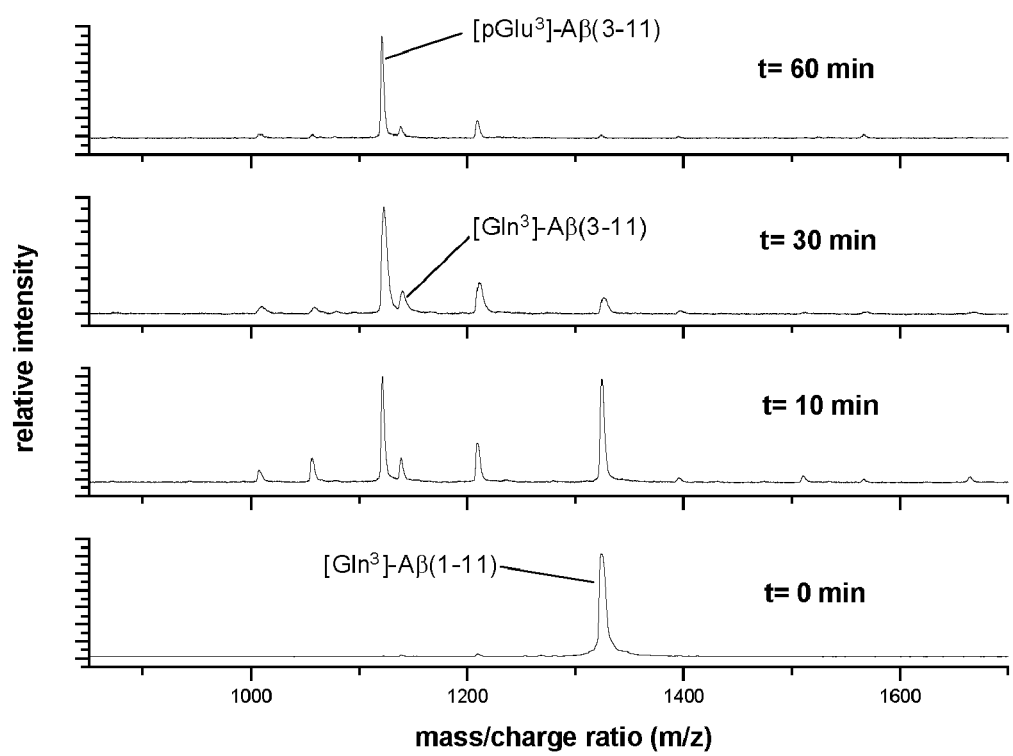
FIG. 11 shows the formation of [pGlu3]Aβ(3-11) from [Gln3]Aβ(1-11) after consecutive catalysis by DP IV and QC. At the times indicated, samples were removed from the assay tube, mixed with matrix solution (1:1 v/v) and subsequently the mass spectra recorded.
Figure 12:
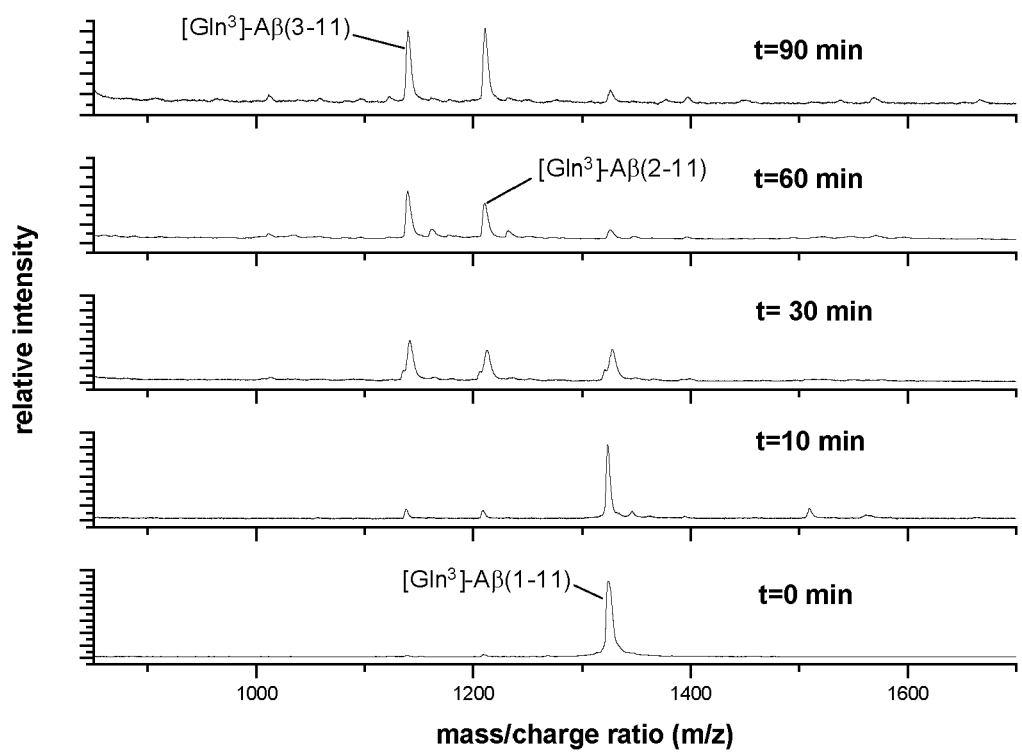
FIG. 12 shows the inhibition of [pGlu3]Aβ(3-11) formation from [Gln3]Aβ(1-11) by the QC-inhibitor 1,10-phenanthroline in the presence of catalytically active DP IV and QC. At the times indicated, samples were removed from the assay tube, mixed with matrix solution (1:1 v/v) and subsequently the mass spectra recorded.
Figure 13:
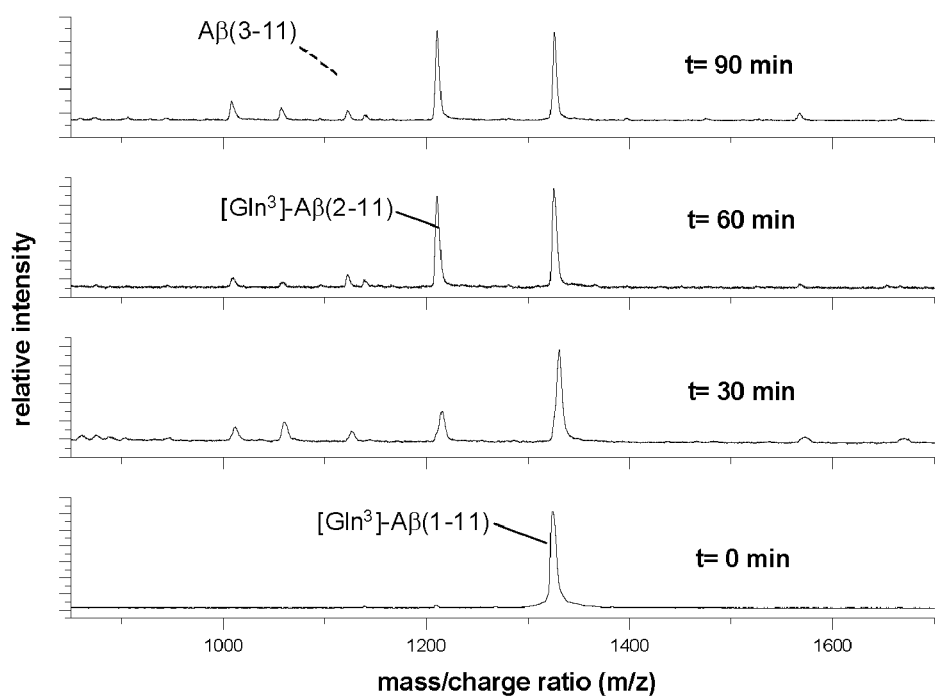
FIG. 13 shows the reduction of [pGlu3]Aβ(3-11) formation from [Gln3]Aβ(1-11) by the DP IV-inhibitor Val-Pyrr in the presence of catalytically active DP IV and QC. At the times indicated, samples were removed from the assay mixture, mixed with matrix solution (1:1 v/v) and subsequently the mass spectra recorded.

3. Consecutive Catalysis of DPIV and QC Resulting in Formation of [pGlu³]Aβ3-11a and Prevention by Val-Pyrr and 1,10-Phenanthroline Formation of [pGlu³]Aβ3-11a from [Gln³]Aβ1-11a takes place after consecutive catalysis by DP IV and QC, measured in crude homogenate of porcine pituitary with added DPIV from porcine kidney (FIG. 11). [pGlu³]Aβ3-11a was not formed when the QC-inhibitor 1,10-phenanthroline (FIG. 12) or the DP IV-inhibitor Val-Pyrr was added (FIG. 13). The slight appearance of [pGlu³]Aβ3-11a is due to aminopeptidase cleavage and following cyclization of the glutamine residue, also indicated by formation of [Gln³]Aβ2-11a.

4. Formation of [pGlu³]Aβ3-11a in Crude Pituitary Homogenate by Catalysis of Aminopeptidase(s)

Figure 14:
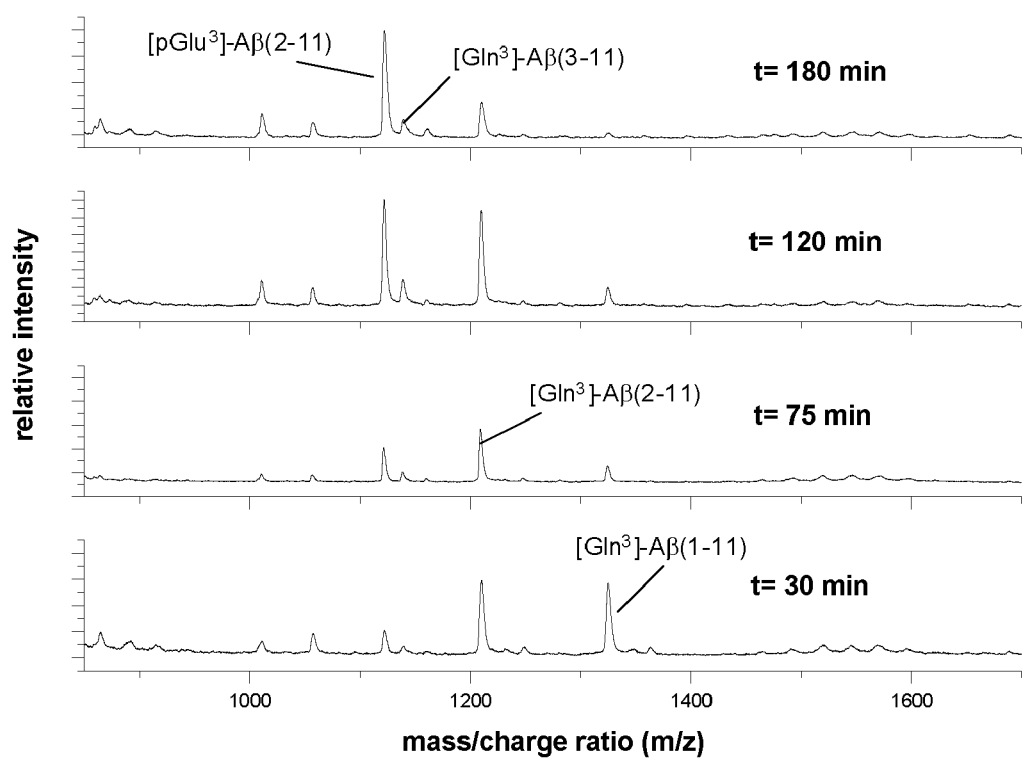
FIG. 14 shows the formation of [pGlu3]Aβ(3-11) from [Gln3]Aβ(1-11) after consecutive catalysis by aminopeptidase(s) and QC that are present in porcine pituitary homogenate. At the times indicated, samples were removed from the assay tube, mixed with matrix solution (1:1 v/v) and subsequently the mass spectra recorded.

Due to the formation of [pGlu³]Aβ3-11a that was not dependent on DPIV catalysis, degradation of [Gln³] Aβ1-11a was investigated in crude pituitary homogenate without the addition of DPIV (FIG. 14) . . . \PrimaryData\Massenspektren\APP3-11_QC-I.doc. As expected from the data in section 4, formation of [pGlu³]Aβ3-11a was observed. The data show that the degradation of [Gln³]Aβ1-11a may also be catalyzed by aminopeptidase(s), resulting in [pGlu³]Aβ3-11a. Hence, the results show that pyroglutamyl formation is an endpoint of N-terminal peptide degradation in this tissue, further supporting the role of QC in plaque formation.

Example 9

Turnover of [Gln³]Aβ3-11a; 3-21a and 3-40 by Recombinant Human QC

All [Gln³]Aβ derived peptides tested, were efficiently converted by human QC into the corresponding pyroglutamyl forms (Table 8). Due to the poor solubility of [Gln³]Aβ3-21a and [Gln³]Aβ3-40 in aqueous solution, the determinations were carried out in presence of 1% DMSO. The higher solubility of [Gln³]Aβ3-11a, however, allowed the kinetic analysis of the QC-catalyzed turnover in presence and absence of DMSO (Table 8). Taken together, the investigation of the Aβ peptides as QC-substrates with chain-length of 8, 18 and 37 amino acids (see Table 8) confirmed the observation that human QC-activity increases with the length of its substrates. Accordingly, Gln¹-gastrin, Gln¹-neurotensin, Gln¹-GnRH are among the best QC-substrates taking the specificity constants into account. Similarly, [Gln³]Aβ3-40 and glucagon, the largest QC-substrates investigated thus far, exhibited high second order rate constants (449 mM$^{-1}$s$^{-1}$ and 526 mM$^{-1}$s$^{-1}$ respectively) even in presence of 1% DMSO (Table 8).

Interestingly, the kinetic parameters for the conversion of the investigated amyloid peptides did not change dramatically with increasing size, suggesting only moderate effects of the C-terminal part of Aβ on QC catalysis. Therefore, due to better solubility and experimental handling, the further investigations concerning N-terminal aminopeptidase processing of these peptides were performed using the smaller fragments of Aβ, [Gln$^3$]Aβ1-11a, [Gln$^3$]Aβ3-11a and Aβ3-11a.

TABLE 8

Kinetic parameters for conversion of N-terminally Gln-containing peptides by recombinant human QC in buffer solution containing 1% DMSO

| Peptide | K$_M$ (µM) | k$_{cat}$ (s$^{-1}$) | k$_{cat}$/K$_M$ (mM$^{-1}$s$^{-1}$) |
|---|---|---|---|
| [Gln$^3$]Aβ3-11a | 87 ± 3# | 55 ± 1# | 632 ± 10# |
| [Gln$^3$]Aβ3-11a | 155 ± 4 | 41.4 ± 0.4 | 267 ± 4 |
| [Gln$^3$]Aβ3-21a | 162 ± 12 | 62 ± 3 | 383 ± 10 |
| [Gln$^3$]Aβ3-40 | 89 ± 10 | 40 ± 2 | 449 ± 28 |
| Glucagon(3-29) | 19 ± 1 | 10.0 ± 0.2 | 526 ± 17 |

Determined in absence of DMSO

Example 10

Turnover of Aβ3-11a and Aβ3-21a by Recombinant Human QC

In contrast to previous work, the incubation of Aβ3-11a and Aβ3-21a in presence of QC revealed that glutamate-containing peptides can also serve as QC-substrates (FIGS. 15C and D). The QC-catalyzed formation of [pGlu$^3$]Aβ3-11a and [pGlu$^3$]Aβ3-21a was investigated at pH 5.2 and 6.5, respectively. If the QC-inhibitor benzimidazole was added to the solution before starting the assay by addition of QC, substrate conversion resulting in [pGlu$^3$]Aβ3-11a or [pGlu$^3$]Aβ3-21a was suppressed (FIGS. 15E and F). If QC was boiled before addition, formation of the pGlu-peptides was negligible (FIGS. 15A and B).

Example 11 pH-Dependency of the Papaya QC-Catalyzed Cyclization of Gln-βNA and Glu-βNA

Papaya QC converted Glu-βNA in a concentration range up to 2 mM (which was limited by substrate solubility) in accordance with Michaelis-Menten kinetics (FIG. 16). Inspection of turnover versus substrate concentration diagrams for the QC-catalyzed conversion of Glu-βNA, studied between pH 6.1 and 8.5, revealed that for this Glu-substrate both parameters, K$_M$ and k$_{cat}$, changed in a pH-dependent manner (FIG. 16). This is in contrast to the previously described QC-catalyzed glutamine cyclization, for which only changes in K$_M$ were observed over the given pH range (Gololobov, M. Y., Song, I., Wang, W., and Bateman, R. C. (1994) *Arch Biochem Biophys* 309, 300-307).

Subsequently, to study the impact of the proton concentration during Glu- and Gln-cyclization, the pH-dependence of cyclization of Glu-βNA and Gln-βNA under first-order rate-law conditions (i.e. substrate concentrations far below K$_M$ values) was investigated (FIG. 17). The cyclization of glutamine has a pH-optimum at pH 8.0, in contrast to the cyclization of glutamic acid which showed a pH-optimum of pH 6.0. While the specificity constants at the respective pH-optima differ approximately 80,000-fold, the ratio of QC versus EC activity around pH 6.0 is only about 8,000.

The nonenzymatic pGlu-formation from Gln-βNA investigated at pH 6.0, was followed for 4 weeks and revealed a first-order rate constant of 1.2*10$^{-7}$ s$^{-1}$. However, during the same time period, no pGlu-βNA was formed from Glu-βNA, allowing to estimate a limiting rate constant for turnover of 1.0*10$^{-9}$ s$^{-1}$.

Example 12

Enzyme Inactivation/Reactivation Procedures

An aliquot of human QC (0.1-0.5 mg, 1 mg/ml) was inactivated overnight by dialysis against a 3000-fold excess of 5 mM 1,10-phenanthroline or 5 mM dipicolinic acid in 0.05 M Bis-Tris/HCl, pH 6.8. Subsequently, the inactivating agent was carefully removed by dialysis (3 cycles, 2000-fold excess) of the samples against 0.05 M Bis-Tris/HCl, pH 6.8, containing 1 mM EDTA. Reactivation experiments were performed at room temperature for 15 minutes using Zn$^{++}$, Mn$^{++}$, Ni$^{++}$, Ca$^{++}$, K$^+$ and Co$^{++}$ ions at concentrations of 1.0, 0.5, 0.25 mM in 0.025 M Bis-Tris, pH 6.8 containing 0.5 mM EDTA. QC activity assays were performed in 0.05 M Tris/HCl, pH 8.0, containing 2 mM EDTA, in order to avoid a rapid reactivation by traces of metal ions present in buffer solutions.

Human QC was almost completely inactivated after extensive dialysis against 5 mM 1,10-phenanthroline or 5 mM dipicolinic acid. After repeated dialysis overnight against chelator-free buffer solutions, QC activity was partially reactivated up to 50-60%. However, when dialyzed against buffers containing 1 mM EDTA, no reactivation was observed.

Near-total restoration of QC activity after inactivation by either dipicolinic acid or 1,10-phenanthroline was achieved by incubating the protein for 10 minutes with 0.5 mM ZnSO$_4$ in presence of 0.5 mM EDTA (FIG. 20). Partial restoration of QC activity was similarly obtained using Co$^{++}$ and Mn$^{++}$ ions for reactivation. Even in the presence of 0.25 mM Zn$^{++}$ a reactivation up to 25% of the original activity was possible. No reactivation was observed applying Ni$^{++}$, Ca$^{++}$ or K$^+$ ions. Similarly, incubation of fully active QC with these ions had no effect on the enzyme activity.

Example 13

In Vitro Studies

It was the object of the following in vitro studies to provide I) evidence that QC catalyses the cyclization of glutamic acid at the N-terminus of Aβ(3-40/42) in vitro applying isolated recombinant enzyme, II) to prove QC-catalyzed pGlu-Aβ (3-40/42) formation in a cell-culture system and III) to demonstrate efficacy of the inhibitor 1-(3-(1H-imidazole-1-yl) propyl)-3-(3,4-dimethoxy-phenyl)thiourea hydrochloride in both approaches. In a further study, the oligomerization of pGlu-Aβ peptides was characterized.

a) Conversion of Aβ(3-40) by Purified Human QC

QC/EC-catalyzed formation of pGlu-Aβ(3-40) from Aβ(3-40) was analyzed using a specific ELISA. Commercially available microplates, coated with an antibody specifically binding the Aβ40 C-terminus, were applied in combination with a conjugated pGlu-Aβ specific antibody. Samples consisted of Aβ(3-40) (0.1-20 µM) in 100 mM Mes, pH 6.5, containing 0.1% Triton X-100 and 6 units of human QC.

Reactions were incubated at 30° C. for up to 72 h. At indicated times, aliquots were withdrawn, QC was heat-inactivated for 2 min at 100° C. and samples stored at −20° C. until analysis. For suppression of pGlu-Aβ formation, 5 μM 1-(3-(1H-imidazole-1-yl)propyl)-3-(3,4-dimethoxy-phenyl)thiourea hydrochloride was added. Significant pGlu-Aβ formation was observed in presence of active QC from the beginning. At these times, there was no pGlu-Aβ detected in samples, which contained the inhibitor. Little pGlu-Aβ was detected after 72 h of incubation, i.e. at the end of the experiment.

The results clearly indicate that cyclization of glutamic acid at the N-terminus of Aβ(3-40) is a QC-catalyzed process, which can be suppressed by QC-inhibitors (see FIG. 24-1). Thus, QC catalyzes the generation of pGlu-Aβ in vitro by promoting the cyclization of glutamic acid.

b) Analysis of pGlu-Aβ Formation in Cell Culture

Generation of pGlu-Aβ(3-42) was assessed in cell culture, following expression of either Aβ or APP in β-TC3 or HEK293 cells, respectively. Cells were transiently transfected with the respective plasmids, and Aβ present in the medium was analyzed 24 h after transfection, applying ELISAs quantifying total Aβ (Aβ(x-42)) or pGlu-Aβ(3-42). Aβ(x-42) shall here relate to all N-terminal Aβ or truncated Aβ forms.

The direct expression of Aβ in the secretory pathway was achieved by fusion of the coding sequence of Aβ(3-42) C-terminally to the murine TRH-prepro-sequence. The prepro-sequence (SEQ ID No: 1-3) is successively processed in the secretory pathway by signalpeptidase and prohormone convertases, resulting in liberation of Aβ(3-42). In the accompanying approach, plasmids encoding variants of human APP were transfected into HEK293 cells (FIG. 24-2). The processing by β- and γ-secretase yields high amounts of Aβ(3-40/42), which can be detected in the culture medium.

Expression of APP-NL, NLE and NLQ resulted in generation of significant amounts of Aβ (FIG. 24-5, 24-4A). Aβ generation, although at a lower level, was also observed after expression of the mTRH-Aβ constructs (FIG. 24-4B, 24-5B). Interestingly, in case of expression of the Gln³-Aβ constructs, complete conversion into pGlu-Aβ was observed, as evident by a comparison of the Aβ (x-42) and the pGlu-Aβ(3-42) concentrations. Expression of human QC in both experimental settings resulted in conspicuous generation of pGlu-Aβ(3-42), substantiating the involvement of QC in pGlu-formation from N-terminal glutamic acid. The QC-mediated pGlu-Aβ formation was proven by application of the QC-inhibitor 1-(3-(1H-imidazole-1-yl)propyl)-3-(3,4-dimethoxy-phenyl)thiourea hydrochloride in both applied experimental settings. While the total Aβ concentration was not reduced, indicating no general adverse effect on the viability of the cells, the pGlu-Aβ concentration was significantly reduced by 1-(3-(1H-imidazole-1-yl)propyl)-3-(3,4-dimethoxy-phenyl)thiourea hydrochloride (FIG. 24-4).

In an accompanying experiment, the location of the pGlu-Aβ formation was characterized (FIG. 24-3). On the one hand, the DNA-constructs encoding APP NLE and hQC were transfected and co-expressed as before. Additionally, APP NLE was expressed and the medium was spiked with recombinant human QC. A QC activity was chosen that was fairly above the concentration present in the medium of expressing HEK293 cells 24 h after transfection. Both experiments were terminated and the pGlu-Aβ concentration in the medium determined. A significantly higher pGlu-Aβ level was observed in the case of co-transfection, suggesting that pGlu-Aβ formation in the model is facilitated intracellularly, i.e. in I) acidic environment, which favor Glu-cyclisation by QC and II) at high (vesicular) concentrations of APP and hQC.

From the above it becomes clear that human QC catalyzes the generation of pGlu-Aβ ex vivo, the process is favored under intracellular conditions, presumably in the secretory pathway.

c) Oligomerization of pGlu-Aβ Peptides In Vitro

In a first approach to demonstrate the crucial role of pGlu-Aβ peptides with regard to amyloidogenesis, different N-terminally modified Aβ peptides were studied in terms of their velocity of oligomer and fibril formation.

Two different methodologies were applied:

1.) Formation of oligomers and fibrils in vitro, based on native and fluorescence-labelled Aβ(1-42), Aβ(3-42) or pGlu-Aβ(3-42) followed by detection and quantification of the aggregates applying flow cytometry, and 2.) Investigation of the respective Aβ40 peptides using ThioflavineT-mediated fluorescence.

Native Aβ42 was spiked with monomeric Alexa Fluor 488 labeled Aβ peptides (20% of the final concentration) and incubated at a 10 μM total peptide concentration for up to 24 h. At different times, samples were removed, diluted to 10 nM (based on the initial concentration of the monomer), and analyzed by flow cytometry. Only very little fibril formation was detected for Aβ(1-42) after 24 h of incubation. The samples containing the N-truncated variants Aβ(3-42) and pGlu-Aβ(3-42) displayed fibril formation already after a few hours. Fibril formation from monomeric pGlu-Aβ(3-42) was finished already after 2-3 h of incubation, implying an exceptionally high tendency to aggregation (FIG. 24-6A). The results were verified for Aβ(1-42) and pGlu-Aβ(3-42) by another set of experiments using unmodified Aβ peptides and an incubation with a fluorescence-labeled antibody (clone 4G8, Chemicon, Temecula, Calif.) prior to analysis by flow cytometry. As observed with the labeled peptides, fibril formation was virtually finished in the case of pGlu-Aβ(3-42) after 1 h of incubation (FIG. 24-6B). During time, only minor fibril formation was detected for Aβ(1-42). After 24 h, however, fibril concentration appeared to be the same as in case of pGlu-Aβ(3-42) (FIG. 24-6).

Another experimental approach was done to characterize the potential role of N-truncated, modified Aβ for formation of aggregates. Monomeric pGlu-Aβ(3-42) was incubated with labeled Aβ(1-42) and unmodified Aβ(1-42) at a 10 μM final peptide concentration and a relative ratio of 1:2:7, respectively (FIG. 24-6C). Interestingly, fibril formation was detected after 4-5 h in the presence of pGlu-Aβ(3-42). This contrasts with the significantly longer lag phase observed with Aβ(1-42) alone, indicating that the addition of pGlu-Aβ to Aβ(1-42) leads to accelerated seeding of fibril formation of the excess of Aβ(1-42), implying, in turn, that N-truncated and full length Aβ form mixed fibrillar aggregates.

The observations for the Aβ42 peptides were substantiated using a common ThT fluorescence assay (FIG. 24-6D). N-truncated Aβ40 species showed an earlier raise in fluorescence compared to Aβ(1-40), indicating an accelerated oligomerization. pGlu-Aβ(3-40) displayed a much faster aggregation compared to the non-cyclized counterpart, suggesting an influence of the N-terminal modification on the fibril formation, in particular on the seeding process. The progress curves of pGlu-Aβ(3-40) revealed a different shape compared to the N-truncated, unmodified peptides. The typical lag phase, i.e. the thermodynamically unfavorable period, in which the seeds are generated, is displaced by a hyperbolic initial phase. Thus, there is a much higher tendency to formation of ThT positive initial aggregates.

A quantification of the relative initial oligomer formation is provided in Table 9.

Example 14

In Vivo Studies

It was the object of the following studies to provide evidence for a QC-mediated pGlu-Aβ formation in vivo, using a rat model based on cortical injection of Aβ peptides. It was the central goal to prove that QC is responsible for pGlu-Aβ formation in vivo and that inhibitors are even efficacious in state of the art Aβ animal models, which display an under-represented pGlu-Aβ pathology.

a) Formation of Glu-Aβ in a Rat Model Based on Traumatic Brain Injury

Formation of pGlu-Aβ was demonstrated in a rat model (Shin et al., 1997; J. Neurosci. 17: 8187-93). Here, one day after intrahippocampal/intracortical injection of freshly solubilized Aβ (1-40), aggregates could be detected using Congo red birefringence and immunohistochemistry. Aβ (1-40) contained fibrillar structures similar to Aβ. N-termini and C-termini of Aβ were processed in vivo yielding variants starting at Asp1 or at pGlu3 and ending at Val40 or Val39, suggesting that the rat brain produces enzymes that mediate the conversion of Aβ(1-40) into variants similar to those found in human Aβ deposits. This model facilitates efforts to elucidate the mechanisms of Aβ deposition evolving into amyloid plaques in Aβ therefore suggesting its usability as a primary screen for proof of concept (POC) studies in the field.

Specifically, it is the primary goal to characterize the dose, time, and site-specific effects of different QC inhibitors on deep intracortical applied Aβ species in the rat brain.

In initial trials, the effect of the QC-inhibitor 1-(3-(1H-imidazole-1-yl)propyl)-3-(3,4-dimethoxy-phenyl)thiourea hydrochloride on formation of pGlu-Aβ(3-40) after intracerebral (ic) injection of Aβ (1-40) or Aβ(3-40) was assessed, aiming at a first proof that a QC inhibitor is capable to inhibit the cyclization of the Glu3 of Aβ (FIG. 24-7).

Results obtained by ELISA show that pre-treatment with 1-(3-(1H-imidazole-1-yl)propyl)-3-(3,4-dimethoxy-phenyl) thiourea hydrochloride reduced A pE(3-40) levels 24 h after injection, revealed by a reduction of the AβpE(3-40)/Aβ(x-40) ratio. Two dosages of 1-(3-(1H-imidazole-1-yl)propyl)-3-(3,4-dimethoxy-phenyl)thiourea hydrochloride were evaluated, injection of 5 µl of a 1 M solution and injection of 5 µl of a 0.2 M solution. The reduction of the ratio of pGlu-Aβ and total Aβ was significant in case of the higher dose and after injection of Aβ (3-40). Changes were also observed, if the low dose of 1-(3-(1H-imidazole-1-yl)propyl)-3-(3,4-dimethoxy-phenyl)thiourea hydrochloride was injected (FIG. 24-8B). The changes lacked, however, statistical significance. The relative pGlu-Aβ formation after injection of Aβ (1-40) was 5-10 times less compared to injection of Aβ (3-40). Thus, pGlu-Aβ levels are low and consequently, 1-(3-(1H-imidazole-1-yl)propyl)-3-(3,4-dimethoxy-phenyl)thiourea hydrochloride treatment did not result in a clear reduction of pGlu-Aβ. This might be caused by I) quick wash-out of the inhibitor (plasma half-life in rat less than 1 hour) and II) a very slow N-terminal truncation after acute injection. The latter might be also caused by a aggregation of the injected peptide, which hampers further enzymatic degradation. This is also corroborated by the observation that the pGlu-Aβ/total Aβ ratio did not change between 24 and 48 h post-injection (FIG. 24-8).

The results of the ELISA-analysis were entirely substantiated by immunohistochemical staining of pGlu-A following injection of Aβ (3-40) (FIG. 24-9). There was a significant reduction in pGlu-Aβ immunostaining detected, if 1-(3-(1H-imidazole-1-yl)propyl)-3-(3,4-dimethoxy-phenyl)thiourea hydrochloride was injected prior to application of Aβ(3-40).

Major Result:

Thus, it is shown that pGlu-Aβ(3-40) is generated in vivo from Aβ(3-40), after injection of the peptide into rat cortex. pGlu-Aβ formation is prevented by application of QC-inhibitor 1-(3-(1H-imidazole-1-yl)propyl)-3-(3,4-dimethoxy-phenyl)thiourea hydrochloride.

b) Treatment of an Aβ Animal Models with QC-Inhibitors

The efficacy of QC-inhibitors for the treatment of Alzheimer's Disease and, e.g. neurodegeneration in Down Syndrome can be tested in animal models of Aβ.

Suitable animal models of Alzheimer's Disease are reviewed in McGowan et al., TRENDS in Genetics, Vol. 22, No. May 2006, pp 281-289, and are selected from PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP, 3xTgAD.

PDAPP: First mutant APP transgenic model with robust plaque pathology. Mice express a human APP cDNA with the Indiana mutation ($APP_{V717F}$). Plaque pathology begins between 6-9 months in hemizygous PDAPP mice. There is synapse loss but no overt cell loss and not NFT pathology is observed. This model has been used widely in vaccination therapy strategies.

Tg2576: Mice express mutant $APP_{SWE}$ under control of the hamster prion promoter. Plaque pathology is observed from 9 months of age. These mice have cognitive deficits but no cell loss or NFT pathology. It is one of the most widely used transgenic models.

APP23: Mice express mutant $APP_{SWE}$ under control of the Thy1 promoter. Prominent cerebrovascular amyloid, amyloid deposits are observed from 6 months of age and some hippocampal neuronal loss is associated with amyloid plaque formation.

TgCRND8: Mice express multiple APP mutations (Swedish plus Indiana). Cognitive deficits coincide with rapid extracellular plaque development at ~3 months of age. The cognitive deficits can be reversed by Aβ vaccination therapy.

$PSEN_{1M146V}$ or $PSEN_{1M146L}$ (lines 6.2 and 8.9, respectively): These models where the first demonstration in vivo that mutant $PSEN_1$ selectively elevates Aβ42. No overt plaque pathology is observed.

PSAPP (Tg2576×$PSEN_{1M146L}$, PSEN1-A246E+$APP_{SWE}$): Bigenic transgenic mice, addition of the mutant PSEN1 transgene markedly accelerated amyloid pathology compared with singly transgenic mutant APP mice, demonstrating that the PSEN1-driven elevation of Aβ42 enhances plaque pathology.

$APP_{Dutch}$: Mice express APP with the Dutch mutation that causes hereditary cerebral hemorrhage with amyloidosis-Dutch type in humans. $APP_{Dutch}$ mice develop severe congophilic amyloid angiopathy. The addition of a mutant PSEN1 transgene redistributes the amyloid pathology to the parenchyma indicating differing roles for Aβ40 and Aβ42 in vascular and parenchymal amyloid pathology.

BRI-Aβ40 and BRI-Aβ42: Mice express individual Aβ isoforms without APP over-expression. Only mice expressing Aβ42 develop senile plaques and CAA, whereas BRI-Aβ40 mice do not develop plaques, suggesting that Aβ42 is essential for plaque formation.

JNPL3: Mice express 4R0N MAPT with the P301L mutation. This is the first transgenic model, with marked tangle pathology and cell loss, demonstrating that MAPT alone can cause cellular damage and loss. JNPL3 mice develop motor impairments with age owing to severe pathology and motor neutron loss in the spinal cord.

$Tau_{P301S}$: Transgenic mice expressing the shortest isoform of 4R MAPT with the P301S mutation. Homozygous mice develop severe paraparesis at 5-6 months of age with widespread neurofibrillary pathology in the brain and spinal cord and neuronal loss in the spinal cord.

$Tau_{V337M}$: Low level synthesis of 4R MAPT with the V337M mutation (1/10 endogenous MAPT) driven by the promoter of platelet-derived growth factor (PDGF). The development of neurofibrillary pathology in these mice suggests the nature of the MAPT rather than absolute MAPT intracellular concentration drives pathology.

$Tau_{R406W}$: Mice expressing 4R human MAPT with the R406W mutation under control of the CAMKII promoter. Mice develop MAPT inclusions in the forebrain from 18 months of age and have impaired associative memory.

rTg4510: Inducible MAPT transgenic mice using the TET-off system. Abnormal MAPT pathology occurs from one month of age. Mice have progressive NFT pathology and severe cell loss. Cognitive deficits are evident from 2.5 months of age. Turning off the transgene improves cognitive performance but NT pathology worsens.

$H_{tau}$: Transgenic mice expressing human genomic MAPT only (mouse MAPT knocked-out). Htau mice accumulate hyperphosphorylated MAPT form 6 month and develop Thio-S-positive NFT by the time they are 15 months old.

TAPP (Tg2576×JNPL3): Increased MAPT forebrain pathology in TAPP mice compared with JNPL3 suggesting mutant APP and/or Aβ can affect downstream MAPT pathology.

3×TgAD: Triple transgenic model expressing mutant $APP_{SWE}$, $MAPT_{P301L}$ on a $PSEN1_{M146V}$ 'knock-in' background (PSNE1-KI). Mice develop plaques from 6 months and MAPT pathology from the time they are 12 months old, strengthening the hypothesis that APP or Aβ can directly influence neurofibrillary pathology.

Suitable study designs could be as outlined in Tables 10 or 11. QC inhibitors could be applied via the drinking solution or chow, or any other conventional route of administration, e.g. orally, intravenously or subcutaneously.

TABLE 10

Animal groups for the treatment of AD animal models with QC-inhibitors

| Group | Treatment | Mode |
| --- | --- | --- |
| 1.) negative control | vehicle | 10 months old (41-45 weeks) |
| 2.) positive control | Ibuprofen | treatment for 6 months (25-26 weeks) starting at age of 4 months (15-20 weeks) |
| 3.) QC-inhibitor | low dose | treatment for 6 months (25-26 weeks) starting at age of 4 months (15-20 weeks) |
| 4.) QC-inhibitor | high dose | treatment for 6 months (25-26 weeks) starting at age of 4 months (15-20 weeks) |

The sequential extraction of Aβ can be performed as described in the materials section below, and initially, the SDS and formic acid (FA) fractions containing the highest Aβ concentrations can be analyzed using an ELISA quantifying total Aβ(x-42) or Aβ(x-40).

Subsequently after QC-inhibitor treatment, the Aβ animal can be tested regarding behavioral changes. Suitable behavioral test paradigms are, e.g. those, which address different aspects of hippocampus-dependent learning. Examples for such tests are the Morris water maze test and the Fear Conditioning test looking at contextual memory changes (Comery, T A et al, (2005), J Neurosci 25:8898-8902; Jacobsen J S et al, (2006), Proc Natl. Acad. Sci USA 103:5161-5166).

TABLE 11

Animal groups involved, examination of the effect of inhibitors of QC on progression of plaque formation in animal models of AD

| Group | Treatment | Mode |
| --- | --- | --- |
| 1) negative control | Vehicle | 16 months old (67-70 weeks) |
| 2) positive control | Ibuprofen (0.2 mg/ml) | treatment for 5 months (21-22 weeks) starting at the age 11 months (46-49 weeks) |
| 3) QC-inhibitor | low dose | treatment for 5 months (21-22 weeks) starting at age 11 months (46-49 weeks) |
| 4) QC-inhibitor | high dose | treatment for 5 months (21-22 weeks) starting at age 11 months (46-49 weeks) |

Example 15

Preparation and Expression of Human MCP-1 in Mammalian Cell Culture

Cell Lines and Media

Human neuroblastoma cell line SH-SY5Y, human embryonic kidney cell line HEK293 and human monocyte cell line THP-1 were cultured in appropriate cell culture media (DMEM, 10% FBS for SH-SY5Y and HEK293), (RPMI1640, 10% FBS for THP-1), in a humidified atmosphere of 5% CO2 (HEK293, THP-1) or 10% CO2 (SH-SY5Y) at 37° C.

Isolation of Human MCP-1

Full-length cDNA of human MCP-1 was isolated from SH-SY5Y cells using RT-PCR. To achieve this, total RNA of SH-SY5Y cells was reversely transcribed by SuperScript II (Invitrogen) and subsequently, human MCP-1 was amplified on a 1:12.5 dilution of generated cDNA product in a 25 µl reaction with Pfu-DNA-Polymerase (Promega) using primers hMCP-1-1 (sense) and hMCP-1-2 (antisense) (Table 12). The resulting PCR-product was cloned into vector pcDNA 3.1 using HindIII and NotI restriction sites and confirmed by sequencing.

Site-Directed Mutagenesis of Human MCP-1

Deletions of the first (ΔQ1) and first and second (ΔQ1P2) amino acids of the mature human MCP-1 were generated by site-directed mutagenesis using primer ΔQ1-1 and ΔQ1-2 for ΔQ1 (Table 12) and primers ΔQ1P2-1 and ΔQ1P2-2 for ΔQ1P2 (Table 12). Parental DNA was digested with Dpn I. The pcDNA 3.1 plasmids with the deletions ΔQ1 and ΔQ1P2 of the mature human MCP-1 were transformed into E. coli JM109. Ampicillin-resistant clones were confirmed by sequencing and subsequently isolated for cell culture purposes using the EndoFree Maxi Kit (Qiagen).

Expression of N-Terminal Variants of Human MCP-1 in HEK293 Cells

For expression of N-terminal variants of human MCP-1, HEK293 cells were cultured in collagen I coated 6-well dishes and grown until 80% confluency, transfected using Lipofectamin2000 (Invitrogen) according to manufacturer's manual and incubated in the transfection solution for 5 hours. Afterwards, cells were allowed to recover in normal growth media over night. The next day, cells were incubated another 24 h in growth media. When application of QC specific inhibitor chemotactic cytokines (chemokines) was intended, cells were incubated for 24 h in absence or presence of 10 µM chemotactic cytokines (chemokines). After 24 h the media containing the human MCP-1 variants were collected and investigated in a migration assay for chemotactic potency. Furthermore, an aliquot of cell culture supernatant was stored at −80° C. for quantification of human MCP-1 concentration using human MCP-1-ELISA (Pierce).

TransWell Chemotaxis Assay

The chemotaxis assay was performed using 24 well TransWell plates with a pore size of 5 µm (Corning). Media, containing human MCP-1 variants expressed in HEK293, were used as chemoattractant. To this avail, 600 µl of the culture media of N-terminal human MCP-1 variants was applied directly or in dilutions 1:3, 1:10 and 1:30 in RPMI1640 to the lower chamber of the TransWell plate. Furthermore, undiluted media of HEK293 cells transfected with vector control were applied as negative control to the lower chamber. THP-1 cells were harvested and resuspended in RPMI1640 in a concentration of $1*10^6$ cells/100 µl and applied in 100 µl aliquots to the upper chamber. Cells were allowed to migrate towards the chemoattractant for 2 h at 37° C. Subsequently, cells from the upper chamber were discarded and the lower chamber was mixed with 70 mM EDTA in PBS and incubated for 15 min at 37° C. to release cells attached to the membrane. Afterwards, cells migrated to the lower chamber were counted using a cell counter system (Scharfe System). The chemotactic index was calculated by dividing cells migrated to the stimulus from cells migrated to the negative control.

Example 16

Investigations on the Proteolytic Degradation of Human MCP-1$_{(1-76)}$

Methods

N-Terminal Degradation by Recombinant Human DP4

Full length recombinant human MCP-1(1-76) (SEQ ID NO: 5) encoded by the nucleic acid sequence as shown in SEQ ID NO: 4, obtained in Example 15 above, starting with an N-terminal glutamine (Peprotech) was dissolved in 25 mM Tris/HCl pH 7.6 in a concentration of 10 µg/ml. MCP-1 solution was either pre-incubated with recombinant human QC (0.0006 mg/ml) (obtained according to Example 1 above, SEQ ID No: 18 for nucleic acid sequence and SEQ ID No: 19 for amino acid sequence) for 3 h at 30° C. and subsequently incubated with recombinant human DP4 (0.0012 mg/ml) at 30° C. (see FIG. 26) or incubated with DP4 without prior QC application. Resulting DP4 cleavage products were analyzed after 0 min, 15 min, 30 min, 1 h, 4 h and 24 h using Maldi-TOF mass spectrometry.

N-Terminal Degradation by Human Rheumatoid Synovial Fibroblast MMP-1

Human recombinant MCP-1 starting with a N-terminal glutamine (Peprotech) was dissolved in 25 mM Tris/HCl, pH 7.6, in a concentration of 10 µg/ml. MMP-1 proenzyme from human rheumatoid synovial fibroblasts (Calbiochem) was activated using 25 mM p-aminophenylmercuric acetate (APMA), dissolved in 0.1 N NaOH at 37° C. for 3 h in a APMA:enzyme-mixture of 10:1. MCP-1 solution was either pre-incubated with recombinant human QC (0.0006 mg/ml) for 3 h at 30° C. and subsequently incubated with MMP-1 at 30° C. or incubated with MMP-1 without prior QC application. Resulting MMP-1 cleavage products were analyzed after 0 min, 15 min, 30 min, 1 h, 2 h, 4 h and 24 h using Maldi-TOF mass spectrometry (see FIG. 31).

N-Terminal Degradation by Human Rheumatoid Synovial Fibroblast MMP-1 and Recombinant Human DP4

Human recombinant MCP-1 starting with a N-terminal glutamine (Peprotech) was dissolved in 25 mM Tris/HCl pH 7.6 in a concentration of 10 µg/ml. MMP-1 proenzyme from human rheumatoid synovial fibroblasts (Calbiochem) was activated using 25 mM p-aminophenylmercuric acetate (APMA) dissolved in 0.1 N NaOH at 37° C. for 3 h in a APMA:enzyme-mixture of 10:1. MCP-1 solution was either pre-incubated with recombinant human QC (0.0006 mg/ml) for 3 h at 30° C. and subsequently incubated with MMP-1 and DP4 at 30° C. or incubated with MMP-1 and DP4 without QC application. Resulting MMP-1 cleavage products were analyzed after 0 min, 15 min, 30 min, 1 h, 2 h, 4 h and 24 h using Maldi-TOF mass spectrometry (see FIG. 32).

Example 17

Effect of QC Specific Inhibitor 1-(3-(1H-imidazol-1-yl)propyl)-3-(3,4-dimethoxyphenyl)thiourea Hydrochloride on Cuff-Induced Accelerated Atherosclerosis in ApoE3*Leiden Mice Timeline 30 male ApoE3*Leiden mice (age 12 weeks) were fed a mildly hypercholesterolemic diet for 3 weeks prior to surgical cuff placement.

After 3 weeks the mice underwent surgical non-constricting cuff placement (day 0) and were divided into 2 groups, matched for plasma cholesterol levels. The mice either received control (acidified) drinking water or drinking water that contains QC specific inhibitor 1-(3-(1H-imidazol-1-yl) propyl)-3-(3,4-dimethoxyphenyl)thiourea hydrochloride in a concentration of 2.4-mg/ml. 7 days after start of treatment the inhibitor concentration was reduced to 1.2 mg/ml. 5 Mice of each group were sacrificed after 2 days for analysis of monocyte adhesion and infiltration, and 10 mice were sacrificed after 2 weeks for histomorphometric analysis to quantify the inhibition of accelerated atherosclerotic lesions and neointima formation.

Surgical Procedure of Cuff Placement

At the time of surgery, mice were anaesthetized with an intraperitoneal injection of 5 mg/kg Dormicum, 0.5 mg/kg Domitor and 0.05 mg/kg Fentanyl. This cocktail gives complete narcosis for at least one hour and can be quickly antagonized with Antisedan 2.5 mg/kg and Anexate 0.5 mg/kg.

A longitudinal 1 cm incision is made in the internal side of the leg and the femoral artery is dissected for 3 mm length from the femoral nerve and femoral vein. The femoral artery is looped with a ligature and a non-constrictive fine bore polyethylene tubing (0.4 mm inner diameter, 0.8 mm outer diameter, length 2 mm) is longitudinally opened and sleeved loosely around the femoral artery. The cuff is closed up with two ligature knots. The skin is closed with a continued suture.

After surgery, the animals were antagonized and placed in a clean cage on top of a heating pad for a few hours.

Sacrifice of the Animals

For histological analysis, animals were sacrificed either 2 days or 14 days after cuff placement. After anaesthesia, the thorax was opened and a mild pressure-perfusion (100 mmHg) with 4% formaldehyde was performed for 3 minutes by cardiac puncture. After perfusion, a longitudinal 2 cm incision was made in the internal side of the leg and the cuffed femoral artery was harvested as a whole and fixed overnight in 4% formaldehyde and processed to paraffin.

Analysis of Monocyte Adhesion and MCP-1 Expression

Adhesion of leukocytes in general and monocytes/macrophages in particular to the activated endothelium of the cuffed vessel wall was analyzed by microscopic analysis of cross sections harvested 2 days after cuff placement. The number of adhering and/or infiltrating leukocytes in general, identified as adhering cells at the luminal side of the vessel segment, and monocytes/macrophages in particular was counted and illustrated as cells per cross-section or as defined areas per cross section. Monocytes were identified by specific immunohistochemical staining by AIA31240 antibody, recognizing monocytes and macrophages. In addition on these sections a specific immunohistochemical staining for MCP-1 was performed.

Analysis of Vascular Remodeling and Accelerated Athero-Sclerosis

Vessel wall remodeling accelerated atherosclerosis and neoinitima formation were analyzed morphometrically in all mice sacrificed after 14 days. A full comparison between the two groups was performed for all relevant vessel wall parameters (neointima formation, vascular circumference (i.e. outward remodelling), media thickness, lumen stenosis). Accelerated atherosclerosis was analyzed by immunohistochemical staining for macrophages and foam cells in the lesion area by AIA31240 antibody. Furthermore, these sections were also stained for MCP-1.

Results

Preparation and Expression of Human MCP-1 in Mammalian Cell Culture

Amplification of human MCP-1 from neuroblastoma cell line SH-SY5Y RNA resulted in a PCR-product of 300 bp (see FIG. 29). Sequencing of the isolated cDNA revealed a silent single nucleotide polymorphism of codon 105 coding for cysteine 35 (see FIG. 27).

Expression of human MCP-1 variants in HEK293 leads to elevated levels within cell culture supernatant as monitored by human MCP-1 ELISA. Thereby, the level between the expressions of MCP-1 (WT) and MCP-1 (ΔQ1) (FIG. 27C), and MCP-1 (WT) in absence or presence of 10 μM 1-(3-(1H-imidazol-1-yl)propyl)-3-(3,4-dimethoxyphenyl)thiourea hydrochloride (FIG. 28A) are not significantly changed. However, the expression of MCP-1 (ΔQ1P2) is reduced by 28% compared to MCP-1 (WT) (see FIG. 30A). The supernatant was collected and applied in TransWell migration assays (see FIGS. 27D, 28B and 30B in this regard).

TransWell Chemotaxis Assay

Purified human MCP-1 displays a bell-shaped chemotactic dose response curve, when attracting, e.g. monocytes, showing an optimum at approx. 1-50 ng/ml. Therefore, the generated cell culture supernatants containing MCP 1 variants were sequentially diluted in order to achieve the optimal working concentration of MCP-1 for chemotaxis assay attracting THP-1 monocytes.

After expression of MCP-1 (WT) and MCP-1 (ΔQ1), the concentrations of MCP-1 variants did not significantly differ (FIG. 27C). Application of MCP-1 (WT) to the chemotaxis assay led to a chemotactic response of THP-1 cells (FIG. 27D) suggested by the elevated chemotactic index. However, MCP-1 (ΔQ1) failed to induce chemotaxis of THP-1 (FIG. 27D) illustrated by a chemotactic index of approx. 1. These results support previous suggestions, that N-truncated MCP-1 is inactive. The finding that MCP-1 (ΔQ1P2) also fails to induce chemotaxis of THP-1 cells further corroborates this (FIG. 30B). Expression of MCP-1 (WT) in HEK293 cells has no influence on MCP-1 concentration in absence or presence of 1-(3-(1H-imidazole-1-yl)propyl)-3-(3,4-dimethoxyphenyl)thiourea hydrochloride (see FIG. 28A). However, the application of 1-(3-(1H-imidazole-1-yl)propyl)-3-(3,4-dimethoxy-phenyl)thiourea hydrochloride leads to significantly lower chemotaxis of THP 1 cells at dilutions 1:3 and 1:10 (FIG. 28B). This suggests a prevention of N-terminal pGlu-formation of MCP-1 (WT) by QC-specific inhibitor 1-(3-(1H-imidazol-1-yl)propyl)-3-(3,4-dimethoxyphenyl) thiourea hydrochloride and, therefore, an inactivation of MCP-1 (WT), either by N-terminal proteolytic degradation or by the sole prevention of pGlu formation.

Investigations on the Proteolytic Degradation of Human MCP-1 (1-76)

Within the circulation, MCP-1 is protected by a N-terminal pGlu-residue giving a resistance against N-terminal post-proline-cleaving aminopeptidases, e.g. DP4. However, the unprotected N-terminus, resulting e.g. from QC inhibitor administration, is readily cleaved by DP4 and thus, inactivating human MCP-1 (FIG. 26). MMP-1 inactivates mature MCP-1 by cleaving the 4 N-terminal amino acids (pE/Q-P-D-A) independent from the presence of a N-terminal pGlu residue. This process reflects the situation of MCP-1 inactivation within the circulation (FIG. 31). The resulting cleavage product MCP 1(5-76) has been shown to be present within plasma and resembles a naturally occurring CCR2 receptor antagonist. The present experiments point to the finding that MMP-1 cleavage is slightly faster in case of a N-terminal glutamine residue (FIG. 31A: 2 h, 4 h vs. 31B: 2 h, 4 h). Furthermore, incubation of human N1Gln-MCP-1 (FIG. 32 A) with human DP4 and human MMP-1 shows an accelerated degradation in comparison to N1pGlu-MCP-1 (FIG. 32 B). Taken together, the N-terminal pGlu residue displays a protection mechanism against N-terminal degradation by post-proline cleaving enzymes, e.g. DP4 and prevention of N-terminal pGlu formation by QC inhibitor application leads to a faster processing and, thus, inactivation of human MCP-1.

Analysis of Vascular Remodeling and Accelerated Atherosclerosis in ApoE3*Leiden Mice Treatment of cuff-induced accelerated atherosclerosis in ApoE3*Leiden mice had no effect on the total area within the outer diameter of the vessel segment (FIG. 36A) and no statistically significant effect on the remaining lumen (FIG. 36 B), although a slight increase in the remaining lumen can be observed. However, 1-(3-(1H-imidazol-1-yl)propyl)-3-(3, 4-dimethoxyphenyl)thiourea hydrochloride shows a profound reduction of 40% on the percentage of lumen stenosis (FIG. 37A) and 45% reduction of the area of neointima formation (FIG. 37B). Both values are statistically significant. Furthermore, the inhibitor also reduced the area of the media (FIG. 38A) and the intima/media ratio (FIG. 38B), although the reduction in intima/media ration lacks statistically significance (P<0.102).

The analysis of the cellular composition in the specific vessel wall layers shows no differences in relative contribution of smooth muscle cells and macrophages/foam cells to the composition of both the media and the adventitia after 2 days and 14 days (FIG. 43). Although one could expect a more specific effect on monocyte/macrophage content in the vessel wall due to the effect of 1-(3-(1H-imidazol-1-yl)propyl)-3-(3,4-dimethoxyphenyl)thiourea hydrochloride on MCP-1, and therefore on monocyte attraction, it should be noted that MCP-1 also has a direct effect on smooth muscle cell proliferation as recently has been discovered and published.

Analysis of Monocyte Adhesion and MCP-1 Expression

Treatment of the mildly hypercholesterolemic ApoE3*Leiden mice (plasma cholesterol levels 12-15 mM) with 1-(3-(1H-imidazol-1-yl)propyl)-3-(3,4-dimethoxyphenyl)thiourea hydrochloride resulted in a profound reduction of total adhering cells by 45%, (p<0.05) after 2 days. Specific analysis of adhering monocytes revealed an even stronger reduction of 67% (p<0.05) to the treated cuffed vessel segments (FIG. 39).

MCP-1 expression was reduced in the vessel segments of 1-(3-(1H-imidazol-1-yl)propyl)-3-(3,4-dimethoxyphenyl) thiourea hydrochloride treated mice 2 days after surgery, the moment of the highest elevation of MCP-1 expression in the model used (FIG. 40, 41A, 42A). These results indicate that early after vascular injury within the lesions a reduction of MCP-1 expression can be detected in both the media and the intima (i.e inside the Lamina elastica interna) of the vessel wall segment, when 1-(3-(1H-imidazol-1-yl)propyl)-3-(3,4-dimethoxyphenyl)thiourea hydrochloride is administered. Analysis of the relative area of the cross sections positive for MCP-1 revealed a 52% (P=0.01) reduction of MCP 1 expression in the media and a 36% (P=0.001) reduction in the intima (FIG. 42A). Analysis of the absolute area positive for MCP-1 (expressed in μm² positive per cross section) reveals a similar reduction of MCP-1 expression in the media (41% reduction, p=0.09) and the intima (40% reduction, p=0.05), although the reduction within the media is statistically not significant (Student's T-test) (FIG. 41A).

At the later time point of 14 days, when the neointima formation/accelerated atherosclerosis has progressed, the overall MCP-1 expression is lower than observed for the early time point and in contrast, no reduction of MCP-1 expression can be monitored, in the media or in the neointima (FIG. 41B, 42B) suggesting an effect of 1-(3-(1H-imidazol-1-yl)propyl)-3-(3,4-dimethoxyphenyl)thiourea hydrochloride only for the time of strong induction of MCP-1.

Taken together, these data indicate that oral dosing of 1-(3-(1H-imidazol-1-yl)propyl)-3-(3,4-dimethoxyphenyl)thiourea hydrochloride has a beneficial effect on post interventional vascular remodelling and accelerated atherosclerosis in the ApoE3*Leiden cuff model.

TABLE 12

Utilized primers

| Primer | Sequence (5'→3') | Application | SEQ ID NO |
|---|---|---|---|
| hMCP-1-1 | <u>ATAT AAGCTT</u> ATGAAAGTCTCTGCCGCCCTTC | Isolation of human MCP-1 | 12 |
| hMCP-1-2 | ATAT GCGGCCGC TCAAGTCTTCGGAGTTTGGG | Isolation of human MCP-1 | 13 |
| ΔQ1-1 | CATTCCCCAAGGGCTCGCTCCAGATGCAATCAATGCC | Site-directed mutagenesis ΔQ1 | 14 |
| ΔQI-2 | GGCATTGATTGCATCTGGAGCGAGCCCTTGGGGAATG | Site-directed mutagenesis ΔQ1 | 15 |
| ΔQ1P2-1 | CATTCCCCAAGGGCTCGCTGATGCAATCAATGCCCAG | Site-directed mutagenesis ΔQ1P2 | 16 |
| ΔQ1P2-2 | CTGGGGCATTGATTGCATCAGCGAGCCCTTGGGGAATG | Site-directed mutagenesis ΔQ1P2 | 17 |

Example 18

Deciphering Molecular Pathways Leading to Generation of N-Truncated and pGlu-Modified Aβ-Peptides In addition to the APP plasmid constructs, which were employed in example 13 (FIGS. 24-2, 24-3, 24-4, 24-5), also plasmid constructs were implicated, used to delineate the formation of the precursors of pGlu-Aβ. The constructs are depicted in FIG. 33. The APP-encoding plasmids differed with respect to the sequence surrounding the β-secretase cleavage site, i.e. either carried the swedish mutation (KM595/596NL) or the wild-type sequence (K595M596) at the β-secretase-cleavage site. Furthermore, the constructs encoded either the London (V6421) or wild-type sequence (V642) near the γ-secretase cleavage site. The swedish mutation leads to an elevated generation of Aβ due to enhanced cleavage by the β-secretase BACE I. The London mutation mediates enhanced formation of Aβ42 peptides compared to the wild-type sequence without affecting the total Aβ generation.

Additionally, a mutation was introduced (E599Q) leading to a change at amino acid position three of Aβ. Instead of glutamic acid, the N3Q construct contains a glutamine. The N3Q mutation has a monitoring function, since glutamine displays enhanced pGlu-formation compared to the wild-type glutamate. Therefore, upon cleavage leading to the liberation of the glutamine, it will be readily cyclized by Glutaminyl Cyclase and can be measured using highly specific ELISA.

Interestingly, massive pGlu-Aβ formation was observed for the conditioned medium of APP-WT (N3Q)-transfected HEK-293 cells (FIG. 34A,B). Apparently, the fraction of pGlu-modified peptides was larger for Aβ42, however, in total the Aβ40 concentration was higher (FIG. 34C,D). The formation of N-terminal pGlu was strongly dependent on the transfected construct, i.e. the wild type-sequence at the β-secretase cleavage site in the APP-WT and APP-London constructs provoked the generation of pGlu-Aβ from APP (N3Q). In contrast, the pGlu-formation was found to be negligible, if the swedish mutation was introduced at the β-secretase cleavage site. The results were entirely corroborated with a glial cell line, LNZ-308 (FIG. 34 D, E). Concluding, apparently caused by the APP sequence at the β-secretase cleavage site the APP molecule is susceptible to cleavage by other proteases. Caused by the alternative cleavage, N-terminally truncated Aβ species are generated after following cleavage by γ-secretase. Thus, these alternative, near the β-site cleaving enzyme(s) are therapeutic targets (in addition to QC as outlined in detail in this invention) in order to prevent the formation of pGlu-Aβ(3-40) and pGlu-Aβ(3-42).

In order to substantiate the role of these newly discovered enzyme activity generating the molecular precursor of pGlu-Aβ peptides, inhibitors of the known β-secretase BACE I were employed in experiments based on transient expression of the plasmid constructs outlined in FIG. 33. Similar to the observations with the APP(N3Q) constructs, N-terminally truncated peptides were generated mainly after APP-WT and APP-London expression. Thus, the influence of the primary structure at the β-cleavage site is highly influential in either case, as evidenced by:

- a highly potent BACE-Inhibitor (BACE IV, Calbiochem) did not influence the total Aβ40-concentration significantly in HEK293 cells and displayed only marginal efficacy in total Aβ lowering in LNZ-308 cells (FIG. 34)
- the inhibitor reduced the N-terminally intact Aβ-peptides, i.e. Aβ(1-40) and Aβ(1-42) significantly, indicating BACE I is α-site cleaving enzyme which generates mainly Aβ(1-40/42) peptides.

The results clearly point to a direct, presumably an endoproteolytic, formation of the N-terminus of N-truncated peptides. These alternative processing pathways lead to the identification of other target proteases exhibiting β-secretase activity, which are potential targets to treat the formation of N-truncated Aβ peptides, preferably Aβ(3-42) and Aβ(3-40).

Material and Methods

Cell Lines, Media and Cultivation

Human neuroblastoma cell line SH-SY5Y, human embryonic kidney cell line HEK293 and human monocyte cell line THP-1 were cultured in appropriate cell culture media (DMEM, 10% FBS for SH-SY5Y and HEK293), (RPMI1640, 10% FBS for THP-1), in a humidified atmosphere of 5% $CO_2$ (HEK293, THP-1) or 10% $CO_2$ (SH-SY5Y) at 37° C.

Aβ Synthesis and Analytics

Synthesis and Purification of Aβ Peptides. Peptides were synthesized in a 50 μmol scale on an Fmoc-Val/Ala-NovaSyn®TGA resin (0.15 mmol/g) using an automated Symphony Synthesizer (Rainin). Fmoc-amino acids (five fold excess, double couplings) were activated with equimolar amounts of TBTU/NMM in DMF. Fmoc-deprotection was achieved by 20% piperidine in DMF. Fmoc-Gly-Ser(ΨMe, Mepro)-OH was introduced instead of Gly25-Ser26 in order to disrupt aggregation of the peptide chain. Global cleavage and deprotection was carried out by using a mixture of TFA/EDT/TIS/Water (94:2.5:2.5:1) for 4 h. The crude peptides were dissolved in HFIP for preparative HPLC. Preparative HPLC was performed with a gradient of solvent B (60% acetonitril, 40% solvent A) in solvent A (0.1% $NH_4OH$ (25%) in $H_2O$, pH 9.0): 10% B for 2 min, 10 to 100% B until 35 min) on a 250×10 Gemini C18 column, 10 μm (Phenomenex). Prior to labeling, all Aβ peptides were treated as reported previously (Stine W B, Jr., Dahlgren K N, Krafft G A, LaDu M J 2003 In vitro characterization of conditions for amyloid-beta peptide oligomerization and fibrillogenesis. J Biol Chem 278:11612-11622) to obtain seedless material and further purified by RP-HPLC (column: Source 5RPC 4.6/150 ST (Amersham); solvent A: 0.1% $NH_4OH$ (25%) in $H_2O$, pH 9.0; solvent B: 60% acetonitril, 40% solvent A; gradient: 25-56% solvent B in 31 min; flow rate: 1.0 ml/min) and lyophilized. Peptide purity and identity was confirmed by analytical HPLC (150×4.6, 5μ Source or Gemini) and MALDI-MS.

Fluorescence Labeling. The peptides Aβ(1-42), Aβ(3-42) and pGlu-Aβ(3-42) were labeled with the fluorescence dye Alexa Fluor 488 according to the manufacturer's instructions (Alexa Fluor 488 5-TFP; Invitrogen). The different reaction products were then separated by RP-HPLC as described above, analyzed by HPLC-MS and lyophilized in the dark. The content of each peptide was determined by amino acid analysis (ZPA Bingen, Germany). The anti-Aβ antibody 4G8 (Chemicon Temecula, Calif.) was labeled with the fluorescence dye Alexa Fluor 488 according to the manufacturer's instructions (Alexa Fluor 488 Monoclonal Antibody Labeling Kit; Invitrogen). Primary amino groups are subjected to derivatization by the fluorescent dye, i.e. the primary amino groups and the lysyl side chains. The reaction mixture was subjected to separation using HPLC, applying the method that was described in the synthesis section. The fractions were analyzed using mass spectrometry, in order to identify the degree of labeling. For the assays, only single and double-labeled peptides were applied (FIG. 25-1).

ELISA analysis. Aβ(x-40), Aβ(x-42) and Aβ(N3pE-42)-specific sandwich ELISAs (all from IBL, Hamburg) were performed according to the manufacturer's manual. Briefly, samples were diluted according to the expected concentration in the brain parts and applied onto a plate precoated with an antibody specific for the respective C-terminus. The samples were incubated overnight. The next day, the plate washed 8 times and incubated for 1 h with a horse radish peroxidase conjugated detection antibody afterwards. Following this incubation the plate washed 10 times and then developed with chromogen (TMB) for 30 min. After applying the stop solution the absorption at 450 nm was measured using a microplate reader (TECAN Sunrise). For preparation of standard curves the respective synthetic peptides supplied with the ELISA kits were used.

The standard curve for Aβ(N3pE-42) was linear from 500 pg/ml to 7.8 pg/ml. Aβ(x-40), Aβ(x-42) was fitted according to an exponential model.

Depending on the assay, the fraction of Aβ extraction and the analyzed model, the following sample dilutions were used:

| | |
|---|---|
| Aβ(x-40), SDS fraction | at least 1:10 |
| Aβ(x-40), formic acid fraction undiluted | |
| Aβ(x-42), SDS fraction | at least 1:10 |
| Aβ(x-42), formic acid fraction undiluted | |

All other samples were analysed undiluted.

For analysis of Aβ in case of the cell culture studies, conditioned medium was diluted using EIA buffer (IBL, Hamburg) as before and diluted samples were subjected to ELISA analysis.

Aβ Extraction from Murine and Rat Brain

Samples for ELISA were prepared from 8 animals per group (total 32 animals). After removal of the brain, the tissue were flushed shortly with ice cold saline and placed shortly on filter paper. The cerebellum were prepared from each brain and stored separately. The brains were weighed and frozen in liquid nitrogen in 2 ml Cryo-tubes and stored at −80° C. until analysis.

For sequential separation of Aβ the following procedures were used:

4. Extraction: TBS
   determination of brain weight
   homogenization (Dounce) in TBS (2.5 ml, 20 mM Tris, 137 mM NaCl, pH 7.6)) containing 1 pill of protease inhibitor cocktail (Complete Mini, Roche) per 10 ml of TBS
   sonification (10 cycles a 30 s) and centrifugation (75,500× g, 1 h, 4° C.)
   separation of supernatant (TBS fraction), storage at −80° C.

2. Extraction: TBS/1% Triton X-100
   resuspension of the pellet in 2.5 ml TBS/1% Triton X-100, sonification
   centrifugation (75,500×g, 1 h, 4° C.)
   separation of supernatant (TBS/Triton fraction), storage at −80° C.

3. Extraction: 2% SDS in Water
   analogous to TBS/1% Triton (SDS fraction)

4. Extraction: Formic Acid, 70%
   resuspension of pellet in 0.5 ml 70% formic acid, sonification
   neutralization of the supernatant using 9.5 ml of 1M Tris, storage of the FA fraction at −80° C.

Expression, Purification and Analysis of Human and Murine QC

Enzyme Assays and Analysis. For determination of mQC and hQC during expression and purification, activity was evaluated using H-Gln-βNA at 30° C. Briefly, the samples consisted of 0.2 mM fluorogenic substrate, 0.1 U pyroglutamyl aminopeptidase in 0.05 M Tris/HCl, pH 8.0 and an appropriately diluted aliquot of QC in a final volume of 250 μl. The excitation/emission wavelength was 320/405 nm. The assay reactions were initiated by addition of QC. One unit is defined as the amount of QC catalyzing the formation of 1.0 μmol pGlu-βNA from H-Gln-βNA per minute under the described conditions.

For inhibitor testing, the sample composition was the same as described above, except for the added putative inhibitory compound and the substrate. Due to the pronounced substrate inhibition by Gln-βNA, inhibitory constants were determined using H-Gln-AMC at a concentration range between 0.25 and 4 $K_M$. The excitation/emission wavelength was adjusted to 380/460 nm. In contrast to H-Gln-βNA, substrate inhibition by H-Gln-AMC is negligible in the applied substrate concentration range and does therefore not interfere with the kinetic evaluation. The fluorometric assay using H-Gln-AMC was also applied to investigate the pH-dependence of the catalytic parameters and inhibitory constants. In these studies, however, the reaction buffer consisted of 0.075 M acetic acid, 0.075 M Mes and 0.15 M Tris, adjusted to the desired pH using HCl or NaOH. This buffer provides a constant ionic strength over a very broad pH-range. Evaluation of the acquired enzyme kinetic data was performed using the following equations:

$$k_{cat}(pH) = k_{cat}(\text{limit}) \tag{1}$$

$$K_M(pH) = K_M(\text{limit}) \ast (1 + [H+]/K_{HS} + K_{E1}/[H+] + K_{E1}/[H+] \ast K_{E2}/[H+]) \tag{2}$$

$$k_{cat}/K_M(pH) = k_{cat}/K_M(\text{limit}) \ast 1/(1 + [H+]/KHS + K_{E1}/[H+] + K_{E1}/[H+] \ast K_{E2}/[H+]) \tag{3}$$

$$K_i(pH) = K_i(\text{limit}) \ast (1 + [H^+]/K_{HI} + K_{E1}/[H^+] + K_{E1}/[H^+] \ast K_{E2}/[H^+]) \tag{4}$$

in which the left expressions denote the pH-dependent (observed) kinetic parameters. The parameters denoted with limit represent the pH-independent ("limiting") values. $K_{HS}$, $K_{HI}$, $K_{E1}$ and $K_{E2}$ denote the dissociation constants of the substrate amino group, the basic nitrogen of the imidazole-based inhibitor and two dissociating groups of the enzyme, respectively. The data of the pH-dependencies of the mQC inhibition by cysteamine derivatives were analyzed by assuming one dissociating group. The measurements were performed with a Novostar (BMG Labtechnologies, Germany) or a SpectraFluor Plus (TECAN, Switzerland) reader for microplates.

For investigation of the substrate specificity, mQC activity was studied spectrophotometrically utilizing glutamic dehydrogenase as the auxiliary enzyme. In contrast to the fluorometric assays, a variety of substrates can be analyzed because of the conversion of ammonia in the coupled reaction. Samples consisted of varying concentrations of the QC substrate (0.25-10 $K_M$), 0.3 mM NADH, 14 mM β-ketoglutaric acid and 30 U/ml glutamic dehydrogenase in a final volume of 250 μl. The reaction buffer was 0.05 M Tris/HCl, pH 8.0. Reactions were started by addition of QC and pursued by monitoring of the decrease in absorbance at 340 nm for 8-15 min. The initial velocities were evaluated and the enzymatic activity was determined from a standard curve of ammonia obtained under assay conditions. All samples were measured at 30° C., using the Sunrise reader for microplates (TECAN, Switzerland). All kinetic data were evaluated using GraFit software (version 5.0.4. for windows, ERITHACUS SOFTWARE Ltd., Horley, UK).

Murine QC (mQC) Expression in *P. pastoris*. 1-2 μg of plasmid DNA were applied for transformation of competent *P. pastoris* cells by electroporation according to the manufacturer's instructions (BioRad). Selection was carried out on plates containing 100 μg/ml Zeocin. In order to test the recombinant yeast clones upon mQC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation.

The expression of mQC was performed in a 5 L reactor (Biostad B. B. Braun biotech, Melsungen, Germany). Fermentation was carried out in basal salts medium supplemented with trace salts at pH 5.5. Initially, biomass was accumulated in a batch and a fed batch phase with glycerol as the sole carbon source for about 28 h. Expression of QC was initiated by methanol feeding according to a three-step profile recommended by Invitrogen for an entire fermentation time of approximately 65 h. Subsequently, cells and turbidity were removed from the mQC-containing supernatant by two sequential centrifugation steps at 6000×g and 38000×g for 15 min and 4 h, respectively.

For purification of mQC, the fermentation broth was diluted with water to a conductivity of about 5 mS/cm and applied in reversed flow direction (15 mL/min) onto a Streamline SP XL column (2.5×100 cm), equilibrated with 0.05 M phosphate buffer, pH 6.4. After a washing step in reversed flow direction with equilibration buffer for 2 column volumes, proteins were eluted at a flow rate of 8 mL/min using 0.15 M Tris buffer, pH 7.6, containing 1.5 M NaCl in forward direction. QC-containing fractions were pooled and ammonium sulfate added to a final concentration of 1 M. The resulting solution was applied onto a Butyl Sepharose FF column (1.6×13 cm) at a flow rate of 4 mL/min. Bound mQC washed with 0.05 M phosphate buffer, pH 6.8 containing 0.75 M ammonium sulfate for 5 column volumes and eluted in reversed flow direction with 0.05 M phosphate buffer, pH 6.8. The fractions containing mQC were pooled and desalted overnight by dialysis against 0.025 M Tris, pH 7.5. Afterwards, the pH was adjusted to 8.0 by addition of NaOH and applied (4.0 mL/min) onto a Uno Q column (Bio Rad), equilibrated with 0.02 M Tris, pH 8.1.

The QC's were stable at 4° C. for up to 1 month. For long-term storage at −20° C., 50% glycerol was added. The protein was applied for determination of inhibitory constants and for protein crystallization.

Analysis of Aβ Oligomerization

Preparation of seedless Aβ stock solutions. Prior to analysis, the lyophilized amyloid peptides were subjected to a disaggregation procedure. The peptides were dissolved in HFIP (1.0 mM) and evaporated in a stream of nitrogen. Residual solvent was removed by evacuation in a speed vac for 10 min. Afterwards, stock solutions of Aβ42 (100 µM) and Aβ40 (5 mM), were prepared in pure DMSO. Aβ solutions treated in this way have been described to be free of oligomeric species (Stine W B, Jr., Dahigren K N, Krafft G A, LaDu M J 2003 In vitro characterization of conditions for amyloid-beta peptide oligomerization and fibrillogenesis. J Biol Chem 278:11612-11622).

Aggregation Assay and Flow Cytometry. Seedless Aβ peptides were diluted to 10 µM (final total peptide concentration) into 50 mM sodium acetate, pH 5.5 containing 2 mM DTT and 100 mM NaCl and incubated at 37° C. without shaking. For fibril formation analysis, the peptides were either used as a mixture of unlabeled peptide (80%) and the respective fluorescence labeled peptide (20%) or as unlabeled peptides alone. For the seeded aggregation, each reaction contained 70% of unlabeled Aβ(1-42), 20% of Alexa Fluor 488 labeled Aβ(1-42) and 10% of unlabeled pGlu-Aβ(3-42). In order to characterize the progress of the reaction, aliquots were removed at the indicated times, diluted to 10 nM into PBS-T (0.05% Tween-20) and analyzed. For reactions containing unlabeled peptides only, prior to flow cytometry aliquots were diluted to 5 nM into PBS-T and incubated with fluorescence labeled antibody 4G8 (Chemicon, Temecula, Calif.) at 1 nM for 1 h at 4° C.

For the detection of Aβ oligomers and fibrils produced during solution phase aggregation, a Cytomics FC500 (Beckman Coulter) flow cytometer equipped with a single 20 mW 488 nm argon-ion laser was used. The green fluorescence of the dye Alexa Fluor 488 was detected by the corresponding FL1 (logarithmic scale) photomultiplier equipped with a 525 bandpass filter. To ensure identical conditions for all measurements, all samples were measured in TruCount Tubes (BD Biosciences) and analysis was stopped after 20,000 beads were counted. Counts were transferred into ANSMS for evaluation (Alzheimer normalized specific measurement signal: event counts from flow cytometry analysis normalized to the size of the particles, i.e. to a mean size of FS Log=250). Since there is a correlation between particle size and intensity of the fluorescence signal, it was possible to discriminate between smaller oligomeric and larger fibrillar structures in a single experiment (FIG. 25-2).

Thus, different regions in a FL1 Log/SS Log dot blot comprising areas of strong or weak fluorescence intensity were assigned to fibrils or oligomers, respectively.

Thioflavin T Assay. Fibril formation analysis using Thioflavin T fluorescence was performed essentially as described previously (Chalifour R J, McLaughlin R W, Lavoie L, Morissette C, Tremblay N, Boule M, Sarazin P, Stea D, Lacombe D, Tremblay P, Gervais F 2003 Stereoselective interactions of peptide inhibitors with the beta-amyloid peptide. J Biol Chem 278:34874-34881). The DMSO stock solution was diluted in PBS to a final concentration of 50 µM of Aβ peptide. The peptide solution was added to an equal volume of ThT solution (20 µM ThT, 0.3 M NaCl, 0.01% NaN$_3$) and applied to a 96-well microplate. Routinely, assays of each peptide were performed in triplicate on one plate. The plate was covered with an adhesive film (EXCEL Scientific, Wrightwood, Calif., USA) and incubated in the plate reader at 30° C. for up to 250 h. The fluorescence was measured every 4 h (excitation 440 nm, emission 590 nm).

Data Evaluation. Aβ data were analyzed according to common algorithms. Fibril formation from monomeric Aβ was evaluated using equation A, $$y = \text{limit}*[1 - 1/(1 + e^{a*t+b})] \qquad \text{A.}$$

The progress curve of the de novo pGlu-Aβ(3-40) fibril formation was analyzed according to equation B, denoting a quick initial first-order aggregation reaction, which is followed by a higher-order fibril formation process:

$$y = \text{limit1} - e^{-a*t+b} + \text{limit2}*[1 - 1/(1 + e^{c*t+d})] \qquad \text{B.}$$

The velocity of initial seed formation was quantified from the derivatives in respect of time, $$y' = (\text{limit}*a*ea^{*t+b})/(1 + e^{a*t+b})^2 \qquad \text{A' and}$$

$$y' = a*e^{-a*t+b} + (\text{limit2}*c*e^{c*t+d})/(1 + e^{c*t+d})^2 \qquad \text{B'.}$$

Behavioral Analyses

Evaluation of Contextual Fear Memory

Procedure:

Day 1:
 from home cage to operant chamber: exploration for 2 minutes
 15 seconds auditory cue/last 2 seconds footshock
 again 15 seconds auditory cue/last 2 seconds footshock
 30 seconds later back to home cage Day 2:
 in operant chamber (context) for 5 minutes; measure freezing (immobility; A)
 back to home cage
 1 hour later: in novel environment for 3 minutes; measure freezing; B
 present auditory cue for 3 minutes; measure freezing; C
 calculate memory for the context: % freezing context−% freezing novel; D

103

Synthesis of the Inhibitors

Synthesis scheme 1: Synthesis of the examples 1-53, 96-102, 136-137

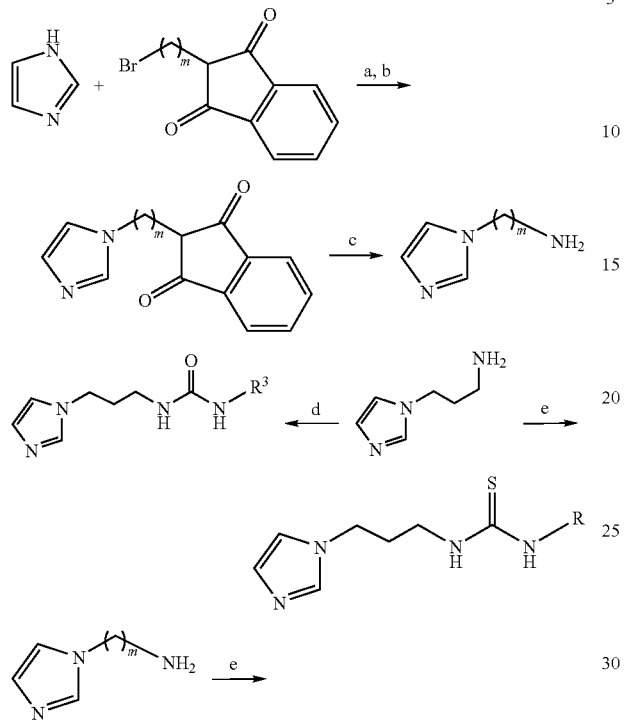

Reagents and conditions: (a) NaH, DMF, 4 h rt.; (b) , 8 h 100° C.; (c) H₂N—NH₂, EtOH, 8 h, reflux then 4N HCl, 6 h, reflux, (d) R³—NCO, EtOH, 6 h, reflux, (e) 3,4 dimethoxy-phenyl-isothiocyanate, Synthesis scheme 2: Synthesis of the examples 54-95

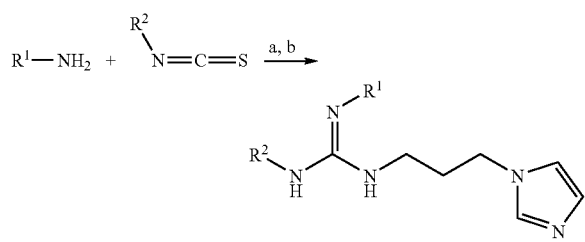

Reagents and conditions: (a) R—NCS, EtOH, 6 h, reflux; (b) WSCD, 1H-imidazole-1-propanamine, DMF, 2 h, r.t.

Synthesis scheme 3: Synthesis of the examples 103-105

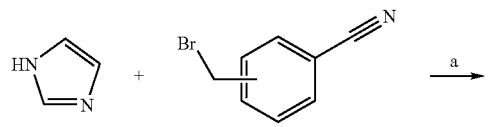

104

-continued

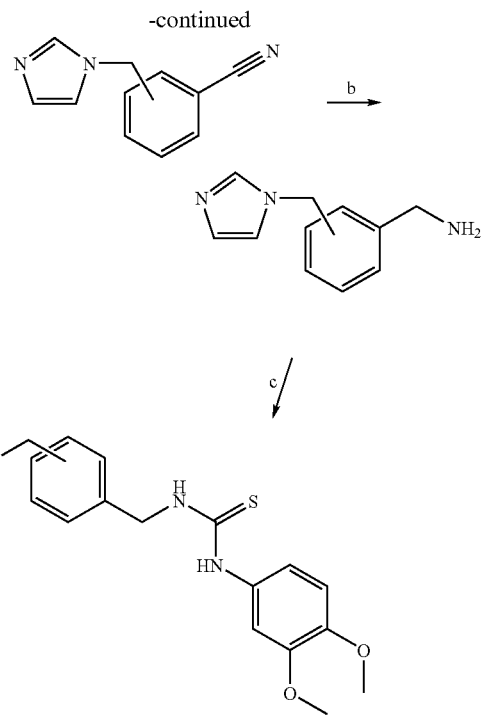

Reagents and conditions: (a) NaH, DMF, rt., 3 h;
(b) LiAlH₄, dioxane, reflux, 1 h;
(c) R-NCS, EtOH, reflux 6 h, Synthesis scheme 4: Synthesis of the examples 106-109

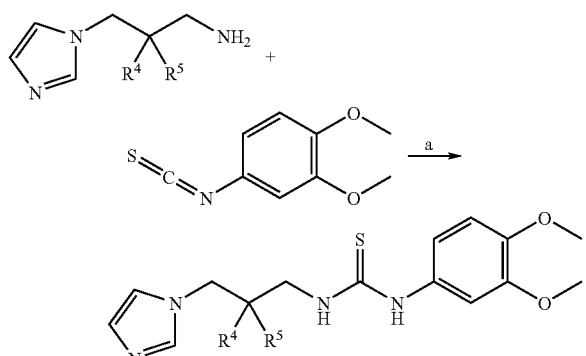

Reagents and conditions: (a) EtOH, 2 h, reflux

Synthesis scheme 5: Synthesis of the examples 110-112

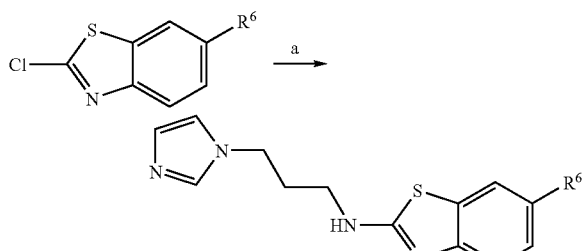

Reagents and conditions: (a) 1H-imidazole-1-propanamine, Triethylamine, Toluene, 12 h, reflux Synthesis scheme 6: Synthesis of the examples 113-132

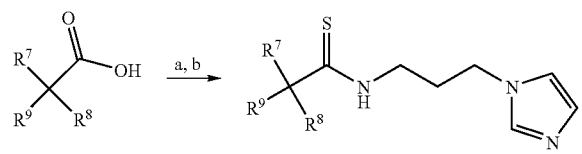

Reagents and conditions: (a) CAIBE, 1H-imidazole-1-propanamine, Dioxan, 0° C., 12 h; (b) Lawesson's Reaent, EtOH, reflux, 8 h Synthesis scheme 7: Synthesis of the examples 133-135

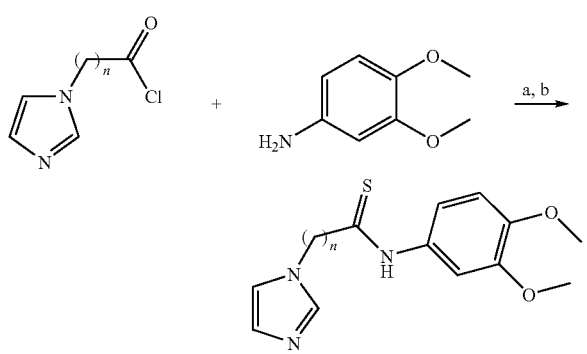

Reagents and conditions: (a) 1H-imidazole-1-propan acidic chloride, CH$_2$Cl$_2$, -10° C., 1 h; (b) Lawesson's Reagent, Dioxane, reflux, 8 h Synthesis scheme 8: Synthesis of the example 138

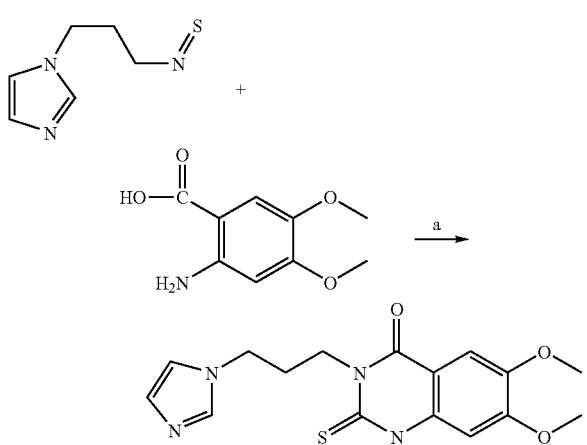

Reagents and conditions: (a) EtOH, reflux, 8 h

Synthesis scheme 9: Synthesis of the example 139

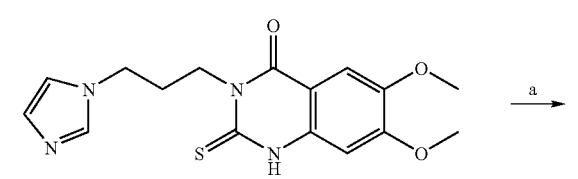

-continued

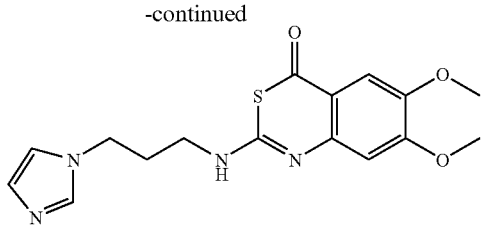

Reagents and conditions: (a) 75% conc. H$_2$SO$_4$, 4 h

Synthesis scheme 10: Synthesis of the example 140

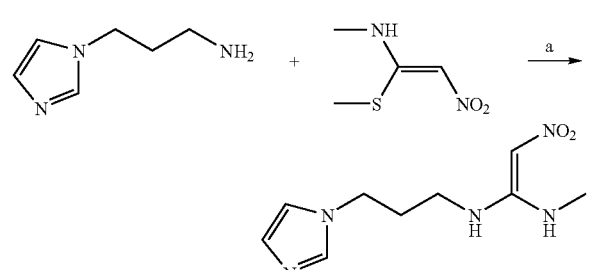

Reagents and conditions: (a) Acetonitrile, reflux 2 h

Synthesis scheme 11: Synthesis of the example 141

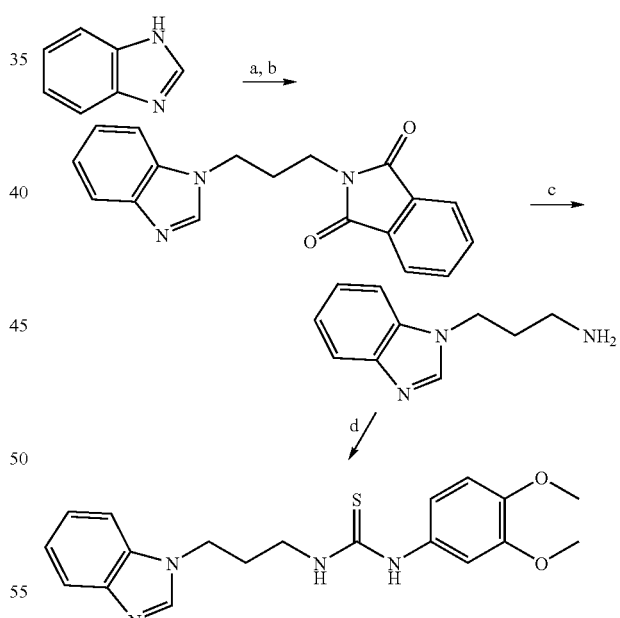

Reagents and conditions: (a) NaH, DMF, 4 h, rt.; (b) , 8 h, 100° C.; (c) H$_2$N—NH$_2$, EtOH, 8 h, reflux then 4N HCl, 6 h, reflux, (d) 3,4 dimethoxy-phenyl-isothiocyanate, EtOH, 6 h, reflux Analytical Conditions ESI-Mass spectra were obtained with a SCIEX API 365 spectrometer (Perkin Elmer). The $^1$H-NMR (500 MHz) data was recorded on a BRUKER AC 500, using DMSO-D$_6$ as solvent. Chemical shifts are expressed as parts per million downfield from tetramethylsilane. Splitting patterns have been designated as follows: s (singlet), d (doublet), dd (doublet of doublet), t (triplet), m (multiplet), and br (broad signal).

Detailed Synthesis Description

Examples 1-12 and 14-53

1H-imidazole-1-propanamine was reacted with the corresponding isothiocyanate in ethanol under reflux for 8 h. After that the solvent was removed and the remaining oil was dissolved in methylene chloride. The organic layer washed twice with a saturated solution of $NaHCO_3$ followed by $NaHSO_4$ and brine, dried then evaporated. The remaining solid was re-crystallized from ethyl acetate, yielding the example thiourea in yields of 80-98%.

Example 13

1-(3-(1H-imidazol-1-yl)propyl)-3-(3,4-dimethoxyphenyl)thiourea 4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol.
Yield: 0.66 g (51.3%); mp: 160.0-161.0° C.
$^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M-$C_3H_3N_2$.)

Examples 96-102

1H-imidazole-1-propanamine was reacted with the corresponding isocyanate in ethanol under reflux for 8 h. After that the solvent was removed and the remaining oil was dissolved in methylene chloride. The organic layer washed twice with a saturated solution of $NaHCO_3$ followed by $NaHSO_4$ and brine, dried then evaporated. The remaining solid was re-crystallized from ethyl acetate, yielding the example urea in yields of 85-90%.

Examples 136, 137

The 1H-imidazole-1-alkylamines were prepared according to the literature from □-brom-alkyl-phthalimides and imidazolium salt and subsequent hydrazinolysis. The resulting products were transformed into the thioureas according to example 1-53 giving a 88% (example 136) and 95% (example 137) yield.

Examples 54-95

All examples were made from the corresponding thioureas by reacting with Water-soluble-carbodiimide (WSCD) and 1H-imidazole-1-propanamine in dry dimethyl form-amide for 2 h at r.t. giving the trisubstituted guanidines with yields from 40-87%.

Examples 103-105

Imidazole was reacted with the corresponding bromomethylphenylcyanide in DMF, utilizing 1 equivalent of NaH for 3 h under rt., giving the 1H-imidazole-1-methylphenylcyanides. The solvent was removed and the resulting oil was re-dissolved in dioxane. The cyanides were converted in the corresponding amines using 1 equivalent of $LiAlH_4$. After adding a saturated solution of $KHSO_4$, dioxane was evaporated and the aqueous layer was extracted by means of $CHCl_3$. The organic layer was concentrated in vacuo and the amine was converted in the corresponding thioureas according to example 1-53 giving a 78% (example 103) and 65% (example 104) and 81% (example 105) yield.

Examples 106-109

Starting from the corresponding methanesulfonate-2-methylpropyl-phthalimides the amines were synthesized as described for the amines in example 136-137. The resulting products were transformed into the thioureas according to example 1-53 giving example 106-109 in total yields of 25-30%.

Examples 110-112

1H-imidazole-1-propanamine was reacted with the corresponding 2-chlorobenzo[d]thiazole in toluol for 24 h at a temperature of 130° C. After removing the solvent and recrystallization from methanol example 110-112 was yielded in an amount of 55-65%.

Examples 113-118, 120-124 and 126-132

1H-imidazole-1-propanamine was reacted with the corresponding 2-phenyl acetic acid in dry dioxane by adding one equivalent of CAIBE and N-methylmorpholine at a temperature of 0° C. After 2 h the mixture was allowed to warm to r.t. and the mixture was stirred for 12 h. After removing the solvent the resulting oil was redissolved in methylene chloride and the organic layer washed by means of an aqueous solution of $NaHCO_3$ and water, dried and the solvent was evaporated. The remaining oil was dissolved in dioxane adding Laweson's Reagent. After stirring for 12 h a saturated solution of $NaHCO_3$ was added. Dioxane was evaporated and the aqueous layer was extracted by means of ethyl acetate. The organic layer was separated, dried and the solvent was evaporated. The remaining solid was crystallized from acetyl acetate/ether, giving 113-118, 120-124 and 126-132 with total yields of 62-85%.

Example 119

N-(3-(1H-imidazol-1-yl)propyl)-2-(3,4-dimethoxyphenyl)ethanethioamide

A mixture of 4.0 mmol triethylamine and 4.0 mmol of 3-(1H-imidazol-1-yl)alkyl-1-amine 20 mL of dioxane was added drop wise to an ice cooled, stirred solution of 4.0 mmol of 2-(3,4-dimethoxyphenyl)acetyl chloride in 30 mL of dioxane. The mixture was allowed to warm to r.t., and then stirred for 1 h. After removing the solvent by reduced pressure, the residue was redissolved in 50 mL of dichloromethane. The organic layer washed by means of 30 mL of saturated aqueous solution of $NaHCO_3$, and water. The organic solution was dried, filtered, and the solvent was removed under reduced pressure. After redissolving in 50 mL of dry dioxane 2.2 mmol of Lawesson's reagent was added, and the mixture was heated to 90° C. and stirred for 8 h. The solvent was removed by reduced pressure, and the residue was redissolved in 50 mL of dichloromethane. The organic layer washed three times by means of a saturated aqueous solution of $NaHCO_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.14 g (10.6%); melting point: 148.0-150.0° C.

$^1$H NMR δ 2.0-2.15 (br m, 2H), 3.4-3.5 (m, 2H), 3.7 (s, 6H), 6.75-6.8 (m, 2H), 4.1-4.2 (m, 2H), 6.8-6.9 (m, 2H), 6.95-7.0 (m, 1H), 7.4 (s, 1H), 7.75-7.85 (br m, 1H), 8.6 (s, 1H), 10.2 (s, 1H); MS m/z 320.2 (M+H), 252.2 (M-C$_3$H$_3$N$_2$.)

Example 125

N-(3-(1H-imidazol-1-yl)propyl)-1-(3,4-dimethoxyphenyl)cyclopropanecarbo-thioamide 11.06 mmol of 3,4-dimethoxyphenyl acetonitrile, 34.8 mmol of 2-Bromo-1-chloroethanole and 1.16 mmol of triethylbenzylammonium hydrochloride were dissolved in 10 mL of an aqueous solution of KOH (60%). The mixture was transferred into an ultrasonic bath and vigorously stirred for 3 h at room temperature. The resulting suspension was diluted with 40 mL of water and extracted three times by means of 20 mL of dichloromethane. The combined organic layers where washed by means of an aqueous solution of hydrochloric acid (1N), dried over Na$_2$SO$_4$ and the solvent was removed under reduced pressure. The remaining oil was purified by flash-chromatography using silica gel and ethyl acetate/heptane as eluting system, resulting in 0.81 g (34.4%) of 1-(3,4-dimethoxyphenyl)cyclopropanecarbonitrile 3.9 mmol of 1-(3,4-dimethoxyphenyl)cyclopropanecarbonitrile and 11.2 mmol of KOH were suspended in 80 mL of ethylene glycol. The mixture was stirred for 12 h under reflux. Then 80 mL of water were added and the aqueous layer was extracted two times with ether. After pH adjustment to a value of pH=4-5 using HCl (1N) the aqueous layer was extracted three times by means of ether, then the combined organic layers were dried over Na$_2$SO$_4$ and the solvent was removed, resulting in 0.81 g (93.5%) of 1-(3,4-dimethoxyphenyl)cyclopropanecarboxylic acid.

3.44 mmol of 1-(3,4-dimethoxyphenyl)cyclopropanecarboxylic acid, 3.5 mmol of N-Methyl morpholine, and 3.5 mmol of isobutyl chloroformiat were dissolved in dry tetrahydrofurane and stirred for 15 min at −15° C. Then 3.5 mmol of 3-(1H-imidazol-1-yl)alkyl-1-amine was added and the mixture was allowed to warm to 0° C. and was stirred for 12 h. The solvent was removed under reduced pressure and the remaining oil was redissolved in chloroform. Then the organic layer washed two times by means of a saturated aqueous solution of NaHCO$_3$, then dried over Na$_2$SO$_4$ and the solvent was removed. Purification was performed by means of centrifugal forced chromatography using a Chromatotron® device (Harrison Research Ltd.) utilizing silica plates of a layer thickness of 2 mm, and a CHCl$_3$/MeOH gradient as eluting system resulting in 0.671 g (59.3%) of N-(3-(1H-imidazol-1-yl)propyl)-1-(3,4-dimethoxyphenyl)cyclopropane-carboxamide.

After redissolving in 30 mL of dry dioxane 1.43 mmol of Lawesson's reagent were added, and the mixture was heated to 90° C. and stirred for 8 h. The solvent was removed by reduced pressure, and the residue was remains were dissolved in 50 mL of dichloromethane. The organic layer washed three times by means of a saturated aqueous solution of NaHCO$_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.33 g (46.2%); melting point: 127.0-127.5° C.

$^1$H NMR δ 1.1-1.2 (t, 2H), 1.55-1.6 (t, 2H), 2.0-2.1 (m, 2H), 3.5-3.6 (m, 2H), 3.7-3.8 (s, 6H), 4.1-4.2 (t, 2H), 6.8-6.9 (m, 3H), 7.65 (s, 1H), 7.75 (s, 1H), 8.8 (m, 1H), 9.05 (s, 1H; MS m/z 346.0 (M+H), 278.2 (M-C$_3$H$_3$N$_2$.), 177.1 (M-C$_6$H$_8$N$_3$S.)

Examples 133-135

A mixture of 1 equivalent triethylamine and 3,4-dimethoxyaniline in dioxane was added to an stirred solution of the corresponding ω-bromoalkyl acidic chloride at a temperature of 0° C. The solution was allowed to warm to r.t. and stirred for 2 h. The solvent was evaporated, and the remaining oil was redissolved in dichloromethane. The organic layer washed by means of water, dried, filtered, and the solvent was removed under reduced pressure.

Imidazole and sodium hydride were suspended in and the mixture was stirred under inert conditions at r.t. for 3 h. ω-Bromo-N-(3,4-dimethoxy-phenyl)alkylamide was added and the mixture was heated to 100° C. and stirred for 8 h. After that, the solvent was evaporated, hot toluene were added and the solution was filtered. Then the solvent was removed under reduced pressure. The transformation into the thioamides was performed as described for example 113-132 by means of Laweson's reagent, giving 133-135 in total yields of 13-20%.

The analytical data for further examples, which were synthesized according to the general synthesis schemes described above, are as follows:

Example 1

1-(3-(1H-imidazol-1-yl)propyl)-3-methylthiourea melting point: 122-122.5° C.

$^1$H NMR δ 1.85-1.95 (m, 2H), 2.8 (s, 3H), 3.2-3.5 (br d, 2H), 3.8-3.9 (m, 2H), 6.85 (d, 1H), 7.15 (d, 1H), 7.3-7.5 (br d, 2H), 7.65 (s, 1H); MS m/z 199.1 (M+H), 221.3 (M+Na), 131.0 (M-C$_3$H$_3$N$_2$.)

Example 2

1-(3-(1H-imidazol-1-yl)propyl)-3-tert-butylthiourea melting point: 147.0-147.5° C.

$^1$H NMR δ 1.3-1.4 (s, 9H), 1.85-1.95 (m, 2H), 3.5 (t, 2H), 3.8 (t, 2H), 6.85 (d, 1H), 7.15 (d, 1H), 7.3-7.5 (br d, 2H), 7.65 (s, 1H); MS m/z 241.1 (M+H), 173.1 (M-C$_3$H$_3$N$_2$.)

Example 3

1-(3-(1H-imidazol-1-yl)propyl)-3-benzylthiourea melting point: 127.0-128.0° C.

$^1$H NMR δ 1.85-1.95 (m, 2H), 3.2-3.5 (br d, 2H), 3.8-3.9 (m, 2H), 4.6 (s, 2H), 6.8 (d, 1H), 7.15 (d, 1H), 7.19-7.35 (m, 5H), 7.5-7.6 (br d, 2H), 7.85 (s, 1H); MS m/z 275.3 (M+H), 207.1 (M-C$_3$H$_3$N$_2$.)

Example 5

1-(3-(1H-imidazol-1-yl)propyl)-3-phenylthiourea melting point: 166.5-167.0° C.

$^1$H NMR δ 1.95-2.05 (m, 2H), 3.3-3.5 (br d, 2H), 3.9-4.0 (m, 2H), 6.85 (d, 1H), 7.05 (m, 1H) 7.15 (d, 1H), 7.25 (m, 2H), 7.35 (m, 2H), 7.6 (s, 1H), 7.8 (br s, 1H), 9.5 (br s, 1H); MS m/z 261.1 (M+H), 193.2 (M-C$_3$H$_3$N$_2$.)

Example 6

1-(3-(1H-imidazol-1-yl)propyl)-3-(4-fluorophenyl) thiourea melting point: 147.0-148.0° C.
$^1$H NMR δ 1.95-2.05 (m, 2H), 3.3-3.5 (br d, 2H), 3.9-4.05 (m, 2H), 6.85 (d, 1H), 7.05-7.15 (m, 3H), 7.3-7.4 (m, 2H), 7.6 (s, 1H), 7.7-7.8 (br s, 1H), 9.4 (br s, 1H); MS m/z 279.3 (M+H), 211.2 (M-$C_3H_3N_2$.)

Example 7

1-(3-(1H-imidazol-1-yl)propyl)-3-(4-ethylphenyl) thiourea melting point: 100.0-100.5° C.
$^1$H NMR δ 1.15-1.2 (t, 3H), 1.9-2.0 (m, 2H), 2.5-2.6 (m, 2H), 3.3-3.5 (br d, 2H), 3.9-4.05 (m, 2H), 6.85 (d, 1H), 7.1-7.2 (m, 3H), 7.25-7.3 (m, 2H), 7.6 (s, 1H), 7.7-7.8 (br s, 1H), 9.4 (br s, 1H); MS m/z 289.3 (M+H), 221.1 (M-$C_3H_3N_2$.)

Example 8

1-(3-(1H-imidazol-1-yl)propyl)-3-(4-(trifluoromethyl)phenyl)thiourea melting point: 154.5-155.0° C.
$^1$H NMR δ 1.9-2.1 (br m, 2H), 3.4-3.6 (br d, 2H), 3.95-4.1 (br m, 2H), 6.85 (d, 1H), 7.2 (d, 1H), 7.6-7.8 (m, 5H), 8.2 (br s, 1H), 9.9 (br s, 1H); MS m/z 329.3 (M+H), 261.2 (M-$C_3H_3N_2$.)

Example 10

1-(3-(1H-imidazol-1-yl)propyl)-3-(4-acetylphenyl) thiourea melting point: 170.0-171.0° C.
$^1$H NMR δ 1.9-2.1 (br m, 2H), 2.4-2.5 (s, 3H), 3.2-3.5 (br m, 2H), 3.9-4.1 (m, 2H), 6.85 (d, 1H), 7.15 (d, 1H), 7.5-7.65 (br m, 3H), 7.8-7.9 (m, 2H), 8.1 (m, 2H), 9.8 (br s, 1H); MS m/z 303.2 (M+H), 235.1 (M-$C_3H_3N_2$.)

Example 11

1-(3-(1H-imidazol-1-yl)propyl)-3-(4-methoxyphenyl)thiourea melting point: 125.0-125.5° C.
$^1$H NMR δ 1.8-2.0 (br m, 2H), 3.2-3.5 (br m, 2H), 3.7 (s, 3H), 3.9-4.0 (m, 2H), 6.7-6.9 (m, 3H), 7.1-7.2 (m, 3H), 7.5 (s, 1H), 7.6 (s, 1H), 9.2 (s, 1H); MS m/z 291.1 (M+H), 223.2 (M-$C_3H_3N_2$.)

Example 14

1-(3-(1H-imidazol-1-yl)propyl)-3-(2,4-dimethoxyphenyl)thiourea melting point: 120.0-120.5° C.
$^1$H NMR δ 1.8-2.0 (br m, 2H), 3.4-3.5 (br m, 2H), 3.75 (s, 6H), 3.9-4.0 (m, 2H), 6.5 (d, 1H), 6.6 (s, 1H), 6.9 (s, 1H), 7.15 (s, 1H), 7.3 (d, 1H), 7.5 (br s, 1H), 7.6 (s, 1H), 9.75 (s, 1H); MS m/z 321.2 (M+H), 253.3 (M-$C_3H_3N_2$.)

Example 15

1-(3-(1H-imidazol-1-yl)propyl)-3-(3,5-dimethoxyphenyl)thiourea melting point: 142.0-143.0° C.
$^1$H NMR δ 1.8-2.0 (br m, 2H), 3.4-3.5 (br m, 2H), 3.6 (s, 6H), 3.95-4.0 (m, 2H), 6.25 (m, 1H), 6.6 (m, 2H), 6.9 (s, 1H), 7.2 (s, 1H), 7.6 (s, 1H), 7.8 (s, 1H), 9.5 (s, 1H); MS m/z 321.2 (M+H), 253.3 (M-$C_3H_3N_2$.)

Example 23

1-(3-(1H-imidazol-1-yl)propyl)-3-(2,3-dihydrobenzo[b][1,4]dioxin-7-yl)-thiourea melting point: 103.0-103.5° C.
$^1$H NMR δ 1.9-2.0 (br m, 2H), 3.3-3.5 (br d, 2H), 3.9-4.0 (m, 2H), 4.2-4.3 (m, 4H), 6.7 (m, 1H), 6.8-6.8 (m, 1H), 6.9 (m, 2H), 7.2 (s, 1H), 7.6 (m, 2H), 9.3 (s, 1H); MS m/z 319.3 (M+H), 251.3 (M-$C_3H_3N_2$.)

Example 24

1-(3-(1H-imidazol-1-yl)propyl)-3-(benzo[d][1,3] dioxol-6-yl)thiourea melting point: 115.0-115.6° C.
$^1$H NMR δ 1.9-2.1 (br m, 2H), 3.4-3.5 (br d, 2H), 4.05-4.15 (m, 2H), 6.0 (s, 2H), 6.7 (m, 1H), 6.8-6.85 (m, 1H), 6.95 (d, 1H), 7.25 (s, 1H), 7.45 (s, 1H), 7.7 (br s, 1H), 8.5 (br s, 1H), 9.4 (br s, 1H); MS m/z 305.2 (M+H), 237.2 (M-$C_3H_3N_2$.)

Example 25

1-(3-(1H-imidazol-1-yl)propyl)-3-(3,4,5-trimethoxyphenyl)thiourea melting point: 124.5-125.5° C.
$^1$H NMR δ 1.8-2.0 (m, 2H), 3.4-3.5 (br m, 2H), 3.6 (s, 3H), 3.7 (s, 6H), 3.9-4.0 (m, 2H), 6.65 (m, 2H), 6.85 (s, 1H), 7.2 (s, 1H), 7.6 (s, 1H), 7.7 (br s, 1H), 9.4 (s, 1H); MS m/z 351.3 (M+H), 283.2 (M-$C_3H_3N_2$.)

Example 26

1-(3-(1H-imidazol-1-yl)propyl)-3-(3-methoxyphenyl)thiourea melting point: 89.5-90.0° C.
$^1$H NMR δ 1.9-2.1 (m, 2H), 3.4-3.5 (br m, 2H), 3.7 (s, 3H), 3.9-4.0 (m, 2H), 6.6-6.7 (m, 1H), 6.8-6.9 (m, 2H), 7.1 (m, 2H), 7.15-7.25 (br m, 1H), 7.6 (s, 1H), 7.8 (br s, 1H), 9.5 (s, 1H); MS m/z 291.1 (M+H), 223.2 (M-$C_3H_3N_2$.)

Example 27

1-(3-(1H-imidazol-1-yl)propyl)-3-(4-ethoxyphenyl) thiourea melting point: 126.0-126.5° C.
$^1$H NMR δ 1.5 (br m, 3H), 1.9-2.0 (br m, 2H), 3.4-3.5 (br m, 2H), 3.9-4.0 (br m, 4H), 6.8-6.9 (m, 2H), 6.95 (s, 1H), 7.15-7.2 (m, 2H), 7.25 (s, 1H), 7.55-7.6 (br s, 1H), 7.8 (s, 1H), 9.3 (s, 1H); MS m/z 305.2 (M+H), 237.2 (M-$C_3H_3N_2$.)

Example 33

1-(3-(1H-imidazol-1-yl)propyl)-3-(4-(methylthio)phenyl)thiourea melting point: 140.0-140.5° C.
$^1$H NMR δ 1.8-2.05 (br m, 2H), 2.5 (s, 3H), 3.3-3.5 (br m, 2H), 3.9-4.1 (m, 2H), 6.9 (m, 1H), 7.1-7.3 (br m, 5H), 7.6 (s, 1H), 7.75 (br s, 1H), 9.4 (s, 1H); MS m/z 307.2 (M+H), 239.2 (M-C$_3$H$_3$N$_2$.)

Example 42

1-(3-(1H-imidazol-1-yl)propyl)-3-(4-nitrophenyl)thiourea melting point: 165.0. 166.0° C.
$^1$H NMR δ 1.9-2.05 (m, 2H), 3.3-3.5 (br d, 2H), 3.95-4.05 (m, 2H), 6.85 (d, 1H), 7.15 (d, 1H), 7.6 (d, 1H), 7.7 (m, 2H), 8.1 (m, 2H), 8.3 (br s, 1H), 10.1 (br s, 1H); MS m/z 306.2 (M+H), 237.9 (M-C$_3$H$_3$N$_2$.)

Example 50

1-(3-(1H-imidazol-1-yl)propyl)-3-(4-(dimethylamino)phenyl)thiourea melting point: 146.5-147.0° C.
$^1$H NMR δ 1.9-2.0 (m, 2H), 2.9 (s, 6H), 3.4 (m, 2H), 3.9-4.0 (m, 2H), 6.7 (m, 2H), 6.9 (s, 1H), 7.05-7.1 (m, 2H), 7.15 (s, 1H), 7.4 (br s, 1H), 7.6 (s, 1H), 9.2 (s, 1H); MS m/z 304.2 (M+H), 236.0 (M-C$_3$H$_3$N$_2$.)

Example 102

1-(3-(1H-imidazol-1-yl)propyl)-3-(3,4-dimethoxyphenyl)urea melting point: 114.5-115.0° C.
$^1$H NMR δ 1.7-1.9 (m, 2H), 2.9-3.1 (m, 2H), 3.7 (2s, 6H), 3.9-4.0 (m, 2H), 6.1 (t, 1H), 6.7 (s, 2H), 6.8 (s, 1H), 7.15 (d, 2H), 7.6 (s, 1H), 8.2 (s, 1H); MS m/z 321.2 (M+H), 253.3 (M-C$_3$H$_3$N$_2$.)

Example 106

1-((S)-3-(1H-imidazol-1-yl)-2-methylpropyl)-3-(3,4-dimethoxyphenyl)-thiourea melting point:: 150.5-151.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.6 (M+H), 267.1 (M-C$_3$H$_3$N$_2$.)

Example 107

1-((R)-3-(1H-imidazol-1-yl)-2-methylpropyl)-3-(3,4-dimethoxyphenyl)-thiourea melting point: 155.0-157.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.4 (M+H), 267.2 (M-C$_3$H$_3$N$_2$.)

Example 109

1-((1-(((1H-imidazol-1-yl)methyl)cyclopropyl)methyl)-3-(3,4-dimethoxy-phenyl)thiourea melting point: 166.5-168.5° C.
$^1$H NMR δ 0.7-0.8 (br m, 2H), 1.85-1.9 (m, 1H), 2.15-2.2 (m, 1H), 2.2-2.3 (m, 1H), 3.4-3.5 (m, 1H), 3.7 (d, 6H), 4.2 (s, 1H), 4.95 (s, 1H), 6.75-6.8 (br m, 1H), 6.85-6.9 (br m, 1H), 7.0 (s, 1H), 7.5 (m, 1H), 7.6 (m, 1H), 7.7 (s, 0.5H), 7.8 (s, 0.5H), 8.85 (s, 0.5H), 9.1 (s, 0.5H), 9.35 (s, 0.5H), 9.45 (s, 0.5H); MS m/z 347.2 (M+H), 279.2 (M-C$_3$H$_3$N$_2$), 137.5 (M-C$_9$H$_{13}$N$_4$S.)

Example 110

N-(3-(1H-imidazol-1-yl)propyl)benzo[d]thiazol-2-amine $^1$H NMR δ 1.95-2.15 (m, 2H), 3.25-3.35 (m, 2H), 4.0-4.1 (t, 2H), 6.9 (s, 1H), 6.95-7.05 (t, 1H), 7.15-7.2 (m, 2H), 7.35-7.4 (d, 1H), 7.60-7.70 (m, 2H), 8.0-8.1 (br s, 1H); MS m/z 259.4 (M+H), 191.3 (M-C$_3$H$_3$N$_2$.)

Example 111

N-(3-(1H-imidazol-1-yl)propyl)-6-chlorobenzo[d]thiazol-2-amine $^1$H NMR δ 1.95-2.15 (m, 2H), 3.25-3.35 (m, 2H), 4.0-4.1 (t, 2H), 6.9 (s, 1H), 7.1-7.2 (d, 2H), 7.3-7.4 (d, 1H), 7.65 (s, 1H), 7.8 (s, 1H), 8.2 (s, 1H); MS m/z 293.3 (M+H), 225.3 (M-C$_3$H$_3$N$_2$.)

Example 112

N-(3-(1H-imidazol-1-yl)propyl)-6-methoxybenzo[d]thiazol-2-amine $^1$H NMR δ 1.9-2.05 (m, 2H), 3.2-3.3 (m, 2H), 3.7 (s, 3H), 4.0-4.1 (t, 2H), 6.7-6.8 (d, 1H), 6.9 (s, 1H), 7.15-7.2 (s, 1H), 7.2-7.3 (m, 2H), 7.65 (s, 1H), 7.8 (s, 1H); MS m/z 289.1 (M+H), 221.4 (M-C$_3$H$_3$N$_2$.)

Example 115

(R)—N-(3-(1H-imidazol-1-yl)propyl)-2-phenylpropanethioamide melting point: 82.0-82.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-C$_3$H$_3$N$_2$.)

Example 116

(S)—N-(3-(1H-imidazol-1-yl)propyl)-2-phenylpropanethioamide melting point: 82.5-83.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-C$_3$H$_3$N$_2$.)

Example 121

N-(3-(1H-imidazol-1-yl)propyl)-1-(4-chlorophenyl) cyclobutanecarbo-thioamide melting point: 137.5-139.0° C.
$^1$H NMR δ1.55-1.75 (br m, 2H), 1.85-1.95 (br m, 2H), 2.4-2.5 (br m, 2H), 2.7-2.85 (br m, 2H), 3.3-3.5 (br m, 2H), 3.8 (m, 2H), 6.9 (s, 1H), 7.0 (s, 1H), 7.3 (m, 2H), 7.45 (s, 1H), 7.5 (m, 2H), 9.6 (t, 1H); MS m/z 334.3 (M+H), 266.1 (M-C$_3$H$_3$N$_2$.)

Example 122

N-(3-(1H-imidazol-1-yl)propyl)-1-(4-chlorophenyl) cyclopentanecarbothioamide melting point: 140.0-141.0° C.
$^1$H NMR δ 1.5-1.65 (br m, 4H), 1.8-1.9 (m, 2H), 2.0-2.1 (m, 2H), 2.6 (m, 2H), 3.4-3.5 (m, 2H), 3.7-3.8 (m, 2H), 6.85 (s, 1H), 7.0 (s, 1H), 7.35 (m, 2H), 7.4 (m, 2H), 7.5 (s, 1H), 9.4 (t, 1H); MS m/z 348.2 (M+H), 280.2 (M-C$_3$H$_3$N$_2$.)

Example 123

N-(3-(1H-imidazol-1-yl)propyl)-1-(4-methoxyphenyl)cyclohexanecarbothioamide melting point: 162.5-164.0° C.
$^1$H NMR δ 1.2-1.3 (m, 1H), 1.35-1.5 (br m, 5H), 1.85-2.0 (br m, 4H), 2.4-2.6 (br m, 2H), 3.4-3.5 (m, 2H), 3.7 (s, 3H), 3.8 (m, 2H), 6.8 (m, 3H), 7.0 (s, 1H), 7.3 (m, 2H), 7.5 (s, 1H), 9.2 (t, 1H); MS m/z 358.3 (M+H), 290.3 (M-C$_3$H$_3$N$_2$.)

Example 124

N-(3-(1H-imidazol-1-yl)propyl)-1-(4-methoxyphenyl)cyclopropanecarbo-thioamide melting point:: 129.0-129.5° C.
$^1$H NMR δ 1.0-1.1 (m, 2H), 1.5-1.6 (m, 2H), 1.9-2.0 (br m, 2H), 3.4-3.5 (m, 2H), 3.7 (s, 3H), 3.9 (m, 2H), 6.9 (m, 3H), 7.1 (s, 1H), 7.2-7.3 (m, 2H), 7.6 (s, 1H), 8.9 (br s, 1H); MS m/z 316.0 (M+H), 248.4 (M-C$_3$H$_3$N$_2$.)

Example 134

5-(1H-imidazol-1-yl)-N-(3,4-dimethoxyphenyl)pentanethioamide melting point:: 128.0-128.5° C.
$^1$H NMR δ 1.65-1.70 (m, 2H), 1.75-1.80 (m, 2H), 2.7-2.75 (m, 2H), 3.7 (s, 3H), 3.75 (s, 3H), 4.0-4.05 (t, 2H), 6.9-7.0 (m, 2H), 7.2 (s, 1H), 7.3 (d, 1H), 7.5 (s, 1H), 7.75 (s, 1H), 11.0 (s, 1H); MS m/z 320.2 (M+H), 252.2 (M-C$_3$H$_3$N$_2$.)

Example 136

1-(2-(1H-imidazol-1-yl)ethyl)-3-(3,4-dimethoxyphenyl)thiourea melting point: 157.5-159.0° C.
$^1$H NMR δ 3.7 (2 s, 6H), 3.8 (m, 2H), 4.2 (m, 2H), 6.7 (m, 1H), 6.85 (m, 1H), 6.9 (m, 2H), 7.15 (s, 1H), 7.5 (br s, 1H), 7.6 (s, 1H), 9.5 (s, 1H); MS m/z 307.2 (M+H), 239.1 (M-C$_3$H$_3$N$_2$.)

---

The invention claimed is:

1. A method of treating a neurodegenerative disease in a mammal, comprising
administering to a mammalian subject a therapeutically effective amount of at least one inhibitor of glutaminyl cyclase (QC) for inhibiting conversion of N-terminal glutamic acid or glutamine residues to pyroglutamyl residues in at least one QC-substrate,
wherein said neurodegenerative disease is selected from the group consisting of mild cognitive impairment (MCI), Alzheimer's disease, neurodegeneration in Down Syndrome, Familial British Dementia, and Familial Danish Dementia.

2. The method according to claim 1 wherein said at least one QC-substrate is selected from the group consisting of Aβ(3-40), Aβ(3-42), [Gln3]Aβ(3-40), [Gln3]Aβ(3-42), [Glu11]Aβ(11-40), [Glu11]Aβ(11-42), [Gln11]Aβ(11-40), [Gln11]Aβ(11-42), ABri, ADan, [Gln$^1$]Gastrins (17 and 34), [Gln$^1$]Neurotensin, [Gln$^1$]FPP, [Gln$^1$]TRH, [Gln$^1$]GnRH, [Gln$^1$]CCL 2, [Gln$^1$]CCL 7, [Gln$^1$]CCL 8, [Gln$^1$]CCL 13, [Gln$^1$]CCL 16, [Gln$^1$]CCL 18, [Gln$^1$]ELA, [Gln$^1$]Fractalkine, [Gln$^1$]Orexin A, [Gln$^3$]glucagon(3-29) and [Gln$^5$]substance P(5-11).

3. The method according to claim 1 wherein said neurodegenerative disease is selected from the grow, consisting of Alzheimer's disease and mild cognitive impairment (MCI).

4. The method according to claim 1 wherein administration of the QC inhibitor results in suppression of myeloid progenitor cell proliferation.

5. The method of claim 1, wherein said QC-inhibitor is a competitive QC-inhibitor.

6. The method of claim 1, wherein said QC-inhibitor selectively binds to an active-site bound metal ion of QC.

7. The method of claim 1 wherein said QC-inhibitor inhibits glutaminyl cyclase with a $K_i$ of 10 μM or less.

8. The method of claim 1, wherein said QC-inhibitor inhibits glutaminyl cyclase with a $K_i$ of 1 μM or less.

9. The method of claim 1, wherein said QC-inhibitor inhibits glutaminyl cyclase with a $K_i$ of 0.1 μM or less.

10. The method of claim 1, wherein said QC-inhibitor inhibits glutaminyl cyclase with a $K_i$ of 0.01 μM or less.

11. The method of claim 1 wherein said QC-inhibitor inhibits glutaminyl cyclase with a $K_i$ of 0.001 μM or less.

12. The method of claim 1, wherein said QC inhibitor or a pharmaceutically acceptable salt, solvate, stereoisomer or polymorph thereof is selected from
(i) a compound of formula 1*:

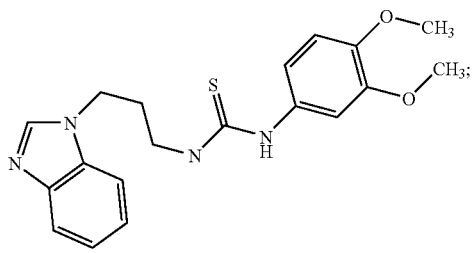

formula 1*

(ii) a compound of formula 1a,

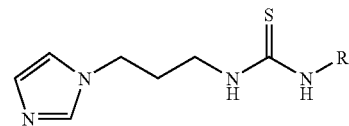

(1a)

wherein R is selected from the group consisting of:

Methyl;
tert-Butyl;
Benzyl;
Phenyl;
4-(fluoro)-pheny;l
4-(chloro)-phenyl;
4-(ethyl)-phenyl;
4-(trifluoromethyl)-phenyl;
4-(methoxy-carbonyl)-Phenyl;
4-(acetyl)-phenyl;
4-(methoxy)-phenyl;
bicyclo[2.2.1]hept-5-en-2-yl;
3,4-(dimethoxy)-phenyl;
2,4-(dimethoxy)-phenyl;
3,5-(dimethoxy)-phenyl;
2-(methoxy-carbonyl)-Phenyl;
4-(oxazol-5-y)-phenyl;
4-(pyrazol-1-yl)-phenyl;
4-(isopropyl)-phenyl;
4-(piperidine-1-sulfonyl)-Phenyl;
4-(morpholin-4-yl)-phenyl;
4-(cyano)-phenyl;
2,3-dihydro-benzo[1,4]dioxin-6-yl;
benzo[1,3]dioxol-5-yl;
3,4,5(trimethoxy)-phenyl;
3-(methoxy)-phenyl;
4-(ethoxy)-phenyl;
4-(benzyloxy)-phenyl;
4-(methoxy)-benzyl;
3,4-(dimethoxy)-benzyl;
2-(methoxy-carbonyl)-thiophene-3-yl;
3-(ethoxy-carbonyl)-4,5,6,7-tetrahydrobenzo[b]thiophene2-yl;
2-(methoxy-carbonyl)-4-(methyl)-thiophene-3-yl;
Benzo[c][1,2,5]thiazol-4-yl;
Benzo[c][1,2,5]thiazol-5-yl;
5-(methyl)-3-(phenyl)-isooxazol-4-yl;
3,5-(dimethyl)-isooxazol-4-yl;
4-(iodo)-phenyl;
4-(bromo)-phenyl;
4-(methyl)-phenyl;
Naphthalen-1-yl;
4-(nitro)-phenyl;
Butyl;
Cyclooctyl;
Furan-2-ylmethyl;
Tetrahydrofuran-2-ylmethyl;
Benzo[1,3]dioxol-5-ylmethyl;
2-(morpholin-4-yl)-ethyl;
4-(methylsulfanyl)-phenyl;
4-(dimethylamino)-phenyl;
4-(trifluoromethoxy)-phenyl;
Benzoyl; and
Pyridin-4-yl;

(iii) a compound of formula 1b,

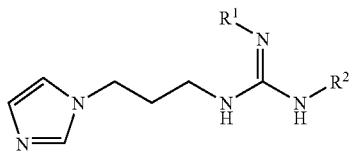
(1b)

wherein $R^1$ and $R^2$ are selected from the group consisting of:

| $R^1$ | $R^2$ |
|---|---|
| Cyano | Methyl |
| Cyano | 3,4-(dimethoxy)-phenyl |
| Cyano | 2,4-(dimethoxy)-phenyl |
| Cyano | 3,5-(dimethoxy)-phenyl |
| Cyano | 2,3-dihydrobenzo[b][1,4]dioxin-7-yl |
| Cyano | Benzo[d][1,3]dioxol-6-yl |
| Cyano | 3,4,5-(trimethoxy)-phenyl |
| Cyano | 3-(methoxy)-phenyl |
| Cyano | 4-(ethoxy)-phenyl |
| Cyano | 4-(benzyloxy)-phenyl |
| Cyano | Phenyl |
| Cyano | 4-(methoxy)-phenyl |
| Cyano | 4-(acetyl)-phenyl |
| Cyano | 4-(nitro)-phenyl |
| Cyano | Benzyl |
| Cyano | Naphthalen-1-yl |
| Cyano | 4-(fluoro)-phenyl |
| Cyano | 4-(iodo)-phenyl |
| Cyano | 4-(bromo)-phenyl |
| Cyano | Cyclooctyl |
| Cyano | tert-butyl |
| Cyano | 4-(methyl)-phenyl |
| Cyano | 4-(methylthio)-phenyl |
| Cyano | 4-(ethyl)-phenyl |
| Cyano | 4-(dimethylamino)-phenyl |
| Cyano | Butyl |
| Cyano | Trityl |
| Cyano | (Benzo[d][1,3]dioxol-6yl)methyl |
| Cyano | (tetrahydrofuran-2yl)methyl |
| Cyano | 4-(trifluoromethyl)-phenyl |
| Cyano | (furan-2-yl)methyl |
| Cyano | 2-(morpholin-4-yl)-ethyl |
| Cyano | 4-(oxazol-5yl)-phenyl |
| Cyano | Pyridin-3-yl |
| Cyano | 4-(cyano)-phenyl |
| Cyano | 4-(trifluoromethoxy)-phenyl |
| Cyano | 4-(piperidinosulfonyl)-phenyl |
| Cyano | 4-(1H-pyrazol-1-yl)phenyl |
| H | 3,4-(dimethoxy)-phenyl |
| Methyl | 3,4-(dimethoxy)-phenyl |
| Cyano | 2,3,4-(trimethoxy)-phenyl |
| Cyano | Cycloheptyl; |

(iv) a compound of formula 1c,

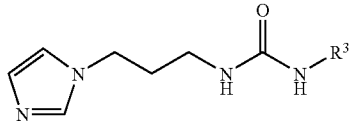
(1c)

wherein $R^3$ is selected from the group consisting of:

| |
|---|
| Ethyl; |
| 6-fluoro-4H-benzo[d][1,3]dioxin-8-yl; |
| 3-(cylopentyloxy)-4-(methoxy)-phenyl; |
| 4-(heptyloxy)-phenyl; |
| 3,4-dihydro-2H-benzo[b][1,4]dioxepin-7-yl; |
| 4-(butoxy)-phenyl; and |
| 3,4-(dimethoxy)-phenyl; |

(v) a compound of formula 1d,

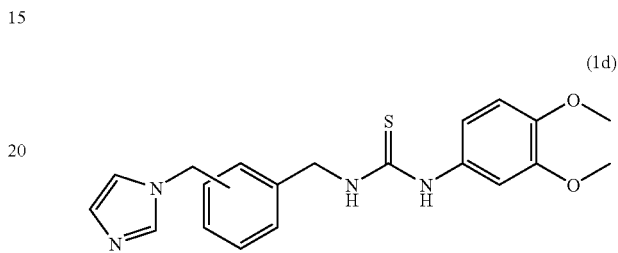
(1d)

wherein the position on the ring is selected from the group consisting of 2, 3, and 4;

(vi) a compound of formula 1e,

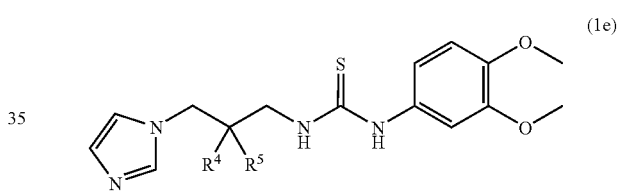
(1e)

wherein $R^4$ and $R^5$ selected from the group consisting of:

| $R^4$ | $R^5$ |
|---|---|
| H | Methyl |
| Methyl | H |
| Methyl | Methyl |
| —CH$_2$—CH$_2$—; | |

(vii) a compound of formula 1f,

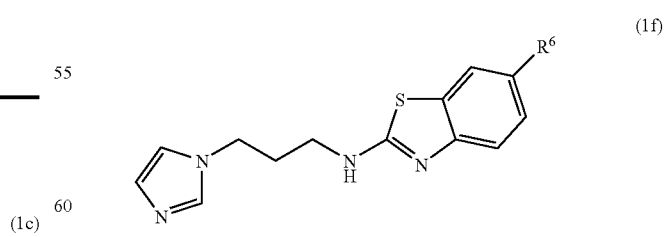
(1f)

wherein $R^6$ is selected from the group consisting of:
H;
Chloro; and
Methoxy;

(viii) a compound of formula 1g,

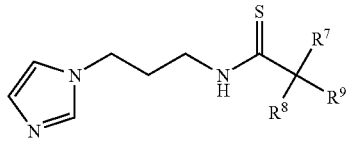

(1g)

wherein $R^7$, $R^8$ and $R^9$ are selected from the group consisting of:

| $R^7$ | $R^8$ | $R^9$ |
|---|---|---|
| Phenyl | H | H |
| Thiophen-2-yl | H | H |
| Phenyl | Methyl | H |
| Phenyl | H | Methyl |
| Phenyl | H | Ethyl |
| Phenyl | H | Phenyl |
| 3,4-(dimethoxy)-Phenyl | H | H |
| 3,4-(dimethoxy)-Phenyl | Methyl | Methyl |
| 4-(chloro)-phenyl | —CH$_2$—CH$_2$—CH$_2$— | |
| 4-(chloro)-phenyl | —CH$_2$—C$_2$H$_4$—CH$_2$— | |
| 4-(methoxy)-phenyl | —CH$_2$—C$_3$H$_6$—CH$_2$— | |
| 4-(methoxy)-phenyl | —CH$_2$—CH$_2$— | |
| 3,4-(dimethoxy)-Phenyl | —CH$_2$—CH$_2$— | |
| 3,4,5-(trimethoxy)-Phenyl | —CH$_2$—CH$_2$— | |
| 2,3,4-(trimethoxy)-Phenyl | —CH$_2$—CH$_2$— | |
| 2-(methoxy)-phenyl- | —CH$_2$—CH$_2$— | |
| 3-(methoxy)-phenyl- | —CH$_2$—CH$_2$— | |
| 2,3-(dimethoxy)-Phenyl | —CH$_2$—CH$_2$— | |
| 3,5-(dimethoxy)-Phenyl | —CH$_2$—CH$_2$— | |
| 2,5-(dimethoxy)-Phenyl; | —CH$_2$—CH$_2$— | |

(ix) a compound of formula 1h,

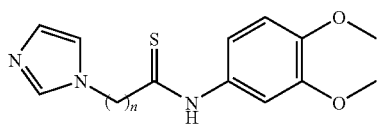

(1h)

wherein n is defined as 3, 4, or 5;

(x) a compound of formula 1i,

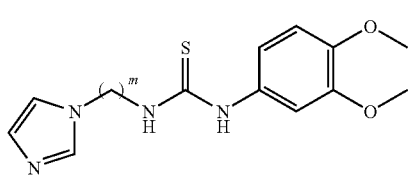

(1i)

wherein m is defined as 2 or 4;

(xi) a compound selected from the group consisting of:

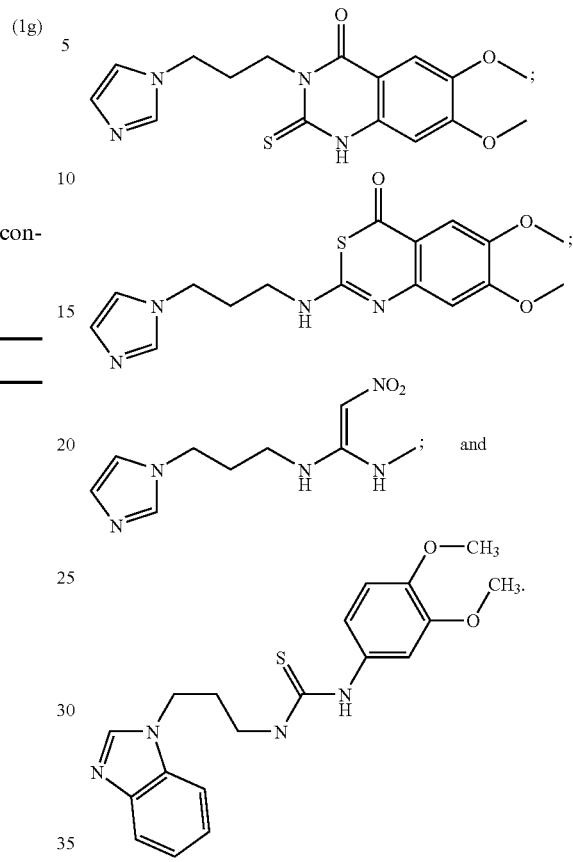

13. The method of claim 1, wherein said QC-inhibitor is 1-(3-(1H-imidazole-1-yl)propyl)-3-(3,4-dimethoxy-phenyl) thiourea hydrochloride.

14. A method of treating a neurodegenerative disease in a mammal comprising:

administering to a mammalian subject a pharmaceutical composition for parenteral, enteral or oral administration comprising at least one inhibitor of glutaminyl cyclase (QC), or a pharmaceutically acceptable salt, solvate, stereoisomer or polymorph thereof, for inhibiting conversion of N-terminal glutamic acid or glutamine residues to pyroglutamyl residues in at least one QC-substrate;

wherein said neurodegenerative disease is selected from the group consisting of mild cognitive impairment (MCI), Alzheimer's disease, neurodegeneration in Down Syndrome, Familial British Dementia, and Familial Danish Dementia.

15. The method according to claim 14 wherein the at least one QC-substrate is selected from the group consisting of Aβ(3-40), Aβ(3-42), [Gln3]Aβ(3-40), [Gln3]Aβ(3-42), [Glu11]Aβ(11-40), [Glu 11]Aβ(11-42), [Gln11]Aβ(11-40), [Gln11]Aβ(11-42), ABri, ADan, [Gln1]Gastrins (17 and 34), [Gln$^1$]Neurotensin, [Gln$^1$]FPP, [Gln$^1$]TRH, [Gln$^1$]GnRH, [Gln$^1$]CCL 2, [Gln$^1$]CCL 7, [Gln$^1$]CCL 8, [Gln$^1$]CCL 13, [Gln$^1$]CCL 16, [Gln$^1$]CCL 18, [Gln$^1$]ELA, [Gln$^1$]Fractalkine, [Gln$^1$]Orexin A, [Gln$^3$]glucagon(3-29) and [Gln$^5$]substance P(5-11).

16. The method according to claim 14 wherein said neurodegenerative disease is selected from the grow, consisting of Alzheimer's disease and mild cognitive impairment (MCI).

17. The method according to claim 14 wherein the pharmaceutical composition further comprises at least one additional agent selected from the group consisting of a beta-amyloid antibody, cysteine protease inhibitor, PEP-inhibitor, LiCl, acetylcholinesterase (AChE) inhibitor, PIMT enhancer, beta secretase inhibitor, gamma secretase inhibitor, aminopeptidase inhibitor, dipeptidyl peptidase inhibitor, neutral endopeptidase inhibitor, Phosphodiesterase-4 (PDE-4) inhibitor, TNFalpha inhibitor, muscarinic M1 receptor antagonist, NMDA receptor antagonist, sigma-1 receptor inhibitor, histamine H3 antagonist, immunomodulatory agent, immunosuppressive agent, MCP-1 antagonist, antegren (natalizumab), Neurelan (fampridine-SR), campath (alemtuzumab), IR 208, NBI 5788/MS P 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

18. The method according to claim 14 wherein the at least one inhibitor of glutaminyl cyclase (QC), or a pharmaceutically acceptable salt, solvate, stereoisomer or polymorph thereof, is selected from:

(i) a compound of formula 1*:

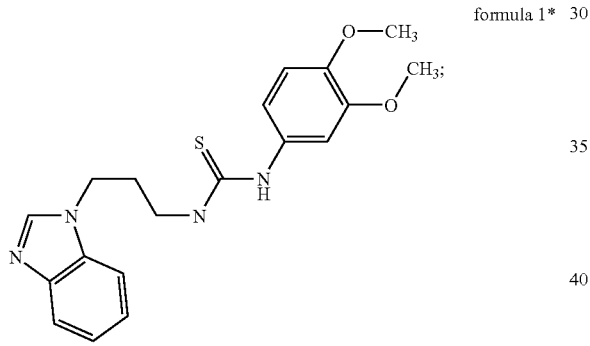

formula 1*

(ii) a compound of formula 1a,

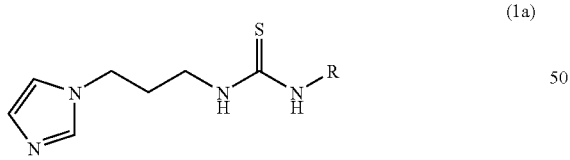

(1a)

wherein R is selected from the group consisting of:

Methyl;
tert-Butyl;
Benzyl;
Phenyl;
4-(fluoro)-phenyl;
4-(chloro)-phenyl;
4-(ethyl)-phenyl;
4-(trifluoromethyl)-phenyl;
4-(methoxy-carbonyl)-Phenyl;
4-(acetyl)-phenyl;

-continued 4-(methoxy)-phenyl;
bicyclo[2.2.1]hept-5-en-2-yl;
3,4-(dimethoxy)-phenyl;
2,4-(dimethoxy)-phenyl;
3,5-(dimethoxy)-phenyl;
2-(methoxy-carbonyl)-Phenyl;
4-(oxazol-5-y)-phenyl;
4-(pyrazol-1-yl)-phenyl;
4-(isopropyl)-phenyl;
4-(piperidine-1-sulfonyl)-Phenyl;
4-(morpholin-4-yl)-phenyl;
4-(cyano)-phenyl;
2,3-dihydro-benzo[1,4]dioxin-6-yl;
benzo[1,3]dioxol-5-yl;
3,4,5(trimethoxy)-phenyl;
3-(methoxy)-phenyl;
4-(ethoxy)-phenyl;
4-(benzyloxy)-phenyl;
4-(methoxy)-benzyl;
3,4-(dimethoxy)-benzyl;
2-(methoxy-carbonyl)-thiophene-3-yl;
3-(ethoxy-carbonyl)-4,5,6,7-tetrahydrobenzo[b]thio-phene2-yl;
2-(methoxy-carbonyl)-4-(methyl)-thiophene-3-yl;
Benzo[c][1,2,5]thiazol-4-yl;
Benzo[c][1,2,5]thiazol-5-yl;
5-(methyl)-3-(phenyl)-isooxazol-4-yl;
3,5-(dimethyl)-isooxazol-4-yl;
4-(iodo)-phenyl;
4-(bromo)-phenyl;
4-(methyl)-phenyl;
Naphthalen-1-yl;
4-(nitro)-phenyl;
Butyl;
Cyclooctyl;
Furan-2-ylmethyl;
Tetrahydrofuran-2-ylmethyl;
Benzo[1,3]dioxol-5-ylmethyl;
2-(morpholin-4-yl)-ethyl;
4-(methylsulfanyl)-phenyl;
4-(dimethylamino)-phenyl;
4-(trifluoromethoxy)-phenyl;
Benzoyl; and
Pyridin-4-yl;

(iii) a compound of formula 1b,

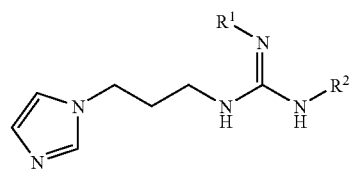

(1b)

wherein R¹ and R² are selected from the group consisting of:

| R¹ | R² |
|---|---|
| Cyano | Methyl |
| Cyano | 3,4-(dimethoxy)-phenyl |
| Cyano | 2,4-(dimethoxy)-phenyl |
| Cyano | 3,5-(dimethoxy)-phenyl |
| Cyano | 2,3-dihydrobenzo[b][1,4]dioxin-7-yl |
| Cyano | Benzo[d][1,3]dioxol-6-yl |
| Cyano | 3,4,5-(trimethoxy)-phenyl |
| Cyano | 3-(methoxy)-phenyl |
| Cyano | 4-(ethoxy)-phenyl |
| Cyano | 4-(benzyloxy)-phenyl |
| Cyano | Phenyl |
| Cyano | 4-(methoxy)-phenyl |

-continued

| R¹ | R² |
|---|---|
| Cyano | 4-(acetyl)-phenyl |
| Cyano | 4-(nitro)-phenyl |
| Cyano | Benzyl |
| Cyano | Naphthalen-1-yl |
| Cyano | 4-(fluoro)-phenyl |
| Cyano | 4-(iodo)-phenyl |
| Cyano | 4-(bromo)-phenyl |
| Cyano | Cyclooctyl |
| Cyano | tert-butyl |
| Cyano | 4-(methyl)-phenyl |
| Cyano | 4-(methylthio)-phenyl |
| Cyano | 4-(ethyl)-phenyl |
| Cyano | 4-(dimethylamino)-phenyl |
| Cyano | Butyl |
| Cyano | Trityl |
| Cyano | (Benzo[d][1,3]dioxol-6yl)methyl |
| Cyano | (tetrahydrofuran-2yl)methyl |
| Cyano | 4-(trifluoromethyl)-phenyl |
| Cyano | (furan-2-yl)methyl |
| Cyano | 2-(morpholin-4-yl)-ethyl |
| Cyano | 4-(oxazol-5yl)-phenyl |
| Cyano | Pyridin-3-yl |
| Cyano | 4-(cyano)-phenyl |
| Cyano | 4-(trifluoromethoxy)-phenyl |
| Cyano | 4-(piperidinosulfonyl)-phenyl |
| Cyano | 4-(1H-pyrazol-1-yl)phenyl |
| H | 3,4-(dimethoxy)-phenyl |
| Methyl | 3,4-(dimethoxy)-phenyl |
| Cyano | 2,3,4-(trimethoxy)-phenyl |
| Cyano | Cycloheptyl; |

(iv) a compound of formula 1c,

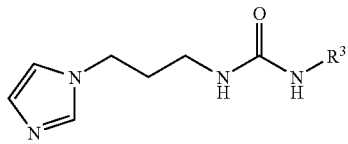

(1c)

wherein $R^3$ is selected from the group consisting of:

Ethyl;
6-fluoro-4H-benzo[d][1,3]dioxin-8-yl;
3-(cylopentyloxy)-4-(methoxy)-phenyl;
4-(heptyloxy)-phenyl;
3,4-dihydro-2H-benzo[b][1,4]dioxepin-7-yl;
4-(butoxy)-phenyl; and
3,4-(dimethoxy)-phenyl;

(v) a compound of formula 1d,

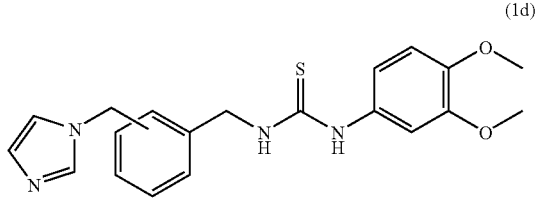

(1d)

wherein the position on the ring is selected from the group consisting of 2, 3, and 4;

(vi) a compound of formula 1e,

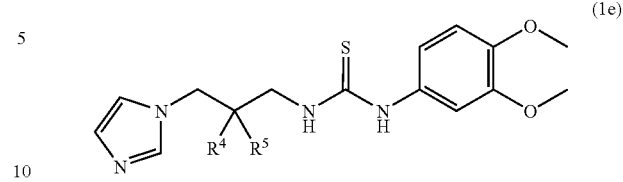

(1e)

wherein $R^4$ and $R^5$ selected from the group consisting of:

| $R^4$ | $R^5$ |
|---|---|
| H | Methyl |
| Methyl | H |
| Methyl | Methyl |
| —CH₂—CH₂—; | |

(vii) a compound of formula if,

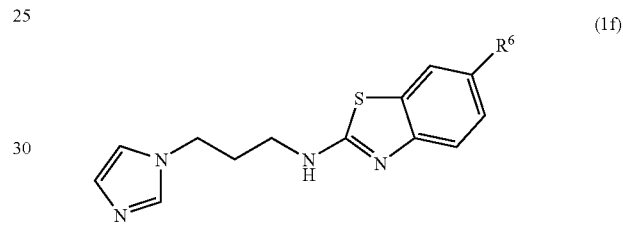

(1f)

wherein $R^6$ is selected from the group consisting of H, chloro, and methoxy;

(viii) a compound of formula 1g,

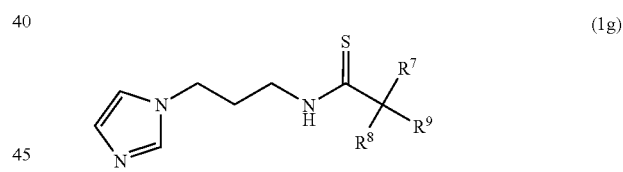

(1g)

wherein $R^7$, $R^8$ and $R^9$ are selected from the group consisting of:

| $R^7$ | $R^8$ | $R^9$ |
|---|---|---|
| Phenyl | H | H |
| Thiophen-2-yl | H | H |
| Phenyl | Methyl | H |
| Phenyl | H | Methyl |
| Phenyl | H | Ethyl |
| Phenyl | H | Phenyl |
| 3,4-(dimethoxy)-Phenyl | H | H |
| 3,4-(dimethoxy)-Phenyl | Methyl | Methyl |
| 4-(chloro)-phenyl | —CH₂—CH₂—CH₂— | |
| 4-(chloro)-phenyl | —CH₂—C₂H₄—CH₂— | |
| 4-(methoxy)-phenyl | —CH₂—C₃H₆—CH₂— | |
| 4-(methoxy)-phenyl | —CH₂—CH₂— | |
| 3,4-(dimethoxy)-Phenyl | —CH₂—CH₂— | |

-continued

| R⁷ | R⁸ | R⁹ |
|---|---|---|
| 3,4,5-(trimethoxy)-Phenyl | | —CH₂—CH₂— |
| 2,3,4-(trimethoxy)-Phenyl | | —CH₂—CH₂— |
| 2-(methoxy)-phenyl | | —CH₂—CH₂— |
| 3-(methoxy)-phenyl | | —CH₂—CH₂— |
| 2,3-(dimethoxy)-Phenyl | | —CH₂—CH₂— |
| 3,5-(dimethoxy)-Phenyl | | —CH₂—CH₂— |
| 2,5-(dimethoxy)-Phenyl; | | —CH₂—CH₂— |

(ix) a compound of formula 1h,

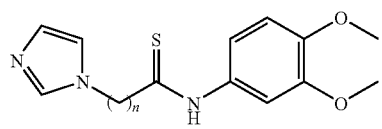

(1h)

wherein n is defined as 3, 4, or 5;

(x) a compound of formula II,

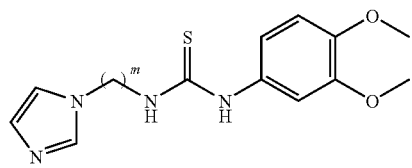

wherein m is defined as 2 or 4; and (xi) a compound selected from the group consisting of:

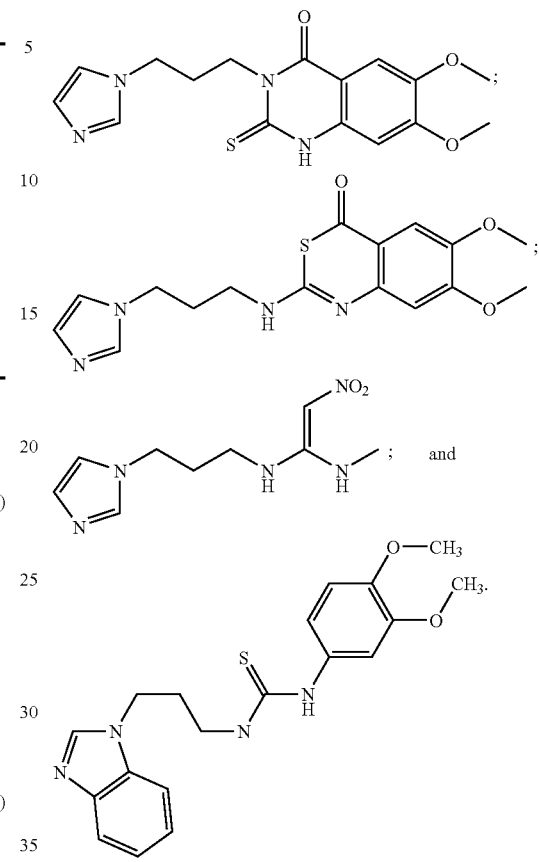

(1i)

19. The method according to claim 14 wherein the at least one inhibitor of glutaminyl cyclase (QC) is 1-(3-(1H-imidazole-1-yl)propyl)-3-(3,4-dimethoxy-phenyl) thiourea hydrochloride.

* * * * *

SEQUENCE LISTING

```
<160> NUMBER OF SEQ ID NOS: 48

<210> SEQ ID NO 1
<211> LENGTH: 371
<212> TYPE: DNA
<213> ORGANISM: Artificial sequence
<220> FEATURE:
<223> OTHER INFORMATION: Synthetic nucleotide

<400> SEQUENCE: 1
aagcttatgc agggaccttg gctgatgatg gctctggctt tgatcttcgt gctaactggt      60
atccccaaat cctgcgcctt gctggaagca gcccaggagg aagtgctgt gactcctgac     120 cttccaggcc tggagaaagt ccaggtccgg ccagaacgtc gattcttgag gaaagacctc    180
cagcgtgtgc gagggacct tggtgctgcc ttagattcct ggatcacaaa acgcgatgca     240
gaattccgac atgactcagg atatgaagtt catcatcaaa aattggtgtt ctttgcagaa    300
gatgtgggtt caaacaaagg tgcaatcatt ggactcatgg tgggcggtgt tgtcatagcg    360
taagcggccg c                                                         371

<210> SEQ ID NO 2
<211> LENGTH: 365
<212> TYPE: DNA
<213> ORGANISM: Artificial sequence
<220> FEATURE:
<223> OTHER INFORMATION: Synthetic nucleotide

<400> SEQUENCE: 2
```

```
aagcttatgc agggaccttg gctgatgatg gctctggctt tgatcttcgt gctaactggt    60
atccccaaat cctgcgcctt gctggaagca gcccaggagg aaggtgctgt gactcctgac   120
cttccaggcc tggagaaagt ccaggtccgg ccagaacgtc gattcttgag gaaagacctc   180
cagcgtgtgc gagggaccct tggtgctgcc ttagattcct ggatcacaaa acgccaattc   240
cgacatgact caggatatga agttcatcat caaaaattgg tgttctttgc agaagatgtg   300
ggttcaaaca aggtgcaat cattggactc atggtgggcg tgttgtcat agcgtaagcg    360 gccgc                                                              365
```

```
<210> SEQ ID NO 3
<211> LENGTH: 365
<212> TYPE: DNA
<213> ORGANISM: Artificial sequence
<220> FEATURE:
<223> OTHER INFORMATION: Synthetic nucleotide

<400> SEQUENCE: 3
```

```
aagcttatgc agggaccttg gctgatgatg gctctggctt tgatcttcgt gctaactggt    60
atccccaaat cctgcgcctt gctggaagca gcccaggagg aaggtgctgt gactcctgac   120
cttccaggcc tggagaaagt ccaggtccgg ccagaacgtc gattcttgag gaaagacctc   180
cagcgtgtgc gagggaccct tggtgctgcc ttagattcct ggatcacaaa acgcgagttc   240
cgacatgact caggatatga agttcatcat caaaaattgg tgttctttgc agaagatgtg   300
ggttcaaaca aggtgcaat cattggactc atggtgggcg tgttgtcat agcgtaagcg    360 gccgc                                                              365
```

```
<210> SEQ ID NO 4
<211> LENGTH: 300
<212> TYPE: DNA
<213> ORGANISM: Homo sapiens

<400> SEQUENCE: 4
```

```
atgaaagtct ctgccgccct tctgtgcctg ctgctcatag cagccacctt cattccccaa    60
gggctcgctc agccagatgc aatcaatgcc ccagtcacct gctgttataa cttcaccaat   120
aggaagatct cagtgcagag gctcgcgagc tatagaagaa tcaccagcag caagtgtccc   180
aaagaagctg tgatcttcaa gaccattgtg gccaaggaga tctgtgctga ccccaagcag   240
aagtgggttc aggattccat ggaccacctg gacaagcaaa cccaaactcc gaagacttga   300
```

```
<210> SEQ ID NO 5
<211> LENGTH: 99
<212> TYPE: PRT
<213> ORGANISM: Homo sapiens

<400> SEQUENCE: 5
```

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

```
Lys Trp Val Gln Asp Ser Met Asp His Leu Asp Lys Gln Thr Gln Thr
            85                  90                  95

Pro Lys Thr
```

<210> SEQ ID NO 6
<211> LENGTH: 300
<212> TYPE: DNA
<213> ORGANISM: Homo sapiens

<400> SEQUENCE: 6

```
atgaaggttt ctgcagcgct tctgtgcctg ctgctcatgg cagccacttt cagccctcag    60
ggacttgctc agccagattc agtttccatt ccaatcacct gctgctttaa cgtgatcaat   120
aggaaaattc ctatccagag gctggagagc tacacaagaa tcaccaacat ccaatgtccc   180
aaggaagctg tgatcttcaa gacccaacgg ggcaaggagg tctgtgctga ccccaaggag   240
agatgggtca gggattccat gaagcatctg gaccaaatat ttcaaaatct gaagccatga   300
```

<210> SEQ ID NO 7
<211> LENGTH: 99
<212> TYPE: PRT
<213> ORGANISM: Homo sapiens

<400> SEQUENCE: 7

```
Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
            20                  25                  30

Thr Cys Cys Phe Asn Val Ile Asn Arg Lys Ile Pro Ile Gln Arg Leu
        35                  40                  45

Glu Ser Tyr Thr Arg Ile Thr Asn Ile Gln Cys Pro Lys Glu Ala Val
    50                  55                  60

Ile Phe Lys Thr Gln Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro
```

<210> SEQ ID NO 8
<211> LENGTH: 300
<212> TYPE: DNA
<213> ORGANISM: Homo sapiens

<400> SEQUENCE: 8

```
atgaaagcct ctgcagcact tctgtgtctg ctgctcacag cagctgcttt cagcccccag    60
gggcttgctc agccagttgg gattaatact tcaactacct gctgctacag atttatcaat   120
aagaaaatcc ctaagcagag gctggagagc tacagaagga ccaccagtag ccactgtccc   180
cgggaagctg taatcttcaa gaccaaactg gacaaggaga tctgtgctga ccccacacag   240
aagtgggtcc aggactttat gaagcacctg gacaagaaaa cccaaactcc aaagctttga   300
```

<210> SEQ ID NO 9
<211> LENGTH: 99
<212> TYPE: PRT
<213> ORGANISM: Homo sapiens

<400> SEQUENCE: 9

```
Met Lys Ala Ser Ala Ala Leu Leu Cys Leu Leu Leu Thr Ala Ala Ala
```

```
                1               5                  10                 15
Phe Ser Pro Gln Gly Leu Ala Gln Pro Val Gly Ile Asn Thr Ser Thr
                    20                  25                 30

Thr Cys Cys Tyr Arg Phe Ile Asn Lys Lys Ile Pro Lys Gln Arg Leu
                    35                  40                 45

Glu Ser Tyr Arg Arg Thr Thr Ser Ser His Cys Pro Arg Glu Ala Val
            50                  55                 60

Ile Phe Lys Thr Lys Leu Asp Lys Glu Ile Cys Ala Asp Pro Thr Gln
65                      70                  75                 80

Lys Trp Val Gln Asp Phe Met Lys His Leu Asp Lys Lys Thr Gln Thr
                            85                  90                 95

Pro Lys Leu

<210> SEQ ID NO 10
<211> LENGTH: 297
<212> TYPE: DNA
<213> ORGANISM: Homo sapiens

<400> SEQUENCE: 10
atgaaagtct ctgcagtgct tctgtgcctg ctgctcatga cagcagcttt caacccccag      60
ggacttgctc agccagatgc actcaacgtc ccatctactt gctgcttcac atttagcagt     120
aagaagatct ccttgcagag gctgaagagc tatgtgatca ccaccagcag gtgtccccag     180
aaggctgtca tcttcagaac caaactgggc aaggagatct gtgctgaccc aaaggagaag     240
tgggtccaga attatatgaa acacctgggc cggaaagctc acacccctgaa gacttga      297

<210> SEQ ID NO 11
<211> LENGTH: 98
<212> TYPE: PRT
<213> ORGANISM: Homo sapiens

<400> SEQUENCE: 11

Met Lys Val Ser Ala Val Leu Leu Cys Leu Leu Leu Met Thr Ala Ala
1               5                  10                 15

Phe Asn Pro Gln Gly Leu Ala Gln Pro Asp Ala Leu Asn Val Pro Ser
                    20                  25                 30

Thr Cys Cys Phe Thr Phe Ser Ser Lys Lys Ile Ser Leu Gln Arg Leu
                    35                  40                 45

Lys Ser Tyr Val Ile Thr Thr Ser Arg Cys Pro Gln Lys Ala Val Ile
            50                  55                 60

Phe Arg Thr Lys Leu Gly Lys Glu Ile Cys Ala Asp Pro Lys Glu Lys
65                      70                  75                 80

Trp Val Gln Asn Tyr Met Lys His Leu Gly Arg Lys Ala His Thr Leu
                            85                  90                 95

Lys Thr

<210> SEQ ID NO 12
<211> LENGTH: 32
<212> TYPE: DNA
<213> ORGANISM: Artificial sequence
<220> FEATURE:
<223> OTHER INFORMATION: DNA primer

<400> SEQUENCE: 12
atataagctt atgaaagtct ctgccgccct tc                                     32

<210> SEQ ID NO 13
```

```
<211> LENGTH: 32
<212> TYPE: DNA
<213> ORGANISM: Artificial sequence
<220> FEATURE:
<223> OTHER INFORMATION: DNA primer

<400> SEQUENCE: 13
atatgcggcc gctcaagtct tcggagtttg gg                              32

<210> SEQ ID NO 14
<211> LENGTH: 37
<212> TYPE: DNA
<213> ORGANISM: Artificial sequence
<220> FEATURE:
<223> OTHER INFORMATION: DNA primer

<400> SEQUENCE: 14
cattccccaa gggctcgctc cagatgcaat caatgcc                         37

<210> SEQ ID NO 15
<211> LENGTH: 37
<212> TYPE: DNA
<213> ORGANISM: Artificial sequence
<220> FEATURE:
<223> OTHER INFORMATION: DNA primer

<400> SEQUENCE: 15
ggcattgatt gcatctggag cgagcccttg gggaatg                         37

<210> SEQ ID NO 16
<211> LENGTH: 38
<212> TYPE: DNA
<213> ORGANISM: Artificial sequence
<220> FEATURE:
<223> OTHER INFORMATION: DNA primer

<400> SEQUENCE: 16
cattccccaa gggctcgctg atgcaatcaa tgccccag                        38

<210> SEQ ID NO 17
<211> LENGTH: 38
<212> TYPE: DNA
<213> ORGANISM: Artificial sequence
<220> FEATURE:
<223> OTHER INFORMATION: DNA primer

<400> SEQUENCE: 17
ctggggcatt gattgcatca gcgagcccct tggggaatg                       38

<210> SEQ ID NO 18
<211> LENGTH: 1086
<212> TYPE: DNA
<213> ORGANISM: human

<400> SEQUENCE: 18
atggcaggcg gaagacaccg gcgcgtcgtg gcaccctcc acctgctgct gctggtggcc   60
gccctgccct gggcatccag gggggtcagt ccgagtgcct cagcctggcc agaggagaag  120
aattaccacc agccagccat tttgaattca tcggctcttc ggcaaattgc agaaggcacc  180
agtatctctg aaatgtggca aaatgactta cagccattgc tgatagagcg atacccggga  240
tcccctggaa gctatgctgc tcgtcagcac atcatgcagc gaattcagag gcttcaggct  300
gactgggtct tggaaataga caccttcttg agtcagacac cctatggtta ccggtctttc  360
tcaaatatca tcagcaccct caatcccact gctaaacgac atttggtcct cgcctgccac  420
```

| | |
|---|---|
| tatgactcca agtatttttc ccactggaac aacagagtgt tgtaggagc cactgattca | 480 |
| gccgtgccat gtgcaatgat gttggaactt gctcgtgcct tagacaagaa actcctttcc | 540 |
| ttaaagactg tttcagactc caagccagat tgtcactcc agctgatctt ctttgatggt | 600 |
| gaagaggctt ttcttcactg gtctcctcaa gattctctct atgggtctcg acacttagct | 660 |
| gcaaagatgg catcgacccc gcacccacct ggagcgagag caccagcca actgcatggc | 720 |
| atggatttat tggtcttatt ggatttgatt ggagctccaa acccaacgtt tcccaatttt | 780 |
| tttccaaact cagccaggtg gttcgaaaga cttcaagcaa ttgaacatga acttcatgaa | 840 |
| tgggtttgc tcaaggatca ctctttggag gggcggtatt tccagaatta cagttatgga | 900 |
| ggtgtgattc aggatgacca tattccattt ttaagaagag gtgttccagt tctgcatctg | 960 |
| ataccgtctc ctttccctga agtctggcac accatggatg acaatgaaga aaatttggat | 1020 |
| gaatcaacca ttgacaatct aaacaaaatc ctacaagtct tgtgttgga atatcttcat | 1080 |
| ttgtaa | 1086 |

<210> SEQ ID NO 19
<211> LENGTH: 361
<212> TYPE: PRT
<213> ORGANISM: human

<400> SEQUENCE: 19

```
Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
                100                 105                 110

Thr Pro Tyr Gly Tyr Arg Ser Phe Ser Asn Ile Ile Ser Thr Leu Asn
            115                 120                 125

Pro Thr Ala Lys Arg His Leu Val Leu Ala Cys His Tyr Asp Ser Lys
        130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
                180                 185                 190

Leu Gln Leu Ile Phe Phe Asp Gly Glu Glu Ala Phe Leu His Trp Ser
            195                 200                 205

Pro Gln Asp Ser Leu Tyr Gly Ser Arg His Leu Ala Ala Lys Met Ala
        210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
```

-continued

```
                245                 250                 255
Phe Pro Asn Phe Pro Asn Ser Ala Arg Trp Phe Glu Arg Leu Gln
            260                 265                 270
Ala Ile Glu His Glu Leu His Glu Leu Gly Leu Leu Lys Asp His Ser
        275                 280                 285
Leu Glu Gly Arg Tyr Phe Gln Asn Tyr Ser Tyr Gly Gly Val Ile Gln
        290                 295                 300
Asp Asp His Ile Pro Phe Leu Arg Arg Gly Val Pro Val Leu His Leu
305                 310                 315                 320
Ile Pro Ser Pro Phe Pro Glu Val Trp His Thr Met Asp Asp Asn Glu
                325                 330                 335
Glu Asn Leu Asp Glu Ser Thr Ile Asp Asn Leu Asn Lys Ile Leu Gln
            340                 345                 350
Val Phe Val Leu Glu Tyr Leu His Leu
        355                 360
```

<210> SEQ ID NO 20
<211> LENGTH: 42
<212> TYPE: PRT
<213> ORGANISM: Homo sapiens

<400> SEQUENCE: 20

```
Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val Ile Ala
        35                  40
```

<210> SEQ ID NO 21
<211> LENGTH: 40
<212> TYPE: PRT
<213> ORGANISM: Homo sapiens

<400> SEQUENCE: 21

```
Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val
        35                  40
```

<210> SEQ ID NO 22
<211> LENGTH: 40
<212> TYPE: PRT
<213> ORGANISM: Homo sapiens

<400> SEQUENCE: 22

```
Glu Phe Arg His Asp Ser Gly Tyr Glu Val His His Gln Lys Leu Val
1               5                   10                  15
Phe Phe Ala Glu Asp Val Gly Ser Asn Lys Gly Ala Ile Ile Gly Leu
            20                  25                  30
Met Val Gly Gly Val Val Ile Ala
        35                  40
```

<210> SEQ ID NO 23
<211> LENGTH: 38
<212> TYPE: PRT
<213> ORGANISM: Homo sapiens

<400> SEQUENCE: 23

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 24
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 24

Asp Ala Glu Phe Arg His Asp Ser Gly Tyr Glu
1               5                   10

<210> SEQ ID NO 25
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (9)..(9)
<223> OTHER INFORMATION: AMIDATION

<400> SEQUENCE: 25

Glu Phe Arg His Asp Ser Gly Tyr Glu
1               5

<210> SEQ ID NO 26
<211> LENGTH: 21
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (21)..(21)
<223> OTHER INFORMATION: AMIDATION

<400> SEQUENCE: 26

Asp Ala Glu Phe Arg His Asp Ser Gly Tyr Glu Val His His Gln Lys
1               5                   10                  15

Leu Val Phe Phe Ala
            20

<210> SEQ ID NO 27
<211> LENGTH: 19
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (19)..(19)
<223> OTHER INFORMATION: AMIDATION

<400> SEQUENCE: 27

```
Glu Phe Arg His Asp Ser Gly Tyr Glu Val His His Gln Lys Leu Val
1               5                   10                  15

Phe Phe Ala

<210> SEQ ID NO 28
<211> LENGTH: 38
<212> TYPE: PRT
<213> ORGANISM: Artificial sequence
<220> FEATURE:
<223> OTHER INFORMATION: Synthetic peptide

<400> SEQUENCE: 28

Gln Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 29
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (19)..(19)
<223> OTHER INFORMATION: AMIDATION

<400> SEQUENCE: 29

Gln Phe Arg His Asp Ser Gly Tyr Glu Val His His Gln Lys Leu Val
1               5                   10                  15

Phe Phe Ala

<210> SEQ ID NO 30
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 30

Asp Ala Gln Phe Arg His Asp Ser Gly Tyr Glu
1               5                   10

<210> SEQ ID NO 31
<211> LENGTH: 9
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 31

Gln Phe Arg His Asp Ser Gly Tyr Glu
1               5

<210> SEQ ID NO 32
<211> LENGTH: 32
<212> TYPE: PRT
<213> ORGANISM: Artificial sequence
<220> FEATURE:
<223> OTHER INFORMATION: synthetic peptide

<400> SEQUENCE: 32

Glu Val His His Gln Lys Leu Val Phe Phe Ala Glu Asp Val Gly Ser
1               5                   10                  15

Asn Lys Gly Ala Ile Ile Gly Leu Met Val Gly Val Ile Ala
            20                  25                  30

<210> SEQ ID NO 33
<211> LENGTH: 30
<212> TYPE: PRT
<213> ORGANISM: Artificial sequence
<220> FEATURE:
<223> OTHER INFORMATION: synthetic peptide

<400> SEQUENCE: 33

Glu Val His His Gln Lys Leu Val Phe Phe Ala Glu Asp Val Gly Ser
1               5                   10                  15

Asn Lys Gly Ala Ile Ile Gly Leu Met Val Gly Val Val
            20                  25                  30

<210> SEQ ID NO 34
<211> LENGTH: 34
<212> TYPE: PRT
<213> ORGANISM: Homo sapiens

<400> SEQUENCE: 34

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 35
<211> LENGTH: 34
<212> TYPE: PRT
<213> ORGANISM: Homo sapiens

<400> SEQUENCE: 35

Glu Ala Ser Asn Cys Phe Ala Ile Arg His Phe Glu Asn Lys Phe Ala
1               5                   10                  15
```

```
Val Glu Thr Leu Ile Cys Phe Asn Leu Phe Leu Asn Ser Gln Glu Lys
            20                  25                  30

His Tyr

<210> SEQ ID NO 36
<211> LENGTH: 34
<212> TYPE: PRT
<213> ORGANISM: Homo sapiens

<400> SEQUENCE: 36

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 37
<211> LENGTH: 34
<212> TYPE: PRT
<213> ORGANISM: Homo sapiens

<400> SEQUENCE: 37

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 38
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 38

Gln Gly Pro Trp Leu Glu Glu Glu Glu Ala Tyr Gly Trp Met Asp
1               5                   10                  15

Phe

<210> SEQ ID NO 39
<211> LENGTH: 13
<212> TYPE: PRT
<213> ORGANISM: Homo sapiens

<400> SEQUENCE: 39

Gln Leu Tyr Glu Asn Lys Pro Arg Arg Pro Tyr Ile Leu
1               5                   10

<210> SEQ ID NO 40
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION
```

-continued

```
<400> SEQUENCE: 40

Gln His Trp Ser Tyr Gly Leu Arg Pro Gly
1               5                   10

<210> SEQ ID NO 41
<211> LENGTH: 97
<212> TYPE: PRT
<213> ORGANISM: Homo sapiens

<400> SEQUENCE: 41

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
        50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 42
<211> LENGTH: 76
<212> TYPE: PRT
<213> ORGANISM: Homo sapiens

<400> SEQUENCE: 42

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
65                  70                  75

<210> SEQ ID NO 43
<211> LENGTH: 68
<212> TYPE: PRT
<213> ORGANISM: Homo sapiens

<400> SEQUENCE: 43

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
            35                  40                  45

Cys Ala Asp Pro Asn Lys Lys Trp Val Gln Lys Tyr Ile Ser Asp Leu
        50                  55                  60

Lys Leu Asn Ala
65
```

<210> SEQ ID NO 44
<211> LENGTH: 373
<212> TYPE: PRT
<213> ORGANISM: Homo sapiens

<400> SEQUENCE: 44

```
Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335
```

```
Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
            355                 360                 365

Val Leu Val Pro Val
        370

<210> SEQ ID NO 45
<211> LENGTH: 76
<212> TYPE: PRT
<213> ORGANISM: Homo sapiens

<400> SEQUENCE: 45

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 46
<211> LENGTH: 33
<212> TYPE: PRT
<213> ORGANISM: Homo sapiens

<400> SEQUENCE: 46

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 47
<211> LENGTH: 11
<212> TYPE: PRT
<213> ORGANISM: Homo sapiens

<400> SEQUENCE: 47

Arg Pro Lys Pro Gln Gln Phe Phe Gly Leu Met
1               5                   10

<210> SEQ ID NO 48
<211> LENGTH: 5
<212> TYPE: PRT
<213> ORGANISM: Artificial sequence
<220> FEATURE:
<223> OTHER INFORMATION: Synthetic peptide

<400> SEQUENCE: 48

Gln Tyr Asn Ala Asp
1               5
```